US009540362B2

(12) United States Patent
Paek et al.

(10) Patent No.: US 9,540,362 B2
(45) Date of Patent: Jan. 10, 2017

(54) SPHINGOSINE-1-PHOSPHATE RECEPTOR AGONISTS, METHODS OF PREPARING THE SAME, AND PHARMACEUTICAL COMPOSITIONS CONTAINING THE SAME AS AN ACTIVE AGENT

(71) Applicant: LG LIFE SCIENCES LTD., Seoul (KR)

(72) Inventors: Seung Yup Paek, Daejeon (KR); Sung Bae Lee, Daejeon (KR); Deok Seong Park, Daejeon (KR); Won Hyung Lee, Daejeon (KR)

(73) Assignee: LG LIFE SCIENCES LTD., Seoul (KR)

( * ) Notice: Subject to any disclaimer, the term of this patent is extended or adjusted under 35 U.S.C. 154(b) by 0 days.

(21) Appl. No.: 14/764,116

(22) PCT Filed: Feb. 19, 2014

(86) PCT No.: PCT/KR2014/001336
§ 371 (c)(1),
(2) Date: Jul. 28, 2015

(87) PCT Pub. No.: WO2014/129796
PCT Pub. Date: Aug. 28, 2014

(65) Prior Publication Data
US 2015/0376173 A1 Dec. 31, 2015

(30) Foreign Application Priority Data
Feb. 20, 2013 (KR) ........................ 10-2013-0018293

(51) Int. Cl.
| C07D 271/12 | (2006.01) |
| C07D 413/04 | (2006.01) |
| A61K 31/4245 | (2006.01) |
| C07D 413/14 | (2006.01) |
| C07D 403/12 | (2006.01) |
| C07D 231/56 | (2006.01) |
| C07D 401/12 | (2006.01) |
| C07D 471/04 | (2006.01) |
| C07D 209/08 | (2006.01) |
| C07D 209/30 | (2006.01) |

(52) U.S. Cl.
CPC ........... *C07D 413/14* (2013.01); *C07D 209/08* (2013.01); *C07D 209/30* (2013.01); *C07D 231/56* (2013.01); *C07D 401/12* (2013.01); *C07D 403/12* (2013.01); *C07D 413/04* (2013.01); *C07D 471/04* (2013.01)

(58) Field of Classification Search
None
See application file for complete search history.

(56) References Cited

U.S. PATENT DOCUMENTS

| 2007/0225275 A1 | 9/2007 | Allison et al. |
| 2008/0153813 A1 | 6/2008 | Chen et al. |
| 2008/0167340 A1 | 7/2008 | DeLong et al. |
| 2008/0200535 A1 | 8/2008 | Ohmori et al. |
| 2010/0040554 A1 | 2/2010 | Li et al. |
| 2011/0152241 A1 | 6/2011 | Nguyen et al. |
| 2011/0183953 A1 | 7/2011 | Boehm et al. |
| 2011/0207704 A1 | 8/2011 | Cusack et al. |

FOREIGN PATENT DOCUMENTS

| EP | 1 535 915 A1 | 6/2005 |
| EP | 1 760 071 A1 | 3/2007 |
| EP | 2 202 232 A1 | 6/2010 |
| WO | WO 9911255 A1 * | 3/1999 |
| WO | WO 2004/063155 A1 | 7/2004 |
| WO | WO 2004/092116 A1 | 10/2004 |
| WO | WO 2006/064757 A1 | 6/2006 |
| WO | WO 2006/081230 A2 | 8/2006 |
| WO | WO 2007/103759 A2 | 9/2007 |
| WO | WO 2008/064320 A2 | 5/2008 |
| WO | WO 2009/011880 A2 | 1/2009 |
| WO | WO 2009/016460 A2 | 2/2009 |
| WO | WO 2009/080724 A1 | 7/2009 |
| WO | WO 2009/151529 A1 | 12/2009 |
| WO | WO 2010/042998 A | 4/2010 |
| WO | WO 2010/069949 A1 | 6/2010 |
| WO | WO 2010/080663 A1 | 7/2010 |
| WO | WO 2010/093191 A2 | 8/2010 |
| WO | WO 2010/112461 A1 | 10/2010 |
| WO | WO 2010/123975 A1 | 10/2010 |

(Continued)

OTHER PUBLICATIONS

Ohmori et al, Chemical Abstracts 148:285196, (2008), Abstract of WO 2008023783.*
Koradin et al., "Synthesis of polyfunctional indoles and related heterocycles mediated by cesium and potassium bases", Tetrahedron, vol. 59, 2003, pp. 1571-1587.
Liu et al., "Synthesis of carbazoles and dibenzofurans via cross-coupling of o-iodoanilines and o-iodophenols with silylaryl triflates and subsequent Pd-catalyzed cyclization", Tetrahedron, vol. 63, 2007 (available online Nov. 13, 2006), pp. 347-355.
Ohta et al., "Construction of Nitrogen Heterocycles Bearing an Aminomethyl Group by Copper-Catalyzed Domino Three-Component Coupling-Cyclization", J. Org. Chem., vol. 74, 2009 (published on web Aug. 12, 2009), pp. 7052-7058.

(Continued)

Primary Examiner — Zinna Northington Davis
(74) Attorney, Agent, or Firm — Birch, Stewart, Kolasch & Birch, LLP

(57) ABSTRACT

The present invention relates to novel compounds of Formula 1 as sphingosine-1-phosphate receptor agonists which can be effectively used for the treatment of autoimmune diseases, a method for preparing the same, and a pharmaceutical composition comprising the same as an active component. The compounds according to the present invention are effective on extensive autoimmune diseases and chronic inflammatory diseases including relapsing-remitting multiple sclerosis, and can also be used for treating or preventing immunoregulation disorders.

12 Claims, No Drawings

(56) References Cited

FOREIGN PATENT DOCUMENTS

| WO | WO 2010/146105 A1 | 12/2010 |
| WO | WO 2010/148649 A1 | 12/2010 |
| WO | WO 2011/060389 A1 | 5/2011 |
| WO | WO 2011/144338 A1 | 11/2011 |

OTHER PUBLICATIONS

Sauerberg et al., "Identification and Synthesis of a Novel Selective Partial PPARδ Agonist with Full Efficacy on Lipid Metabolism In Vitro and In Vivo", J. Med. Chem., vol. 50, 2007 (published on web Mar. 8, 2007), pp. 1495-1503.
Zhang et al., "Synthesis of Trisubstituted Indoles on the Solid Phase via Palladium-Mediated Heteroannulation of Internal Alkynes", Tetrahedron Letters, vol. 38, No. 14, 1997, pp. 2439-2442.
International Search Report issued in PCT/KR2014/001336 dated May 30, 2014.
Supplementary European Search Report issued in EP14753476 dated Sep. 5, 2016.

\* cited by examiner

SPHINGOSINE-1-PHOSPHATE RECEPTOR AGONISTS, METHODS OF PREPARING THE SAME, AND PHARMACEUTICAL COMPOSITIONS CONTAINING THE SAME AS AN ACTIVE AGENT

TECHNICAL FIELD

The present invention relates to novel compounds as sphingosine-1-phosphate receptor agonists which can be effectively used for the treatment of autoimmune diseases such as multiple sclerosis, a method for preparing the same, and a pharmaceutical composition comprising the same as an active component.

BACKGROUND ART

S1P (sphingosine-1-phosphate) is produced via an intracellular ceramide pathway, in which ceramide is the starting material. Ceramide is produced via two pathways, the first of which is de novo biosynthetic pathway. Ceramide is also produced by the degradation of sphingomyelin, a cell membrane constituent, in a cell. The S1P level in each tissue is controlled by two biosynthetic sphingosine kinases (SphKs) and two biodegradable S1P phosphatases (S1P lyase and lysophospholipid phosphatases). S1P, produced via phosphorylation of sphingosine by sphingosine kinase, is known to mediate various cellular responses, such as cell proliferation, cytoskeletal organization and migration, adherence- and tight junction assembly, and morphogenesis. S1P exists as a combined form with plasma protein including albumin at high level (100~1000 nM) in plasma, while it is at a low level in tissues.

S1P binds with S1P receptor, a G-protein coupled receptor, to show various biological functions. As S1P receptor sub-types, S1P1~S1P5 are known up to now and are named endothelial differentiation gene (EDG) receptors 1, 5, 3, 6 and 8, respectively. The S1P receptors are known to be involved in various biological functions such as leukocyte recirculation, neural cell proliferation, morphological changes, migration, endothelial function, vasoregulation and cardiovascular development.

In recent years, many studies have found that the S1P signaling process via these receptors plays an important role in a series of responses related to multiple sclerosis including inflammation response and the repair process, and a non-selective S1P1 agonist was actually approved as a therapeutic agent for multiple sclerosis. S1P receptors are extensively expressed in many cells related to the induction of multiple sclerosis. Especially, S1P1 receptor plays a major role in the immune system. S1P1 receptor is mainly expressed on the surface of lymphocytes such as T cell and B cell, and responds to S1P resulting in involvement in recirculation of lymphocytes. In normal condition, the S1P concentration is higher in body fluid than in lymphoid tissue, and therefore lymphocytes leave lymphoid tissue by the difference of S1P concentration to circulate after efferent lymph circulates. However, if S1P1 receptor in lymphocytes is down-regulated by S1P1 agonist, the egress of lymphocytes from lymphoid tissue does not occur, resulting in reduced infiltration of autoaggressive lymphocytes which cause inflammation and tissue damage in the central nervous system (CNS). As a result, a therapeutic effect on multiple sclerosis is obtained. Fingolimod, a non-selective S1P1 agonist, has been approved as an oral medication for the treatment of multiple sclerosis. When it binds at S1P1 receptor to be activated, the receptor becomes degraded or internalized from the surface of lymphocytes ironically, and thus it acts as a functional S1P1 antagonism.

DISCLOSURE OF INVENTION

Technical Problem

The object of the present invention is to provide novel compounds having superior effect on sphingosine-1-phosphate receptor, or pharmaceutically acceptable salts, isomers or solvates thereof.

Another object of the present invention is to provide a method for preparing the novel compounds.

Still another object of the present invention is to provide a pharmaceutical composition as sphingosine-1-phosphate receptor agonists, comprising as active components the novel compounds or pharmaceutically acceptable salts, isomers or solvates thereof and a pharmaceutically acceptable carrier.

The pharmaceutical composition of the present invention has an especially superior effect on preventing and treating autoimmune disease such as multiple sclerosis.

Solution to Problem

Therefore, the present invention provides the compounds of Formula 1 as sphingosine-1-phosphate receptor agonists, or pharmaceutically acceptable salts, isomers or solvates thereof:

[Formula 1]

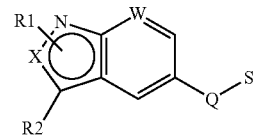

wherein,

X represents C or N,

R1 represents H or optionally substituted alkyl,

R2 represents H, optionally substituted alkyl, halogen, CN, $CF_3$ or $COCF_3$,

W represents C, N, C-alkoxy, C-halogen or C—CN,

Q represents $CH_2O$ or

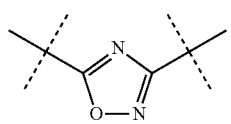

S is selected from the following residues:

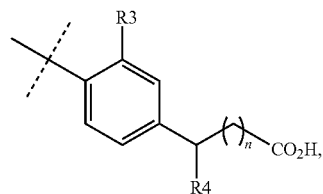

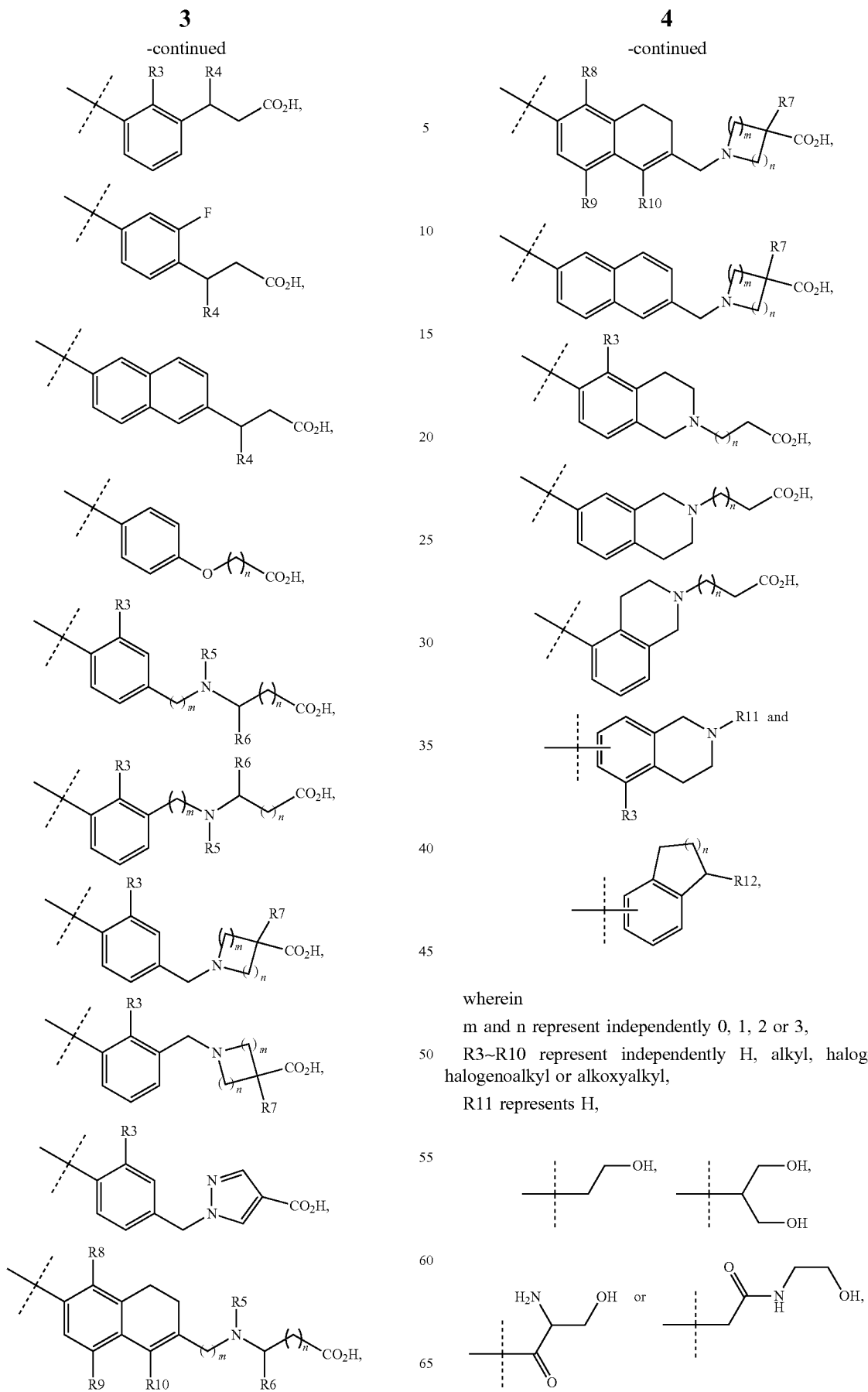
wherein
m and n represent independently 0, 1, 2 or 3,
R3~R10 represent independently H, alkyl, halogen, halogenoalkyl or alkoxyalkyl,
R11 represents H, R12 represents OH, NH$_2$,
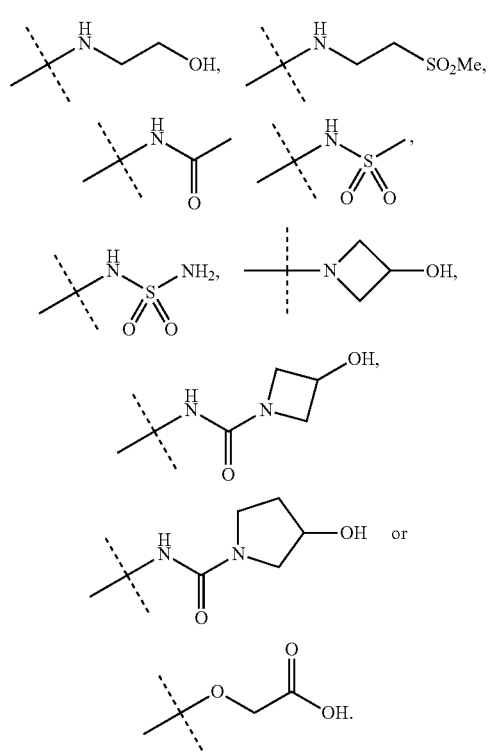
In the preferable compounds of Formula 1 according to the present invention, S is selected from the following groups:
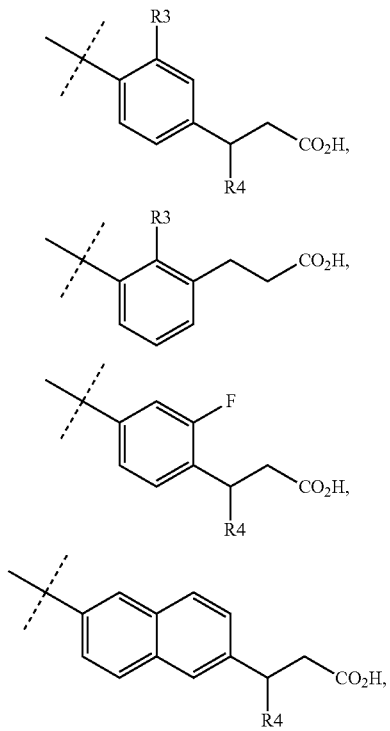
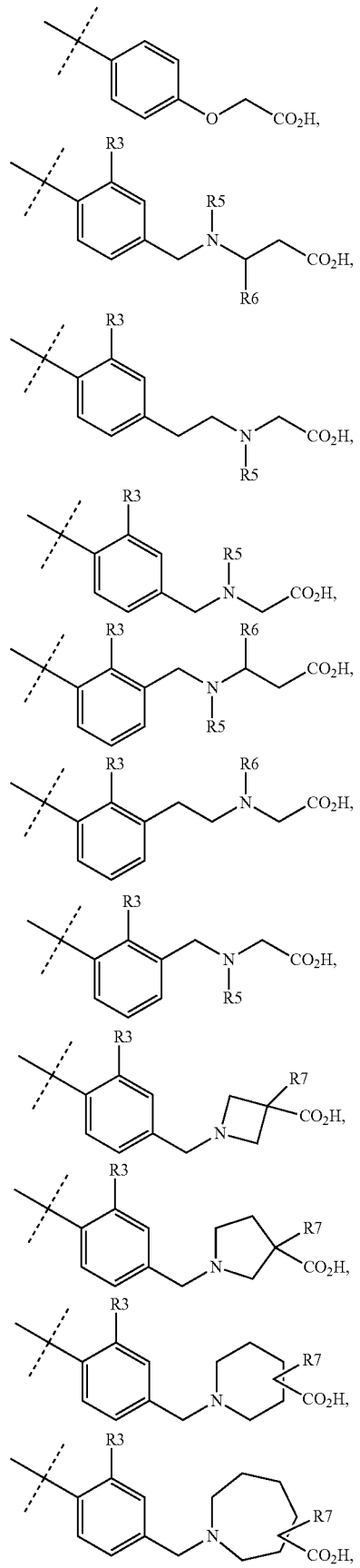

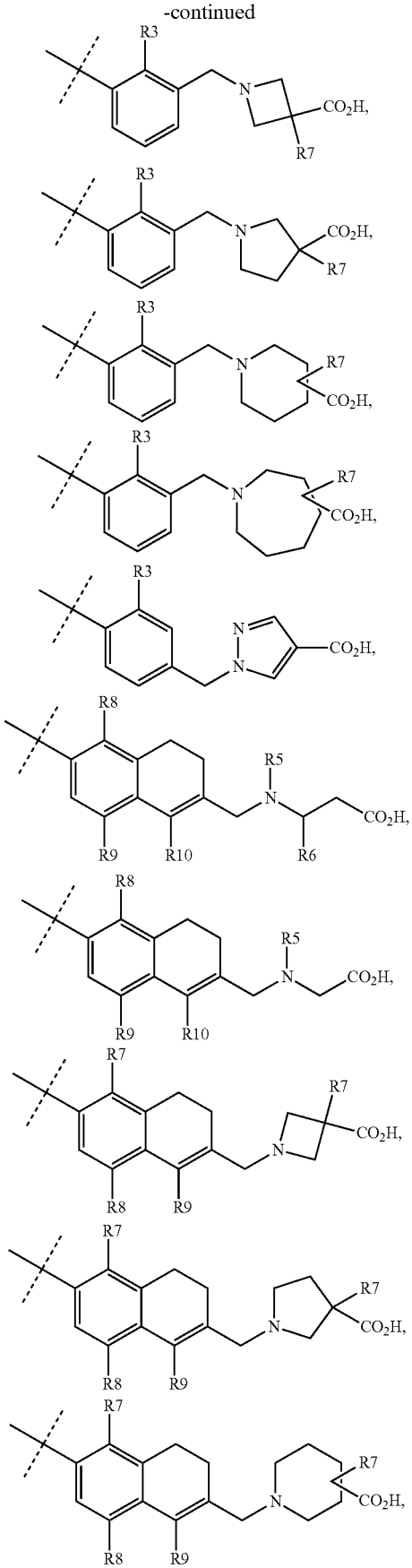
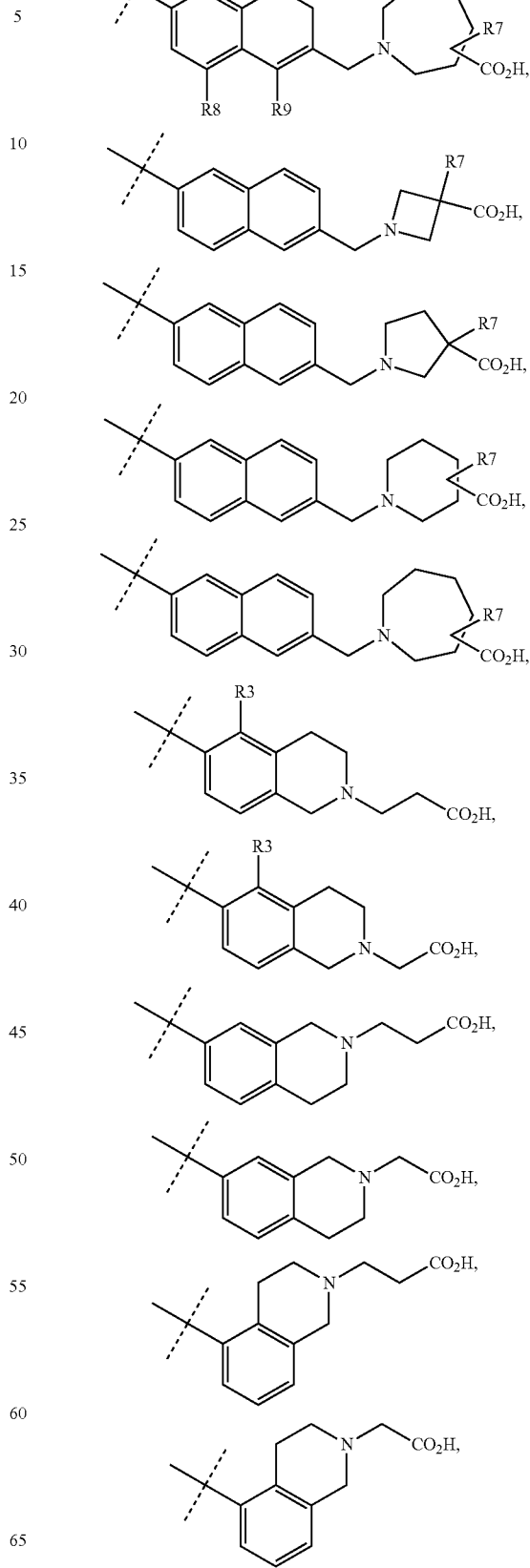

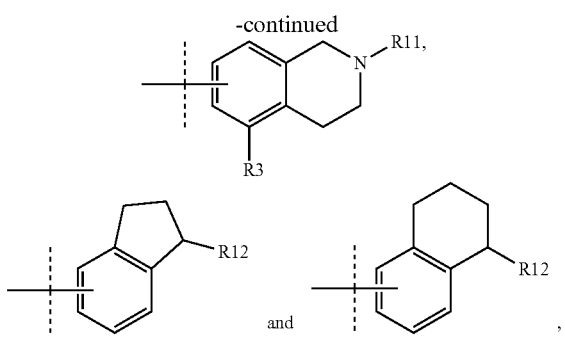

wherein

R3~R10 represent independently H, methyl, ethyl, fluoride, chloride, halogenomethyl, halogenoethyl, alkoxymethyl or alkoxyethyl, R11 represents H,

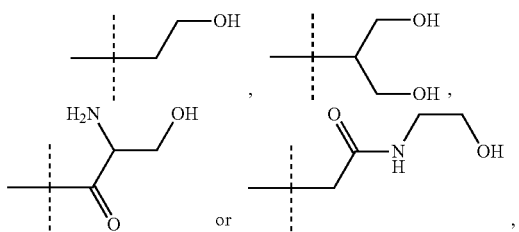

R12 represents OH, NH$_2$,

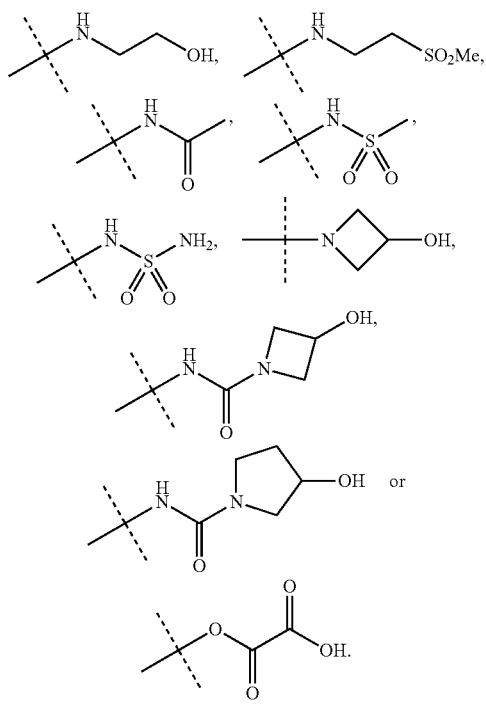

Herein, unless indicated otherwise, the term "the compounds of Formula 1" is used to mean all the compounds of Formula 1, including the pharmaceutically acceptable salts, isomers or solvates thereof.

The terms used in the definition of the compounds of Formula 1 are defined as follows. Unless indicated otherwise, the following definition applies to the terms used individually or as a part of a bigger group herein.

means the position in which a substituent is combined to the ring system.

The term "alkyl," when used alone or in combination such as "heteroalkyl," means straight-chain, branched-chain or cyclic hydrocarbon radical and is preferably a straight-chain or branched-chain saturated hydrocarbon radical having 1 to 6 carbon atoms; a saturated cyclic hydrocarbon radical having 3 to 6 carbon atoms; or a saturated cyclic hydrocarbon radical having 3 to 6 carbon atoms combined with a straight-chain and/or branched-chain saturated hydrocarbon radical having 1 to 6 carbon atoms. Each carbon atom is optionally substituted by at least one of halo(gen), cyano, hydroxyl, $C_1$-$C_6$-alkyloxy, oxo or sulfonyl unsubstituted or substituted by alkyl.

The term "alkoxy" means —O-alkyl, in which alkyl is as defined above.

The term "halo(gen)" means a substituent selected from fluoro, chloro, bromo and iodo groups. The other terms and abbreviations used herein have their original meanings, unless defined otherwise.

The compounds of Formula 1 according to the present invention can form pharmaceutically acceptable salts, which include acid-addition salts which are formed from inorganic acids such as hydrochloric acid, sulfuric acid, nitric acid, phosphoric acid, hydrobromic acid and hydroiodic acid; organic acids such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acids such as methanesulfonic acid, benzenesulfonic acid, p-toluenesulfonic acid or naphthalene-sulfonic acid, which form non-toxic acid-addition salts including pharmaceutically acceptable anion. Preferable acid-addition salts are formed from sulfuric acid, methanesulfonic acid or halogen acid. The compounds of Formula 1 according to the present invention can be converted into their salts by conventional methods.

Furthermore, since the compounds of Formula 1 according to the present invention can have an asymmetric carbon center, they can exist as R- or S-isomers, racemic mixtures or diastereoisomer mixtures and each diastereoisomer, all of which are within the scope of the present invention. That is, in case the compounds of Formula 1 include asymmetric carbon atom(s), they are construed as including all stereoisomers, unless the configuration is indicated specifically.

Representative compounds of Formula 1 according to the present invention include the following compounds:

3-{4-[5-(1-isopropyl-1H-indol-5-yl)-[1,2,4]oxadiazol-3-yl]-3-methyl-phenyl}-propanoic acid;

1-{4-[5-(1-isopropyl-1H-indol-5-yl)-[1,2,4]oxadiazol-3-yl]-benzyl}-azetidine-3-carboxylic acid;

1-{4-[5-(3-chloro-1-isopropyl-1H-indol-5-yl)-[1,2,4]oxadiazol-3-yl]-3-methyl-benzyl}-azetidine-3-carboxylic acid;

1-{4-[5-(3-cyano-1-isopropyl-1H-indol-5-yl)-[1,2,4]oxadiazol-3-yl]-3-methyl-benzyl}-azetidine-3-carboxylic acid;

1-{4-[5-(1-isopropyl-1H-indol-5-yl)-[1,2,4]oxadiazol-3-yl]-3-methyl-benzyl}-azetidine-3-carboxylic acid;

1-(4-{5-[1-isopropyl-3-(2,2,2-trifluoro-acetyl)-1H-indol-5-yl]-[1,2,4]oxadiazol-3-yl}-3-methyl-benzyl)-azetidine-3-carboxylic acid;
1-{4-[5-(1-isobutyl-1H-indol-5-yl)-[1,2,4]oxadiazol-3-yl]-3-methyl-benzyl}-azetidine-3-carboxylic acid;
1-{4-[5-(3-chloro-1-isopropyl-1H-indol-5-yl)-[1,2,4]oxadiazol-3-yl]-benzyl}-1H-pyrazole-4-carboxylic acid;
1-{4-[5-(3-chloro-1-isopropyl-1H-indol-5-yl)-[1,2,4]oxadiazol-3-yl]-3-methyl-benzyl}-1H-pyrazole-4-carboxylic acid;
3-{4-[5-(3-chloro-1-isopropyl-1H-indol-5-yl)-[1,2,4]oxadiazol-3-yl]-benzylamino}-propanoic acid;
{4-[5-(1-isopropyl-1H-indol-5-yl)-[1,2,4]oxadiazol-3-yl]-phenoxy}-acetic acid;
{4-[5-(3-chloro-1-isopropyl-1H-indol-5-yl)-[1,2,4]oxadiazol-3-yl]-phenoxy}-acetic acid;
3-{4-[5-(1-isopropyl-1H-indol-5-yl)-[1,2,4]oxadiazol-3-yl]-phenoxy}-propanoic acid;
(R)-1-{4-[5-(1-isopropyl-1H-indol-5-yl)-[1,2,4]oxadiazol-3-yl]-3-methyl-benzyl}-piperidine-3-carboxylic acid;
(S)-1-{4-[5-(1-isopropyl-1H-indol-5-yl)-[1,2,4]oxadiazol-3-yl]-3-methyl-benzyl}-piperidine-3-carboxylic acid;
1-{4-[5-(1-isopropyl-1H-indol-5-yl)-[1,2,4]oxadiazol-3-yl]-3-methyl-benzyl}-piperidine-4-carboxylic acid;
(S)-1-{4-[5-(1-isopropyl-1H-indol-5-yl)-[1,2,4]oxadiazol-3-yl]-3-methyl-benzyl}-pyrrolidine-3-carboxylic acid;
({4-[5-(1-isopropyl-1H-indol-5-yl)-[1,2,4]oxadiazol-3-yl]-3-methyl-benzyl}-methyl-amino)-acetic acid;
3-{4-[5-(1-isopropyl-1H-indol-5-yl)-[1,2,4]oxadiazol-3-yl]-3-methyl-benzylamino}-propanoic acid;
3-{3-[5-(1-isopropyl-1H-indol-5-yl)-[1,2,4]oxadiazol-3-yl]-2-methyl-phenyl}-propanoic acid;
1-{3-[5-(1-isopropyl-1H-indol-5-yl)-[1,2,4]oxadiazol-3-yl]-benzyl}-azetidine-3-carboxylic acid;
{3-[5-(1-isopropyl-1H-indol-5-yl)-[1,2,4]oxadiazol-3-yl]-benzylamino}-acetic acid;
({3-[5-(1-isopropyl-1H-indol-5-yl)-[1,2,4]oxadiazol-3-yl]-benzyl}-methyl-amino)-acetic acid;
(1S,3R)-3-{4-[5-(1-isopropyl-1H-indol-5-yl)-[1,2,4]oxadiazol-3-yl]-3-methyl-benzyl amino}-cyclopentanecarboxylic acid;
3-({4-[5-(1-isopropyl-1H-indol-5-yl)-[1,2,4]oxadiazol-3-yl]-3-methyl-benzyl}-methyl-amino)-propanoic acid;
1-{3-[5-(1-isopropyl-1H-indol-5-yl)-[1,2,4]oxadiazol-3-yl]-2-methyl-benzyl}-azetidine-3-carboxylic acid;
5-[5-(1-isopropyl-1H-indol-5-yl)-[1,2,4]oxadiazol-3-yl]-1,2,3,4-tetrahydro-isoquinoline, hydrochloride;
{5-[5-(1-isopropyl-1H-indol-5-yl)-[1,2,4]oxadiazol-3-yl]-3,4-dihydro-1H-isoquinolin-2-yl}-acetic acid;
3-{5-[5-(1-isopropyl-1H-indol-5-yl)-[1,2,4]oxadiazol-3-yl]-3,4-dihydro-1H-isoquinolin-2-yl}-propanoic acid;
4-[5-(1-isopropyl-1H-indol-5-yl)-[1,2,4]oxadiazol-3-yl]-indan-1-ol;
2-{4-[5-(1-isopropyl-1H-indol-5-yl)-[1,2,4]oxadiazol-3-yl]-indan-1-ylamino}-ethanol;
(S)-2-amino-3-hydroxy-1-{5-[5-(1-isopropyl-1H-indol-5-yl)-[1,2,4]oxadiazol-3-yl]-3, 4-dihydro-1H-isoquinolin-2-yl}-propan-1-on;
2-{5-[5-(1-isopropyl-1H-indol-5-yl)-[1,2,4]oxadiazol-3-yl]-3,4-dihydro-1H-isoquinolin-2-yl}-propan-1,3-diol;
N—{(S)-4-[5-(1-isopropyl-1H-indol-5-yl)-[1,2,4]oxadiazol-3-yl]-indan-1-yl}-methanesulfonamide;
N—{(S)-4-[5-(1-isopropyl-1H-indol-5-yl)-[1,2,4]oxadiazol-3-yl]-indan-1-yl}-acetamide;
N-{5-[5-(1-isopropyl-1H-indol-5-yl)-[1,2,4]oxadiazol-3-yl]-1,2,3,4-tetrahydro-naphthalen-1-yl}-acetamide;
N-{5-[5-(1-isopropyl-1H-indol-5-yl)-[1,2,4]oxadiazol-3-yl]-1,2,3,4-tetrahydro-naphthalen-1-yl}-methanesulfonamide;
N-{5-[5-(1-isopropyl-1H-indol-5-yl)-[1,2,4]oxadiazol-3-yl]-1,2,3,4-tetrahydro-naphthalen-1-yl}-sulfamide;
3-hydroxy-pyrrolidine-1-carboxylic acid {5-[5-(1-isopropyl-1H-indol-5-yl)-[1,2,4]oxadiazol-3-yl]-1,2,3,4-tetrahydro-naphthalen-1-yl}-amide;
5-[5-(3-chloro-1-isopropyl-1H-indol-5-yl)-[1,2,4]oxadiazol-3-yl]-1,2,3,4-tetrahydro-isoquinoline, hydrochloride;
7-[5-(1-isopropyl-1H-indol-5-yl)-[1,2,4]oxadiazol-3-yl]-1,2,3,4-tetrahydro-isoquinoline, hydrochloride;
3-hydroxy-azetidine-1-carboxylic acid {5-[5-(1-isopropyl-1H-indol-5-yl)-[1,2,4]oxadiazol-3-yl]-1,2,3,4-tetrahydro-naphthalen-1-yl}-amide;
{5-[5-(3-chloro-1-isopropyl-1H-indol-5-yl)-[1,2,4]oxadiazol-3-yl]-3,4-dihydro-1H-isoquinolin-2-yl}-acetic acid, fluoroacetate;
2-{5-[5-(3-chloro-1-isopropyl-1H-indol-5-yl)-[1,2,4]oxadiazol-3-yl]-3,4-dihydro-1H-isoquinolin-2-yl}-ethanol;
5-[5-(1-isopropyl-1H-indol-5-yl)-[1,2,4]oxadiazol-3-yl]-1,2,3,4-tetrahydro-naphthalen-1-ylamine, hydrochloride;
1-{4-[5-(1-isopropyl-1H-indol-5-yl)-[1,2,4]oxadiazol-3-yl]-indan-1-yl}-azetidin-3-ol;
2-{5-[5-(3-chloro-1-isopropyl-1H-indol-5-yl)-[1,2,4]oxadiazol-3-yl]-3,4-dihydro-1H-isoquinolin-2-yl}-N-(2-hydroxy-ethyl)-acetamide;
2-{7-[5-(1-isopropyl-1H-indol-5-yl)-[1,2,4]oxadiazol-3-yl]-3,4-dihydro-1H-isoquinolin-2-yl}-ethanol;
{5-[5-(1-isopropyl-1H-indol-5-yl)-[1,2,4]oxadiazol-3-yl]-1,2,3,4-tetrahydro-naphthalen-1-yl}-(2-methanesulfonyl-ethyl)-amine, hydrochloride;
{7-[5-(1-isopropyl-1H-indol-5-yl)-[1,2,4]oxadiazol-3-yl]-3,4-dihydro-1H-isoquinolin-2-yl}-acetic acid, hydrochloride;
N-(2-hydroxy-ethyl)-2-{7-[5-(1-isopropyl-1H-indol-5-yl)-[1,2,4]oxadiazol-3-yl]-3,4-dihydro-1H-isoquinolin-2-yl}-acetamide;
3-{4-[5-(3-chloro-1-isopropyl-1H-indol-5-yl)-[1,2,4]oxadiazol-3-yl]-3-methyl-phenyl}-propanoic acid;
3-{4-[5-(3-cyano-1-isopropyl-1H-indol-5-yl)-[1,2,4]oxadiazol-3-yl]-3-methyl-phenyl}-propanoic acid;
3-{3-methyl-4-[5-(1-methyl-1H-indol-5-yl)-[1,2,4]oxadiazol-3-yl]-phenyl}-propanoic acid;
5-[5-(1-isopropyl-1H-indol-5-yl)-[1,2,4]oxadiazol-3-yl]-indan-1-ol;
6-[5-(3-chloro-1-isopropyl-1H-indol-5-yl)-[1,2,4]oxadiazol-3-yl]-5-methyl-1,2,3,4-tetrahydro-isoquinoline, hydrochloride;
2-{6-[5-(3-chloro-1-isopropyl-1H-indol-5-yl)-[1,2,4]oxadiazol-3-yl]-5-methyl-3,4-dihydro-1H-isoquinolin-2-yl}-ethanol;
{6-[5-(3-chloro-1-isopropyl-1H-indol-5-yl)-[1,2,4]oxadiazol-3-yl]-5-methyl-3,4-dihydro-1H-isoquinolin-2-yl}-acetic acid, hydrochloride;
{5-[5-(1-isopropyl-1H-indol-5-yl)-[1,2,4]oxadiazol-3-yl]-indan-1-yloxy}-acetic acid;
2-{6-[5-(3-chloro-1-isopropyl-1H-indol-5-yl)-[1,2,4]oxadiazol-3-yl]-5-methyl-3,4-dihydro-1H-isoquinolin-2-yl}-N-(2-hydroxy-ethyl)-acetamide;
6-[5-(1-isopropyl-1H-indol-5-yl)-[1,2,4]oxadiazol-3-yl]-5-methyl-1,2,3,4-tetrahydro-isoquinoline, hydrochloride;
{6-[5-(3-cyano-1-isopropyl-1H-indol-5-yl)-[1,2,4]oxadiazol-3-yl]-5-methyl-3,4-dihydro-1H-isoquinolin-2-yl}-acetic acid, hydrochloride;

{6-[5-(1-isopropyl-1H-indol-5-yl)-[1,2,4]oxadiazol-3-yl]-5-methyl-3,4-dihydro-1H-isoquinolin-2-yl}-acetic acid, hydrochloride;
3-{4-[5-(7-chloro-2-methyl-1H-indol-5-yl)-[1,2,4]oxadiazol-3-yl]-3-methyl-phenyl}-propanoic acid;
1-isopropyl-5-[3-(1,2,3,4-tetrahydro-isoquinolin-5-yl)-[1,2,4]oxadiazol-5-yl]-1H-indol-3-carbonitrile, hydrochloride;
3-{4-[5-(2-cyclopentyl-1H-indol-5-yl)-[1,2,4]oxadiazol-3-yl]-3-methyl-phenyl}-propanoic acid;
{5-[5-(3-cyano-1-isopropyl-1H-indol-5-yl)-[1,2,4]oxadiazol-3-yl]-3,4-dihydro-1H-isoquinolin-2-yl}-acetic acid, hydrochloride;
3-{4-[5-(1-benzyl-1H-indol-5-yl)-[1,2,4]oxadiazol-3-yl]-methyl-phenyl}-propanoic acid;
3-{4-[5-(1-cyclopentyl-1H-indol-5-yl)-[1,2,4]oxadiazol-3-yl]-3-methyl-phenyl}-propanoic acid;
3-{4-[5-(7-cyano-2-methyl-1H-indol-5-yl)-[1,2,4]oxadiazol-3-yl]-3-methyl-phenyl}-propanoic acid;
3-{4-[5-(7-cyano-2-cyclopropyl-1H-indol-5-yl)-[1,2,4]oxadiazol-3-yl]-3-methyl-phenyl}-propanoic acid;
3-{4-[5-(7-cyano-1H-indol-5-yl)-[1,2,4]oxadiazol-3-yl]-3-methyl-phenyl}-propanoic acid;
3-{4-[5-(7-cyano-1-isopropyl-1H-indol-5-yl)-[1,2,4]oxadiazol-3-yl]-3-methyl-phenyl}-propanoic acid;
3-{4-[5-(7-cyano-1-methyl-1H-indol-5-yl)-[1,2,4]oxadiazol-3-yl]-3-methyl-phenyl}-propanoic acid;
3-{5-[5-(3-chloro-1-isopropyl-1H-indol-5-yl)-[1,2,4]oxadiazol-3-yl]-3,4-dihydro-1H-isoquinolin-2-yl}-propanoic acid, hydrochloride;
3-{6-[5-(1-isopropyl-1H-indol-5-yl)-[1,2,4]oxadiazol-3-yl]-5-methyl-3,4-dihydro-1H-isoquinolin-2-yl}-propanoic acid, hydrochloride;
3-{6-[5-(3-chloro-1-isopropyl-1H-indol-5-yl)-[1,2,4]oxadiazol-3-yl]-5-methyl-3,4-dihydro-1H-isoquinolin-2-yl}-propanoic acid, hydrochloride;
3-{4-[5-(7-methoxy-2-methyl-1H-indol-5-yl)-[1,2,4]oxadiazol-3-yl]-3-methyl-phenyl}-propanoic acid;
3-{4-[5-(7-chloro-1-isopropyl-1H-indol-5-yl)-[1,2,4]oxadiazol-3-yl]-3-methyl-phenyl}-propanoic acid;
3-{4-[5-(1-isopropyl-1H-indazol-5-yl)-[1,2,4]oxadiazol-3-yl]-3-methyl-phenyl}-propanoic acid;
{5-[5-(1-isopropyl-1H-indol-5-yl)-[1,2,4]oxadiazol-3-yl]-1,3-dihydro-isoindol-2-yl}-acetic acid;
3-{4-[5-(2-isopropyl-2H-indazol-5-yl)-[1,2,4]oxadiazol-3-yl]-3-methyl-phenyl}-propanoic acid;
{5-[5-(1-isopropyl-1H-indazol-5-yl)-[1,2,4]oxadiazol-3-yl]-3,4-dihydro-1H-isoquinolin-2-yl}-acetic acid;
3-{5-[5-(1-isopropyl-1H-indazol-5-yl)-[1,2,4]oxadiazol-3-yl]-3,4-dihydro-1H-isoquinolin-2-yl}-propanoic acid;
{6-[5-(1-isopropyl-1H-indazol-5-yl)-[1,2,4]oxadiazol-3-yl]-5-methyl-3,4-dihydro-1H-isoquinolin-2-yl}-acetic acid, trifluoroacetate;
3-{6-[5-(1-isopropyl-1H-indazol-5-yl)-[1,2,4]oxadiazol-3-yl]-5-methyl-3,4-dihydro-1H-isoquinolin-2-yl}-propanoic acid, trifluoroacetate;
{5-[5-(2-isopropyl-2H-indazol-5-yl)-[1,2,4]oxadiazol-3-yl]-3,4-dihydro-1H-isoquinolin-2-yl}-acetic acid, trifluoroacetate;
3-{5-[5-(2-isopropyl-2H-indazol-5-yl)-[1,2,4]oxadiazol-3-yl]-3,4-dihydro-1H-isoquinolin-2-yl}-propanoic acid, trifluoroacetate;
6-[5-(1-isopropyl-1H-indazol-5-yl)-[1,2,4]oxadiazol-3-yl]-5-methyl-1,2,3,4-tetrahydro-isoquinoline, hydrochloride;
5-[5-(2-isopropyl-2H-indazol-5-yl)-[1,2,4]oxadiazol-3-yl]-1,2,3,4-tetrahydro-isoquinoline, hydrochloride;
6-[5-(2-isopropyl-2H-indazol-5-yl)-[1,2,4]oxadiazol-3-yl]-5-methyl-1,2,3,4-tetrahydro-isoquinoline, hydrochloride;
6-[5-(3-chloro-1-isopropyl-1H-indazol-5-yl)-[1,2,4]oxadiazol-3-yl]-5-methyl-1,2,3,4-tetrahydro-isoquinoline, hydrochloride;
{6-[5-(3-chloro-1-isopropyl-1H-indazol-5-yl)-[1,2,4]oxadiazol-3-yl]-5-methyl-3,4-dihydro-1H-isoquinolin-2-yl}-acetic acid, trifluoroacetate;
3-{6-[5-(3-chloro-1-isopropyl-1H-indazol-5-yl)-[1,2,4]oxadiazol-3-yl]-5-methyl-3,4-dihydro-1H-isoquinolin-2-yl}-propanoic acid, trifluoroacetate;
{6-[5-(1-isopropyl-1H-pyrazolo[3,4-b]pyridin-5-yl)-[1,2,4]oxadiazol-3-yl]-5-methyl-3,4-dihydro-1H-isoquinolin-2-yl}-acetic acid;
5-[5-(1-isopropyl-1H-indazol-5-yl)-[1,2,4]oxadiazol-3-yl]-1,2,3,4-tetrahydro-isoquinoline, hydrochloride;
{6-[5-(2-isopropyl-2H-indazol-5-yl)-[1,2,4]oxadiazol-3-yl]-5-methyl-3,4-dihydro-1H-isoquinolin-2-yl}-acetic acid, trifluoroacetate;
3-{6-[5-(2-isopropyl-2H-indazol-5-yl)-[1,2,4]oxadiazol-3-yl]-5-methyl-3,4-dihydro-1H-isoquinolin-2-yl}-propanoic acid, trifluoroacetate;
{5-[5-(1-isopropyl-1H-pyrazolo[3,4-b]pyridin-5-yl)-[1,2,4]oxadiazol-3-yl]-3,4-dihydro-1H-isoquinolin-2-yl}-acetic acid;
({4-[5-(1-isopropyl-1H-indazol-5-yl)-[1,2,4]oxadiazol-3-yl]-3-methyl-benzyl}-methyl-amino)-acetic acid, trifluoroacetate;
5-[5-(3-chloro-1-isopropyl-1H-indazol-5-yl)-[1,2,4]oxadiazol-3-yl]-1,2,3,4-tetrahydro-isoquinoline, hydrochloride;
{5-[5-(3-chloro-1-isopropyl-1H-indazol-5-yl)-[1,2,4]oxadiazol-3-yl]-3,4-dihydro-1H-isoquinolin-2-yl}-acetic acid, trifluoroacetate;
3-{5-[5-(3-chloro-1-isopropyl-1H-indazol-5-yl)-[1,2,4]oxadiazol-3-yl]-3,4-dihydro-1H-isoquinolin-2-yl}-propanoic acid, trifluoroacetate;
{5-[5-(1-isopropyl-1H-pyrrolo[2,3-b]pyridin-5-yl)-[1,2,4]oxadiazol-3-yl]-3,4-dihydro-1H-isoquinolin-2-yl}-acetic acid;
6-[5-(3-chloro-1-isopropyl-1H-indazol-5-yl)-[1,2,4]oxadiazol-3-yl]-5-methyl-3,4-dihydro-1H-isoquinoline-2-sulfonic acid amide;
{6-[5-(1-isopropyl-1H-pyrrolo[2,3-b]pyridin-5-yl)-[1,2,4]oxadiazol-3-yl]-5-methyl-3,4-dihydro-1H-isoquinolin-2-yl}-acetic acid;
1-{4-[5-(1-isopropyl-1H-indazol-5-yl)-[1,2,4]oxadiazol-3-yl]-3-methyl-benzyl}-azetidine-3-carboxylic acid;
5-[5-(3-chloro-1-isopropyl-1H-indazol-5-yl)-[1,2,4]oxadiazol-3-yl]-3,4-dihydro-1H-isoquinoline-2-sulfonic acid amide;
{6-[5-(1-isopropyl-1H-indazol-5-yl)-[1,2,4]oxadiazol-3-yl]-3,4-dihydro-1H-isoquinolin-2-yl}-acetic acid, trifluoroacetate;
({4-[5-(1-isopropyl-1H-indazol-5-yl)-[1,2,4]oxadiazol-3-yl]-indan-1-yl}-methyl-amino)-acetic acid;
3-{6-[5-(1-isopropyl-1H-indazol-5-yl)-[1,2,4]oxadiazol-3-yl]-3,4-dihydro-1H-isoquinolin-2-yl}-propanoic acid, trifluoroacetate;
(R)-2-{4-[5-(1-isopropyl-1H-indazol-5-yl)-[1,2,4]oxadiazol-3-yl]-3-methyl-benzylamino}-propanoic acid;
{4-[5-(1-isopropyl-1H-indazol-5-yl)-[1,2,4]oxadiazol-3-yl]-3-methyl-benzylamino}-acetic acid, trifluoroacetate;
(ethyl-{4-[5-(1-isopropyl-1H-indazol-5-yl)-[1,2,4]oxadiazol-3-yl]-3-methyl-benzyl}-amino)-acetic acid, trifluoroacetate;

(R)-2-({4-[5-(1-isopropyl-1H-indazol-5-yl)-[1,2,4]oxadiazol-3-yl]-3-methyl-benzyl}-methyl-amino)-propanoic acid;

({4-[5-(1-isopropyl-1H-indazol-5-yl)-[1,2,4]oxadiazol-3-yl]-benzyl}-methyl-amino)-acetic acid, trifluoroacetate;

{6-[5-(1-isopropyl-3-methyl-1H-indazol-5-yl)-[1,2,4]oxadiazol-3-yl]-5-methyl-3,4-dihydro-1H-isoquinolin-2-yl}-acetic acid, trifluoroacetate;

({3-[5-(3-chloro-1-isopropyl-1H-indol-5-yl)-[1,2,4]oxadiazol-3-yl]-benzyl}-methyl-amino)-acetic acid, trifluoroacetate;

3-({3-[5-(3-chloro-1-isopropyl-1H-indol-5-yl)-[1,2,4]oxadiazol-3-yl]-benzyl}-methyl-amino)-propanoic acid, trifluoroacetate;

({3-[5-(3-chloro-1-isopropyl-1H-indol-5-yl)-[1,2,4]oxadiazol-3-yl]-2-methyl-benzyl}-methyl-amino)-acetic acid, trifluoroacetate;

3-{3-[5-(3-chloro-1-isopropyl-1H-indol-5-yl)-[1,2,4]oxadiazol-3-yl]-2-methyl-benzylamino}-propanoic acid, trifluoroacetate;

3-({3-[5-(3-chloro-1-isopropyl-1H-indol-5-yl)-[1,2,4]oxadiazol-3-yl]-2-methyl-benzyl}-methyl-amino)-propanoic acid, trifluoroacetate;

3-{4-[5-(3-chloro-1-isopropyl-1H-indazol-5-yl)-[1,2,4]oxadiazol-3-yl]-3-methyl-phenyl}-propanoic acid;

({3-[5-(3-chloro-1-isopropyl-1H-indazol-5-yl)-[1,2,4]oxadiazol-3-yl]-2-methyl-benzyl}-methyl-amino)-acetic acid, trifluoroacetate;

1-{3-[5-(3-chloro-1-isopropyl-1H-indazol-5-yl)-[1,2,4]oxadiazol-3-yl]-2-methyl-benzyl}-azetidine-3-carboxylic acid;

[(2-{3-[5-(3-chloro-1-isopropyl-1H-indol-5-yl)-[1,2,4]oxadiazol-3-yl]-phenyl}-ethyl)-methyl-amino]-acetic acid, trifluoroacetate;

1-(2-{3-[5-(3-chloro-1-isopropyl-1H-indol-5-yl)-[1,2,4]oxadiazol-3-yl]-phenyl}-ethyl)-piperidine-4-carboxylic acid;

3-{6-[5-(3-cyclopropyl-1-isopropyl-1H-indazol-5-yl)-[1,2,4]oxadiazol-3-yl]-5-methyl-3,4-dihydro-1H-isoquinolin-2-yl}-propanoic acid, trifluoroacetate;

3-{4-[5-(3-chloro-1-isopropyl-1H-indazol-5-yl)-[1,2,4]oxadiazol-3-yl]-3-methyl-phenyl}-butyric acid, trifluoroacetate;

3-{4-[5-(3-chloro-1-isopropyl-1H-indol-5-yl)-[1,2,4]oxadiazol-3-yl]-3-methyl-phenyl}-butyric acid, trifluoroacetate;

1-[4-(1-isopropyl-1H-indol-5-ylmethoxy)-benzyl]-azetidine-3-carboxylic acid;

3-[4-(1-isopropyl-1H-indol-5-ylmethoxy)-phenyl]-propanoic acid;

1-[4-(3-chloro-1-isopropyl-1H-indol-5-ylmethoxy)-3-methyl-benzyl]-azetidine-3-carboxylic acid;

[5-(1-isopropyl-1H-indazol-5-ylmethoxy)-3,4-dihydro-1H-isoquinolin-2-yl]-acetic acid, trifluoroacetate;

[6-(1-isopropyl-1H-indazol-5-ylmethoxy)-5-methyl-3,4-dihydro-1H-isoquinolin-2-yl]-acetic acid, trifluoroacetate;

[6-(2-isopropyl-2H-indazol-5-ylmethoxy)-5-methyl-3,4-dihydro-1H-isoquinolin-2-yl]-acetic acid, trifluoroacetate;

[5-(2-isopropyl-2H-indazol-5-ylmethoxy)-3,4-dihydro-1H-isoquinolin-2-yl]-acetic acid, trifluoroacetate;

3-[4-(3-chloro-1-isopropyl-1H-indol-5-ylmethoxy)-2-fluoro-phenyl]-propanoic acid;

3-[5-(1-isopropyl-1H-indazol-5-ylmethoxy)-3,4-dihydro-1H-isoquinolin-2-yl]-propanoic acid, trifluoroacetate;

3-[6-(3-chloro-1-isopropyl-1H-indol-5-ylmethoxy)-naphthalen-2-yl]-propanoic acid;

1-[6-(3-chloro-1-isopropyl-1H-indazol-5-ylmethoxy)-naphthalen-2-ylmethyl]-azetidine-3-carboxylic acid;

{[6-(3-chloro-1-isopropyl-1H-pyrrolo[2,3-b]pyridin-5-ylmethoxy)-naphthalen-2-ylmethyl]-methyl-amino}-acetic acid;

{[6-(3-chloro-1-isopropyl-1H-indazol-5-ylmethoxy)-naphthalen-2-ylmethyl]-methyl-amino}-acetic acid;

{[6-(3-chloro-1-isopropyl-1H-indazol-5-ylmethoxy)-1-methyl-3,4-dihydro-naphthalen-2-ylmethyl]-methyl-amino}-acetic acid;

1-[6-(3-chloro-1-isopropyl-1H-indazol-5-ylmethoxy)-1-methyl-3,4-dihydro-naphthalen-2-ylmethyl]-azetidine-3-carboxylic acid;

1-[6-(3-chloro-1-isopropyl-1H-pyrazolo[3,4-b]pyridin-5-ylmethoxy)-naphthalen-2-ylmethyl]-azetidine-3-carboxylic acid;

1-[6-(3-chloro-1-isopropyl-1H-indazol-5-ylmethoxy)-1-methyl-3,4-dihydro-naphthalen-2-ylmethyl]-piperidine-4-carboxylic acid;

1-[6-(3-chloro-1-isopropyl-1H-indazol-5-ylmethoxy)-1-methyl-3,4-dihydro-naphthalen-2-ylmethyl]-azepane-4-carboxylic acid;

1-[1-chloro-6-(3-chloro-1-isopropyl-1H-indazol-5-ylmethoxy)-3,4-dihydro-naphthalen-2-ylmethyl]-pyrrolidine-3-carboxylic acid;

(R)-1-[1-chloro-6-(3-chloro-1-isopropyl-1H-indazol-5-ylmethoxy)-3,4-dihydro-naphthalen-2-ylmethyl]-pyrrolidine-3-carboxylic acid;

1-[1-chloro-6-(3-chloro-1-isopropyl-1H-indazol-5-ylmethoxy)-3,4-dihydro-naphthalen-2-ylmethyl]-3-methyl-pyrrolidine-3-carboxylic acid;

1-[1-chloro-6-(3-chloro-1-isopropyl-1H-indazol-5-ylmethoxy)-3,4-dihydro-naphthalen-2-ylmethyl]-piperidine-4-carboxylic acid;

1-[1-chloro-6-(3-chloro-1-isopropyl-1H-indazol-5-ylmethoxy)-3,4-dihydro-naphthalen-2-ylmethyl]-4-fluoro-piperidine-4-carboxylic acid;

1-[1-chloro-6-(3-chloro-1-isopropyl-1H-indazol-5-ylmethoxy)-3,4-dihydro-naphthalen-2-ylmethyl]-piperidine-3-carboxylic acid;

(S)-1-[1-chloro-6-(3-chloro-1-isopropyl-1H-indazol-5-ylmethoxy)-3,4-dihydro-naphthalen-2-ylmethyl]-piperidine-3-carboxylic acid;

(R)-1-[1-chloro-6-(3-chloro-1-isopropyl-1H-indazol-5-ylmethoxy)-3,4-dihydro-naphthalen-2-ylmethyl]-piperidine-3-carboxylic acid;

1-[1-chloro-6-(3-chloro-1-isopropyl-1H-indazol-5-ylmethoxy)-3,4-dihydro-naphthalen-2-ylmethyl]-3-fluoro-piperidine-3-carboxylic acid;

1-[1-chloro-6-(3-chloro-1-isopropyl-1H-pyrazolo[3,4-b]pyridin-5-ylmethoxy)-3,4-dihydro-naphthalen-2-ylmethyl]-piperidine-4-carboxylic acid;

1-[6-(1-sec-butyl-3-chloro-1H-pyrazolo[3,4-b]pyridin-5-ylmethoxy)-1-chloro-3,4-dihydro-naphthalen-2-ylmethyl]-piperidine-4-carboxylic acid; and 1-[1-chloro-6-(3-chloro-1-isopropyl-1H-indazol-5-ylmethoxy)-3,4-dihydro-naphthalen-2-ylmethyl]-3-fluoro-pyrrolidine-3-carboxylic acid.

The present invention also provides a method for preparing the compounds of Formula 1. Hereinafter, the method for preparing the compounds of Formula 1 is explained based on exemplary reactions in order to illustrate the present invention. However, a person skilled in the art could prepare the compounds of Formula 1 by various methods based on the structure of Formula 1, and such methods should be interpreted as being within the scope of the present invention. That is, the compounds of Formula 1 may be prepared by the methods described herein or by combining various methods disclosed in the prior art, which should be interpreted as being within the scope of the present invention.

The compounds of Formula 1 according to the present invention may be obtained by cyclization reaction of Compound 2 or by coupling reaction of Compound 5 with Compound 6.

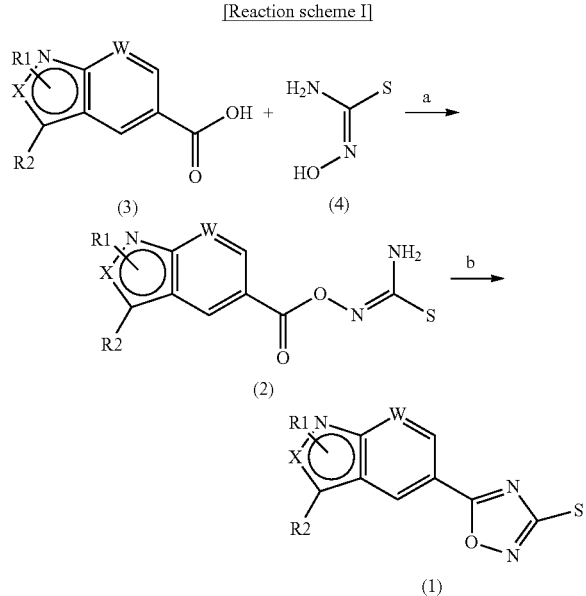

wherein a represents hydroxybenzotriazole (HOBT), diisopropylcarbodiimide (DIC), b represents tetrabutylammoniumflouoride (TBAF), and R1, R2, W and S are as described in the definition of the compounds of Formula 1.

The compounds of Formula 1 according to the present invention may be obtained by a two-step process, as shown in reaction scheme 1. In the first step, a carboxylic acid compound (Compound 3) is coupled with an aryl amidoxime compound (Compound 4) to produce a substituted amidoxime compound (Compound 2). The coupling condition is well-known in this field, and various processes and reagents may be used. Among them, coupling reaction of a carboxylic acid compound (Compound 3) with an aryl amidoxime compound (Compound 4) using hydroxybenzotriazole (HOBT) and diisopropylcarbodiimide (DIC) as standard coupling agents is included. Preferable solvents are dimethylformamide, tetrahydrofuran, dichloromethane, etc. Alternatively, Compound 2 may be produced by a coupling reaction of carboxylic acid derivatives obtained by a well-known method and condition with aryl amidoxime compound (Compound 4) in the presence of a base such as triethylamine. In the second step, cyclization of the substituted amidoxime and dehydration is carried out to produce oxadiazole (Compound 1). The reaction is preferably carried out in the presence of a base such as tetrabutylammoniumfluoride (TBAF). Preferable solvents include tetrahydrofuran, acetonitrile and dimethylformamide. Alternatively, thermal decomposition, which is a well-known method in this field, may be used. A microwave oven may also be used.

Compound 3 is obtainable by the method as shown in reaction scheme 3, and Compound 4 can be prepared by a conventional method.

The compounds of Formula 1 according to the present invention can be also obtained by the following method.

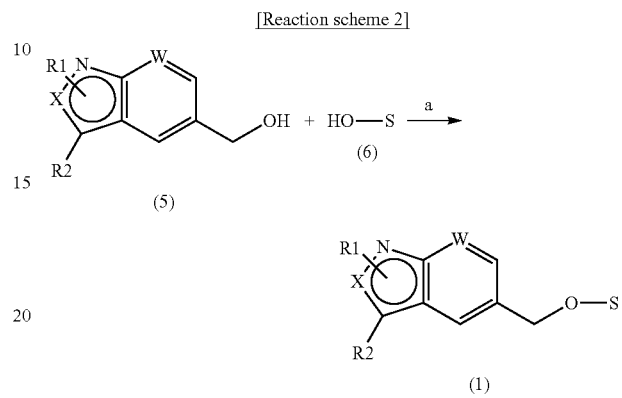

wherein a represents 1,1'-(azodicarbonyl)dipiperidine (ADD), tributylphosphine ($Bu_3P$), R1, R2, W and S are as described in the definition of the compounds of Formula 1.

The compounds of Formula 1 according to the present invention may be obtained by the coupling reaction of Compound 5 with Compound 6 in the Mitsunobu condition. The Mitsunobu condition is well-known in this field, and various processes and reagents may be used. Among them, a coupling reaction of an alcohol compound (Compound 5) with a phenol compound (Compound 6) using phosphines such as tributyl phosphine, triphenyl phosphine and 1,1'-(azodicarbonyl)dipiperidine (ADD) or dimethyl azodicarboxylate (DEAD) as coupling reagents is included. Preferable solvents are toluene, tetrahydrofuran, etc. Alternatively, the alcohol radical in Compound 5 is converted into a leaving group by using appropriate brominating reagents, chlorinating reagents or methanesulfonylating reagents, and then a coupling reaction of Compound 5 with the phenol compound (Compound 6) may be carried out in the presence of a base such as potassium carbonate to obtain the compound of Formula 1.

Compound 5 is obtainable by the method as shown in reaction scheme 4, and Compound 6 can be prepared by a conventional method.

In reaction scheme 1, Compound 3 can also be obtained by the following method.

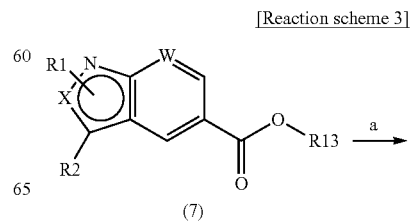

-continued

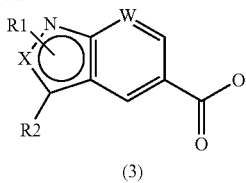

(3)

wherein a represents metal hydroxide—for example, sodium hydroxide,

R1, R2 and W are as described in the definition of the compounds of Formula 1, and R13 represents methyl or ethyl.

Compound 3 can be obtained by reacting Compound 7 in the presence of a base at room temperature or under a heated condition. Preferable bases are sodium hydroxide or lithium hydroxide in aqueous solution. Preferable solvents are tetrahydrofuran, alcohol such as methanol, or mixtures thereof.

In the above reaction scheme 2, Compound 5 can be obtained by the following method.

[Reaction scheme 4]

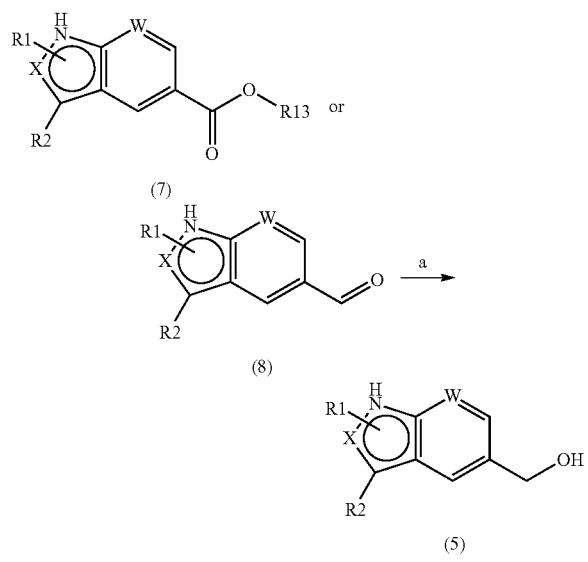

wherein a represents sodium borohydride (NaBH$_4$), lithium borohydride (LiBH$_4$) or lithium aluminum hydride (LiAlH$_4$), R1, R2 and W are as described in the definition of the compounds of Formula 1, and R13 represents methyl or ethyl.

Compound 5 may be obtained by reduction of an ester radical of Compound 7 or an aldehyde radical of Compound 8 using reducing agents. Sodium borohydride (NaBH$_4$), lithium borohydride (LiBH$_4$) or lithium aluminum hydride (LiAlH$_4$) may be used as reducing agents. Tetrahydrofuran is a preferable solvent.

Compounds 7 and 8 can be prepared by the following method.

[Reaction scheme 5]

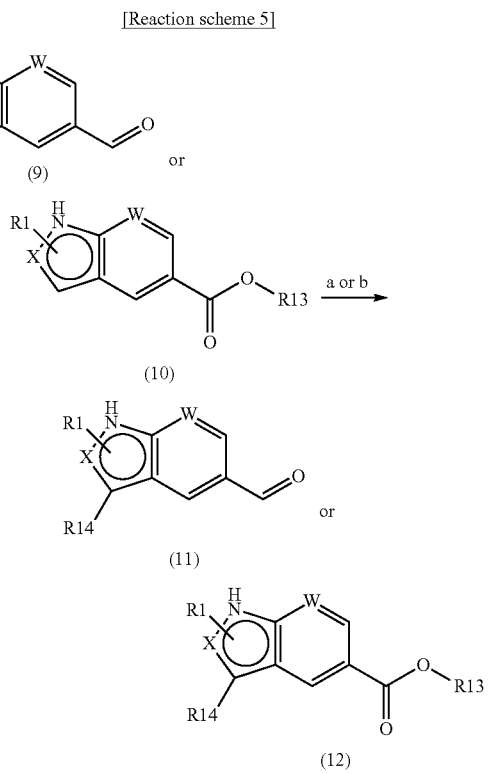

wherein a represents N-chlorosuccinimide, b represents oxalyl chloride, dimethylformamide; hydroxyamine, pyridine; thiocarbonyldiimidazole, R1 and W are as described in the definition of the compounds of Formula 1, R13 represents methyl or ethyl, and R14 represents chloride or nitrile.

Compound 11 or 12 may be obtained under the reaction condition a or b.

In the above reaction scheme 5, halogenation of Compound 9 or 10 (reaction condition a) is carried out by using fluorinating reagents (e.g., N-fluoro-2,4,6-trimethylpyridinium triflate), chlorinating reagents (e.g., N-chlorosuccinimide) or brominating reagents (e.g., N-bromosuccinimide).

Nitrilation of Compound 9 or 10 (reaction condition b) is carried out by formylation of indole compound, conversion into oxime by using hydroxylamine, and then dehydration using thiocarbonylimidazole.

Compound 9 or 10 can be prepared by the following method.

[Reaction scheme 6]

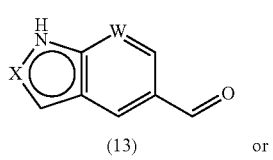

(13)      or

-continued

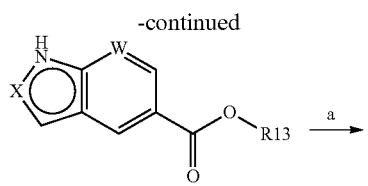
(14)

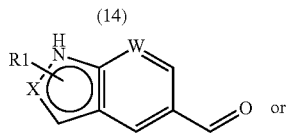
(9)

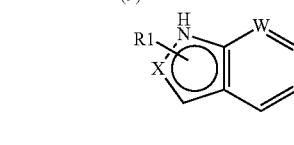
(10)

wherein a represents R1-OSO₂CH₃ or R1-halogen, sodium hydride,

R1 and W are as described in the definition of the compounds of Formula 1, and

R13 represents methyl or ethyl.

In reaction scheme 6, Compound 9 or 10 may be obtained by alkylation of Compound 13 or 14. The condition of alkylation is well-known in this field. For example, Compound 13 or 14 can be reacted with alkylating reagents having a leaving group such as halogen or methanesulfonate in the presence of a base such as sodium hydride or potassium carbonate in solvent. Preferable solvents are tetrahydrofuran, dimethylformamide or mixtures thereof.

Compound 13 or 14 is commercially available or can be prepared by conventional methods.

Compound 7 can be prepared by the following method.

[Reaction scheme 7]

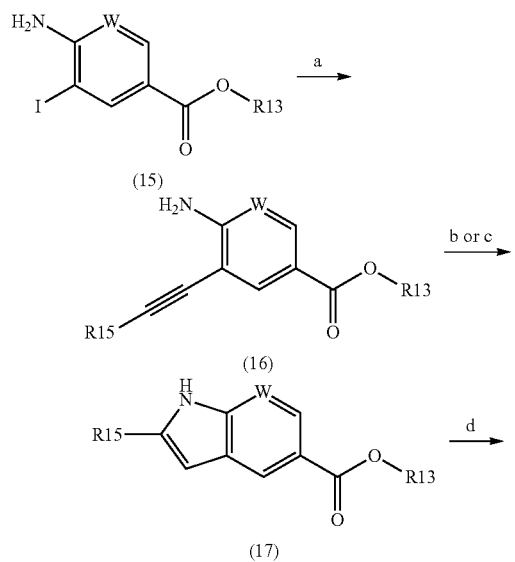

-continued

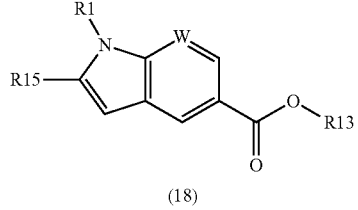
(18)

wherein a represents R13-C≡CH, copper (I) iodide (CuI), bis(triphenylphosphine) palladium (II) dichloride [Pd(Ph₃P)₂Cl₂], b represents acetyl chloride; tetrabutyl ammonium fluoride, c represents potassium tert-butoxide, d represents R1-OSO₂CH₃ or R1-halogen, sodium hydride, R1 and W are as described in the definition of the compounds of Formula 1, R13 represents methyl or ethyl, and R15 represents H, trimethylsilyl [(CH₃)₃Si], alkyl.

Compound 15 is commercially available or may be prepared by the method described in Tetrahedron Letters, 38(14), 2439, 1997.

Compound 16 can be obtained by reacting R13-C≡CH with Compound 15 in the presence of copper (I) iodide (CuI), bis(triphenylphosphine)palladium (II) dichloride [Pd(Ph₃P)₂Cl₂] and a base, according to the method described in the Journal of Organic Chemistry, 4(18), 7052, 2009. Preferable bases are triethylamine, diethylamine, and as solvents dimethylformamide and tetrahydrofuran may be used.

Compound 17 can be obtained by cyclization reaction of Compound 16. The condition of cyclization reaction is well-known in this field. Compound 17 may be obtained by reacting Compound 16 with tetrabutylammonium fluoride (reaction condition b), as described in WO 2010123975, Example 58. Alternatively, potassium tert-butoxide or DBU (reaction condition c) may be used as a base, according to the method described in Tetrahedron, 59, 1571, 2003. Preferable solvents are tetrahydrofuran, N-methylpyrrolidone and dimethylformamide.

Compound 18 can be obtained by alkylation of Compound 17 as in the preparation method of Compound 10.

Compound 7 can also be prepared by the following method.

[Reaction scheme 8]

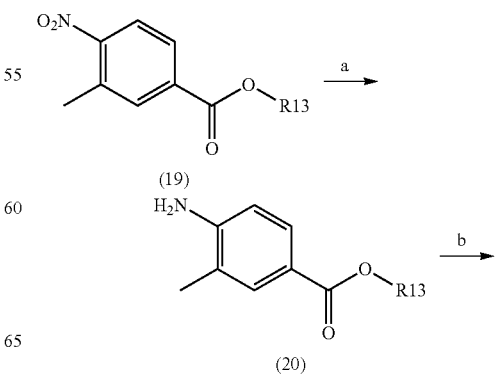

-continued

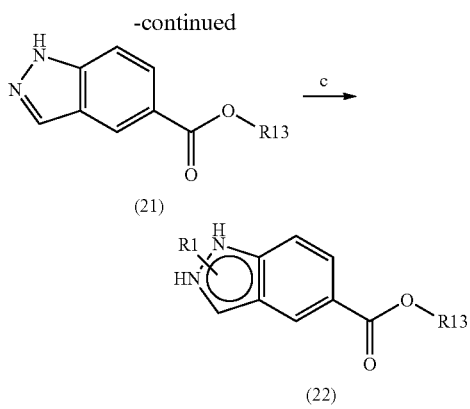

wherein
a represents palladium/carbon (Pd/C), hydrogen,
b represents acetic anhydride (Ac$_2$O), isoamyl nitrite, potassium acetate (KOAc),
c represents R1-OSO$_2$CH$_3$ or R1-halogen, sodium hydride,
R1 is as described in the definition of the compounds of Formula 1, and
R13 represents methyl or ethyl.

Compound 19 is commercially available or may be prepared by the method described in US 20100040554.

Compound 20 may be prepared by reducing Compound 19 by using hydrogen gas in the presence of a Pd/C catalyst.

Compound 21 can be prepared by using indazole synthesis which is well-known in this field. The condition of indazole synthesis includes the reaction condition in which 1-amino-2-alkylphenyl compound (Compound 19) is reacted with acetic anhydride (Ac$_2$O) in the presence of potassium acetate (KOAc), and then reacted with isoamyl nitrite.

Compound 22 can be obtained by alkylation of Compound 21 as in the preparation method of Compound 10.

Compound 7 can also be prepared by the following method.

[Reaction scheme 9]

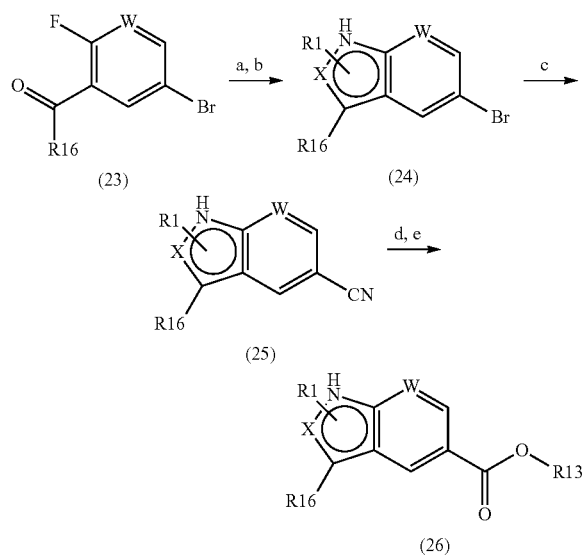

wherein
a represents hydrazine,
b represents R1-OSO$_2$CH$_3$ or R1-halogen, sodium hydride,
c represents zinc cyanide (ZnCN$_2$), palladium tetrakistriphenylphosphine [Pd(Ph$_3$P)$_4$],
d represents sodium hydroxide,
e represents diazomethane (CH$_2$N$_2$),
R1 and W are as described in the definition of the compounds of Formula 1,
R13 represents methyl or ethyl, and
R16 represents H, alkyl.

Compound 23 is commercially available or may be prepared by the method described in US 20080153813.

Compound 24 may be obtained by reacting Compound 23 with hydrazine, and then reacting with alkylating reagents having a leaving group such as halogen or methanesulfonate in the presence of a base such as sodium hydride or potassium carbonate in solvent. Preferable solvents are tetrahydrofuran, dimethylformamide or mixtures thereof.

Compound 25 can be prepared by reacting Compound 24 with zinc cyanide in the presence of palladium tetrakistriphenylphosphine catalyst.

Compound 26 may be obtained by the method in which a carbonitrile radical of Compound 25 is converted into an acid radical by using acidic or alkaline aqueous solution, and then the resulting compound is esterified with methanol or ethanol in the presence of an acid catalyst such as anhydrous sulfuric acid or hydrochloric acid. Alternatively, Compound can also be obtained by methylesterification of an acid radical and diazomethane in the presence of tetrahydrofuran or dichloromethane solvent.

The compounds of Formula 1 obtained by the above methods can be separated or purified from the reaction products by conventional methods such as recrystallization, ionospheresis, silica gel column chromatography or ion-exchange chromatography.

As described above, the compounds according to the present invention, starting materials or intermediates for the preparation thereof can be prepared by a variety of methods, which should be interpreted as being within the scope of the present invention.

The compounds of Formula 1 according to the present invention, or pharmaceutically acceptable salts, isomers or solvates thereof are effectively used for the treatment or prevention of the diseases related to sphingosine-1-phosphate receptor.

The present invention also provides a pharmaceutical composition as sphingosine-1-phosphate receptor agonists, comprising an effective amount of the compounds or Formula 1, or pharmaceutically acceptable salts, isomers or solvates thereof and a pharmaceutically acceptable carrier.

The pharmaceutical composition of the present invention can be used for the treatment or prevention of diseases caused by undesired lymphocyte infiltration related to sphingosine-1-phosphate.

Exemplary diseases which can be treated by the pharmaceutical composition according to the present invention include extensive autoimmune diseases and chronic inflammatory diseases including relapsing-remitting multiple sclerosis.

The pharmaceutical composition of the present invention can be used for the treatment or prevention of immunoregulation disorders. Herein, the immunoregulation disorders include systemic lupus erythematosus, chronic rheumatoid arthritis, inflammatory bowel diseases, multiple sclerosis, amyotrophic lateral sclerosis (ALS), arteriosclerosis, atherosclerosis, scleroderma and autoimmune hepatitis.

In addition, the present invention provides a method for preparing the composition for preventing or treating extensive autoimmune diseases and chronic inflammatory diseases including relapsing-remitting multiple sclerosis, which comprises the step of mixing the compound of Formula 1, or a pharmaceutically acceptable salt, an isomer or a solvate thereof as an active component and a pharmaceutically acceptable carrier.

According to the present invention, the "pharmaceutical composition" can include other components such as diluents, carriers, etc., in addition to the active component of the present invention. Accordingly, the pharmaceutical composition can include pharmaceutically acceptable carriers, diluents, excipients or combinations thereof as necessary. The pharmaceutical composition facilitates the administration of compounds into the body. Various methods for administering the compounds include, but are not limited to, oral, injection, aerosol, parenteral and local administration.

Herein, "carriers" mean compounds that facilitate the addition of compounds into the cell or tissue. For example, dimethylsulfoxide (DMSO) is a conventional carrier facilitating the administration of many organic compounds into living cells or tissues.

Herein, "diluents" mean compounds that not only stabilize a biologically active form but are diluted in solvent dissolving the compounds. Dissolved salts in buffer are used as diluents in this field. A conventionally used buffer is a phosphate buffer saline mimicking salt form in body fluid. Since a buffer solution can control the pH of the solution at low concentration, buffer diluents hardly modify the biological activity of compounds.

Herein, "pharmaceutically acceptable" means a property that does not impair the biological activity and physical property of compounds.

The compounds according to the present invention can be formulated as various pharmaceutically administered dosage forms. In the preparation of the pharmaceutical composition of the present invention, an active component—specifically, the compound of Formula 1 or a pharmaceutically acceptable salt, isomer or solvate thereof—is mixed with selected pharmaceutically acceptable carriers considering the dosage form to be prepared. For example, the pharmaceutical composition of the present invention can be formulated as injections, oral preparations and the like, as needed.

The compounds of the present invention can be formulated by conventional methods using known pharmaceutical carriers and excipients, and inserted into a single-unit or multi-unit containers. The formulations may be solution, suspension or emulsion in oil or aqueous solvent and include conventional dispersing agents, suspending agents or stabilizing agents. In addition, the compounds may be, for example, dry powder form which is dissolved in sterilized pyrogen-free water before use. The compounds of the present invention can be formulated into suppositories by using a conventional suppository base such as cocoa butter or other glycerides. Solid forms for oral administration include capsules, tablets, pills, powders and granules. Capsules and tablets are preferred. Tablets and pills are preferably enteric-coated. Solid forms are manufactured by mixing the compounds of the present invention with at least one carrier selected from inert diluents such as sucrose, lactose or starch, lubricants such as magnesium stearate, disintegrating agents, binders and the like.

The compounds according to the present invention can be administered in combination with other drugs—for example, other medications for immune disorders—as required.

The dose of the compounds according to the present invention is determined by a physician's prescription considering the patient's sex, body weight, age, and disease condition and severity. A typical dose for adults is in the range of about 0.1 to 500 mg per day according to the frequency and intensity of administration. A typical daily dose of intramuscular or intravenous administration for adults is in the range of about 0.1 to 300 mg per day which can be administered in divided unit dosages. Some patients need a higher daily dose.

Herein, the term "treatment" is used to mean deterring, delaying or ameliorating the progress of diseases in a subject exhibiting symptoms of those diseases. The term "prevention" is used to mean deterring, delaying or ameliorating the sign of diseases in a subject at risk of exhibiting symptoms of diseases, even if he or she does not exhibit the symptoms.

Advantageous Effects of Invention

The compounds of Formula 1 according to the present invention act as a sphingosine-1-phosphate receptor agonist, and accordingly they are effective on extensive autoimmune diseases and chronic inflammatory diseases including relapsing-remitting multiple sclerosis, and can also be used for treating or preventing immunoregulation disorders.

MODE FOR THE INVENTION

The present invention is explained in more detail by the following Preparation Examples and Examples. However, the scope of the present invention is not limited by them. When preparing the compounds of the present invention, it is possible to appropriately change the reaction sequence. That is, it is possible to run first optional processes or insert optional processes to change substituents, and use any reagents other than the exemplified reagents as needed. Compounds obtained in each process can be separated or purified by conventional methods such as recrystallization, distillation or silica gel column chromatography. Furthermore, the compound obtained in each process can be used in the next step without further purification or separation.

In the following reaction schemes, unless indicated otherwise, all substituents are as previously defined above. Reagents and starting materials can be obtained readily commercially. Others can be produced by synthetic methods described in the following Preparation Examples and Examples, including known synthetic methods for structurally similar compounds. Unless otherwise noted, compounds used as starting materials are known ones or those which can be prepared by known synthetic methods or similar methods from known compounds.

Hereinafter, M means molar concentration, N means normal concentration and "room temperature" means 1 to 40° C.

PREPARATION EXAMPLE 1-1

Synthesis of 1-isopropyl-1H-indole-5-carboxylic acid methyl ester 1H-indole-5-carboxylic acid methyl ester (1 g, 5.71 mmol) was dissolved in dimethylformamide (20 mL), and isopropyl iodide (1.14 mL, 11.42 mmol) and sodium hydride (205 mg, 8.56 mmol) were slowly added dropwise thereto at 0° C. The mixture was stirred at 50° C. for 8 hours, added with 1N hydrochloric acid solution and extracted with ethyl acetate. The extract was washed with brine, dried with anhydrous magnesium sulfate and filtered. The filtrate was distilled under reduced pressure and separated by column chromatography to obtain the title compound (1.1 g, 89%).

NMR: 1H-NMR (400 HMz, CDCl$_3$); δ 8.39 (s, 1H), 7.90 (dd, 1H), 7.37 (d, 1H), 7.27 (d, 1H), 6.60 (d, 1H), 4.70 (m, 1H), 3.93 (s, 3H), 1.54 (d, 6H)

PREPARATION EXAMPLE 1-2

Synthesis of 1-isopropyl-1H-indole-5-carboxylic acid

The compound (1.1 g, 5.06 mmol) obtained from Preparation Example 1-1 was dissolved in a mixed solution of tetrahydrofuran and methanol (2/1, 20 mL), and 1N sodium hydroxide aqueous solution (10 mL, 10.12 mmol) was slowly added dropwise thereto. The mixture was stirred for 18 hours at room temperature, added with 1N hydrochloric acid solution, and extracted with ethyl acetate. The extract was washed with brine, dried with anhydrous magnesium sulfate and filtered. The filtrate was distilled under reduced pressure to obtain the title compound (900 mg, 88%).

NMR: 1H-NMR (400 HMz, CDCl$_3$); δ 8.49 (s, 1H), 7.98 (dd, 1H), 7.41 (d, 1H), 7.30 (d, 1H), 6.64 (d, 1H), 4.72 (m, 1H), 1.56 (d, 6H)

PREPARATION EXAMPLE 1-3

Synthesis of 3-[4-(N-hydroxycarbimidoyl)-3-methyl-phenyl]-propanoic acid ethyl ester The title compound was obtained according to the method described in EP 2202232.

PREPARATION EXAMPLE 1-4

Synthesis of 3-{4-[5-(1-isopropyl-1H-indol-5-yl)-[1,2,4]oxadiazol-3-yl]-3-methyl-phenyl}-propanoic acid ethyl ester 1-Isopropyl-1H-indole-5-carboxylic acid (933 mg, 4.59 mmol) obtained from Preparation Example 1-2 and 3-[4-(N-hydroxycarbimidoyl)-3-methyl-phenyl]-propanoic acid ethyl ester (1.15 g, 4.59 mmol) obtained from Preparation Example 1-3 were dissolved in dimethylformamide (15 mL). The solution was added with hydroxybenzotriazole (HOBT, 843 mg, 5.51 mmol) and diisopropylcarbodiimide (DIC, 0.86 mL, 5.51 mmol), and the mixture was stirred for 18 hours at room temperature. After completion of the reaction, the solvent was removed by distillation under reduced pressure. The residue was added with water and extracted with ethyl acetate. The extract was washed with brine, dried with anhydrous magnesium sulfate and filtered. The filtrate was distilled under reduced pressure. The residue was separated by column chromatography to obtain amidoxime compound (1.5 g, 75%).

The obtained amidoxime compound (1.5 g, 3.44 mmol) was dissolved in tetrahydrofuran (10 mL), and then 1M tetrabutylammonium fluoride solution in tetrahydrofuran (TBAF, 6.88 mL, 6.88 mmol) was added dropwise thereto. The mixture was stirred for 18 hours at 50° C., added with water and extracted with ethyl acetate. The extract was washed with brine, dried with anhydrous magnesium sulfate and filtered. The filtrate was distilled under reduced pressure. The residue was separated by column chromatography to obtain the title compound (880 mg, 61%).

NMR: 1H-NMR (400 HMz, CDCl$_3$); δ 8.52 (s, 1H), 8.03 (m, 2H), 7.48 (d, 1H), 7.32 (d, 1H), 7.17 (m, 2H), 6.66 (d, 1H), 4.73 (m, 1H), 4.13 (q, 2H), 2.98 (t, 2H), 2.65 (m, 5H), 1.55 (d, 6H), 1.24 (t, 3H)

EXAMPLE 1

Synthesis of 3-{4-[5-(1-isopropyl-1H-indol-5-yl)-[1,2,4]oxadiazol-3-yl]-3-methyl-phenyl}-propanoic acid

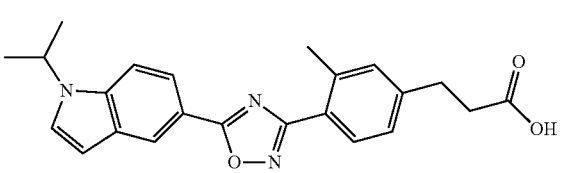 [SMILES: Cc1cc(CCC(=O)O)ccc1-c1noc(-c2ccc3c(ccn3C(C)C)c2)n1]

The compound (880 mg, 2.11 mmol) obtained from Preparation Example 1-4 was dissolved in a mixed solution of tetrahydrofuran and methanol (2/1, 20 mL), and 6N sodium hydroxide aqueous solution (1 mL, 6.32 mmol) was slowly added dropwise thereto. The mixture was stirred for 3 hours at room temperature, added with 1N hydrochloric acid solution and extracted with ethyl acetate. The extract was washed with brine, dried with anhydrous magnesium sulfate and filtered. The filtrate was distilled under reduced pressure to obtain the title compound (720 mg, 88%).

NMR: 1H-NMR (400 HMz, CDCl$_3$); δ 8.53 (d, 1H), 8.05 (m, 2H), 7.48 (d, 1H), 7.32 (d, 1H), 7.20 (m, 2H), 6.66 (d, 1H), 4.73 (m, 1H), 3.00 (t, 2H), 2.73 (t, 2H), 2.68 (s, 3H), 1.56 (d, 6H)

PREPARATION EXAMPLE 2-1

Synthesis of 1-[4-(N-hydroxycarbimidoyl)-benzyl]-azetidine-3-carboxylic acid t-butyl ester The title compound was obtained according to the method described in WO 2010085581 A1.

NMR: 1H-NMR (400 HMz, DMSO-d6); δ 7.59 (d, 1H), 7.23 (d, 1H), 5.74 (s, 2H), 3.62 (s, 1H), 3.53 (s, 2H), 3.22-3.12 (m, 5H), 1.40 (s, 9H)

EXAMPLE 2

Synthesis of 1-{4-[5-(1-isopropyl-1H-indol-5-yl)-[1,2,4]oxadiazol-3-yl]-benzyl}-azetidine-3-carboxylic acid

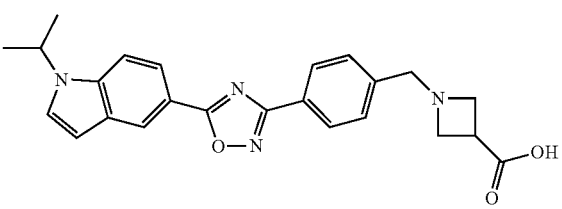 [SMILES: CC(C)n1ccc2cc(-c3nc(-c4ccc(CN5CC(C(=O)O)C5)cc4)no3)ccc21]

1-Isopropyl-1H-indole-5-carboxylic acid methyl ester (75 mg, 0.346 mmol) obtained from Preparation Example 1-1 and 1-[4-(N-hydroxycarbimidoyl)-benzyl]-azetidine-3-carboxylic acid t-butyl ester (71 mg, 0.231 mmol) obtained from Preparation Example 2-1 were dissolved in ethanol (10 mL), and sodium ethoxide (53 mg, 2.31 mmol) was slowly added dropwise thereto. The mixture was stirred for 18 hours under reflux, added with saturated ammonium chloride aqueous solution and extracted with ethyl acetate. The extract was washed with brine, dried with anhydrous magnesium sulfate and filtered. The filtrate was distilled under reduced pressure. The residue was separated by column chromatography to obtain the title compound (6 mg, 6%).

NMR: 1H-NMR (400 HMz, DMSO-d6); δ 8.46 (s, 1H), 8.04 (d, 2H), 7.95 (d, 1H), 7.78 (d, 1H), 7.71 (d, 1H), 7.48 (d, 2H), 6.72 (d, 1H), 4.88-4.83 (m, 1H), 3.61 (s, 2H), 3.25-3.16 (m, 4H), 3.05 (br, s, 1H), 1.50 (d, 6H)

PREPARATION EXAMPLE 3-1

Synthesis of
3-chloro-1-isopropyl-1H-indole-5-carboxylic acid methyl ester

1-Isopropyl-1H-indole-5-carboxylic acid methyl ester (412 mg, 1.90 mmol) obtained from Preparation Example 1-1 was dissolved in dimethylformamide, and N-chlorosuccinimide (NCS, 253 mg, 1.90 mmol) was added dropwise. The mixture was stirred for 18 hours at room temperature. Water was added thereto and the mixture was extracted with ethyl acetate. The extract was washed with brine, dried with anhydrous magnesium sulfate and filtered. The filtrate was distilled under reduced pressure. The residue was separated by column chromatography to obtain the title compound (428 mg, 90%).

NMR: 1H-NMR (400 HMz, CDCl₃); δ 8.38 (d, 1H), 7.94 (dd, 1H), 7.36 (d, 1H), 7.24 (s, 1H), 4.66 (m, 1H), 3.94 (s, 3H), 1.51 (d, 6H)

PREPARATION EXAMPLE 3-2

Synthesis of
3-chloro-1-isopropyl-1H-indole-5-carboxylic acid

The compound (428 mg, 1.7 mmol) obtained from Preparation Example 3-1 was dissolved in a mixed solution of tetrahydrofuran, methanol and water (1/1/1, 24 mL), and lithium hydroxide (143 mg, 3.4 mmol) was slowly added dropwise. The mixture was stirred for 18 hours at room temperature, added with 1N hydrochloric acid solution and extracted with ethyl acetate. The extract was washed with brine, dried with anhydrous magnesium sulfate and filtered. The filtrate was distilled under reduced pressure to obtain the title compound (362 mg, 90%).

NMR: 1H-NMR (400 HMz, DMSO-d6); δ 8.13 (d, J=1.2 Hz, 1H), 7.85 (s, 1H), 7.82 (dd, J=1.2, 1.6 Hz, 1H), 7.68 (d, 1H), 4.87-4.80 (m, 1H), 1.46 (d, 6H)

PREPARATION EXAMPLE 3-3

Synthesis of 1-[4-(N-hydroxycarbimidoyl)-3-methyl-benzyl]-azetidine-3-carboxylic acid t-butyl ester The title compound was obtained according to the method described in WO 2010085581 A1.

NMR: 1H-NMR (400 HMz, CDCl₃); δ 7.32 (d, 1H), 7.14 (s, 1H), 7.11 (d, 1H), 4.76 (br, s, 2H), 3.58 (s, 2H), 3.52 (br, s, 2H), 3.24 (br, s, 2H), 2.42 (s, 3H), 1.45 (s, 9H)

PREPARATION EXAMPLE 3-4

Synthesis of 4-[5-(3-chloro-1-isopropyl-1H-indol-5-yl)-[1,2,4]oxadiazol-3-yl]-3-methyl-benzaldehyde 3-Chloro-1-isopropyl-1H-indole-5-carboxylic acid (24 mg, 0.1 mmol) obtained from Preparation Example 3-2 and 1-[4-(N-hydroxycarbimidoyl)-3-methyl-benzyl]-azetidine-3-carboxylic acid t-butyl ester (38.5 mg, 0.12 mmol) obtained from Preparation Example 3-3 were dissolved in a mixed solution of dichloromethane and dimethylformamide (3/1, 4 mL). Hydroxybenzotriazole (HOBT, 16.4 mg, 0.12 mmol) and diisopropylcarbodiimide (DIC, 0.019 mL, 0.12 mmol) were added thereto and the mixture was stirred for 4 hours at room temperature. After completion of the reaction, the solvent was removed by distillation under reduced pressure. The residue was added with water and extracted with ethyl acetate. The extract was washed with brine, dried with anhydrous magnesium sulfate and filtered. The filtrate was distilled under reduced pressure. The residue was dissolved in dimethylformamide (1 mL) and the solution was stirred for 5 hours at 139° C. The solvent was removed by distillation under reduced pressure and the residue was separated by column chromatography to obtain the title compound (5 mg, 13%).

NMR: 1H-NMR (400 HMz, CDCl₃); δ 10.09 (s, 1H), 8.54 (s, 1H), 8.33 (d, 1H), 8.10 (d, 1H), 7.86 (br, s, 2H), 7.50 (d, 1H), 7.31 (s, 1H), 4.76-4.70 (m, 1H), 2.80 (s, 3H), 1.57 (d, 6H)

EXAMPLE 3

Synthesis of 1-{4-[5-(3-chloro-1-isopropyl-1H-indol-5-yl)-[1,2,4]oxadiazol-3-yl]-3-methyl-benzyl}-azetidine-3-carboxylic acid

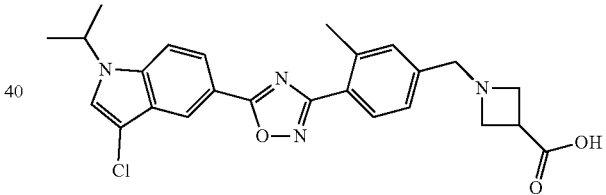

4-[5-(3-Chloro-1-isopropyl-1H-indol-5-yl)-[1,2,4]oxadiazol-3-yl]-3-methyl-benzaldehyde (5 mg, 0.013 mmol) obtained from Preparation Example 3-4 and azetidine-3-carboxylic acid (1.5 mg, 0.014 mmol) were dissolved in methanol (5 mL), and sodium cyanoborohydride (1.6 mg, 0.026 mmol) and a catalytic amount of acetic acid were added thereto. The mixture was stirred for 18 hours at room temperature. The solvent was removed by distillation under reduced pressure and the residue was separated by column chromatography to obtain the title compound (2.4 mg, 39%).

NMR: 1H-NMR (400 HMz, CDCl₃); δ 8.51 (s, 1H), 8.13 (d, 1H), 8.07 (dd, 1H), 7.49 (d, 1H), 7.40 (br, s, 2H), 7.30 (s, 1H), 4.76-4.69 (m, 1H), 4.14 (br, s, 4H), 3.92 (t, 2H), 3.32 (br, s, 1H), 2.70 (s, 3H), 1.55 (d, 6H)

PREPARATION EXAMPLE 4-1

Synthesis of
3-formyl-1-isopropyl-1H-indole-5-carboxylic acid methyl ester

Oxalyl chloride (0.13 mL, 1.51 mmol) and dimethylformamide (0.12 mL, 1.51 mmol) were dissolved in dichloromethane (10 mL) at 0° C., and the solution was stirred for 30 minutes at room temperature. 1-Isopropyl-1H-indole-5-carboxylic acid methyl ester (252 mg, 1.16 mmol) obtained from Preparation Example 1-1 was dissolved in dichloromethane (5 mL) and added thereto. The mixture was stirred for 18 hours at room temperature. The solvent was removed by distillation under reduced pressure, and the residue was added with tetrahydrofuran (20 mL), ammonium acetate (800 mg) and water (10 mL). The mixture was stirred for 30 minutes under reflux, added with saturated sodium hydrogen carbonate aqueous solution and extracted with ethyl acetate. The extract was washed with brine, dried with anhydrous magnesium sulfate and filtered. The filtrate was distilled under reduced pressure to obtain the title compound (267 mg, 94%).

NMR: 1H-NMR (400 HMz, CDCl$_3$); δ 10.06 (s, 1H), 9.01 (s, 1H), 8.06 (dd, 1H), 7.92 (s, 1H), 7.45 (d, 1H), 4.78-4.71 (m, 1H), 3.95 (s, 3H), 1.62 (d, 6H)

PREPARATOIN EXAMPLE 4-2

Synthesis of 3-(hydroxyimino-methyl)-1-isopropyl-1H-indole-5-carboxylic acid methyl ester 3-Formyl-1-isopropyl-1H-indole-5-carboxylic acid methyl ester (267 mg, 1.09 mmol) obtained from Preparation Example 4-1 was dissolved in pyridine (5 mL) and hydroxylamine hydrochloride (114 mg, 1.64 mmol) was added dropwise thereto. The mixture was stirred under reflux for 3 hours at 110° C., added with 1N hydrochloric acid solution and extracted with ethyl acetate. The extract was washed with brine, dried with anhydrous magnesium sulfate and filtered. The filtrate was distilled under reduced pressure to obtain the title compound (255 mg, 90%).

NMR: 1H-NMR (500 HMz, CDCl$_3$); δ 8.51 (s, 1H), 8.03 (dd, J=1.85 Hz, 1H), 7.78 (s, 1H), 7.47 (d, 1H), 4.75-4.71 (m, 1H), 3.95 (s, 3H), 1.58 (d, 6H)

PREPARATION EXAMPLE 4-3

Synthesis of 3-cyano-1-isopropyl-1H-indole-5-carboxylic acid methyl ester 3-(Hydroxyimino-methyl)-1-isopropyl-1H-indole-5-carboxylic acid methyl ester (170 mg, 0.65 mmol) obtained from Preparation Example 4-2 was dissolved in tetrahydrofuran (10 mL), and thiocarbonyldiimidazole (290 mg, 1.63 mmol) was added dropwise thereto. The mixture was stirred for 1 hour at room temperature. The solvent was removed by distillation under reduced pressure. The residue was added with water and extracted with ethyl acetate. The extract was washed with brine, dried with anhydrous magnesium sulfate and filtered. The filtrate was distilled under reduced pressure to obtain the title compound (157 mg, 99%).

NMR: 1H-NMR (500 HMz, CDCl$_3$); δ 8.51 (s, 1H), 8.03 (dd, J=1.85 Hz, 1H), 7.78 (s, 1H), 7.47 (d, 1H), 4.75-4.72 (m, 1H), 3.95 (s, 3H), 1.58 (d, 6H)

PREPARATION EXAMPLE 4-4

Synthesis of 3-cyano-1-isopropyl-1H-indole-5-carboxylic acid

According to the method described in Preparation Example 3-2, 3-cyano-1-isopropyl-1H-indole-5-carboxylic acid methyl ester (157 mg, 0.65 mmol) obtained from Preparation Example 4-3 was used to obtain the title compound (125 mg, 85%).

NMR: 1H-NMR (400 HMz, DMSO-d6); δ 8.59 (s, 1H), 8.23 (s, 1H), 7.92 (dd, J=1.6 Hz, 1H), 7.83 (d, 1H), 4.95-4.88 (m, 1H), 1.50 (d, 6H)

PREPARATION EXAMPLE 4-5

Synthesis of 5-[3-(4-formyl-2-methyl-phenyl)-[1,2,4]oxadiazol-5-yl]-1-isopropyl-1H-indole-3-carbonitrile According to the method described in Preparation Example 3-4, 3-cyano-1-isopropyl-1H-indole-5-carboxylic acid (21 mg, 0.094 mmol) obtained from Preparation Example 4-4 and 1-[4-(N-hydroxycarbimidoyl)-3-methyl-benzyl]-azetidine-3-carboxylic acid t-butyl ester (30 mg, 0.094 mmol) obtained from Preparation Example 3-3 were used to obtain the title compound (3 mg, 9%)

NMR: 1H-NMR (400 HMz, CDCl$_3$); δ 10.09 (s, 1H), 8.71 (s, 1H), 8.34 (d, 1H), 8.20 (dd, 1H), 7.88-7.85 (m, 3H), 7.62 (d, 1H), 4.82-4.78 (m, 1H), 2.81 (s, 3H), 1.63 (d, 6H)

EXAMPLE 4

Synthesis of 1-{4-[5-(3-cyano-1-isopropyl-1H-indol-5-yl)-[1,2,4]oxadiazol-3-yl]-3-methyl-benzyl}-azetidine-3-carboxylic acid

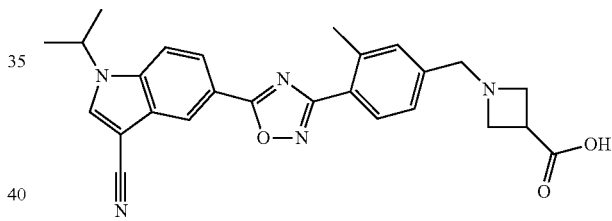

According to the method described in Example 3, 5-[3-(4-formyl-2-methyl-phenyl)-[1,2,4]oxadiazol-5-yl]-1-isopropyl-1H-indole-3-carbonitrile (3 mg, 0.008 mmol) obtained from Preparation Example 4-5 was used to obtain the title compound (3.5 mg, 95%).

NMR: 1H-NMR (400 HMz, CDCl$_3$); δ 8.65 (s, 1H), 8.20 (dd, J=1.6 Hz, 1H), 8.08 (d, 1H), 7.70 (d, 1H), 7.33 (br, s, 2H), 4.87-4.82 (m, 1H), 3.85 (s, 2H), 3.71 (t, 2H), 3.59 (t, 2H), 3.26 (t, 1H), 2.70 (s, 3H), 1.65 (d, 6H)

PREPARTION EXAMPLE 5-1

Synthesis of 1-{4-[5-(1-isopropyl-1H-indol-5-yl)-[1,2,4]oxadiazol-3-yl]-3-methyl-benzyl}-azetidine-3-carboxylic acid t-butyl ester According to the method described in Preparation Example 1-4, 1-isopropyl-1H-indole-5-carboxylic acid (20 mg, 0.094 mmol) obtained from Preparation Example 1-2 and 1-[4-(N-hydroxycarbimidoyl)-3-methyl-benzyl]-azetidine-3-carboxylic acid t-butyl ester (30 mg, 0.094 mmol) obtained from Preparation Example 3-3 were used to obtain the title compound (23.5 mg, 51.4%).

NMR: 1H-NMR (400 HMz, CDCl$_3$); δ 8.53 (s, 1H), 8.05 (d, 2H), 7.48 (d, 1H), 7.33 (d, 1H), 7.26 (s, 1H), 7.25 (d, 1H), 6.67 (d, 1H), 4.77-4.71 (m, 1H), 3.65 (s, 2H), 3.55 (br, s, 2H), 3.27 (br, s, 3H), 2.68 (s, 3H), 1.57 (d, 6H), 1.46 (s, 9H)

EXAMPLE 5

Synthesis of 1-{4-[5-(1-isopropyl-1H-indol-5-yl)-[1,2,4]oxadiazol-3-yl]-3-methyl-benzyl}-azetidine-3-carboxylic acid

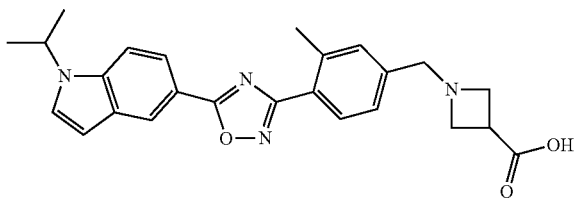 [SMILES: Cc1cc(CN2CC(C(=O)O)C2)ccc1-c1noc(-c2ccc3c(ccn3C(C)C)c2)n1]

EXAMPLE 6

Synthesis of 1-(4-{5-[1-isopropyl-3-(2,2,2-trifluoro-acetyl)-1H-indol-5-yl]-[1,2,4]oxadiazol-3-yl}-3-methyl-benzyl)-azetidine-3-carboxylic acid

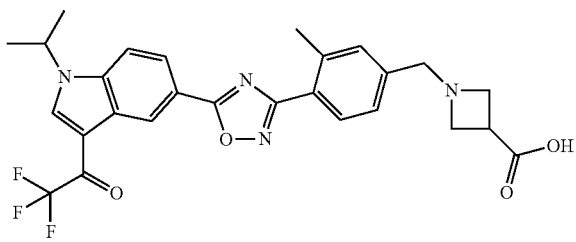 [SMILES: Cc1cc(CN2CC(C(=O)O)C2)ccc1-c1noc(-c2ccc3c(c2)c(C(=O)C(F)(F)F)cn3C(C)C)n1]

1-{4-[5-(1-Isopropyl-1H-indol-5-yl)-[1,2,4]oxadiazol-3-yl]-3-methyl-benzyl}-azetidine-3-carboxylic acid t-butyl ester (22 mg, 0.045 mmol) obtained from Preparation Example 5-1 was dissolved in 20% trifluoroacetic acid solution in dichloromethane (2 mL), and the solution was stirred for 18 hours at room temperature. The solvent was removed by distillation under reduced pressure. The residue was added with saturated sodium hydrogen carbonate and extracted with a mixed solution of dichloromethane and methanol (9/1). The extract was washed with brine, dried with anhydrous magnesium sulfate and filtered. The filtrate was distilled under reduced pressure. The residue was separated by column chromatography to obtain 1-{4-[5-(1-isopropyl-1H-indol-5-yl)-[1,2,4]oxadiazol-3-yl]-3-methyl-benzyl}-azetidine -3-carboxylic acid (3.5 mg, 18%) which passed firstly through column chromatography (Compound of Example 5), and 1-(4-{5-[1-isopropyl-3-(2,2,2-trifluoro-acetyl)-1H-indol-5-yl]-[1,2,4]oxadiazol-3-yl}-3-methyl-benzyl)-azetidine-3-carboxylic acid (4.7 mg, 19%) which passed secondly through column chromatography (Compound of Example 6).

NMR: 1H-NMR (400 HMz, CDCl$_3$); δ 8.49 (s, 1H), 8.07 (d, 1H), 8.01 (d, 1H), 7.47 (d, 1H), 7.32-7.29 (m, 3H), 6.65 (d, 1H), 4.74-4.69 (m, 1H), 3.90-3.69 (m, 6H), 3.26 (br, s, 1H), 2.66 (s, 3H), 1.55 (d, 6H)

NMR: 1H-NMR (400 HMz, CDCl$_3$); δ 9.24 (s, 1H), 8.22 (d, 1H), 8.12 (s, 1H), 8.10 (d, 1H), 7.62 (d, 1H), 7.32 (br, s, 2H), 4.84-4.80 (m, 1H), 3.90-3.71 (m, 6H), 3.27 (br, s, 1H), 2.69 (s, 3H), 1.69 (d, 6H)

PREPARATION EXAMPLE 7-1

Synthesis of 1-isobutyl-1H-indole-5-carboxylic acid methyl ester

According to the method described in Preparation Example 1-1, 1H-indole-5-carboxylic acid methyl ester (960 mg, 5.48 mmol) and isobutyl iodide (4 g, 21.92 mmol) were used to obtain the title compound (370 mg, 30%).

NMR: 1H-NMR (400 HMz, CDCl$_3$); δ 8.39 (s, 1H), 7.90 (dd, J=1.6 Hz, 1H), 7.32 (d, 1H), 7.12 (d, 1H), 6.58 (d, 1H), 3.93 (t, 5H), 2.24-2.15 (m, 1H), 0.92 (d, 6H)

PREPARATION EXAMPLE 7-2

Synthesis of 1-isobutyl-1H-indole-5-carboxylic acid

According to the method described in Preparation Example 3-2, 1-isobutyl-1H-indole-5-carboxylic acid methyl ester (100 mg, 0.43 mmol) obtained from Preparation Example 7-1 was used to obtain the title compound (95 mg, 99%).

NMR: 1H-NMR (400 HMz, CDCl$_3$); δ 8.49 (d, J=1.2 Hz, 1H), 7.97 (dd, J=1.6 Hz, 1H), 7.36 (d, 1H), 7.15 (d, 1H), 6.62 (d, 1H), 3.95 (d, 2H), 2.26-2.16 (m, 1H), 0.94 (d, 6H)

PPEPARATION EXAMPLE 7-3

Synthesis of 1-{4-[5-(1-isobutyl-1H-indol-5-yl)-[1,2,4]oxadiazol-3-yl]-3-methyl-benzyl}-azetidine-3-carboxylic acid t-butyl ester According to the method described in Preparation Example 1-4, 1-isobutyl-1H-indole-5-carboxylic acid (31 mg, 0.14 mmol) obtained from Preparation Example 7-2 and 1-[4-(N-hydroxycarbimidoyl)-3-methyl-benzyl]-azetidine-3-carboxylic acid t-butyl ester (45 mg, 0.14 mmol) obtained from Preparation Example 3-3 were used to obtain the title compound (17.5 mg, 30%).

NMR: 1H-NMR (400 HMz, CDCl$_3$); δ 8.53 (s, 1H), 8.06-8.03 (m, 2H), 7.44 (d, 1H), 7.26 (s, 1H), 7.24 (d, 1H), 7.17 (d, 1H), 6.64 (d, 1H), 3.97 (d, 1H), 3.65 (s, 2H), 3.55 (br, s, 2H), 3.289 (br, s, 3H), 2.68 (s, 3H), 2.27-2.17 (m, 1H), 1.46 (s, 9H), 0.95 (d, 6H)

EXAMPLE 7

Synthesis of 1-{4-[5-(1-isobutyl-1H-indol-5-yl)-[1,2,4]oxadiazol-3-yl]-3-methyl-benzyl}-azetidine-3-carboxylic acid

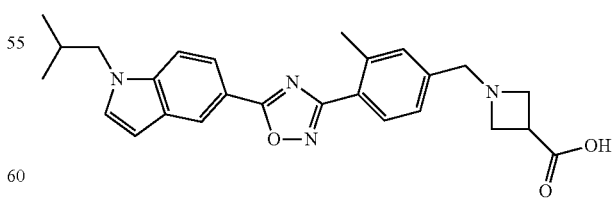

According to the method described in Example 5, 1-{4-[5-(1-isobutyl-1H-indol-5-yl)-[1,2,4]oxadiazol-3-yl]-3-methyl-benzyl}-azetidine-3-carboxylic acid t-butyl ester (17.5 mg, 0.035 mmol) obtained from Preparation Example 7-3 was used to obtain the title compound (9.9 mg, 64%).

NMR: 1H-NMR (400 HMz, CDCl₃); δ 8.40 (s, 1H), 8.03 (d, 1H), 7.91 (d, 1H), 7.33-7.25 (m, 3H), 7.07 (d, 1H), 6.54 (d, 1H), 3.85-3.68 (m, 9H), 3.25 (br, s, 1H), 2.58 (s, 3H), 2.17-2.10 (m, 1H), 0.88 (d, 6H)

PREPARATION EXAMPLE 8-1

Synthesis of 1-[4-(N-hydroxycarbimidoyl)-3-methyl-benzyl]-1H-pyrazole-4-carboxylic acid t-butyl ester The title compound was obtained according to the method described in WO 2010085581 A1.

NMR: 1H-NMR (400 HMz, CDCl₃); δ 7.88 (s, 1H), 7.81 (s, 1H), 7.61 (d, 2H), 7.25 (d, 2H), 5.31 (s, 2H), 4.86 (br, s 2H), 1.53 (s, 9H)

PREPARATION EXAMPLE 8-2

Synthesis of 1-{4-[5-(3-chloro-1-isopropyl-1H-indol-5-yl)-[1,2,4]oxadiazol-3-yl]-benzyl}-1H-pyrazole-4-carboxylic acid t-butyl ester According to the method described in Preparation Example 1-4, 3-chloro-1-isopropyl-1H-indole-5-carboxylic acid (21.5 mg, 0.09 mmol) obtained from Preparation Example 3-2 and 1-[4-(N-hydroxycarbimidoyl)-3-methyl-benzyl]-1H-pyrazole-4-carboxylic acid t-butyl ester (28.5 mg, 0.09 mmol) obtained from Preparation Example 8-1 were used to obtain the title compound (17.5 mg, 37.5%).

NMR: 1H-NMR (400 HMz, CDCl₃); δ 8.53 (d, J=1.2 Hz, 1H), 8.20 (d, 2H), 8.08 (dd, J=1.6, 2.0 Hz, 1H), 7.91 (s, 1H), 7.84 (s, 1H), 7.49 (d, 1H), 7.37 (d, 1H), 7.29 (s, 1H), 5.38 (s, 2H), 4.76-4.69 (m, 1H), 1.56 (d, 6H), 1.54 (s, 9H)

EXAMPLE 8

Synthesis of 1-{4-[5-(3-chloro-1-isopropyl-1H-indol-5-yl)-[1,2,4]oxadiazol-3-yl]-benzyl}-1H-pyrazole-4-carboxylic acid

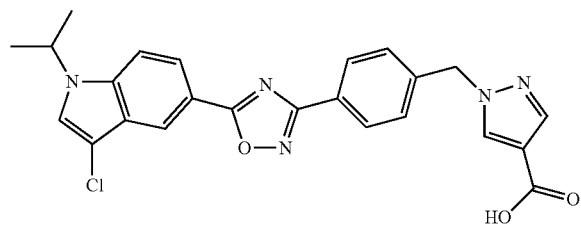 [SMILES: CC(C)n1cc(Cl)c2cc(-c3nc(-c4ccc(Cn5cc(C(=O)O)cn5)cc4)no3)ccc21]

According to the method described in Example 5, 1-{4-[5-(3-chloro-1-isopropyl-1H-indol-5-yl)-[1,2,4]oxadiazol-3-yl]-benzyl}-1H-pyrazole-4-carboxylic acid t-butyl ester (17.5 mg, 0.034 mmol) obtained from Preparation Example 8-2 was used to obtain the title compound (14.6 mg, 93%).

NMR: 1H-NMR (400 HMz, CDCl₃); δ 8.51 (d, J=1.2 Hz, 1H), 8.17 (d, 2H), 8.07 (dd, J=1.6 Hz, 1H), 7.92 (d, 2H), 7.52 (d, 1H), 7.37 (d, 1H), 7.32 (s, 1H), 5.38 (s, 2H), 4.77-4.70 (m, 1H), 1.56 (d, 6H)

PREPARATION EXAMPLE 9-1

Synthesis of 4-[1,3]dioxolan-2-yl-2-methyl-benzonitrile

The title compound was obtained according to the method described in European Journal of Organic Chemistry, 25, 4277, 2008.

NMR: 1H-NMR (400 HMz, CDCl₃); δ 7.62 (d, 1H), 7.44 (s, 1H), 7.36 (d, 1H), 5.81 (s, 1H), 4.16-4.02 (m, 4H), 2.57 (s, 3H)

PREPARATION EXAMPLE 9-2

Synthesis of 4-[1,3]dioxolan-2-yl-N-hydroxy-2-methyl-benzamidine

4-[1,3]Dioxolan-2-yl-2-methyl-benzonitrile (750 mg, 3.51 mmol) obtained from Preparation Example 9-1 was dissolved in ethanol (10 mL), and 50% hydroxylamine aqueous solution (700 mg) was added dropwise thereto. The mixture was stirred under reflux for 18 hours and distilled under reduced pressure to obtain the title compound (890 mg, 100%).

NMR: 1H-NMR (400 HMz, CDCl₃); δ 7.39-7.29 (m, 3H), 5.79 (s, 1H), 4.16-4.01 (m, 4H), 2.37 (s, 3H)

PREPARATION EXAMPLE 9-3

Synthesis of 3-chloro-5-[3-(4-[1,3]dioxolan-2-yl-2-methyl-phenyl)-[1,2,4]oxadiazol-5-yl]-1-isopropyl-1H-indole According to the method described in Preparation Example 1-4, 3-chloro-1-isopropyl-1H-indole-5-carboxylic acid (840 mg, 3.51 mmol) obtained from Preparation Example 3-2 and 4-[1,3]dioxolan-2-yl-N-hydroxy-2-methyl-benzamidine (890 mg, 3.51 mmol) obtained from Preparation Example 9-2 were used to obtain the title compound (790 mg, 53%).

NMR: 1H-NMR (400 HMz, CDCl₃); δ 8.53 (d, J=1.6 Hz, 1H), 8.15 (d, 1H), 8.09 (dd, J=1.6 Hz, 1H), 7.47 (t, 3H), 7.29 (s, 1H), 5.88 (s, 1H), 4.76-4.69 (m, 1H), 4.19-4.03 (m, 4H), 2.73 (s, 3H), 1.56 (d, 6H),

PREPARATION EXAMPLE 9-4

Synthesis of 4-[5-(3-chloro-1-isopropyl-1H-indol-5-yl)-[1,2,4]oxadiazol-3-yl]-3-methyl-benzaldehyde 3-Chloro-5-[3-(4-[1,3]dioxolan-2-yl-2-methyl-phenyl)-[1,2,4]oxadiazol-5-yl]-1-isopropyl-1H-indole (300 mg, 0.71 mmol) obtained from Preparation Example 9-3 was dissolved in tetrahydrofuran, and 50% acetic acid aqueous solution (10 mL) was added dropwise thereto. The mixture was stirred for 18 hours at room temperature, further stirred for 3 hours under reflux at 80° C. and distilled under reduced pressure to obtain the title compound (300 mg, 99%).

NMR: 1H-NMR (400 HMz, CDCl₃); δ 10.09 (s, 1H), 8.55 (d, J=1.2 Hz, 1H), 8.34 (d, 1H), 8.10 (dd, J=1.6 Hz, 1H), 7.87 (br, s, 2H), 7.51 (d, 1H), 7.31 (s, 1H), 4.77-4.70 (m, 1H), 3.49 (s, 1H), 2.80 (s, 3H), 1.56 (d, 6H)

PREPARATION EXAMPLE 9-5

Synthesis of {4-[5-(3-chloro-1-isopropyl-1H-indol-5-yl)-[1,2,4]oxadiazol-3-yl]-3-methyl-phenyl}-methanol 4-[5-(3-Chloro-1-isopropyl-1H-indol-5-yl)-[1,2,4]oxadiazol-3-yl]-3-methyl-benzaldehyde (200 mg, 0.53 mmol) obtained from Preparation Example 9-4 was dissolved in a mixed solution of methanol and dichloromethane (2/1, 15 mL), and sodium borohydride (30 mg, 0.79 mmol) was added dropwise thereto at 0° C. The mixture was stirred for 1 hour at 0° C., added with water and extracted with ethyl acetate. The extract was distilled under reduced pressure to obtain the title compound (200 mg, 99%).

PREPARATION EXAMPLE 9-6

Synthesis of 5-[3-(4-bromomethyl-2-methyl-phenyl)-[1,2,4]oxadiazol-5-yl]-3-chloro-1-isopropyl-1H-indole {4-[5-(3-Chloro-1-isopropyl-1H-indol-5-yl)-[1,2,4]oxadiazol-3-yl]-3-methyl-phenyl}-methanol (200 mg, 0.52 mmol) obtained from Preparation Example 9-5 was dissolved in tetrahydrofuran, and PBr3 (0.03 mL, 0.32 mmol) was slowly added dropwise at 0° C. The mixture was stirred for 18 hours at room temperature and distilled under reduced pressure. The residue was separated by column chromatography to obtain the title compound (200 mg, 86%).

NMR: 1H-NMR (400 HMz, CDCl₃); δ 8.53 (d, J=1.2 Hz, 1H), 8.12 (d, 1H), 8.09 (dd, J=1.6, 2.0 Hz, 1H), 7.49 (d, 1H), 7.38 (br, s, 2H), 7.30 (s, 1H), 4.76-4.69 (m, 1H), 4.52 (s, 2H), 2.71 (s, 3H), 1.55 (d, 6H)

PREPARATION EXAMPLE 9-7

Synthesis of 1-{4-[5-(3-chloro-1-isopropyl-1H-indol-5-yl)-[1,2,4]oxadiazol-3-yl]-3-methyl-benzyl}-1H-pyrazole-4-carboxylic acid ethyl ester Sodium hydride (40 mg, 0.9 mmol) and pyrazole-4-carboxylic acid ethyl ester (76 mg, 0.54 mmol) were dissolved in dimethylformamide (10 mL) and the solution was stirred for 30 minutes at 0° C. 5-[3-(4-Bromomethyl-2-methyl-phenyl)-[1,2,4]oxadiazol-5-yl]-3-chloro-1-isopropyl-1H-indole (200 mg, 0.45 mmol) obtained from Preparation Example 9-6 was added to the resulting solution, and the mixture was stirred for 2 hours at room temperature. The mixture was added with saturated ammonium chloride aqueous solution and extracted with ethyl acetate. The extract was washed with brine, dried with anhydrous magnesium sulfate and filtered. The filtrate was distilled under reduced pressure. The residue was separated by column chromatography to obtain the title compound (60 mg, 26%).

NMR: 1H-NMR (400 HMz, CDCl₃); δ 8.53 (d, J=1.2 Hz, 1H), 8.13 (d, 1H), 8.08 (dd, J=1.6 Hz, 1H), 7.98 (s, 1H), 7.90 (s, 1H), 7.49 (d, 1H), 7.30 (s, 1H), 7.22 (s, 1H), 5.35 (s, 2H), 4.75-4.69 (m, 1H), 4.29 (q, 2H), 2.69 (s, 3H), 1.56 (d, 6H), 1.34 (t, 3H)

EXAMPLE 9

Synthesis of 1-{4-[5-(3-chloro-1-isopropyl-1H-indol-5-yl)-[1,2,4]oxadiazol-3-yl]-3-methyl-benzyl}-1H-pyrazole-4-carboxylic acid

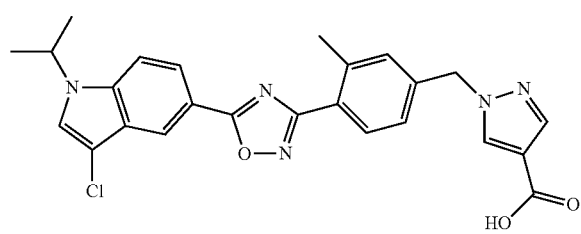 [SMILES: Cc1cc(Cn2cc(C(=O)O)cn2)ccc1-c1noc(-c2ccc3c(c2)c(Cl)cn3C(C)C)n1]

According to the method described in Example 1, 1-{4-[5-(3-chloro-1-isopropyl-1H-indol-5-yl)-[1,2,4]oxadiazol-3-yl]-3-methyl-benzyl}-1H-pyrazole-4-carboxylic acid ethyl ester (60 mg, 0.12 mmol) obtained from Preparation Example 9-7 was used to obtain the title compound (60 mg, 99%).

NMR: ¹H-NMR (400 MHz, DMSO-d6) δ 8.44 (s, 1H), 8.33 (d, J=1.6 Hz, 1H), 8.07 (d, 1H), 8.04 (dd, J=1.6 Hz, 1H), 7.99 (s, 1H), 7.91 (s, 1H), 7.86 (s, 1H), 7.35 (s, 1H), 7.31 (1H), 5.45 (s, 1H), 4.94-4.91 (m, 1H), 2.63 (s, 3H), 1.50 (d, 6H)

PREPARATION EXAMPLE 10-1

Synthesis of N-hydroxy-4-hydroxymethyl-benzamidine

The title compound was obtained according to the method described in WO 2010142628 A1.

NMR: ¹H-NMR (400 HMz, MeOD); δ 7.60 (d, 2H), 7.36 (s, 2H), 4.61 (s, 2H)

PPREPARTION EXAMPLE 10-2

Synthesis of {4-[5-(3-chloro-1-isopropyl-1H-indol-5-yl)-[1,2,4]oxadiazol-3-yl]-phenyl}-methanol According to the method described in Preparation Example 1-4, 3-chloro-1-isopropyl-1H-indole-5-carboxylic acid (200 mg, 0.84 mmol) obtained from Preparation Example 3-2 and N-hydroxy-4-hydroxymethyl-benzamidine (139 mg, 0.84 mmol) obtained from Preparation Example 10-1 were used to obtain the title compound (70 mg, 23%).

NMR: ¹H-NMR (400 HMz, CDCl₃); δ 8.58 (s, 1H), 8.25 (d, 2H), 8.14 (dd, J=1.6 Hz, 1H), 7.57 (d, 2H), 7.53 (d, 1H), 7.34 (s, 1H), 4.84 (s, 2H), 4.76-4.71 (m, 1H), 1.60 (d, 6H)

PREPARATION EXAMPLE 10-3

Synthesis of 4-[5-(3-chloro-1-isopropyl-1H-indol-5-yl)-[1,2,4]oxadiazol-3-yl]-benzaldehyde {4-[5-(3-Chloro-1-isopropyl-1H-indol-5-yl)-[1,2,4]oxadiazol-3-yl]-phenyl}-methanol (70 mg, 0.19 mmol) obtained from Preparation Example 10-2 was dissolved in dichloromethane, and 15 wt % Dess-Martin periodinane (1 g, 0.38 mmol) was added dropwise thereto. The mixture was stirred for 1 hour at room temperature and added with dichloromethane, and washed with saturated sodium thiosulfate aqueous solution and saturated sodium hydrogen carbonate aqueous solution. The organic layer was dried with anhydrous magnesium sulfate and filtered. The filtrate was distilled under reduced pressure to obtain the title compound (70 mg, 99%).

EXAMPLE 10

Synthesis of 3-{4-[5-(3-chloro-1-isopropyl-1H-indol-5-yl)-[1,2,4]oxadiazol-3-yl]-benzylamino}-propanoic acid

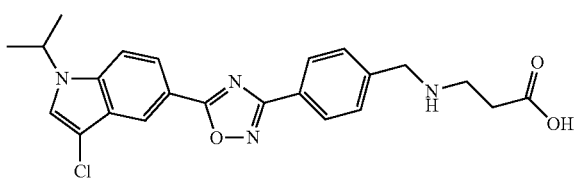 [SMILES: CC(C)n1cc(Cl)c2cc(-c3nc(-c4ccc(CNCCC(=O)O)cc4)no3)ccc21]

According to the method described in Example 3, 4-[5-(3-chloro-1-isopropyl-1H-indol-5-yl)-[1,2,4]oxadiazol-3-yl]-benzaldehyde (70 mg, 0.22 mmol) obtained from Preparation Example 10-3 and beta-alanine (23 mg, 0.26 mmol) were used to obtain the title compound (33 mg, 34%).

NMR: $^1$H-NMR (500 MHz, MeOD-d4) δ 8.35 (d, J=1.2 Hz, 1H), 8.22 (d, 2H), 8.02 (dd, J=1.8 1.3 Hz, 1H), 7.68-7.65 (m, 3H), 7.58 (s, 1H), 4.87-4.83 (m, 1H), 4.30 (s, 2H), 3.23 (t, 2H), 2.55 (t, 2H), 1.52 (d, 6H)

PREPARATION EXAMPLE 11-1

Synthesis of (4-cyano-phenoxy)-acetic acid ethyl ester

The title compound was obtained according to the method described in US 20080167340 A1.

NMR: $^1$H-NMR (400 HMz, CDCl$_3$); δ 7.55 (d, 2H), 6.92 (d, 2H), 4.63 (s, 2H), 4.22 (q, 2H), 1.23 (t, 3H)

PREPARATION EXAMPLE 11-2

Synthesis of [4-(N-hydroxycarbimidoyl)-phenoxy]-acetic acid ethyl ester

According to the method described in Preparation Example 9-2, (4-cyano-phenoxy)-acetic acid ethyl ester (3.5 g, 17.05 mmol) obtained from Preparation Example 11-1 was used to obtain the title compound (3 g, 74%).

NMR: $^1$H-NMR (400 HMz, MeOD); δ 7.62 (d, 2H), 7.00 (d, 2H), 4.74 (s, 2H), 4.23 (q, 2H), 1.29 (t, 3H)

PREPARATION EXAMPLE 11-3

Synthesis of {4-[5-(1-isopropyl-1H-indol-5-yl)-[1,2,4]oxadiazol-3-yl]-phenoxy}-acetic acid ethyl ester According to the method described in Preparation Example 1-4, 1-isopropyl-1H-indole-5-carboxylic acid (600 mg, 2.95 mmol) obtained from Preparation Example 1-2 and [4-(N-hydroxycarbimidoyl)-phenoxy]-acetic acid ethyl ester (703 mg, 2.95 mmol) obtained from Preparation Example 11-2 were used to obtain the title compound (390 mg, 33%).

NMR: $^1$H-NMR (400 HMz, CDCl$_3$); δ 8.52 (s, 1H), 8.14 (d, 2H), 8.03 (d, 1H), 7.47 (d, 1H), 7.31 (d, 1H), 7.02 (d, 2H), 6.66 (d, 1H), 4.71 (m, 5H), 4.29 (q, 2H), 1.55 (d, 6H), 1.30 (t, 3H)

EXAMPLE 11

Synthesis of {4-[5-(1-isopropyl-1H-indol-5-yl)-[1,2,4]oxadiazol-3-yl]-phenoxy}-acetic acid

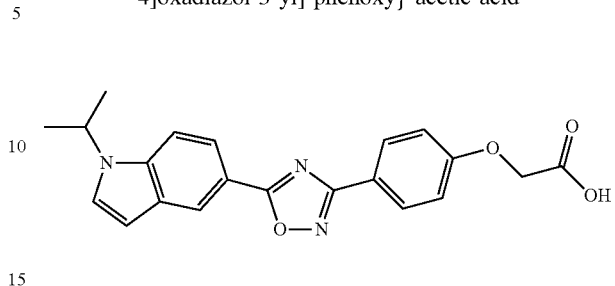

According to the method described in Example 1, {4-[5-(1-isopropyl-1H-indol-5-yl)-[1,2,4]oxadiazol-3-yl]-phenoxy}-acetic acid ethyl ester (390 mg, 0.96 mmol) obtained from Preparation Example 11-3 was used to obtain the title compound (300 mg, 83%).

NMR: $^1$H-NMR (400 HMz, DMSO$_{d6}$); δ 8.42 (s, 1H), 8.00 (d, 2H), 7.89 (d, 1H), 7.73 (d, 1H), 7.67 (d, 1H), 7.08 (d, 2H), 6.68 (d, 1H), 4.83 (m, 1H), 4.75 (s, 2H), 1.45 (d, 6H)

PREPARATION EXAMPLE 12-1

Synthesis of {4-[5-(3-chloro-1-isopropyl-1H-indol-5-yl)-[1,2,4]oxadiazol-3-yl]-phenoxy}-acetic acid ethyl ester According to the method described in Preparation Example 1-4, 3-chloro-1-isopropyl-1H-indole-5-carboxylic acid (269 mg, 1.13 mmol) obtained from Preparation Example 3-2 and [4-(N-hydroxycarbimidoyl)-phenoxy]-acetic acid ethyl ester (270 mg, 1.13 mmol) obtained from Preparation Example 11-2 were used to obtain the title compound (100 mg, 20%).

NMR: $^1$H-NMR (400 HMz, CDCl$_3$); δ 8.51 (s, 1H), 8.15 (d, 2H), 8.07 (d, 1H), 7.47 (d, 1H), 7.28 (s, 1H), 7.02 (d, 2H), 4.71 (m, 5H), 4.29 (q, 2H), 1.55 (d, 6H), 1.31 (t, 3H)

EXAMPLE 12

Synthesis of {4-[5-(3-chloro-1-isopropyl-1H-indol-5-yl)-[1,2,4]oxadiazol-3-yl]-phenoxy}-acetic acid

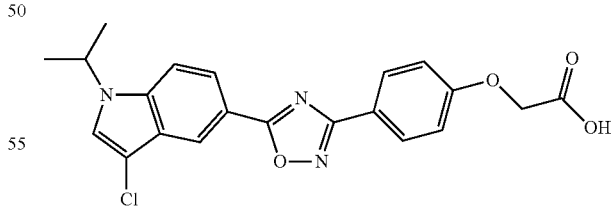

According to the method described in Example 1, {4-[5-(3-chloro-1-isopropyl-1H-indol-5-yl)-[1,2,4]oxadiazol-3-yl]-phenoxy}-acetic acid ethyl ester (100 mg, 0.23 mmol) obtained from Preparation Example 12-1 was used to obtain the title compound (85 mg, 89%).

NMR: $^1$H-NMR (400 HMz, DMSO$_{d6}$); δ 8.27 (s, 1H), 8.02 (d, 2H), 7.98 (d, 1H), 7.95 (s, 1H), 7.85 (d, 1H), 7.09 (d, 2H), 4.88 (m, 1H), 4.76 (s, 2H), 1.45 (d, 6H)

PREPARATION EXAMPLE 13-1

Synthesis of 3-(4-cyano-phenoxy)-propanoic acid ethyl ester

The title compound was obtained according to the method described in US 20080167340 A1.

PREPARATION EXAMPLE 13-2

Synthesis of 3-[4-(N-hydroxycarbimidoyl)-phenoxy]-propanoic acid ethyl ester According to the method described in Preparation Example 9-2, 3-(4-cyano-phenoxy)-propanoic acid ethyl ester (3.5 g, 15.0 mmol) obtained from Preparation Example 13-1 was used to obtain the title compound (3 g, 75%).

PREPARATION EXAMPLE 13-3

Synthesis of 3-{4-[5-(1-isopropyl-1H-indol-5-yl)-[1,2,4]oxadiazol-3-yl]-phenoxy}-propanoic acid ethyl ester According to the method described in Preparation Example 1-4, 1-isopropyl-1H-indole-5-carboxylic acid (300 mg, 1.48 mmol) obtained from Preparation Example 1-2 and 3-[4-(N-hydroxycarbimidoyl)-phenoxy]-propanoic acid ethyl ester (393 mg, 1.48 mmol) obtained from Preparation Example 13-2 were used to obtain the title compound (368 mg, 57%).

EXAMPLE 13

Synthesis of 3-{4-[5-(1-isopropyl-1H-indol-5-yl)-[1,2,4]oxadiazol-3-yl]-phenoxy}-propanoic acid

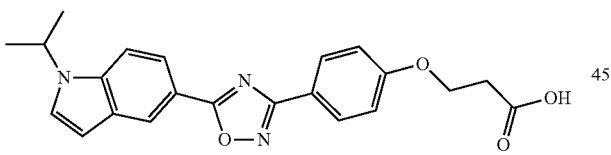

According to the method described in Example 1, 3-{4-[5-(1-isopropyl-1H-indol-5-yl)-[1,2,4]oxadiazol-3-yl]-phenoxy}-propanoic acid ethyl ester (368 mg, 0.85 mmol) obtained from Preparation Example 13-3 was used to obtain the title compound (310 mg, 90%).

NMR: $^1$H-NMR (400 HMz, DMSO$_{d6}$); δ 8.42 (s, 1H), 8.00 (d, 2H), 7.89 (d, 1H), 7.73 (d, 1H), 7.67 (d, 1H), 7.09 (d, 2H), 6.68 (d, 1H), 4.83 (m, 1H), 4.05 (t, 2H), 2.38 (t, 2H), 1.95 (m, 2H), 1.45 (d, 6H)

PREPARATION EXAMPLE 14-1

Synthesis of N-hydroxy-4-hydroxymethyl-2-methyl-benzamidine

The title compound was obtained according to the method described in WO 2010112461 A1.

PREPARATION EXAMPLE 14-2

Synthesis of {4-[5-(1-isopropyl-1H-indol-5-yl)-[1,2,4]oxadiazol-3-yl]-3-methyl-phenyl}-methanol According to the method described in Preparation Example 1-4, 1-isopropyl-1H-indole-5-carboxylic acid (1.0 g, 4.92 mmol) obtained from Preparation Example 1-2 and N-hydroxy-4-hydroxymethyl-2-methyl-benzamidine (887 mg, 4.92 mmol) obtained from Preparation Example 14-1 were used to obtain the title compound (1.0 g, 56%).

NMR: $^1$H-NMR (400 HMz, CDCl$_3$); δ 8.53 (s, 1H), 8.10 (d, 1H), 8.04 (dd, 1H), 7.49 (d, 1H), 7.33 (m, 3H), 6.67 (d, 1H), 4.74 (m, 3H), 2.70 (s, 3H), 1.55 (d, 6H)

PREPARATION EXAMPLE 14-3

Synthesis of 4-[5-(1-isopropyl-1H-indol-5-yl)-[1,2,4]oxadiazol-3-yl]-3-methyl-benzaldehyde {4-[5-(1-Isopropyl-1H-indol-5-yl)-[1,2,4]oxadiazol-3-yl]-3-methyl-phenyl}-methanol (400 mg, 1.09 mmol) obtained from Preparation Example 14-2 was dissolved in dichloromethane (30 mL), and pyridinium chlorochromate (PCC, 283 mg, 1.31 mmol) was added dropwise thereto. The mixture was stirred for 3 hours at room temperature, added with ethyl acetate and filtered by celite. The filtrate was added with water and extracted with ethyl acetate. The extract was washed with brine, dried with anhydrous magnesium sulfate and filtered. The filtrate was distilled under reduced pressure. The residue was separated by column chromatography to obtain the title compound (315 mg, 84%).

PREPARATION EXAMPLE 14-4

Synthesis of (R)-1-{4-[5-(1-isopropyl-1H-indol-5-yl)-[1,2,4]oxadiazol-3-yl]-3-methyl-benzyl}-piperidine-3-carboxylic acid ethyl ester 4-[5-(1-Isopropyl-1H-indol-5-yl)-[1,2,4]oxadiazol-3-yl]-3-methyl-benzaldehyde (50 mg, 0.14 mmol) obtained from Preparation Example 14-3 and (R)-piperidine-3-carboxylic acid ethyl ester (27 mg, 0.17 mmol) were dissolved in dichloroethane (10 mL), and sodium triacetoxy borohydride (46 mg, 0.22 mmol) was added thereto. The mixture was stirred for 5 hours at room temperature. After completion of the reaction, the reactant was added with water and extracted with ethyl acetate. The extract was dried with anhydrous magnesium sulfate and filtered. The filtrate was distilled under reduced pressure. The residue was separated by column chromatography to obtain the title compound (57 mg, 85%).

NMR: $^1$H-NMR (400 HMz, CDCl$_3$); δ 8.54 (s, 1H), 8.05 (m, 2H), 7.50 (d, 1H), 7.32 (m, 3H), 6.67 (d, 1H), 4.75 (m, 1H), 4.11 (q, 2H), 3.70 (m, 2H), 3.14 (m, 1H), 2.96 (m, 1H), 2.71 (m, 3H), 2.30 (m, 1H), 2.11 (m, 1H), 2.06 (s, 3H), 1.98 (m, 1H), 1.71 (m, 2H), 1.56 (d, 6H), 1.47 (m, 1H), 1.23 (t, 3H)

EXAMPLE 14

Synthesis of (R)-1-{4-[5-(1-isopropyl-1H-indol-5-yl)-[1,2,4]oxadiazol-3-yl]-3-methyl-benzyl}-piperidine-3-carboxylic acid

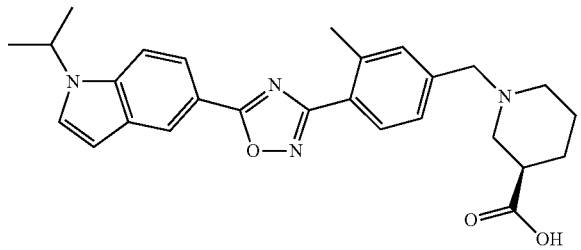 [SMILES: Cc1cc(CN2CCC[C@@H](C(=O)O)C2)ccc1-c1noc(-c2ccc3c(ccn3C(C)C)c2)n1]

According to the method described in Example 1, (R)-1-{4-[5-(1-isopropyl-1H-indol-5-yl)-[1,2,4]oxadiazol-3-yl]-3-methyl-benzyl}-piperidine-3-carboxylic acid ethyl ester (57 mg, 0.12 mmol) obtained from Preparation Example 14-4 was used to obtain the title compound (50 mg, 91%).

NMR: $^1$H-NMR (400 HMz, CDCl$_3$); δ 8.52 (s, 1H), 8.10 (d, 1H), 8.04 (dd, 1H), 7.48 (d, 1H), 7.31 (m, 3H), 6.66 (d, 1H), 4.73 (m, 1H), 3.76 (s, 2H), 3.06 (m, 1H), 2.87 (m, 1H), 2.75 (m, 1H), 2.64 (m, 1H), 2.43 (m, 1H), 1.82 (m, 2H), 1.70 (m, 2H), 1.56 (d, 6H)

PREPARATION EXAMPLE 15-1

Synthesis of (S)-1-{4-[5-(1-isopropyl-1H-indol-5-yl)-[1,2,4]oxadiazol-3-yl]-3-methyl-benzyl}-piperidine-3-carboxylic acid ethyl ester According to the method described in Preparation Example 14-4, 4-[5-(1-isopropyl-1H-indol-5-yl)-[1,2,4]oxadiazol-3-yl]-3-methyl-benzaldehyde (50 mg, 0.14 mmol) obtained from Preparation Example 14-3 and (S)-piperidine-3-carboxylic acid ethyl ester (27 mg, 0.17 mmol) were used to obtain the title compound (52 mg, 78%).

EXAMPLE 15

Synthesis of (S)-1-{4-[5-(1-isopropyl-1H-indol-5-yl)-[1,2,4]oxadiazol-3-yl]-3-methyl-benzyl}-piperidine-3-carboxylic acid

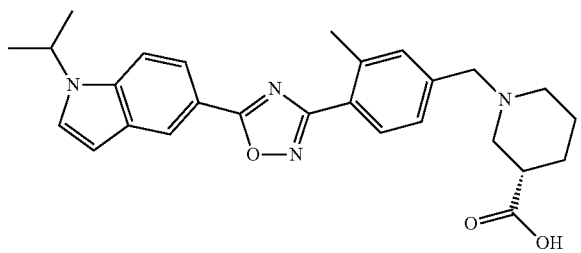 [SMILES: Cc1cc(CN2CCC[C@H](C(=O)O)C2)ccc1-c1noc(-c2ccc3c(ccn3C(C)C)c2)n1]

According to the method described in Example 1, (S)-1-{4-[5-(1-isopropyl-1H-indol-5-yl)-[1,2,4]oxadiazol-3-yl]-3-methyl-benzyl}-piperidine-3-carboxylic acid ethyl ester (52 mg, 0.11 mmol) obtained from Preparation Example 15-1 was used to obtain the title compound (45 mg, 90%).

NMR: $^1$H-NMR (400 HMz, CDCl$_3$); δ 8.52 (s, 1H), 8.10 (d, 1H), 8.04 (dd, 1H), 7.48 (d, 1H), 7.31 (m, 3H), 6.66 (d, 1H), 4.73 (m, 1H), 3.76 (s, 2H), 3.06 (m, 1H), 2.87 (m, 1H), 2.75 (m, 1H), 2.64 (m, 1H), 2.43 (m, 1H), 1.82 (m, 2H), 1.70 (m, 2H), 1.56 (d, 6H)

PREPARATION EXAMPLE 16-1

Synthesis of 1-{4-[5-(1-isopropyl-1H-indol-5-yl)-[1,2,4]oxadiazol-3-yl]-3-methyl-benzyl}-piperidine-4-carboxylic acid methyl ester According to the method described in Preparation Example 14-4, 4-[5-(1-isopropyl-1H-indol-5-yl)-[1,2,4]oxadiazol-3-yl]-3-methyl-benzaldehyde (50 mg, 0.14 mmol) obtained from Preparation Example 14-3 and piperidine-4-carboxylic acid methyl ester hydrochloride (31 mg, 0.17 mmol) were used to obtain the title compound (55 mg, 83%).

EXAMPLE 16

Synthesis of 1-{4-[5-(1-isopropyl-1H-indol-5-yl)-[1,2,4]oxadiazol-3-yl]-3-methyl-benzyl}-piperidine-4-carboxylic acid

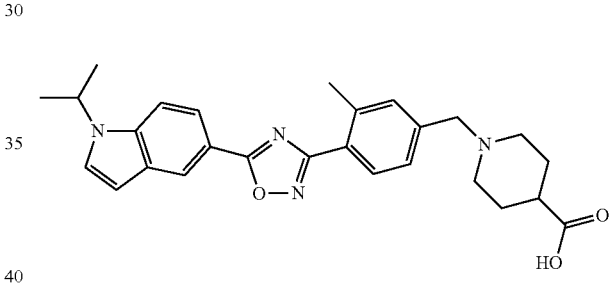

According to the method described in Example 1, 1-{4-[5-(1-isopropyl-1H-indol-5-yl)-[1,2,4]oxadiazol-3-yl]-3-methyl-benzyl}-piperidine-4-carboxylic acid methyl ester (55 mg, 0.12 mmol) obtained from Preparation Example 16-1 was used to obtain the title compound (48 mg, 87%).

NMR: $^1$H-NMR (400 HMz, CDCl$_3$); δ 8.67 (s, 1H), 8.05 (m, 2H), 7.51 (d, 1H), 7.34 (m, 3H), 6.67 (d, 1H), 4.75 (m, 1H), 3.84 (s, 2H), 3.14 (m, 2H), 2.37 (m, 3H), 2.01 (m, 2H), 1.88 (m, 2H), 1.57 (d, 6H)

PREPARATION EXAMPLE 17-1

Synthesis of (S)-1-{4-[5-(1-isopropyl-1H-indol-5-yl)-[1,2,4]oxadiazol-3-yl]-3-methyl-benzyl}-pyrrolidine-3-carboxylic acid methyl ester According to the method described in Preparation Example 14-4, 4-[5-(1-isopropyl-1H-indol-5-yl)-[1,2,4]oxadiazol-3-yl]-3-methyl-benzaldehyde (50 mg, 0.14 mmol) obtained from Preparation Example 14-3 and (S)-pyrrolidine-3-carboxylic acid methyl ester hydrochloride (29 mg, 0.17 mmol) were used to obtain the title compound (55 mg, 85%).

EXAMPLE 17

Synthesis of (S)-1-{4-[5-(1-isopropyl-1H-indol-5-yl)-[1,2,4]oxadiazol-3-yl]-3-methyl-benzyl}-pyrrolidine-3-carboxylic acid

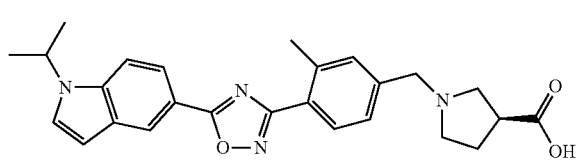 [SMILES: Cc1cc(CN2CC[C@H](C(=O)O)C2)ccc1-c1noc(-c2ccc3c(ccn3C(C)C)c2)n1]

According to the method described in Example 1, (S)-1-{4-[5-(1-isopropyl-1H-indol-5-yl)-[1,2,4]oxadiazol-3-yl]-3-methyl-benzyl}-pyrrolidine-3-carboxylic acid methyl ester (55 mg, 0.12 mmol) obtained from Preparation Example 17-1 was used to obtain the title compound (48 mg, 90%).

NMR: $^1$H-NMR (400 HMz, CDCl$_3$); δ 8.49 (s, 1H), 8.10 (d, 1H), 8.00 (dd, 1H), 7.44 (m, 3H), 7.30 (d, 1H), 6.64 (d, 1H), 4.70 (m, 1H), 4.11 (dd, 2H), 3.52 (m, 1H), 3.18 (m, 3H), 3.00 (m, 1H), 2.67 (s, 3H), 2.30 (m, 2H), 1.54 (d, 6H)

PREPARATION EXAMPLE 18-1

Synthesis of ({4-[5-(1-isopropyl-1H-indol-5-yl)-[1,2,4]oxadiazol-3-yl]-3-methyl-benzyl}-methyl-amino)-acetic acid ethyl ester According to the method described in Preparation Example 14-4, 4-[5-(1-isopropyl-1H-indol-5-yl)-[1,2,4]oxadiazol-3-yl]-3-methyl-benzaldehyde (40 mg, 0.12 mmol) obtained from Preparation Example 14-3 and sarcosine ethyl ester hydrochloride (27 mg, 0.17 mmol) were used to obtain the title compound (43 mg, 80%).

EXAMPLE 18

Synthesis of ({4-[5-(1-isopropyl-1H-indol-5-yl)-[1,2,4]oxadiazol-3-yl]-3-methyl-benzyl}-methyl-amino)-acetic acid

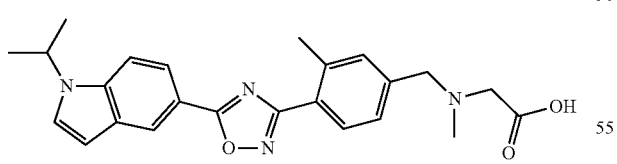

According to the method described in Example 1, ({4-[5-(1-isopropyl-1H-indol-5-yl)-[1,2,4]oxadiazol-3-yl]-3-methyl-benzyl}-methyl-amino)-acetic acid ethyl ester (43 mg, 0.096 mmol) obtained from Preparation Example 18-1 was used to obtain the title compound (39 mg, 97%).

NMR: $^1$H-NMR (400 HMz, CDCl$_3$); δ 8.48 (s, 1H), 8.14 (d, 1H), 8.00 (dd, 1H), 7.46 (m, 3H), 7.30 (d, 1H), 6.64 (d, 1H), 4.70 (m, 1H), 4.30 (s, 2H), 3.59 (s, 2H), 2.78 (s, 3H), 2.68 (s, 3H), 1.55 (d, 6H)

EXAMPLE 19

Synthesis of 3-{4-[5-(1-isopropyl-1H-indol-5-yl)-[1,2,4]oxadiazol-3-yl]-3-methyl-benzylamino}-propanoic acid

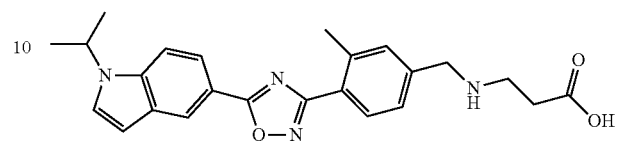

According to the method described in Preparation Example 14-4, 4-[5-(1-isopropyl-1H-indol-5-yl)-[1,2,4]oxadiazol-3-yl]-3-methyl-benzaldehyde (75 mg, 0.22 mmol) obtained from Preparation Example 14-3 and beta-alanine (19 mg, 0.22 mmol) were used to obtain the title compound (3 mg).

NMR: $^1$H-NMR (400 HMz, CDCl$_3$); δ 8.47 (s, 1H), 8.12 (d, 1H), 8.00 (dd, 1H), 7.43 (m, 3H), 7.30 (d, 1H), 6.64 (d, 1H), 4.70 (m, 1H), 4.14 (s, 2H), 3.05 (m, 2H), 2.67 (s, 3H), 2.60 (m, 2H), 1.55 (d, 6H)

PREPARTION EXAMPLE 20-1

Synthesis of 3-[3-(N-hydroxycarbimidoyl)-2-methyl-phenyl]-propanoic acid ethyl ester The title compound was obtained according to the method described in EP 2202232.

PREPARATION EXAMPLE 20-2

Synthesis of 3-{3-[5-(1-isopropyl-1H-indol-5-yl)-[1,2,4]oxadiazol-3-yl]-2-methyl-phenyl}-propanoic acid ethyl ester According to the method described in Preparation Example 1-4, 1-isopropyl-1H-indole-5-carboxylic acid (200 mg, 0.98 mmol) obtained from Preparation Example 1-2 and 3-[3-(N-hydroxycarbimidoyl)-2-methyl-phenyl]-propanoic acid ethyl ester (250 mg, 0.98 mmol) obtained from Preparation Example 20-1 were used to obtain the title compound (103 mg, 25%).

EXAMPLE 20

Synthesis of 3-{3-[5-(1-isopropyl-1H-indol-5-yl)-[1,2,4]oxadiazol-3-yl]-2-methyl-phenyl}-propanoic acid

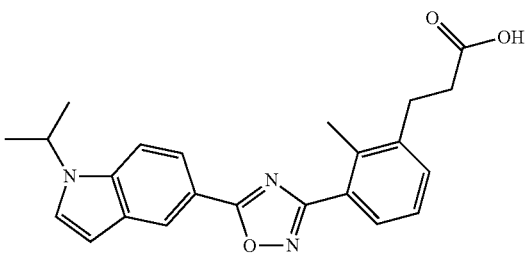 [SMILES: Cc1c(CCC(=O)O)cccc1-c1noc(-c2ccc3c(ccn3C(C)C)c2)n1]

According to the method described in Example 1, 3-{3-[5-(1-isopropyl-1H-indol-5-yl)-[1,2,4]oxadiazol-3-yl]-2-methyl-phenyl}-propanoic acid ethyl ester (103 mg, 0.25 mmol) obtained from Preparation Example 20-2 was used to obtain the title compound (95 mg, 97%).

NMR: $^1$H-NMR (400 HMz, CDCl$_3$); δ 8.53 (s, 1H), 8.04 (dd, 1H), 7.81 (dd, 1H), 7.49 (d, 1H), 7.30 (m, 3H), 6.67 (d, 1H), 4.74 (m, 1H), 3.09 (t, 2H), 2.68 (t, 2H), 1.56 (d, 6H)

PREPARATION EXAMPLE 21-1

Synthesis of N-hydroxy-3-hydroxymethyl-benzamidine

The title compound was obtained according to the method described in WO 2009080663 A1.

PREPARATION EXAMPLE 21-2

Synthesis of {3-[5-(1-isopropyl-1H-indol-5-yl)-[1,2,4]oxadiazol-3-yl]-phenyl}-methanol According to the method described in Preparation Example 1-4, 1-isopropyl-1H-indole-5-carboxylic acid (500 mg, 2.46 mmol) obtained from Preparation Example 1-2 and N-hydroxy-3-hydroxymethyl-benzamidine (409 mg, 2.46 mmol) obtained from Preparation Example 21-1 were used to obtain the title compound (730 mg, 89%).

PREPARATION EXAMPLE 21-3

Synthesis of 3-[5-(1-isopropyl-1H-indol-5-yl)-[1,2,4]oxadiazol-3-yl]-benzaldehyde According to the method described in Preparation Example 14-3, {3-[5-(1-isopropyl-1H-indol-5-yl)-[1,2,4]oxadiazol-3-yl]-phenyl}-methanol (730 mg, 2.19 mmol) obtained from Preparation Example 21-2 was used to obtain the title compound (590 mg, 81%)

EXAMPLE 21

Synthesis of 1-{3-[5-(1-isopropyl-1H-indol-5-yl)-[1,2,4]oxadiazol-3-yl]-benzyl}-azetidine-3-carboxylic acid

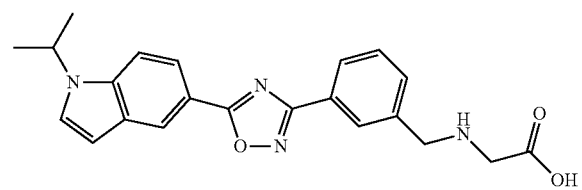 [SMILES: CC(C)n1ccc2cc(-c3nc(-c4cccc(CNCC(=O)O)c4)no3)ccc21]

According to the method described in Preparation Example 14-4, 3-[5-(1-isopropyl-1H-indol-5-yl)-[1,2,4]oxadiazol-3-yl]-benzaldehyde (50 mg, 0.15 mmol) obtained from Preparation Example 21-3 and azetidine-3-carboxylic acid (23 mg, 0.23 mmol) were used to obtain the title compound (25 mg, 40%).

NMR: $^1$H-NMR (400 HMz, CDCl$_3$); δ 8.45 (s, 1H), 8.24 (s, 1H), 8.14 (d, 1H), 7.95 (dd, 1H), 7.58 (d, 1H), 7.45 (m, 2H), 7.27 (d, 1H), 6.60 (d, 1H), 4.67 (m, 1H), 4.31 (s, 2H), 4.19 (m, 4H), 3.53 (m, 1H), 1.51 (d, 6H)

PREPARATION EXAMPLE 22-1

Synthesis of {3-[5-(1-isopropyl-1H-indol-5-yl)-[1,2,4]oxadiazol-3-yl]-benzylamino}-acetic acid methyl ester According to the method described in Preparation Example 14-4, 3-[5-(1-isopropyl-1H-indol-5-yl)-[1,2,4]oxadiazol-3-yl]-benzaldehyde (50 mg, 0.15 mmol) obtained from Preparation Example 21-3 and glycine methyl ester hydrochloride (28 mg, 0.23 mmol) were used to obtain the title compound (46 mg, 75%).

EXAMPLE 22

Synthesis of {3-[5-(1-isopropyl-1H-indol-5-yl)-[1,2,4]oxadiazol-3-yl]-benzylamino}-acetic acid

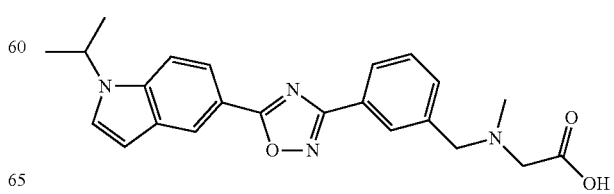

According to the method described in Example 1, {3-[5-(1-isopropyl-1H-indol-5-yl)-[1,2,4]oxadiazol-3-yl]-benzylamino}-acetic acid methyl ester (46 mg, 0.11 mmol) obtained from Preparation Example 22-1 was used to obtain the title compound (40 mg, 93%).

NMR: $^1$H-NMR (400 HMz, CDCl$_3$); δ 8.46 (s, 1H), 8.21 (s, 1H), 8.15 (d, 1H), 7.97 (d, 1H), 7.57 (m, 2H), 7.47 (d, 1H), 7.34 (d, 1H), 6.64 (d, 1H), 4.72 (m, 1H), 4.20 (s, 2H), 3.47 (s, 2H), 1.56 (d, 6H)

PREPARATION EXAMPLE 23-1

Synthesis of ({3-[5-(1-isopropyl-1H-indol-5-yl)-[1,2,4]oxadiazol-3-yl]-benzyl}-methyl-amino)-acetic acid ethyl ester According to the method described in Preparation Example 14-4, 3-[5-(1-isopropyl-1H-indol-5-yl)-[1,2,4]oxadiazol-3-yl]-benzaldehyde (50 mg, 0.15 mmol) obtained from Preparation Example 21-3 and N-methyl glycine methyl ester hydrochloride (35 mg, 0.23 mmol) were used to obtain the title compound (51 mg, 81%).

EXAMPLE 23

Synthesis of ({3-[5-(1-isopropyl-1H-indol-5-yl)-[1,2,4]oxadiazol-3-yl]-benzyl}-methyl-amino)-acetic acid According to the method described in Example 1, ({3-[5-(1-isopropyl-1H-indol-5-yl)-[1,2,4]oxadiazol-3-yl]-benzyl}-methyl-amino)-acetic acid ethyl ester (51 mg, 0.12 mmol) obtained from Preparation Example 23-1 was used to obtain the title compound (45 mg, 93%).

NMR: ¹H-NMR (400 HMz, CDCl₃); δ 8.47 (s, 1H), 8.24 (s, 1H), 8.19 (d, 1H), 7.99 (d, 1H), 7.56 (m, 3H), 7.35 (d, 1H), 6.66 (d, 1H), 4.74 (m, 1H), 4.38 (s, 2H), 3.64 (s, 2H), 2.85 (s, 3H), 1.56 (d, 6H)

PREPARATION EXAMPLE 24-1

Synthesis of (1S, 3R)-3-{4-[5-(1-isopropyl-1H-indol-5-yl)-[1,2,4]oxadiazol-3-yl]-3-methyl-benzylamino}-cyclopentanecarboxylic acid methyl ester According to the method described in Preparation Example 14-4, 4-[5-(1-isopropyl-1H-indol-5-yl)-[1,2,4]oxadiazol-3-yl]-3-methyl-benzaldehyde (50 mg, 0.14 mmol) obtained from Preparation Example 14-3 and aminocyclopentane carboxylic acid methyl ester hydrochloride (39 mg, 0.22 mmol) were used to obtain the title compound (30 mg, 45%).

EXAMPLE 24

Synthesis of (1S, 3R)-3-{4-[5-(1-isopropyl-1H-indol-5-yl)-[1,2,4]oxadiazol-3-yl]-3-methyl-benzylamino}-cyclopentanecarboxylic acid

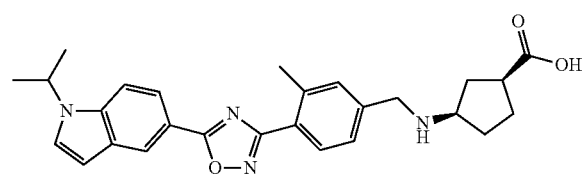 [SMILES: Cc1cc(CN[C@@H]2CC[C@H](C(=O)O)C2)ccc1-c1noc(-c2ccc3c(ccn3C(C)C)c2)n1]

According to the method described in Example 1, (1S, 3R)-3-{4-[5-(1-isopropyl-1H-indol-5-yl)-[1,2,4]oxadiazol-3-yl]-3-methyl-benzylamino}-cyclopentanecarboxylic acid methyl ester (30 mg, 0.06 mmol) obtained from Preparation Example 24-1 was used to obtain the title compound (25 mg, 91%).

NMR: ¹H-NMR (400 HMz, CDCl₃); δ 8.48 (s, 1H), 8.09 (d, 1H), 7.99 (d, 1H), 7.50 (d, 1H), 7.42 (m, 2H), 7.35 (d, 1H), 6.66 (d, 1H), 4.73 (m, 1H), 4.11 (d, 1H), 3.93 (d, 1H), 3.52 (m, 1H), 2.95 (m, 1H), 2.67 (s, 3H), 2.00 (m, 6H), 1.56 (d, 6H)

PREPARATION EXAMPLE 25-1

Synthesis of 3-{4-[5-(1-isopropyl-1H-indol-5-yl)-[1,2,4]oxadiazol-3-yl]-3-methyl-benzylamino}-propanoic acid methyl ester According to the method described in Preparation Example 14-4, 4-[5-(1-isopropyl-1H-indol-5-yl)-[1,2,4]oxadiazol-3-yl]-3-methyl-benzaldehyde (139 mg, 0.41 mmol) obtained from Preparation Example 14-3 and beta-alanine methyl ester hydrochloride (93 mg, 0.62 mmol) were used to obtain the title compound (139 mg, 79%).

PREPARATION EXAMPLE 25-2

Synthesis of 3-{4-[5-(1-isopropyl-1H-indol-5-yl)-[1,2,4]oxadiazol-3-yl]-3-methyl-benzyl}methyl-amino)-propanoic acid methyl ester According to the method described in Preparation Example 14-4, 3-{4-[5-(1-isopropyl-1H-indol-5-yl)-[1,2,4]oxadiazol-3-yl]-3-methyl-benzylamino}-propanoic acid methyl ester (80 mg, 0.18 mmol) obtained from Preparation Example 25-1 and 37% formaldehyde aqueous solution (0.02 mL, 0.24 mmol) were used to obtain the title compound (65 mg, 81%).

EXAMPLE 25

Synthesis of 3-({4-[5-(1-isopropyl-1H-indol-5-yl)-[1,2,4]oxadiazol-3-yl]-3-methyl-benzyl}-methyl-amino)-propanoic acid

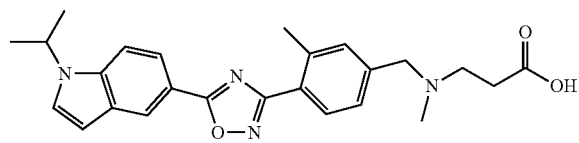 [SMILES: Cc1cc(CN(C)CCC(=O)O)ccc1-c1noc(-c2ccc3c(ccn3C(C)C)c2)n1]

According to the method described in Example 1, 3-{4-[5-(1-isopropyl-1H-indol-5-yl)-[1,2,4]oxadiazol-3-yl]-3-methyl-benzyl}methyl-amino)-propanoic acid methyl ester (65 mg, 0.15 mmol) obtained from Preparation Example 25-2 was used to obtain the title compound (56 mg, 86%).

NMR: ¹H-NMR (400 HMz, CDCl₃); δ 8.53 (s, 1H), 8.12 (d, 1H), 8.04 (dd, 1H), 7.49 (d, 1H), 7.32 (m, 3H), 6.66 (d, 1H), 4.73 (m, 1H), 3.81 (s, 3H), 2.93 (t, 2H), 2.70 (s, 3H), 2.60 (t, 2H), 2.40 (s, 3H), 1.56 (d, 6H)

PREPARATION EXAMPLE 26-1

Synthesis of N-hydroxy-3-hydroxymethyl-2-methyl-benzamidine

The title compound was obtained according to the method described in WO 2010148649 A1.

PREPARATION EXAMPLE 26-2

Synthesis of {3-[5-(1-isopropyl-1H-indol-5-yl)-[1,2,4]oxadiazol-3-yl]-2-methyl-phenyl}-methanol According to the method described in Preparation Example 1-4, 1-isopropyl-1H-indole-5-carboxylic acid (500 mg, 2.46 mmol) obtained from Preparation Example 1-2 and N-hydroxy-3-hydroxymethyl-2-methyl-benzamidine (443 mg, 2.46 mmol) obtained from Preparation Example 26-1 were used to obtain the title compound (900 mg, 99%).

NMR: ¹H-NMR (400 HMz, CDCl₃); δ 8.53 (s, 1H), 8.04 (dd, 1H), 7.87 (d, 1H), 7.58 (d, 1H), 7.49 (d, 1H), 7.33 (2H), 6.67 (d, 1H), 4.81 (s, 2H), 4.72 (m, 1H), 2.59 (s, 3H), 1.58 (d, 6H)

PREPARATION EXAMPLE 26-3

Synthesis of 3-[5-(1-isopropyl-1H-indol-5-yl)-[1,2,4]oxadiazol-3-yl]-2-methyl-benzaldehyde According to the method described in Preparation Example 14-3, {3-[5-(1-isopropyl-1H-indol-5-yl)-[1,2,4]

oxadiazol-3-yl]-2-methyl-phenyl}-methanol (900 mg, 2.46 mmol) obtained from Preparation Example 26-2 was used to obtain the title compound (750 mg, 88%).

EXAMPLE 26

Synthesis of 1-{3-[5-(1-isopropyl-1H-indol-5-yl)-[1,2,4]oxadiazol-3-yl]-2-methyl-benzyl}-azetidine-3-carboxylic acid

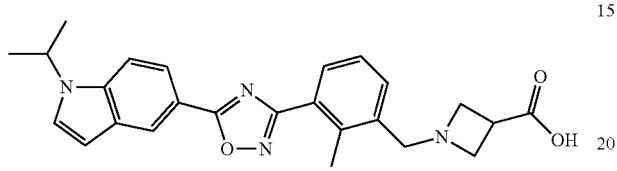

According to the method described in Example 3, 3-[5-(1-isopropyl-1H-indol-5-yl)-[1,2,4]oxadiazol-3-yl]-2-methyl-benzaldehyde (50 mg, 0.14 mmol) obtained from Preparation Example 26-3 and azetidine-3-carboxylic acid (22 mg, 0.22 mmol) were used to obtain the title compound (20 mg, 33%).

NMR: $^1$H-NMR (400 HMz, CDCl$_3$); δ 8.47 (s, 1H), 7.98 (d, 1H), 7.90 (d, 1H), 7.53 (d, 1H), 7.43 (d, 1H), 7.30 (m, 2H), 6.62 (d, 1H), 4.68 (m, 1H), 4.25 (s, 2H), 4.09 (m, 4H), 3.45 (m, 1H), 2.62 (s, 3H), 1.52 (d, 6H)

PEPARATION EXAMPLE 27-1

Synthesis of 5-(N-hydroxycarbimidoyl)-3,4-dihydro-1H-isoquinoline-2-carboxylic acid t-butyl ester The title compound was obtained according to the method described in WO 2010146105 A1.

PREPARATION EXAMPLE 27-2

Synthesis of 5-[5-(1-isopropyl-1H-indol-5-yl)-[1,2,4]oxadiazol-3-yl]-3,4-dihydro-1H-isoquinoline-2-carboxylic acid t-butyl ester According to the method described in Preparation Example 1-4, 1-isopropyl-1H-indole-5-carboxylic acid (700 mg, 3.42 mmol) obtained from Preparation Example 1-2 and 5-(N-hydroxycarbimidoyl)-3,4-dihydro-1H-isoquinoline-2-carboxylic acid t-butyl ester (1.0 g, 3.42 mmol) obtained from Preparation Example 27-1 were used to obtain the title compound (1.0 g, 64%).

NMR: $^1$H-NMR (400 HMz, CDCl$_3$); δ 8.53 (s, 1H), 8.04 (dd, 1H), 7.98 (d, 1H), 7.49 (d, 1H), 7.34 (m, 2H), 7.28 (s, 1H), 6.68 (d, 1H), 4.74 (m, 1H), 4.66 (s, 2H), 3.68 (t, 2H), 3.28 (t, 2H), 1.58 (d, 6H), 1.50 (s, 9H)

EXAMPLE 27

Synthesis of 5-[5-(1-isopropyl-1H-indol-5-yl)-[1,2,4]oxadiazol-3-yl]-1,2,3,4-tetrahydro-isoquinoline, hydrochloride

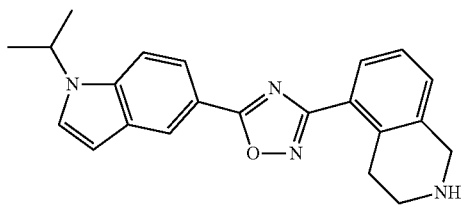 [SMILES: CC(C)n1ccc2cc(-c3nc(-c4cccc5c4CCNC5)no3)ccc21]

5-[5-(1-Isopropyl-1H-indol-5-yl)-[1,2,4]oxadiazol-3-yl]-3,4-dihydro-1H-isoquinoline -2-carboxylic acid t-butyl ester (1.0 g, 2.18 mmol) obtained from Preparation Example 27-2 was dissolved in dichloromethane (50 mL) and then 4N hydrochloric acid solution in dioxane (2.2 mL, 8.72 mmol) was added dropwise thereto. The mixture was stirred for 5 hours at room temperature. The solvent was removed by distillation under reduced pressure, and the residue was washed with diethyl ether to obtain the title compound (800 mg, 93%).

NMR: $^1$H-NMR (400 HMz, DMSO$_{d6}$); δ 9.66 (s, 2H), 8.47 (s, 1H), 8.05 (m, 1H), 7.95 (m, 1H), 7.78 (d, 1H), 7.72 (d, 1H), 7.48 (m, 2H), 6.72 (d, 1H), 4.88 (m, 1H), 4.38 (s, 2H), 3.42 (m, 4H), 1.50 (d, 6H)

PREPARATION EXAMPLE 28-1

Synthesis of {5-[5-(1-isopropyl-1H-indol-5-yl)-[1,2,4]oxadiazol-3-yl]-3,4-dihydro-1H-isoquinolin-2-yl}-acetic acid ethyl ester 5-[5-(1-Isopropyl-1H-indol-5-yl)-[1,2,4]oxadiazol-3-yl]-1,2,3,4-tetrahydro-isoquinoline, hydrochloride (100 mg, 0.25 mmol) obtained from Example 27 was dissolved in dimethylformamide (4 mL), and ethyl bromoacetate (0.04 mL, 0.45 mmol) and cesium carbonate (248 mg, 0.75 mmol) were added dropwise thereto. The mixture was stirred for 1 hour at room temperature, added with excess ethyl acetate and filtered by celite. The filtrate was distilled under reduced pressure. The residue was added with water and extracted with ethyl acetate. The extract was dried with anhydrous magnesium sulfate and filtered. The filtrate was distilled under reduced pressure. The residue was separated by column chromatography to obtain the title compound (90 mg, 81%).

NMR: $^1$H-NMR (400 HMz, CDCl$_3$); δ 8.52 (s, 1H), 8.03 (m, 2H), 7.47 (d, 1H), 7.28 (m, 2H), 7.16 (d, 1H), 6.66 (d, 1H), 4.71 (m, 1H), 4.22 (q, 2H), 3.89 (s, 2H), 3.43 (s, 2H), 3.36 (t, 2H), 2.94 (t, 2H), 1.55 (d, 6H), 1.28 (t, 3H)

EXAMPLE 28

Synthesis of {5-[5-(1-isopropyl-1H-indol-5-yl)-[1,2,4]oxadiazol-3-yl]-3,4-dihydro-1H-isoquinolin-2-yl}-acetic acid

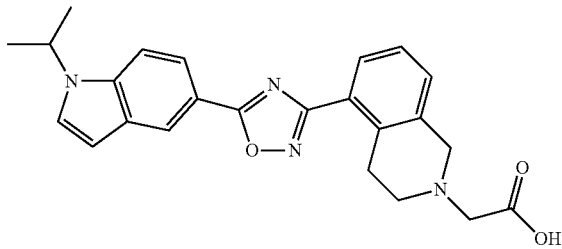

According to the method described in Example 1, {5-[5-(1-isopropyl-1H-indol-5-yl)-[1,2,4]oxadiazol-3-yl]-3,4-dihydro-1H-isoquinolin-2-yl}-acetic acid ethyl ester (90 mg, 0.20 mmol) obtained from Preparation Example 28-1 was used to obtain the title compound (55 mg, 66%)

NMR: $^1$H-NMR (400 HMz, CDCl$_3$); δ 8.43 (s, 1H), 8.02 (d, 1H), 7.94 (d, 1H), 7.40 (d, 1H), 7.25 (m, 2H), 7.15 (m, 1H), 6.60 (d, 1H), 4.65 (m, 1H), 4.33 (m, 1H), 3.48 (m, 6H), 1.51 (d, 6H)

PREPARATION EXAMPLE 29-1

Synthesis of 3-{5-[5-(1-isopropyl-1H-indol-5-yl)-[1,2,4]oxadiazol-3-yl]-3,4-dihydro-1H-isoquinolin-2-yl}-propanoic acid ethyl ester 5-[5-(1-Isopropyl-1H-indol-5-yl)-[1,2,4]oxadiazol-3-yl]-1,2,3,4-tetrahydro-isoquinoline, hydrochloride (100 mg, 0.25 mmol) obtained from Example 27 was dissolved in acetonitrile (10 mL), and ethyl acrylate (38 mg, 0.38 mmol) and 1,8-diazabicycloundec-7-ene (DBU, 231 mg, 1.50 mmol) were added dropwise thereto. The mixture was stirred for 1 hour at 70° C., added with water and extracted with ethyl acetate. The extract was dried with anhydrous magnesium sulfate and filtered. The filtrate was distilled under reduced pressure. The residue was separated by column chromatography to obtain the title compound (110 mg, 96%)

NMR: $^1$H-NMR (400 HMz, CDCl$_3$); δ 8.52 (s, 1H), 8.02 (m, 2H), 7.47 (d, 1H), 7.28 (m, 2H), 7.16 (d, 1H), 6.65 (d, 1H), 4.71 (m, 1H), 4.14 (q, 2H), 3.74 (s, 2H), 3.30 (t, 2H), 2.88 (t, 2H), 2.82 (t, 2H), 2.62 (t, 2H), 1.53 (d, 6H), 1.24 (t, 3H)

EXAMPLE 29

Synthesis of 3-{5-[5-(1-isopropyl-1H-indol-5-yl)-[1,2,4]oxadiazol-3-yl]-3,4-dihydro-1H-isoquinolin-2-yl}-propanoic acid

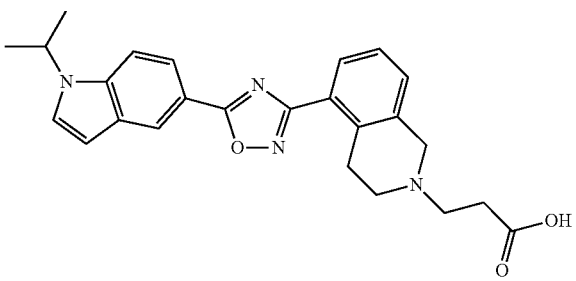 [SMILES: CC(C)n1ccc2cc(-c3nc(-c4cccc5c4CCN(CCC(=O)O)C5)no3)ccc21]

According to the method described in Example 1, 3-{5-[5-(1-isopropyl-1H-indol-5-yl)-[1,2,4]oxadiazol-3-yl]-3,4-dihydro-1H-isoquinolin-2-yl}-propanoic acid ethyl ester (110 mg, 0.24 mmol) obtained from Preparation Example 29-1 was used to obtain the title compound (72 mg, 70%).

NMR: $^1$H-NMR (400 HMz, CDCl$_3$); δ 8.52 (s, 1H), 8.03 (m, 2H), 7.48 (d, 1H), 7.32 (m, 2H), 7.20 (d, 1H), 6.66 (d, 1H), 4.73 (m, 1H), 3.98 (s, 2H), 3.42 (t, 2H), 3.08 (t, 2H), 2.97 (t, 2H), 2.63 (t, 2H), 1.55 (d, 6H)

PREPARATION EXAMPLE 30-1

Synthesis of 1,N-dihydroxy-indane-4-carboxamidine

The title compound was obtained according to the method described in WO 2009151529 A1.

EXAMPLE 30

Synthesis of 4-[5-(1-isopropyl-1H-indol-5-yl)-[1,2,4]oxadiazol-3-yl]-indan-1-ol

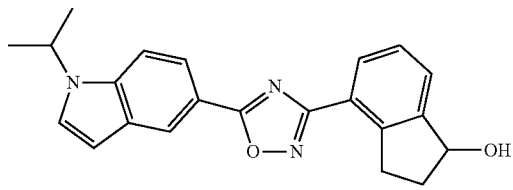 [SMILES: CC(C)n1ccc2cc(-c3nc(-c4cccc5c4CCC5O)no3)ccc21]

According to the method described in Preparation Example 1-4, 1-isopropyl-1H-indole-5-carboxylic acid (254 mg, 1.25 mmol) obtained from Preparation Example 1-2 and 1,N-dihydroxy-indane-4-carboxamidine (240 mg, 1.25 mmol) obtained from Preparation Example 30-1 were used to obtain the title compound (350 mg, 78%).

NMR: $^1$H-NMR (400 HMz, CDCl$_3$); δ 8.54 (s, 1H), 8.19 (d, 1H), 8.05 (dd, 1H), 7.58 (1H), 7.49 (d, 1H), 7.43 (m, 1H), 7.33 (d, 1H), 6.67 (d, 1H), 5.33 (m, 1H), 4.74 (m, 1H), 3.55 (m, 1H), 3.26 (m, 1H), 2.60 (m, 1H), 2.04 (m, 1H), 1.57 (d, 6H)

PREPARATION EXAMPLE 31-1

Synthesis of 4-[5-(1-isopropyl-1H-indol-5-yl)-[1,2,4]oxadiazol-3-yl]-indan-1-one According to the method described in Preparation Example 14-3, 4-[5-(1-isopropyl-1H-indol-5-yl)-[1,2,4]oxadiazol-3-yl]-indan-1-ol (300 mg, 0.83 mmol) obtained from Example 30 was used to obtain the title compound (170 mg, 61%).

EXAMPLE 31

Synthesis of 2-{4-[5-(1-isopropyl-1H-indol-5-yl)-[1,2,4]oxadiazol-3-yl]-indan-1-ylamino}-ethanol

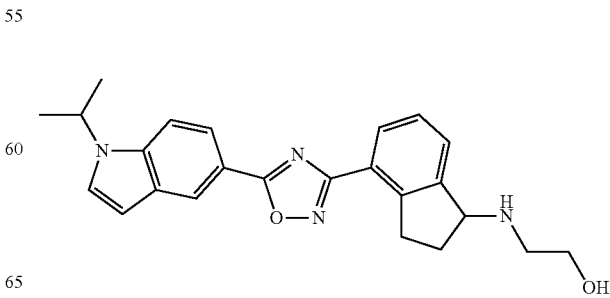

4-[5-(1-Isopropyl-1H-indol-5-yl)-[1,2,4]oxadiazol-3-yl]-indan-1-one (50 mg, 0.15 mmol) obtained from Preparation Example 31-1 was dissolved in toluene (40 mL), and ethanolamine (18 mg, 0.30 mmol) and a catalytic amount of p-toluene sulfonic acid were added. The mixture was stirred under reflux for 18 hours using Dean-Stark apparatus. The solvent was removed by distillation under reduced pressure and the residue was dissolved in dichloroethane (20 mL). The solution was added with sodium acetoxy borohydride (64 mg, 0.30 mmol) and stirred for 3 hours at room temperature. The mixture was added with saturated sodium hydrogen carbonate aqueous solution and extracted with ethyl acetate. The extract was dried with anhydrous magnesium sulfate and filtered. The filtrate was distilled under reduced pressure. The residue was separated by column chromatography to obtain the title compound (20 mg, 33%).

NMR: $^1$H-NMR (400 HMz, CDCl$_3$); δ 8.53 (s, 1H), 8.13 (d, 1H), 8.03 (dd, 1H), 7.50 (m, 2H), 7.37 (m, 1H), 7.25 (d, 1H), 6.66 (d, 1H), 4.72 (m, 1H), 4.33 (t, 1H), 3.69 (m, 2H), 3.50 (m, 1H), 3.23 (m, 1H), 2.92 (m, 2H), 2.50 (m, 1H), 2.27 (s, 2H), 1.92 (m, 1H), 1.55 (d, 6H)

PREPARATION EXAMPLE 32-1

Synthesis of ((S)-1-hydroxymethyl-2-{5-[5-(1-isopropyl-1H-indol-5-yl)-[1,2,4]oxadiazol-3-yl]-3,4-dihydro-1H-isoquinolin-2-yl}-2-oxo-ethyl)-carbamic acid t-butyl ester 5-[5-(1-Isopropyl-1H-indol-5-yl)-[1,2,4]oxadiazol-3-yl]-1,2,3,4-tetrahydro-isoquinoline, hydrochloride (100 mg, 0.25 mmol) obtained from Example 27 was dissolved in dimethylformamide (10 mL) and N-ethylmorpholine (0.06 mL, 0.50 mmol), Boc-serine (43 mg, 0.25 mmol), hydroxybenzotriazole (HOBT, 35 mg, 0.30 mmol) and 1-ethyl-3-(3-dimethylaminopropyl)carbodiimide (EDC, 49 mg, 0.30 mmol) were added dropwise thereto. The mixture was stirred for 18 hours at room temperature. The solvent was removed by distillation under reduced pressure. The residue was added with excess ethyl acetate. The resulting solution was washed with saturated sodium hydrogen carbonate aqueous solution and 1N hydrochloric acid aqueous solution, and then with brine, dried with anhydrous magnesium sulfate and filtered. The filtrate was distilled under reduced pressure. The residue was separated by column chromatography to obtain the title compound (85 mg, 62%).

NMR: $^1$H-NMR (400 HMz, CDCl$_3$); δ 8.52 (s, 1H), 8.02 (m, 2H), 7.48 (d, 1H), 7.33 (m, 3H), 6.66 (d, 1H), 5.78 (m, 1H), 4.78 (m, 4H), 3.86 (m, 4H), 3.39 (m, 2H), 1.56 (d, 6H), 1.45 (s, 9H)

EXAMPLE 32

Synthesis of (S)-2-amino-3-hydroxy-1-{5-[5-(1-isopropyl-1H-indol-5-yl)-[1,2,4]oxadiazol-3-yl]-3,4-dihydro-1H-isoquinolin-2-yl}-propan-1-one

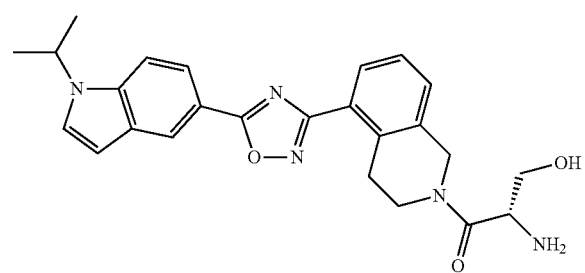 [SMILES: CC(C)n1ccc2cc(-c3nc(-c4cccc5c4CCN(C(=O)[C@@H](N)CO)C5)no3)ccc21]

According to the method described in Example 27, ((S)-1-hydroxymethyl-2-{5-[5-(1-isopropyl-1H-indol-5-yl)-[1,2,4]oxadiazol-3-yl]-3,4-dihydro-1H-isoquinolin-2-yl}-2-oxo-ethyl)-carbamic acid t-butyl ester (85 mg, 0.16 mmol) obtained from Preparation Example 32-1 was used to obtain the title compound (56 mg, 78%).

NMR: $^1$H-NMR (400 HMz, CDCl$_3$); δ 8.52 (s, 1H), 8.02 (d, 2H), 7.47 (d, 1H), 7.33 (m, 3H), 6.65 (d, 1H), 4.85 (m, 2H), 4.71 (m, 1H), 4.01 (m, 1H), 3.80 (m, 3H), 3.60 (m, 1H), 3.38 (m, 2H), 2.63 (s, 3H), 1.56 (d, 6H)

EXAMPLE 33

Synthesis of 2-{5-[5-(1-isopropyl-1H-indol-5-yl)-[1,2,4]oxadiazol-3-yl]-3,4-dihydro-1H-isoquinolin-2-yl}-propan-1,3-diol

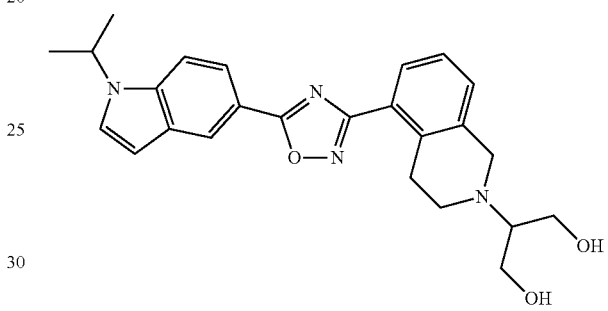

According to the method described in Preparation Example 14-4, 5-[5-(1-isopropyl-1H-indol-5-yl)-[1,2,4]oxadiazol-3-yl]-1,2,3,4-tetrahydro-isoquinoline, hydrochloride (100 mg, 0.25 mmol) obtained from Example 27 and 2,2-dimethyl-1,3-dioxan-5-one (132 mg, 1.00 mmol) were used to obtain 2-(2,2-dimethyl-[1,3]dioxan-5-yl)-5-[5-(1-isopropyl-1H-indol-5-yl)-[1,2,4]oxadiazol-3-yl]-1,2,3,4-tetrahydro-isoquinoline (85 mg, 72%).

The obtained 2-(2,2-dimethyl-[1,3]dioxan-5-yl)-5-[5-(1-isopropyl-1H-indol-5-yl)-[1,2,4]oxadiazol-3-yl]-1,2,3,4-tetrahydro-isoquinoline (85 mg, 0.18 mmol) was dissolved in a mixed solution of dichloromethane and methanol (2/1, 10 mL), and 1N hydrochloric acid aqueous solution (1 mL) was added dropwise thereto. The mixture was stirred for 2 hours at room temperature, added with saturated sodium hydrogen carbonate aqueous solution and extracted with ethyl acetate. The extract was dried with anhydrous magnesium sulfate and filtered. The filtrate was distilled under reduced pressure. The residue was separated by column chromatography to obtain the title compound (60 mg, 77%).

NMR: $^1$H-NMR (400 HMz, CDCl$_3$); δ 8.52 (s, 1H), 8.00 (m, 2H), 7.48 (d, 1H), 7.32 (m, 2H), 7.17 (d, 1H), 6.66 (d, 1H), 4.71 (m, 1H), 4.12 (s, 2H), 3.77 (m, 4H), 3.29 (t, 2H), 3.03 (t, 2H), 2.94 (m, 1H), 1.55 (d, 6H)

PREPARATION EXAMPLE 34-1

Synthesis of [(R)-4-(N-hydroxycarbaimidoyl)-indan-1-yl]-carbamic acid t-butyl ester The title compound was obtained according to the method described in WO 2011060389 A1.

PREPARATION EXAMPLE 34-2

Synthesis of {(S)-4-[5-(1-isopropyl-1H-indol-5-yl)-[1,2,4]oxadiazol-3-yl]-indan-1-yl}-carbamic acid t-butyl ester According to the method described in Preparation Example 1-4, 1-isopropyl-1H-indole-5-carboxylic acid (215 mg, 1.06 mmol) obtained from Preparation Example 1-2 and [(R)-4-(N-hydroxycarbaimidoyl)-indan-1-yl]-carbamic acid t-butyl ester (310 mg, 1.06 mmol) obtained from Preparation Example 34-1 were used to obtain the title compound (320 mg, 66%).

NMR: $^1$H-NMR (400 HMz, CDCl$_3$); δ 8.54 (s, 1H), 8.15 (d, 1H), 8.05 (d, 1H), 7.49 (m, 2H), 7.39 (m, 1H), 7.33 (d, 1H), 6.67 (d, 1H), 5.28 (m, 1H), 4.74 (m, 2H), 3.50 (m, 1H), 3.24 (m, 1H), 2.66 (m, 1H), 1.88 (m, 1H), 1.56 (d, 6H), 1.50 (s, 9H)

PREPARATION EXAMPLE 34-3

Synthesis of (S)-4-[5-(1-isopropyl-1H-indol-5-yl)-[1,2,4]oxadiazol-3-yl]-indan-1-yl amine, hydrochloride According to the method described in Example 27, {(S)-4-[5-(1-isopropyl-1H-indol-5-yl)-[1,2,4]oxadiazol-3-yl]-indan-1-yl}-carbamic acid t-butyl ester (300 mg, 0.65 mmol) obtained from Preparation Example 34-2 was used to obtain the title compound (127 mg, 49%).

EXAMPLE 34

Synthesis of N—{(S)-4-[5-(1-isopropyl-1H-indol-5-yl)-[1,2,4]oxadiazol-3-yl]-indan-1-yl}-methanolsulfonamide

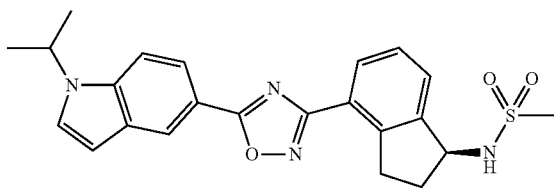 [SMILES: CC(C)n1ccc2cc(-c3nc(-c4cccc5c4CC[C@@H]5NS(C)(=O)=O)no3)ccc21]

(S)-4-[5-(1-Isopropyll-1H-indol-5-yl)-[1,2,4]oxadiazol-3-yl]-indan-1-ylamine, hydrochloride (40 mg, 0.10 mmol) obtained from Preparation Example 34-3 was dissolved in dichloromethane (5 mL), and then triethylamine (0.04 mL, 0.30 mmol) and methansulfonyl chloride (0.009 mL, 0.11 mmol) were added dropwise thereto at 0° C. The mixture was stirred for 1 hour at 0° C., added with 1N hydrochloric acid aqueous solution and extracted with ethyl acetate. The extract was dried with anhydrous magnesium sulfate and filtered. The filtrate was distilled under reduced pressure. The residue was separated by column chromatography to obtain by the title compound (31 mg, 71%).

NMR: $^1$H-NMR (400 HMz, CDCl$_3$); δ 8.52 (s, 1H), 8.19 (d, 1H), 8.03 (dd, 1H), 7.58 (d, 1H), 7.49 (d, 1H), 7.42 (t, 1H), 7.33 (d, 1H), 6.66 (d, 1H), 5.07 (m, 1H), 4.72 (m, 1H), 3.55 (m, 1H), 3.25 (m, 1H), 3.10 (s, 3H), 2.72 (m, 1H), 2.00 (m, 1H), 1.55 (d, 6H)

EXAMPLE 35

Synthesis of N—{(S)-4-[5-(1-isopropyl-1H-indol-5-yl)-[1,2,4]oxadiazol-3-yl]-indan-1-yl}-acetamide

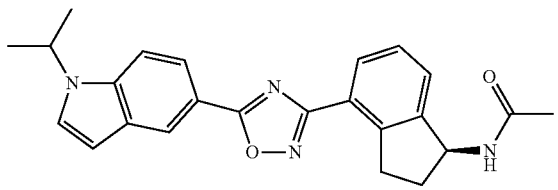 [SMILES: CC(=O)N[C@H]1CCc2c(-c3noc(-c4ccc5c(ccn5C(C)C)c4)n3)cccc21]

According to the method described in Example 34, (S)-4-[5-(1-isopropyl-1H-indol-5-yl)-[1,2,4]oxadiazol-3-yl]-indan-1-yl amine, hydrochloride (47 mg, 0.12 mmol) obtained from Preparation Example 34-3 and acetyl chloride (9 mg, 0.13 mmol) were used to obtain the title compound (32 mg, 67%).

NMR: $^1$H-NMR (400 HMz, CDCl$_3$); δ 8.52 (s, 1H), 8.15 (d, 1H), 8.04 (dd, 1H), 7.40 (m, 4H), 6.67 (d, 1H), 5.79 (d, 1H), 5.57 (m, 1H), 4.73 (m, 1H), 3.50 (m, 1H), 3.22 (m, 1H), 2.67 (m, 1H), 2.05 (s, 3H), 1.87 (m, 1H), 1.57 (d, 6H)

PREPARATION EXAMPLE 36-1

Synthesis of [5-(N-hydroxycarbimidoyl)-1,2,3,4-tetrahydro-naphthalen-1-yl]-carbamic acid t-butyl ester The title compound was obtained according to the method described in WO 2011060389 A1.

PREPARATION EXAMPLE 36-2

Synthesis of {5-[5-(1-isopropyl-1H-indol-5-yl)-[1,2,4]oxadiazol-3-yl]-1,2,3,4-tetrahydro-naphthalen-1-yl}-carbamic acid t-butyl ester According to the method described in Preparation Example 1-4, 1-isopropyl-1H-indole-5-carboxylic acid (431 mg, 2.12 mmol) obtained from Preparation Example 1-2 and [5-(N-hydroxycarbimidoyl)-1,2,3,4-tetrahydro-naphthalen-1-yl]-carbamic acid t-butyl ester (647 mg, 2.12 mmol) obtained from Preparation Example 36-1 were used to obtain the title compound (590 mg, 59%).

EXAMPLE 36

Synthesis of N-{5-[5-(1-isopropyl-1H-indol-5-yl)-[1,2,4]oxadiazol-3-yl]-1,2,3,4-tetrahydro-naphthalen-1-yl}-acetamide

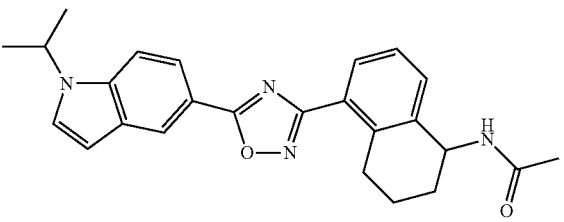 [SMILES: CC(=O)NC1CCCc2c(-c3noc(-c4ccc5c(ccn5C(C)C)c4)n3)cccc21]

According to the method described in Example 34, 5-[5-(1-isopropyl-1H-indol-5-yl)-[1,2,4]oxadiazol-3-yl]-1,2,3,4-tetrahydro-naphthalen-1-ylamine, hydrochloride (60 mg, 0.15 mmol) obtained from Example 45 and acetyl chloride (17 mg, 0.22 mmol) were used to obtain the title compound (45 mg, 72%).

NMR: $^1$H-NMR (400 HMz, CDCl$_3$); δ 8.52 (s, 1H), 8.04 (d, 1H), 7.95 (d, 1H), 7.48 (d, 1H), 7.46 (d, 1H), 7.33 (m, 2H), 6.66 (d, 1H), 5.73 (d, 1H), 5.30 (m, 1H), 4.74 (m, 1H), 3.20 (m, 1H), 3.05 (m, 1H), 2.05 (s, 3H), 1.87 (m, 4H), 1.56 (d, 6H)

EXAMPLE 37

Synthesis of N-{5-[5-(1-isopropyl-1H-indol-5-yl)-[1,2,4]oxadiazol-3-yl]-1,2,3,4-tetrahydro-naphthalen-1-yl}-methanolsulfonamide

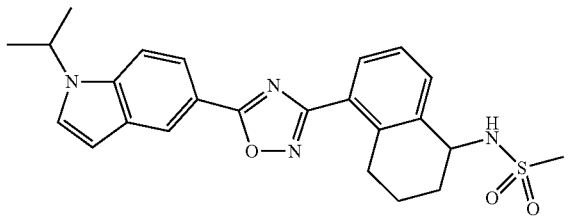 [SMILES: CC(C)n1ccc2cc(-c3nc(-c4cccc5c4CCCC5NS(C)(=O)=O)no3)ccc21]

According to the method described in Example 34, 5-[5-(1-isopropyl-1H-indol-5-yl)-[1,2,4]oxadiazol-3-yl]-1,2,3,4-tetrahydro-naphthalen-1-ylamine, hydrochloride (60 mg, 0.15 mmol) obtained from Example 45 and methansulfonyl chloride (25 mg, 0.22 mmol) were used to obtain the title compound (51 mg, 75%).

NMR: $^1$H-NMR (400 HMz, CDCl$_3$); δ 8.51 (s, 1H), 8.02 (d, 1H), 7.98 (d, 1H), 7.63 (d, 1H), 7.48 (d, 1H), 7.35 (m, 2H), 6.66 (d, 1H), 4.75 (m, 2H), 4.62 (d, 1H), 3.21 (m, 1H), 3.08 (m, 4H), 2.12 (m, 1H), 1.98 (m, 3H), 1.56 (d, 6H)

EXAMPLE 38

Synthesis of N-{5-[5-(1-isopropyl-1H-indol-5-yl)-[1,2,4]oxadiazol-3-yl]-1,2,3,4-tetrahydro-naphthalen-1-yl}-sulfamide

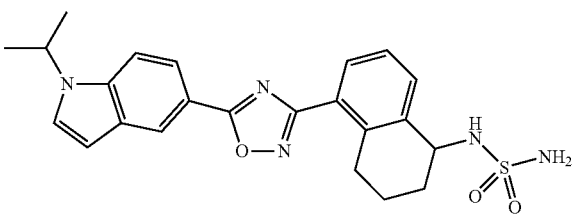 [SMILES: CC(C)n1ccc2cc(-c3nc(-c4cccc5c4CCCC5NS(N)(=O)=O)no3)ccc21]

According to the method described in Example 34, 5-[5-(1-isopropyl-1H-indol-5-yl)-[1,2,4]oxadiazol-3-yl]-1,2,3,4-tetrahydro-naphthalen-1-ylamine, hydrochloride (100 mg, 0.24 mmol) obtained from Example 45 and sulfamide (28 mg, 0.29 mmol) were used to obtain the title compound (35 mg, 32%).

NMR: $^1$H-NMR (400 HMz, MeOD); δ 8.44 (d, 1H), 7.98 (dd, 1H), 7.84 (d, 1H), 7.80 (d, 1H), 7.63 (d, 1H), 7.51 (d, 1H), 7.35 (t, 1H), 6.66 (d, 1H), 4.84 (m, 1H), 4.61 (m, 1H), 3.12 (m, 1H), 3.00 (m, 1H), 2.14 (m, 1H), 2.02 (m, 2H), 1.84 (m, 1H), 1.54 (d, 6H)

EXAMPLE 39

Synthesis of 3-hydroxy-pyrrolidine-1-carboxylic acid {5-[5-(1-isopropyl-1H-indol-5-yl)-[1,2,4]oxadiazol-3-yl]-1,2,3,4-tetrahydro-naphthalen-1-yl}-amide

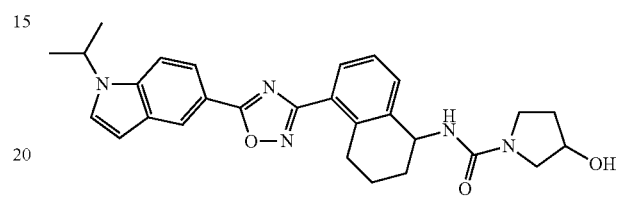

5-[5-(1-Isopropyl-1H-indol-5-yl)-[1,2,4]oxadiazol-3-yl]-1,2,3,4-tetrahydro-naphthalen-1-ylamine, hydrochloride (60 mg, 0.15 mmol) obtained from Example 45 was dissolved in dichloromethane, and triphosgene (22 mg, 0.075 mmol) was added dropwise thereto at 0° C. The mixture was stirred for 18 hours at room temperature. The mixture was added with triethylamine (76 mg, 0.75 mmol) and pyrrolidine-3-ol (13 mg, 0.15 mmol) and stirred for 3 hours at room temperature. The mixture was added with water and extracted with dichloromethane. The extract was dried with anhydrous magnesium sulfate and filtered. The filtrate was distilled under reduced pressure. The residue was separated by column chromatography to obtain the title compound (36 mg, 49%).

NMR: $^1$H-NMR (400 HMz, CDCl$_3$); δ 8.52 (s, 1H), 8.04 (d, 1H), 7.90 (d, 1H), 7.54 (d, 1H), 7.48 (d, 1H), 7.30 (m, 2H), 6.66 (d, 1H), 5.18 (s, 1H), 4.73 (m, 1H), 4.51 (s, 1H), 3.50 (m, 4H), 3.20 (m, 4H), 2.3 (m, 1H), 1.94 (m, 6H), 1.56 (d, 6H)

PREPARATION EXAMPLE 40-1

Synthesis of 5-[5-(3-chloro-1-isopropyl-1H-indol-5-yl)-[1,2,4]oxadiazol-3-yl]-3,4-dihydro-1H-isoquinoline-2-carboxylic acid t-butyl ester According to the method described in Preparation Example 1-4, 3-chloro-1-isopropyl-1H-indole-5-carboxylic acid (1.5 g, 6.31 mmol) obtained from Preparation Example 3-2 and 5-(N-hydroxycarbimidoyl)-3,4-dihydro-1H-isoquinoline-2-carboxylic acid t-butyl ester (1.84 g, 6.31 mmol) obtained from Preparation Example 27-1 were used to obtain the title compound (2.35 g, 76%).

NMR: $^1$H-NMR (400 HMz, CDCl$_3$); δ 8.53 (d, J=1.6 Hz, 1H), 8.09 (dd, J=1.6 Hz, 1H), 8.00 (d, 1H), 7.49 (d, 1H), 7.36 (t, 1H), 7.30 (s, 1H), 7.28 (d, 1H), 4.76-4.70 (m, 1H), 4.67 (s, 2H), 3.69 (t, 2H), 3.29 (t, 2H), 1.55 (d, 6H), 1.51 (s, 9H)

EXMPLE 40

Synthesis of 5-[5-(3-chloro-1-isopropyl-1H-indol-5-yl)-[1,2,4]oxadiazol-3-yl]-1,2,3,4-tetrahydro-isoquinoline, hydrochloride

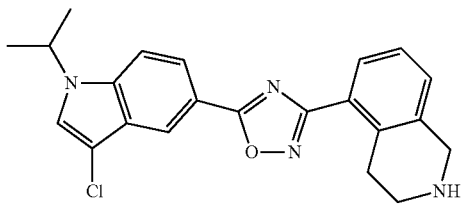 [SMILES: CC(C)n1cc(Cl)c2cc(-c3nc(-c4cccc5c4CCNC5)no3)ccc21]

According to the method described in Example 27, 5-[5-(3-chloro-1-isopropyl-1H-indol-5-yl)-[1,2,4]oxadiazol-3-yl]-3,4-dihydro-1H-isoquinoline-2-carboxylic acid t-butyl ester (1.35 g, 2.74 mmol) obtained from Preparation Example 40-1 was used to obtain the title compound (1.2 g, 100%).

NMR: $^1$H-NMR (400 MHz, CDCl$_3$) δ 8.33 (d, J=1.6 Hz, 1H), 8.05 (q, 2H), 7.99 (s, 1H), 7.91 (d, 1H), 7.54-7.48 (m, 2H), 4.94-4.90 (m, 1H), 4.40 (s, 2H), 3.45-3.39 (m, 4H), 1.49 (d, 6H)

PREPARATION EXAMPLE 41-1

Synthesis of 7-(N-hydroxycarbimidoyl)-3,4-dihydro-1H-isoquinoline-2-carboxylic acid t-butyl ester The title compound was obtained according to the method described in WO 2010069949 A1.

NMR: $^1$H-NMR (400 HMz, DMSO-d$_6$); δ 9.56 (s, 1H), 7.48-7.44 (m, 2H), 7.14 (d, 1H), 5.76 (s, 2H), 4.50 (br, s, 2H), 3.55 (t, 2H), 2.77 (t, 2H), 1.43 (s, 9H)

PREPARATION EXAMPLE 41-2

Synthesis of 7-[5-(1-isopropyl-1H-indol-5-yl)-[1,2,4]oxadiazol-3-yl]-3,4-dihydro-1H-isoquinoline-2-carboxylic acid t-butyl ester According to the method described in Preparation Example 1-4, 1-isopropyl-1H-indole-5-carboxylic acid (700 mg, 3.54 mmol) obtained from Preparation Example 1-2 and 7-(N-hydroxycarbimidoyl)-3,4-dihydro-1H-isoquinoline-2-carboxylic acid t-butyl ester (880 mg, 3.02 mmol) obtained from Preparation Example 41-1 were used to obtain the title compound (1.2 g, 87%).

NMR: $^1$H-NMR (400 HMz, CDCl$_3$); δ 8.54 (s, 1H), 8.05 (dd, J=1.6 Hz, 1H), 7.99 (d, 1H), 7.96 (s, 1H), 7.49 (d, 1H), 7.34 (d, 1H), 7.28 (d, 1H), 6.67 (d, 1H), 4.78-4.72 (m, 1H), 4.68 (s, 2H), 3.70 (br, s, 2H), 2.91 (br, s, 2H), 1.57 (d, 6H), 1.51 (s, 9H)

EXAMPLE 41

Synthesis of 7-[5-(1-isopropyl-1H-indol-5-yl)-[1,2,4]oxadiazol-3-yl]-1,2,3,4-tetrahydro-isoquinoline, hydrochloride

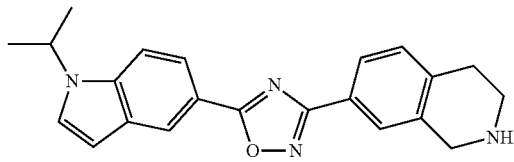 [SMILES: CC(C)n1ccc2cc(-c3nc(-c4ccc5c(c4)CNCC5)no3)ccc21]

According to the method described in Example 27, 7-[5-(1-isopropyl-1H-indol-5-yl)-[1,2,4]oxadiazol-3-yl]-3,4-dihydro-1H-isoquinoline-2-carboxylic acid t-butyl ester (1.2 g, 2.62 mmol) obtained from Preparation Example 41-2 was used to obtain the title compound (1.02 g, 98%).

NMR: $^1$H-NMR (400 MHz, CDCl$_3$) δ 8.47 (d, J=1.6 Hz, 1H), 8.00 (d, 2H), 7.94 (dd, J=1.6 Hz, 1H), 7.80 (d, 1H), 7.72 (d, 1H), 7.47 (d, 1H), 6.73 (d, 1H), 4.90-4.85 (m, 1H), 4.42 (br, s, 2H), 3.42 (br, s, 2H), 3.11 (t, 2H), 1.50 (d, 6H)

EXAMPLE 42

Synthesis of 3-hydroxy-azetidine-1-carboxylic acid {5-[5-(1-isopropyl-1H-indol-5-yl)-[1,2,4]oxadiazol-3-yl]-1,2,3,4-tetrahydro-naphthalen-1-yl}-amide

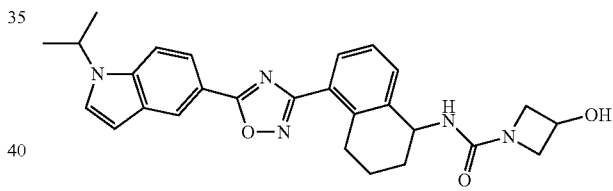

According to the method described in Example 39, 5-[5-(1-isopropyl-1H-indol-5-yl)-[1,2,4]oxadiazol-3-yl]-1,2,3,4-tetrahydro-naphthalen-1-ylamine, hydrochloride (70 mg, 0.17 mmol) obtained from Example 45 and azetidin-3-ol hydrochloride (19 mg, 0.17 mmol) were used to obtain the title compound (38 mg, 47%).

NMR: $^1$H-NMR (400 HMz, MeOD); δ 8.43 (s, 1H), 7.96 (d, 1H), 7.82 (d, 1H), 7.62 (d, 1H), 7.50 (d, 1H), 7.47 (d, 1H), 7.32 (t, 1H), 6.72 (d, 1H), 6.66 (d, 1H), 5.00 (m, 1H), 4.82 (m, 1H), 4.51 (m, 1H), 4.15 (m, 2H), 3.75 (dd, 2H), 3.07 (m, 2H), 2.00 (m, 2H), 1.80 (m, 2H), 1.54 (d, 6H)

PREPARATION EXAMPLE 43-1

Synthesis of {5-[5-(3-chloro-1-isopropyl-1H-indol-5-yl)-[1,2,4]oxadiazol-3-yl]-3,4-dihydro-1H-isoquinolin-2-yl}-acetic acid t-butyl ester According to the method described in Preparation Example 28-1, 5-[5-(3-chloro-1-isopropyl-1H-indol-5-yl)-[1,2,4]oxadiazol-3-yl]-1,2,3,4-tetrahydro-isoquinoline, hydrochloride (600 mg, 1.40 mmol) obtained from Example 40 and t-butyl bromoacetate (0.23 mL, 1.54 mmol) were used to obtain the title compound (510 mg, 77%).

NMR: ¹H-NMR (400 HMz, CDCl₃); δ 8.53 (d, J=1.2 Hz, 1H), 8.08 (dd, J=1.6 Hz, 1H), 8.02 (d, 1H), 7.49 (d, 1H), 7.29 (t, 2H), 7.18 (d, 1H), 4.75-4.69 (m, 1H), 3.90 (s, 2H), 3.37 (s, 2H), 3.35 (t, 2H), 2.96 (t, 2H), 1.55 (d, 6H), 1.50 (s, 9H)

EXAMPLE 43

Synthesis of {5-[5-(3-chloro-1-isopropyl-1H-indol-5-yl)-[1,2,4]oxadiazol-3-yl]-3,4-dihydro-1H-isoquinolin-2-yl}-acetic acid, trifluoroacetate

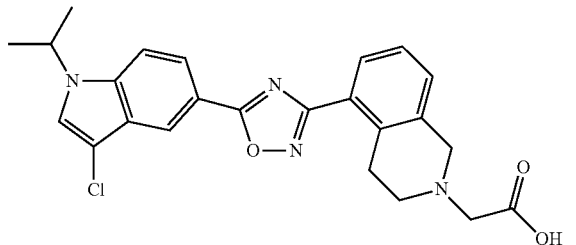 [SMILES: CC(C)n1cc(Cl)c2cc(-c3nc(-c4cccc5c4CCN(CC(=O)O)C5)no3)ccc21]

According to the method described in Example 5, {5-[5-(3-chloro-1-isopropyl-1H-indol-5-yl)-[1,2,4]oxadiazol-3-yl]-3,4-dihydro-1H-isoquinolin-2-yl}-acetic acid t-butyl ester (510 mg, 1.08 mmol) obtained from Preparation Example 43-1 was used to obtain the title compound (650 mg, 114%).
NMR: ¹H-NMR (400 MHz, CDCl₃) δ 8.47 (d, J=1.2 Hz, 1H), 8.21 (d, 1H), 8.04 (d, 1H), 7.48-7.42 (m, 2H), 7.28 (d, 1H), 4.72-4.64 (m, 3H), 4.05 (br, s, 2H), 3.75 (br, s, 2H), 3.66 (br, s, 2H), 1.55 (d, 6H)

PREPRATION EXAMPLE 44-1

Synthesis of {5-[5-(3-chloro-1-isopropyl-1H-indol-5-yl)-[1,2,4]oxadiazol-3-yl]-3,4-dihydro-1H-isoquinolin-2-yl}-acetic acid ethyl ester According to the method described in Preparation Example 28-1, 5-[5-(3-chloro-1-isopropyl-1H-indol-5-yl)-[1,2,4]oxadiazol-3-yl]-1,2,3,4-tetrahydro-isoquinoline, hydrochloride (600 mg, 1.40 mmol) obtained from Example 40 and ethyl bromoacetate (0.17 mL, 1.54 mmol) were used to obtain the title compound (510 mg, 77%).
NMR: ¹H-NMR (400 HMz, CDCl₃); δ 8.53 (d, J=1.2 Hz, 1H), 8.08 (dd, J=1.6 Hz, 1H), 8.03 (d, 1H), 7.49 (d, 1H), 7.30 (t, 1H), 7.29 (s, 1H), 7.18 (d, 1H), 4.76-4.70 (m, 1H), 4.24 (q, 2H), 3.91 (s, 2H), 3.45 (s, 2H), 3.37 (t, 2H), 2.97 (t, 2H), 1.56 (d, 6H), 1.31 (t, 3H)

EXAMPLE 44

Synthesis of 2-{5-[5-(3-chloro-1-isopropyl-1H-indol-5-yl)-[1,2,4]oxadiazol-3-yl]-3,4-dihydro-1H-isoquinolin-2-yl}-ethanol

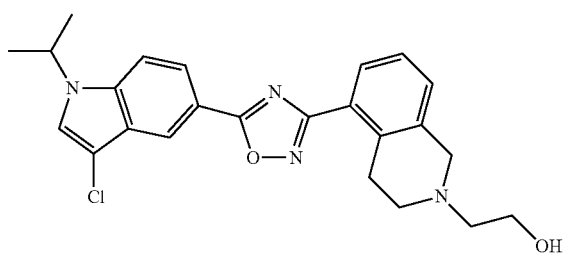 [SMILES: CC(C)n1cc(Cl)c2cc(-c3nc(-c4cccc5c4CCN(CCO)C5)no3)ccc21]

{5-[5-(3-Chloro-1-isopropyl-1H-indol-5-yl)-[1,2,4]oxadiazol-3-yl]-3,4-dihydro-1H-isoquinolin-2-yl}-acetic acid ethyl ester (50 mg, 0.10 mmol) obtained from Preparation Example 44-1 was dissolved in tetrahydrofuran, and lithium aluminium borohydride (8 mg, 0.20 mmol) was added dropwise thereto. The mixture was stirred for 1 hour at room temperature, sequentially added with water (1 mL), 6N sodium hydroxide aqueous solution (1 mL) and water (3 mL), and filtered with Celite. The filtrate was distilled under reduced pressure. The residue was separated by column chromatography to obtain the title compound (20 mg, 46%).
NMR: ¹H-NMR (400 MHz, CDCl₃) δ 8.54 (d, J=1.6 Hz, 1H), 8.09 (d, 1H), 8.03 (d, 1H), 7.49 (d, 1H), 7.31 (d, 2H), 7.20 (d, 1H), 4.75-4.70 (m, 1H), 3.82 (s, 2H), 3.75 (t, 2H), 3.33 (t, 2H), 2.90 (t, 2H), 2.76 (t, 2H), 1.56 (d, 6H)

EXAMPLE 45

Synthesis of 5-[5-(1-isopropyl-1H-indol-5-yl)-[1,2,4]oxadiazol-3-yl]-1,2,3,4-tetrahydro-naphthalen-1-ylamine, hydrochloride

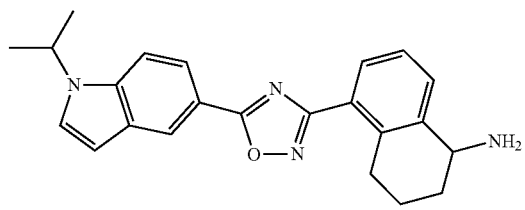 [SMILES: CC(C)n1ccc2cc(-c3nc(-c4cccc5c4CCCC5N)no3)ccc21]

According to the method described in Example 27, {5-[5-(1-isopropyl-1H-indol-5-yl)-[1,2,4]oxadiazol-3-yl]-1,2,3,4-tetrahydro-naphthalen-1-yl}-carbamic acid t-butyl ester (590 mg, 1.25 mmol) obtained from Preparation Example 36-2 was used to obtain the title compound (500 mg, 98%).
NMR: ¹H-NMR (400 HMz, MeOD); δ 8.45 (s, 1H), 8.04 (d, 1H), 7.97 (d, 1H), 7.64 (d, 1H), 7.60 (d, 1H), 7.51 (d, 1H), 7.48 (t, 1H), 6.66 (d, 1H), 4.84 (m, 1H), 4.62 (t, 1H), 3.10 (m, 2H), 2.21 (m, 1H), 2.07 (m, 1H), 1.97 (m, 2H), 1.54 (d, 6H)

PREPARATION EXAMPLE 46-1

Synthesis of 1-oxo-indane-4-carbonitrile

The title compound was synthesized according to the method described in WO 2010129379 A1.

PREPARATION EXAMPLE 46-2

Synthesis of 1-(3-hydroxy-azetidin-1-yl)-indane-4-carbonitrile

According to the method described in Example 3, 1-oxo-indane-4-carbonitrile (210 mg, 1.33 mmol) obtained from Preparation Example 46-1 and azetidine-3-ol hydrochloride (220 mg, 2.00 mmol) were used to obtain the title compound (190 mg, 67%).

PREPARATION EXAMPLE 46-3

Synthesis of N-hydroxy-1-(3-hydroxy-azetidin-1-yl)-indane-4-carboxamidine

According to the method described in Preparation Example 9-2, 1-(3-hydroxy-azetidin-1-yl)-indane-carbonitrile (190 mg, 0.89 mmol) obtained from Preparation Example 46-2 was used to obtain the title compound (160 mg, 73%).

EXAMPLE 46

Synthesis of 1-{4-[5-(1-isopropyl-1H-indol-5-yl)-[1,2,4]oxadiazol-3-yl]-indan-1-yl}-azetidin-3-ol

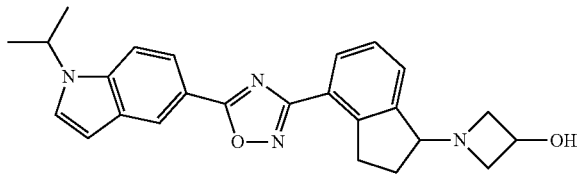 [SMILES: CC(C)n1ccc2cc(-c3nc(-c4cccc5c4CCC5N4CC(O)C4)no3)ccc21]

According to the method described in Preparation Example 1-4, 1-isopropyl-1H-indole-5-carboxylic acid (132 mg, 0.65 mmol) obtained from Preparation Example 1-2 and N-hydroxy-1-(3-hydroxy-azetidin-1-yl)-indane-4-carboxamidine (160 mg, 0.65 mmol) obtained from Preparation Example 46-3 were used to obtain the title compound (125 mg, 46%).

NMR: $^1$H-NMR (400 HMz, DMSO$_{d6}$); δ 8.43 (s, 1H), 7.99 (d, 1H), 7.91 (d, 1H), 7.75 (d, 1H), 7.68 (d, 1H), 7.46 (d, 1H), 7.36 (t, 1H), 6.69 (d, 1H), 5.28 (d, 1H), 4.84 (m, 1H), 4.11 (m, 1H), 3.82 (m, 1H), 3.48 (m, 1H), 3.38 (m 1H), 3.18 (m, 2H), 2.94 (t, 1H), 2.81 (t, 1H), 2.05 (m, 1H), 1.90 (m, 1H), 1.47 (d, 6H)

EXAMPLE 47

Synthesis of 2-{5-[5-(3-chloro-1-isopropyl-1H-indol-5-yl)-[1,2,4]oxadiazol-3-yl]-3,4-dihydro-1H-isoquinolin-2-yl}-N-(2-hydroxy-ethyl)-acetamide

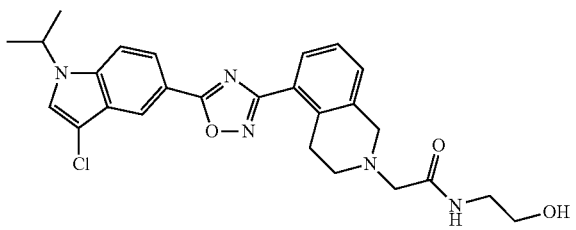 [SMILES: CC(C)n1cc(Cl)c2cc(-c3nc(-c4cccc5c4CCN(CC(=O)NCCO)C5)no3)ccc21]

{5-[5-(3-Chloro-1-isopropyl-1H-indol-5-yl)-[1,2,4]oxadiazol-3-yl]-3,4-dihydro-1H-isoquinolin-2-yl}-acetic acid, hydrochloride (50 mg, 0.10 mmol) obtained from Example 43 was dissolved in dimethylformamide (5 mL), and 2-aminoethanol (0.007 mL, 0.11 mmol), O-(7-azabenzotriazol-1-yl)-N,N,N',N'-tetramethyluronium hexafluorophosphate (HATU, 78 mg, 0.20 mmol) and diisopropylethylamine (0.089 mL, 0.50 mmol) were added dropwise thereto. The mixture was stirred for 3 hours at room temperature. The solvent was removed by distillation under reduced pressure. The residue was added with water and extracted with ethyl acetate. The extract was dried with anhydrous magnesium sulfate and filtered. The filtrate was distilled under reduced pressure. The residue was separated by column chromatography to obtain the title compound (32 mg, 65%).

NMR: $^1$H-NMR (400 MHz, CDCl$_3$) δ 8.54 (s, 1H), 8.09 (d, 1H), 8.05 (d, 1H), 7.50 (d, 1H), 7.36-7.30 (m, 2H), 7.20 (d, 1H), 4.75-4.72 (m, 1H), 3.75 (q, 2H), 3.48 (q, 2H), 3.35 (t, 2H), 2.26 (s, 2H), 2.90 (t, 2H), 2.81 (br, s, 1H) 1.57 (d, 6H)

PREPARATION EXAMPLE 48-1

Synthesis of {7-[5-(1-isopropyl-1H-indol-5-yl)-[1,2,4]oxadiazol-3-yl]-3,4-dihydro-1H-isoquinolin-2-yl}-acetic acid ethyl ester According to the method described in Preparation Example 28-1, 7-[5-(1-isopropyl-1H-indol-5-yl)-[1,2,4]oxadiazol-3-yl]-1,2,3,4-tetrahydro-isoquinoline, hydrochloride (600 mg, 1.40 mmol) obtained from Example 41 and ethyl bromoacetate (0.19 mL, 1.54 mmol) were used to obtain the title compound (620 mg, 99%).

NMR: $^1$H-NMR (400 HMz, CDCl$_3$); δ 8.53 (s, 1H), 8.05 (dd, J=1.6 Hz, 1H), 7.96 (d, 1H), 7.88 (s, 1H), 7.49 (d, 1H), 7.33 (d, 1H), 7.24 (d, 1H), 6.67 (d, 1H), 4.76-4.71 (m, 1H), 4.24 (q, 2H), 3.91 (s, 2H), 3.46 (s, 2H), 3.02-2.95 (m, 4H), 1.57 (d, 6H), 1.32 (t, 3H)

EXAMPLE 48

Synthesis of 2-{7-[5-(1-isopropyl-1H-indol-5-yl)-[1,2,4]oxadiazol-3-yl]-3,4-dihydro-1H-isoquinolin-2-yl}-ethanol

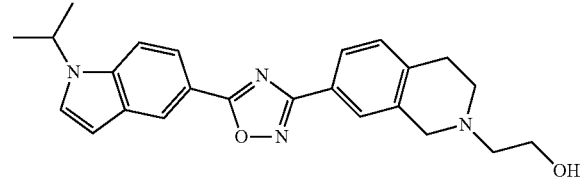 [SMILES: CC(C)n1ccc2cc(-c3nc(-c4ccc5c(c4)CN(CCO)CC5)no3)ccc21]

According to the method described in Example 44, {7-[5-(1-isopropyl-1H-indol-5-yl)-[1,2,4]oxadiazol-3-yl]-3,4-dihydro-1H-isoquinolin-2-yl}-acetic acid ethyl ester (50 mg, 0.11 mmol) obtained from Preparation Example 48-1 was used to obtain the title compound (20 mg, 45%).

NMR: $^1$H-NMR (400 MHz, CDCl$_3$) δ 8.54 (d, J=1.6 Hz, 1H), 8.05 (dd, J=1.6 Hz, 1H), 7.97 (d, 1H), 7.89 (s, 1H), 7.49 (d, 1H), 7.33 (d, 1H), 7.25 (d, 1H), 6.67 (d, 1H), 4.78-4.71 (m, 1H), 3.82 (s, 2H), 3.75 (t, 2H), 2.99 (t, 2H), 2.88 (t, 2H), 2.77 (t, 2H), 1.57 (d, 6H)

EXAMPLE 49

Synthesis of {5-[5-(1-isopropyl-1H-indol-5-yl)-[1,2,4]oxadiazol-3-yl]-1,2,3,4-tetrahydro-naphthalen-1-yl}-(2-methanolsulfonyl-ethyl)-amine, hydrochloride

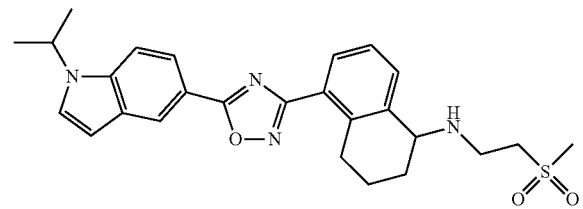 [SMILES: CC(C)n1ccc2cc(-c3nc(-c4cccc5c4CCCC5NCCS(C)(=O)=O)no3)ccc21]

According to the method described in Example 34, 5-[5-(1-isopropyl-1H-indol-5-yl)-[1,2,4]oxadiazol-3-yl]-1,2,3,4-tetrahydro-naphthalen-1-ylamine, hydrochloride (110 mg, 0.27 mmol) obtained from Example 45 and methyl vinyl sulfone (287 mg, 2.70 mmol) were used to obtain the title compound (85 mg, 61%).

NMR: $^1$H-NMR (400 HMz, DMSO$_{d6}$); δ 8.48 (s, 1H), 8.07 (d, 1H), 7.95 (d, 1H), 7.91 (d, 1H), 7.80 (d, 1H), 7.74 (d, 1H), 7.55 (t, 1H), 6.72 (d, 1H), 4.89 (m, 1H), 4.70 (m, 1H), 3.71 (m, 2H), 3.38 (m, 2H), 3.18 (m, 4H), 3.05 (m, 2H), 2.27 (m, 1H), 2.07 (m, 2H), 1.87 (m, 1H), 1.51 (d, 6H)

EXAMPLE 50

Synthesis of {7-[5-(1-isopropyl-1H-indol-5-yl)-[1,2,4]oxadiazol-3-yl]-3,4-dihydro-1H-isoquinolin-2-yl}-acetic acid, hydrochloride

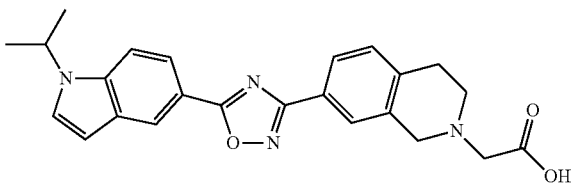 [SMILES: CC(C)n1ccc2cc(-c3nc(-c4ccc5c(c4)CN(CC(=O)O)CC5)no3)ccc21]

According to the method described in Example 1, {7-[5-(1-isopropyl-1H-indol-5-yl)-[1,2,4]oxadiazol-3-yl]-3,4-dihydro-1H-isoquinolin-2-yl}-acetic acid ethyl ester (800 mg, 1.80 mmol) obtained from Preparation Example 48-1 was used to obtain the title compound (330 mg, 44%).

NMR: $^1$H-NMR (400 MHz, DMSO-d6) δ 8.47 (s, 1H), 8.01-7.93 (m, 3H), 7.79 (d, 1H), 7.73 (d, 1H), 7.48 (d, 1H), 6.73 (d, 1H), 4.91-4.85 (m, 1H), 4.56 (br, s, 2H), 4.20 (br, s, 2H), 3.56 (br, s, 2H), 3.20 (br, s, 2H), 1.50 (d, 6H)

EXAMPLE 51

Synthesis of N-(2-hydroxy-ethyl)-2-{7-[5-(1-isopropyl-1H-indol-5-yl)-[1,2,4]oxadiazol-3-yl]-3,4-dihydro-1H-isoquinolin-2-yl}-acetamide

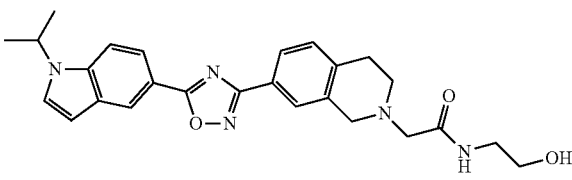 [SMILES: CC(C)n1ccc2cc(-c3nc(-c4ccc5c(c4)CN(CC(=O)NCCO)CC5)no3)ccc21]

According to the method described in Example 47, {7-[5-(1-isopropyl-1H-indol-5-yl)-[1,2,4]oxadiazol-3-yl]-3,4-dihydro-1H-isoquinolin-2-yl}-acetic acid, hydrochloride (46 mg, 0.10 mmol) obtained from Example 50 was used to obtain the title compound (18 mg, 39%).

NMR: $^1$H-NMR (400 MHz, CDCl$_3$) δ 8.53 (d, J=1.6 Hz, 1H), 8.04 (dd, J=1.6 Hz, 1H), 7.99 (d, 1H), 7.88 (s, 1H), 7.64 (br, s, 1H), 7.50 (d, 1H), 7.34 (d, 1H), 7.27 (d, 1H), 6.67 (d, 1H), 4.78-4.71 (m, 1H), 3.83 (s, 2H), 3.76 (t, 2H), 3.48 (q, 2H), 3.27 (s, 2H), 3.01 (t, 2H), 2.89 (t, 2H), 1.57 (d, 6H)

PREPARATION EXAMPLE 52-1

Synthesis of 3-{4-[5-(3-chloro-1-isopropyl-1H-indol-5-yl)-[1,2,4]oxadiazol-3-yl]-3-methyl-phenyl}-propanoic acid ethyl ester According to the method described in Preparation Example 1-4, 3-chloro-1-isopropyl-1H-indole-5-carboxylic acid (100 mg, 0.42 mmol) obtained from Preparation Example 3-2 and 3-[4-(N-hydroxycarbimidoyl)-3-methyl-phenyl]-propanoic acid ethyl ester (105 mg, 0.42 mmol) obtained from Preparation Example 1-3 were used to obtain the title compound (65 mg, 34%).

NMR: $^1$H-NMR (400 HMz, CDCl$_3$); δ 8.538 (s, 1H), 8.09 (dd, J=1.6 Hz, 1H), 8.04 (d, 1H), 7.49 (d, 1H), 7.29 (s, 1H), 7.19 (br, s, 1H), 4.76-4.70 (m, 1H), 4.15 (q, 2H), 3.00 (t, 2H), 2.68 (s, 3H), 2.66 (t, 2H), 1.56 (d, 6H), 1.26 (t, 3H)

EXAMPLE 52

Synthesis of 3-{4-[5-(3-chloro-1-isopropyl-1H-indol-5-yl)-[1,2,4]oxadiazol-3-yl]-3-methyl-phenyl}-propanoic acid According to the method described in Example 1, 3-{4-[5-(3-chloro-1-isopropyl-1H-indol-5-yl)-[1,2,4]oxadiazol-3-yl]-3-methyl-phenyl}-propanoic acid ethyl ester (65 mg, 0.14 mmol) obtained from Preparation Example 52-1 was used to obtain the title compound (60 mg, 100%).

NMR: $^1$H-NMR (400 MHz, CDCl$_3$) δ 8.53 (d, J=1.2 Hz, 1H), 8.09 (dd, J=1.6 Hz, 1H), 8.06 (d, 1H), 7.49 (d, 1H), 7.29 (s, 1H), 7.21 (d, 2H), 4.76-4.68 (m, 1H), 3.02 (t, 2H), 2.74 (t, 2H), 2.69 (s, 3H), 1.56 (d, 6H)

PREPARATION EXAMPLE 53-1

Synthesis of 3-{4-[5-(3-cyano-1-isopropyl-1H-indol-5-yl)-[1,2,4]oxadiazol-3-yl]-3-methyl-phenyl}-propanoic acid ethyl ester According to the method described in Preparation Example 1-4, 3-cyano-1-isopropyl-1H-indole-5-carboxylic acid (200 mg, 0.88 mmol) obtained from Preparation Example 4-4 and 3-[4-(N-hydroxycarbimidoyl)-3-methyl-phenyl]-propanoic acid ethyl ester (221 mg, 0.88 mmol) obtained from Preparation Example 1-3 were used to obtain the title compound (90 mg, 23%).

EXAMPLE 53

Synthesis of 3-{4-[5-(3-cyano-1-isopropyl-1H-indol-5-yl)-[1,2,4]oxadiazol-3-yl]-3-methyl-phenyl}-propanoic acid

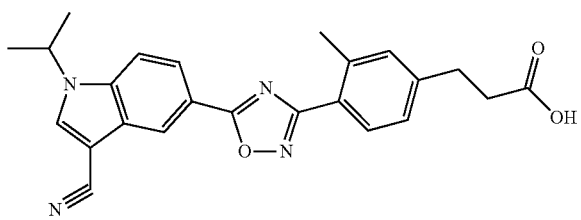 [SMILES: Cc1cc(CCC(=O)O)ccc1-c1noc(-c2ccc3c(c2)c(C#N)cn3C(C)C)n1]

According to the method described in Example 1, 3-{4-[5-(3-cyano-1-isopropyl-1H-indol-5-yl)-[1,2,4]oxadiazol-3-yl]-3-methyl-phenyl}-propanoic acid ethyl ester (90 mg, 0.20 mmol) obtained from Preparation Example 53-1 was used to obtain the title compound (75 mg, 90%).

NMR: $^1$H-NMR (400 HMz, DMSO$_{d6}$); δ 8.67 (s, 1H), 8.39 (s, 1H), 8.08 (d, 1H), 8.00 (d, 1H), 7.96 (d, 1H), 7.27 (s, 1H), 7.24 (d, 1H), 4.94 (m, 1H), 2.85 (t, 2H), 2.57 (s, 3H), 2.52 (t, 2H), 1.49 (d, 6H)

PREPARATION EXAMPLE 54-1

Synthesis of 1-methyl-1H-indole-5-carboxylic acid methyl ester

According to the method described in Preparation Example 1-1, 1H-indole-5-carboxylic acid methyl ester (300 mg, 1.71 mmol) and methyl iodide (485 mg, 3.42 mmol) were used to obtain the title compound (300 mg, 93%).

PREPARATION EXAMPLE 54-2

Synthesis of 1-methyl-1H-indole-5-carboxylic acid

According to the method described in Preparation Example 1-2, 1-methyl-1H-indole-5-carboxylic acid methyl ester (300 mg, 1.59 mmol) obtained from Preparation Example 54-1 was used to obtain the title compound (200 mg, 72%).

PREPARATION EXAMPLE 54-3

Synthesis of 3-{3-methyl-4-[5-(1-methyl-1H-indol-5-yl)-[1,2,4]oxadiazol-3-yl]-phenyl}-propanoic acid ethyl ester According to the method described in Preparation Example 1-4, 1-methyl-1H-indole-5-carboxylic acid (90 mg, 0.51 mmol) obtained from Preparation Example 54-2 and 3-[4-(N-hydroxycarbimidoyl)-3-methyl-phenyl]-propanoic acid ethyl ester (128 mg, 0.51 mmol) obtained from Preparation Example 1-3 were used to obtain the title compound (70 mg, 35%).

NMR: $^1$H-NMR (400 HMz, CDCl$_3$); δ 8.53 (s, 1H), 8.05 (m, 2H), 7.43 (d, 1H), 7.17 (m, 2H), 7.15 (d, 1H), 6.63 (d, 1H), 4.13 (m, 2H), 3.85 (s, 3H), 2.98 (t, 2H), 2.65 (m, 5H), 1.24 (t, 3H)

EXAMPLE 54

Synthesis of 3-{3-methyl-4-[5-(1-methyl-1H-indol-5-yl)-[1,2,4]oxadiazol-3-yl]-phenyl}-propanoic acid

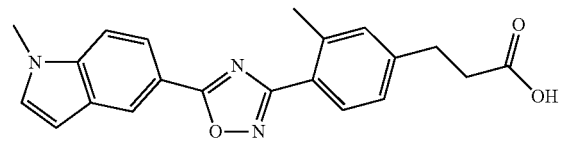 [SMILES: Cc1cc(CCC(=O)O)ccc1-c1noc(-c2ccc3c(ccn3C)c2)n1]

According to the method described in Example 1, 3-{3-methyl-4-[5-(1-methyl-1H-indol-5-yl)-[1,2,4]oxadiazol-3-yl]-phenyl}-propanoic acid ethyl ester (33 mg, 0.08 mmol) obtained from Preparation Example 54-3 was used to obtain the title compound (25 mg, 86%).

NMR: $^1$H-NMR (400 HMz, MeOD); δ 8.44 (s, 1H), 7.99 (d, 1H), 7.94 (d, 1H), 7.56 (d, 1H), 7.31 (d, 1H), 7.24 (s, 1H), 7.22 (d, 1H), 6.62 (d, 1H), 3.86 (s, 3H), 2.95 (t, 2H), 2.64 (t, 2H), 2.61 (s, 3H)

PREPARATION EXAMPLE 55-1

Synthesis of 1-hydroxy-indane-5-carbonitrile

The title compound was obtained according to the method described in WO 2004092116 A1

PREPARATION EXAMPLE 55-2

Synthesis of 1,N-dihydroxy-indane-5-carboxamidine

According to the method described in Preparation Example 9-2, 1-hydroxy-indane-5-carbonitrile (220 mg, 1.38 mmol) obtained from Preparation Example 55-1 was used to obtain the title compound (200 mg, 75%).

EXAMPLE 55

Synthesis of 5-[5-(1-isopropyl-1H-indol-5-yl)-[1,2,4]oxadiazol-3-yl]-indan-1-ol

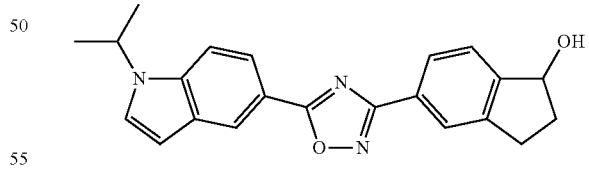

According to the method described in Preparation Example 1-4, 1-isopropyl-1H-indole-5-carboxylic acid (211 mg, 1.04 mmol) obtained from Preparation Example 1-2 and 1,N-dihydroxy-indane-5-carboxamidine (200 mg, 1.04 mmol) obtained from Preparation Example 55-2 were used to obtain the title compound (280 mg, 75%).

NMR: $^1$H-NMR (400 HMz, CDCl$_3$); δ 8.53 (s, 1H), 8.18 (d, 1H), 8.04 (d, 1H), 7.55 (d, 1H), 7.48 (d, 1H), 7.40 (t, 1H), 7.32 (d, 1H), 6.66 (d, 1H), 5.31 (t, 1H), 4.72 (m, 1H), 3.52 (m, 1H), 3.24 (m, 1H), 2.57 (m, 1H), 2.16 (b, 1H), 2.01 (m, 1H), 1.55 (d, 6H)

PREPARATION EXAMPLE 56-1

Synthesis of 6-(N-hydroxycarbimidoyl)-5-methyl-3,4-dihydro-1H-isoquinoline-2-carboxylic acid t-butyl ester The title compound was obtained according to the method described in WO 2010146105 A1.

NMR: $^1$H-NMR (400 HMz, DMSO-$d_6$); δ 9.24 (s, 1H), 7.07 (d, 1H), 7.00 (d, 1H), 5.68 (s, 2H), 3.58 (t, 2H), 2.67 (t, 2H), 2.20 (s, 3H), 1.42 (s, 9H)

PREPARATION EXAMPLE 56-2

Synthesis of 6-[5-(3-chloro-1-isopropyl-1H-indol-5-yl)-[1,2,4]oxadiazol-3-yl]-5-methyl-3,4-dihydro-1H-isoquinoline-2-carboxylic acid t-butyl ester According to the method described in Preparation Example 1-4, 3-chloro-1-isopropyl-1H-indole-5-carboxylic acid (600 mg, 2.52 mmol) obtained from Preparation Example 3-2 and 6-(N-hydroxycarbimidoyl)-5-methyl-3,4-dihydro-1H-isoquinoline-2-carboxylic acid t-butyl ester (770 mg, 2.52 mmol) obtained from Preparation Example 56-1 were used to obtain the title compound (1.05 g, 82%).

NMR: $^1$H-NMR (400 HMz, CDCl$_3$); δ 8.53 (d, J=1.6 Hz, 1H), 8.09 (dd, J=1.6 Hz, 1H), 7.80 (d, 1H), 7.48 (d, 1H), 7.30 (d, 1H), 7.29 (s, 1H), 7.11 (d, 1H), 4.76-4.69 (m, 1H), 4.64 (s, 2H), 3.72 (t, 2H), 2.85 (t, 2H), 2.55 (s, 3H), 1.56 (d, 6H), 1.51 (s, 9H)

EXAMPLE 56

Synthesis of 6-[5-(3-chloro-1-isopropyl-1H-indol-5-yl)-[1,2,4]oxadiazol-3-yl]-5-methyl-1,2,3,4-tetrahydro-isoquinoline, hydrochloride

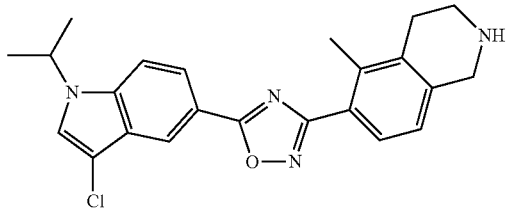 [SMILES: Cc1c(-c2noc(-c3ccc4c(c3)c(Cl)cn4C(C)C)n2)ccc2c1CCNC2]

According to the method described in Example 27, 6-[5-(3-chloro-1-isopropyl-1H-indol-5-yl)-[1,2,4]oxadiazol-3-yl]-5-methyl-3,4-dihydro-1H-isoquinoline-2-carboxylic acid t-butyl ester (1.05 g, 2.07 mmol) obtained from Preparation Example 56-2 was used to obtain the title compound (750 mg, 86%).

NMR: $^1$H-NMR (400 MHz, DMSO-d6) δ 8.31 (s, 1H), 8.02 (dd, J=1.6 Hz, 1H), 7.98 (s, 1H), 7.89 (d, 1H), 7.82 (d, 1H), 7.29 (d, 1H), 4.94-4.89 (m, 1H), 4.36 (s, 2H), 3.46 (t, 2H), 3.00 (t, 2H), 2.50 (s, 3H), 1.49 (d, 6H)

PREPARATION EXAMPLE 57-1

Synthesis of {6-[5-(3-chloro-1-isopropyl-1H-indol-5-yl)-[1,2,4]oxadiazol-3-yl]-5-methyl-3,4-dihydro-1H-isoquinolin-2-yl}-acetic acid ethyl ester According to the method described in Preparation Example 28-1, 6-[5-(3-chloro-1-isopropyl-1H-indol-5-yl)-[1,2,4]oxadiazol-3-yl]-5-methyl-1,2,3,4-tetrahydro-isoquinoline, hydrochloride (630 mg, 1.42 mmol) obtained from Example 56 and ethyl bromoacetate (0.17 mL, 1.56 mmol) were used to obtain the title compound (503 mg, 72%).

NMR: $^1$H-NMR (400 HMz, CDCl$_3$); δ 8.53 (d, J=1.2 Hz, 1H), 8.09 (dd, J=1.6 Hz, 1H), 7.77 (d, 1H), 7.48 (d, 1H), 7.29 (s, 1H), 7.02 (d, 1H), 4.76-4.69 (m, 1H), 4.24 (q, 2H), 3.86 (s, 2H), 3.44 (s, 2H), 2.97-2.91 (m, 4H), 2.53 (s, 3H), 1.56 (d, 6H), 1.31 (t, 3H)

EXAMPLE 57

Synthesis of 2-{6-[5-(3-chloro-1-isopropyl-1H-indol-5-yl)-[1,2,4]oxadiazol-3-yl]-5-methyl-3,4-dihydro-1H-isoquinolin-2-yl}-ethanol

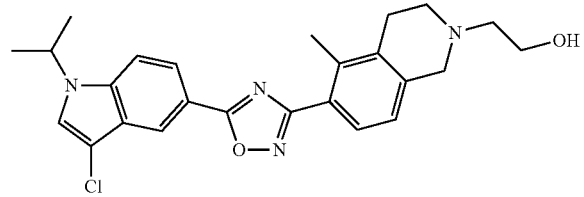 [SMILES: Cc1c(-c2noc(-c3ccc4c(c3)c(Cl)cn4C(C)C)n2)ccc2c1CCN(CCO)C2]

According to the method described in Example 44, {6-[5-(3-chloro-1-isopropyl-1H-indol-5-yl)-[1,2,4]oxadiazol-3-yl]-5-methyl-3,4-dihydro-1H-isoquinolin-2-yl}-acetic acid ethyl ester (53 mg, 0.11 mmol) obtained from Preparation Example 57-1 was used to obtain the title compound (37 mg, 76%).

NMR: $^1$H-NMR (400 MHz, CDCl$_3$) δ 8.53 (d, 1H), 8.09 (dd, J=1.6 Hz, 1H), 7.78 (d, 1H), 7.48 (d, 1H), 7.29 (s, 1H), 7.04 (d, 1H), 4.76-4.69 (m, 1H), 3.78 (s, 2H), 3.75 (t, 2H), 2.90 (s, 4H), 2.76 (t, 2H), 2.53 (s, 3H), 1.56 (d, 6H)

EXAMPLE 58

Synthesis of {6-[5-(3-chloro-1-isopropyl-1H-indol-5-yl)-[1,2,4]oxadiazol-3-yl]-5-methyl-3,4-dihydro-1H-isoquinolin-2-yl}-acetic acid, hydrochloride

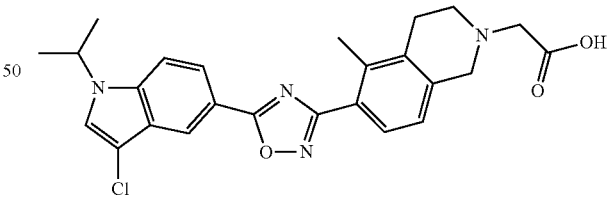

According to the method described in Example 1, {6-[5-(3-chloro-1-isopropyl-1H-indol-5-yl)-[1,2,4]oxadiazol-3-yl]-5-methyl-3,4-dihydro-1H-isoquinolin-2-yl}-acetic acid ethyl ester (450 mg, 0.91 mmol) obtained from Preparation Example 57-1 was used to obtain the title compound (410 mg, 90%).

NMR: $^1$H-NMR (400 MHz, CDCl$_3$) δ 8.31 (d, 1H), 8.02 (dd, J=1.6 Hz, 1H), 7.98 (s, 1H), 7.89 (d, 1H), 7.76 (d, 1H), 7.19 (d, 1H), 4.93-4.89 (m, 1H), 4.15 (br, 2H), 3.76 (br, s, 2H), 3.25 (br. s, 2H), 2.95 (br, s, 2H), 2.48 (s, 3H), 1.49 (d, 6H)

PREPARATION EXAMPLE 59-1

Synthesis of {5-[5-(1-isopropyl-1H-indol-5-yl)-[1,2,4]oxadiazol-3-yl]-indan-1-yloxy}-acetic acid ethyl ester According to the method described in Preparation Example 1-1, 5-[5-(1-isopropyl-1H-indol-5-yl)-[1,2,4]oxadiazol-3-yl]-indan-1-ol (150 mg, 0.42 mmol) obtained from Example 55 and ethyl bromoacetate (139 mg, 0.84 mmol) were used to obtain the title compound (30 mg, 16%).

NMR: $^1$H-NMR (400 HMz, CDCl$_3$); δ 8.54 (s, 1H), 8.07 (m, 3H), 7.60 (d, 1H), 7.48 (d, 1H), 7.33 (d, 1H), 6.66 (d, 1H), 5.12 (m, 1H), 4.74 (m, 1H), 4.22 (m, 2H), 4.18 (s, 2H), 3.17 (m, 1H), 2.92 (m, 1H), 2.43 (m, 1H), 2.22 (m, 1H), 1.56 (d, 6H), 1.30 (t, 3H)

EXAMPLE 59

Synthesis of {5-[5-(1-isopropyl-1H-indol-5-yl)-[1,2,4]oxadiazol-3-yl]-indan-1-yloxy}-acetic acid

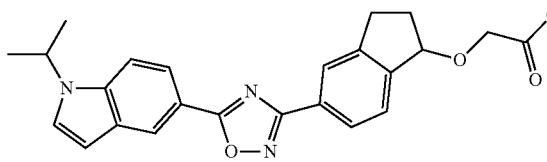

According to the method described in Example 1, {5-[5-(1-isopropyl-1H-indol-5-yl)-[1,2,4]oxadiazol-3-yl]-indan-1-yloxy}-acetic acid ethyl ester (30 mg, 0.07 mmol) obtained from Preparation Example 59-1 was used to obtain the title compound (25 mg, 86%).

NMR: $^1$H-NMR (400 HMz, MeOD); δ 8.42 (s, 1H), 8.00 (s, 1H), 7.97 (d, 1H), 7.95 (d, 1H), 7.60 (m, 2H), 7.49 (d, 1H), 6.65 (d, 1H), 5.06 (m, 1H), 4.81 (m, 1H), 4.18 (s, 2H), 3.11 (m, 1H), 2.88 (m, 1H), 2.40 (m, 1H), 2.14 (m, 1H), 1.53 (d, 6H)

EXAMPLE 60

Synthesis of 2-{6-[5-(3-chloro-1-isopropyl-1H-indol-5-yl)-[1,2,4]oxadiazol-3-yl]-5-methyl-3,4-dihydro-1H-isoquinolin-2-yl}-N-(2-hydroxy-ethyl)-acetamide

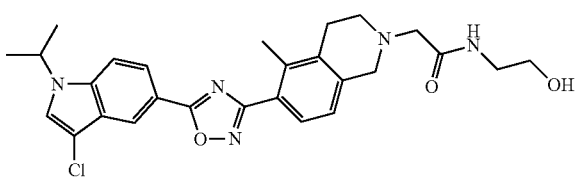 [SMILES: Cc1c(-c2noc(-c3ccc4c(c3)c(Cl)cn4C(C)C)n2)ccc2c1CCN(CC(=O)NCCO)C2]

According to the method described in Example 47, {6-[5-(3-chloro-1-isopropyl-1H-indol-5-yl)-[1,2,4]oxadiazol-3-yl]-5-methyl-3,4-dihydro-1H-isoquinolin-2-yl}-acetic acid, hydrochloride (50 mg, 0.10 mmol) obtained from Example 58 was used to obtain the title compound (22 mg, 63%).

NMR: $^1$H-NMR (400 MHz, CDCl$_3$) δ 8.53 (d, 1H), 8.09 (d, 1H), 7.79 (d, 1H), 7.64 (br, s, 1H), 7.49 (d, 1H), 7.29 (s, 1H), 7.03 (d, 1H), 4.75-4.71 (m, 1H), 3.80 (s, 2H), 3.76 (q, 2H), 3.49 (q, 2H), 3.25 (s, 2H), 2.92 (s, 4H), 2.68 (t, 1H), 2.54 (s, 3H), 1.55 (d, 6H))

PREPARATION EXAMPLE 61-1

Synthesis of 6-[5-(1-isopropyl-1H-indol-5-yl)-[1,2,4]oxadiazol-3-yl]-5-methyl-3,4-dihydro-1H-isoquinoline-2-carboxylic acid t-butyl ester According to the method described in Preparation Example 1-4, 1-isopropyl-1H-indole-5-carboxylic acid (230 mg, 0.97 mmol) obtained from Preparation Example 1-2 and 6-(N-hydroxycarbimidoyl)-5-methyl-3,4-dihydro-1H-isoquinoline-2-carboxylic acid t-butyl ester (300 mg, 0.97 mmol) obtained from Preparation Example 56-1 were used to obtain the title compound (360 mg, 79%).

NMR: $^1$H-NMR (400 HMz, CDCl$_3$); δ 8.53 (s, 1H), 8.05 (dd, J=1.6, 1.2 Hz, 1H), 7.79 (d, 1H), 7.49 (d, 1H), 7.33 (d, 1H), 7.10 (d, 1H), 6.67 (d, 1H), 4.78-4.71 (m, 1H), 4.64 (s, 2H), 3.72 (t, 2H), 2.85 (t, 2H), 2.54 (s, 3H), 1.57 (d, 6H), 1.51 (s, 9H)

EXAMPLE 61

Synthesis of 6-[5-(1-isopropyl-1H-indol-5-yl)-[1,2,4]oxadiazol-3-yl]-5-methyl-1,2,3,4-tetrahydro-isoquinoline, hydrochloride

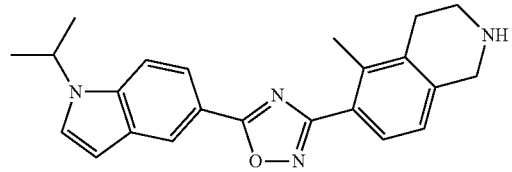 [SMILES: Cc1c(-c2noc(-c3ccc4c(ccn4C(C)C)c3)n2)ccc2c1CCNC2]

According to the method described in Example 27, 6-[5-(1-isopropyl-1H-indol-5-yl)-[1,2,4]oxadiazol-3-yl]-5-methyl-3,4-dihydro-1H-isoquinoline-2-carboxylic acid t-butyl ester (360 mg, 0.76 mmol) obtained from Preparation Example 61-1 was used to obtain the title compound (260 mg, 84%).

NMR: $^1$H-NMR (400 MHz, CDCl$_3$) δ 8.53 (d, 1H), 8.05 (dd, J=1.6 Hz, 1H), 7.80 (d, 1H), 7.49 (s, 1H), 7.33 (d, 1H), 7.06 (d, 1H), 6.67 (d, 1H), 4.77-4.71 (m, 1H), 4.21 (s, 2H), 3.35 (t, 2H), 2.92 (t, 2H), 2.53 (s, 3H), 1.57 (d, 6H)

PREPARATION EXAMPLE 62-1

Synthesis of 6-[5-(3-cyano-1-isopropyl-1H-indol-5-yl)-[1,2,4]oxadiazol-3-yl]-5-methyl-3,4-dihydro-1H-isoquinoline-2-carboxylic acid t-butyl ester According to the method described in Preparation Example 1-4, 3-cyano-1-isopropyl-1H-indole-5-carboxylic acid (66 mg, 0.29 mmol) obtained from Preparation Example 4-4 and 6-(N-hydroxycarbimidoyl)-5-methyl-3,4-dihydro-1H-isoquinoline-2-carboxylic acid t-butyl ester (88 mg, 0.29 mmol) obtained from Preparation Example 56-1 were used to obtain the title compound (60 mg, 42%).

NMR: $^1$H-NMR (400 HMz, CDCl$_3$); δ 8.69 (s, 1H), 8.18 (dd, J=1.6 Hz, 1H), 7.83 (s, 1H), 7.81 (d, 1H), 7.59 (d, 1H), 7.12 (d, 1H), 4.82-4.76 (m, 1H), 4.65 (s, 2H), 3.72 (t, 2H), 2.86 (t, 2H), 2.55 (s, 3H), 1.63 (d, 6H), 1.51 (s, 9H)

PREPARATION EXAMPLE 62-2

Synthesis of 1-isopropyl-5-[3-(5-methyl-1,2,3,4-tetrahydro-isoquinolin-6-yl)-[1,2,4]oxadiazol-5-yl]-1H-indole-3-carbonitrile, hydrochloride According to the method described in Example 27, 6-[5-(3-cyano-1-isopropyl-1H-indol-5-yl)-[1,2,4]oxadiazol-3-yl]-5-methyl-3,4-dihydro-1H-isoquinoline-2-carboxylic acid t-butyl ester (60 mg, 0.12 mmol) obtained from Preparation Example 62-1 was used to obtain the title compound (40 mg, 77%).

NMR: $^1$H-NMR (400 HMz, DMSO-d$_6$); δ 9.17 (br, s, 1H), 8.71 (s, 1H), 8.45 (s, 1H), 8.13 (d, 1H), 8.05 (d, 1H), 7.84 (d, 1H), 7.30 (d, 1H), 5.01-4.96 (m, 1H), 4.37 (s, 2H), 3.48 (t, 2H), 3.00 (t, 2H), 2.50 (s, 3H), 1.53 (d, 6H),

PREPARATION EXAMPLE 62-3

Synthesis of {6-[5-(3-cyano-1-isopropyl-1H-indol-5-yl)-[1,2,4]oxadiazol-3-yl]-5-methyl-3,4-dihydro-1H-isoquinolin-2-yl}-acetic acid ethyl ester According to the method described in Preparation Example 28-1, 1-isopropyl-5-[3-(5-methyl-1,2,3,4-tetrahydro-isoquinolin-6-yl)-[1,2,4]oxadiazol-5-yl]-1H-indole-3-carbonitrile, hydrochloride (40 mg, 0.09 mmol) obtained from Preparation Example 62-2 and ethyl bromoacetate (0.015 mL, 0.13 mmol) were used to obtain the title compound (17 mg, 39%).

NMR: $^1$H-NMR (400 HMz, CDCl$_3$); δ 8.67 (s, 1H), 8.18 (dd, J=1.6, 1.2 Hz, 1H), 7.83 (s, 1H), 7.78 (d, 1H), 7.59 (d, 1H), 7.03 (d, 1H), 4.81-4.75 (m, 1H), 4.25 (q, 2H), 3.88 (s, 2H), 3.45 (s, 2H), 3.00-2.91 (m 4H), 2.53 (s, 3H), 1.62 (d, 6H), 1.31 (t, 3H)

EXAMPLE 62

Synthesis of {6-[5-(3-cyano-1-isopropyl-1H-indol-5-yl)-[1,2,4]oxadiazol-3-yl]-5-methyl-3,4-dihydro-1H-isoquinolin-2-yl}-acetic acid, hydrochloride

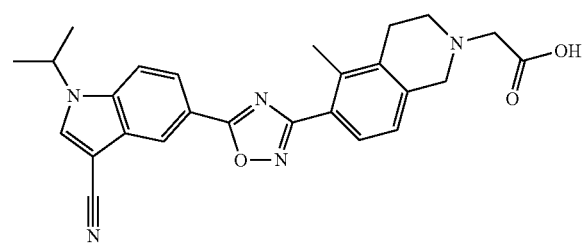 [SMILES: Cc1c(-c2noc(-c3ccc4c(c3)c(C#N)cn4C(C)C)n2)ccc2c1CCN(CC(=O)O)C2]

According to the method described in Example 1, {6-[5-(3-cyano-1-isopropyl-1H-indol-5-yl)-[1,2,4]oxadiazol-3-yl]-5-methyl-3,4-dihydro-1H-isoquinolin-2-yl}-acetic acid ethyl ester (17 mg, 0.035 mmol) obtained from Preparation Example 62-3 was used to obtain the title compound (5 mg, 29%).

NMR: $^1$H-NMR (400 MHz, DMSO-d6) δ 8.69 (s, 1H), 8.43 (s, 1H), 8.12 (d, 1H), 8.03 (d, 1H), 7.72 (d, 1H), 7.12 (d, 1H), 5.01-4.95 (m, 1H), 3.83 (s, 2H), 3.37 (s, 3H), 2.94 (br s, 2H), 2.83 (br s, 2H), 2.46 (s, 2H), 1.53 (d, 6H)

PREPARATION EXAMPLE 63-1

Synthesis of {6-[5-(1-isopropyl-1H-indol-5-yl)-[1,2,4]oxadiazol-3-yl]-5-methyl-3,4-dihydro-1H-isoquinolin-2-yl}-acetic acid ethyl ester According to the method described in Preparation Example 28-1, 6-[5-(1-isopropyl-1H-indol-5-yl)-[1,2,4]oxadiazol-3-yl]-5-methyl-1,2,3,4-tetrahydro-isoquinoline, hydrochloride (160 mg, 0.39 mmol) obtained from Example 61 and ethyl bromoacetate (0.048 mL, 0.43 mmol) were used to obtain the title compound (70 mg, 39%).

NMR: $^1$H-NMR (400 HMz, CDCl$_3$); δ 8.53 (s, 1H), 8.05 (dd, J=1.6 Hz, 1H), 7.76 (d, 1H), 7.48 (d, 1H), 7.32 (d, 1H), 7.02 (d, 1H), 6.66 (d, 1H), 4.75-4.71 (m, 1H), 4.24 (q, 2H), 3.86 (s, 2H), 3.43 (s, 2H), 2.98-2.91 (m, 4H), 2.52 (s, 3H), 1.57 (d, 6H), 1.31 (t, 3H)

EXAMPLE 63

Synthesis of {6-[5-(1-isopropyl-1H-indol-5-yl)-[1,2,4]oxadiazol-3-yl]-5-methyl-3,4-dihydro-1H-isoquinolin-2-yl}-acetic acid, hydrochloride

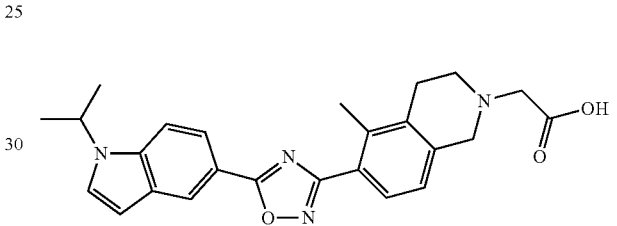

According to the method described in Example 1, {6-[5-(1-isopropyl-1H-indol-5-yl)-[1,2,4]oxadiazol-3-yl]-5-methyl-3,4-dihydro-1H-isoquinolin-2-yl}-acetic acid ethyl ester (70 mg, 0.15 mmol) obtained from Preparation Example 63-1 was used to obtain the title compound (60 mg, 84%).

NMR: $^1$H-NMR (500 MHz, CDCl$_3$) δ 8.50 (s, 1H), 8.01 (d, 1H), 7.83 (d, 1H), 7.47 (d, 1H), 7.31 (d, 1H), 7.08 (d, 1H), 6.65 (d, 1H), 4.74-4.70 (m, 1H), 4.36 (s, 2H), 3.66 (s, 2H), 3.47 (br. s, 2H), 3.08 (br, s, 2H), 2.54 (s, 3H), 1.55 (d, 6H)

PREPARATION EXAMPLE 64-1

Synthesis of 4-amino-3-chloro-5-iodo-benzoic acid methyl ester

The title compound was obtained according to the method described in WO 2010093191 A2.

PREPARATION EXAMPLE 64-2

Synthesis of 4-amino-3-chloro-5-prop-1-ynyl-benzoic acid methyl ester

4-Amino-3-chloro-5-iodo-benzoic acid methyl ester (3.4 g, 10.91 mmol) obtained from Preparation Example 64-1 was dissolved in tetrahydrofuran (150 mL), and methyl acetylene (900 mg, 21.82 mmol), cupper (I) iodide (206 mg, 1.09 mmol), bis(triphenylphosphine)palladium(II) dichloride (Pd(Ph$_3$P)$_2$Cl$_2$, 760 mg, 1.09 mmol) and triethylamine (4.5 mL, 32.73 mmol) were added dropwise thereto. The mixture was stirred for 18 hours at room temperature, added with water and extracted with ethyl acetate. The extract was washed with brine, dried with anhydrous magnesium sulfate and filtered. The filtrate was distilled under reduced pressure. The residue was separated by column chromatography to obtain the title compound (2.4 g, 98%).

NMR: $^1$H-NMR (400 HMz, CDCl$_3$); δ 7.87 (d, 2H), 4.99 (s, 2H), 3.85 (s, 3H), 2.11 (s, 3H)

PREPARTION EXAMPLE 64-3

Synthesis of 7-chloro-2-methyl-1H-indole-5-carboxylic acid methyl ester

4-Amino-3-chloro-5-prop-1-ynyl-benzoic acid methyl ester (1.7 g, 7.6 mmol) obtained from Preparation Example 64-2 was dissolved in N-methylpyrrolidone, and potassium t-butoxide (840 mg, 7.6 mmol) was slowly added dropwise thereto. The mixture was stirred for 18 hours at room temperature, added with 1N hydrochloric acid aqueous solution and extracted with ethyl acetate. The extract was washed with brine, dried with anhydrous magnesium sulfate and filtered. The filtrate was distilled under reduced pressure. The residue was separated by column chromatography to obtain the title compound (1.4 g, 82%).

NMR: $^1$H-NMR (400 HMz, CDCl$_3$); δ 8.30 (s, 1H), 8.17 (s, 1H), 7.83 (s, 1H), 6.35 (s, 1H), 3.92 (s, 3H), 2.49 (s, 3H)

PREPARATION EXAMPLE 64-4

Synthesis of 7-chloro-2-methyl-1H-indole-5-carboxylic acid

According to the method described in Preparation Example 1-2, 7-chloro-2-methyl-1H-indole-5-carboxylic acid methyl ester (300 mg, 1.34 mmol) obtained from Preparation Example 64-3 was used to obtain the title compound (230 mg, 82%).

PREPARATION EXAMPLE 64-5

Synthesis of 3-{4-[5-(7-chloro-2-methyl-1H-indol-5-yl)-[1,2,4]oxadiazol-3-yl]-3-methyl-phenyl}-propanoic acid ethyl ester

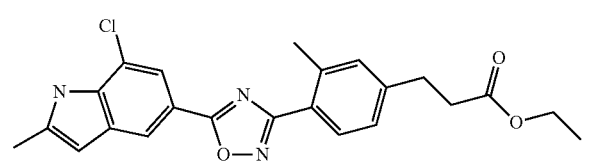 [SMILES: CCOC(=O)CCc1ccc(-c2noc(-c3cc(Cl)c4[nH]c(C)cc4c3)n2)c(C)c1]

According to the method described in Preparation Example 1-4, 7-chloro-2-methyl-1H-indole-5-carboxylic acid (230 mg, 1.1 mmol) obtained from Preparation Example 64-4 and 3-[4-(N-hydroxycarbimidoyl)-3-methyl-phenyl]-propanoic acid ethyl ester (275 mg, 1.1 mmol) obtained from Preparation Example 1-3 were used to obtain the title compound (318 mg, 68%).

EXAMPLE 64

Synthesis of 3-{4-[5-(7-chloro-2-methyl-1H-indol-5-yl)-[1,2,4]oxadiazol-3-yl]-3-methyl-phenyl}-propanoic acid

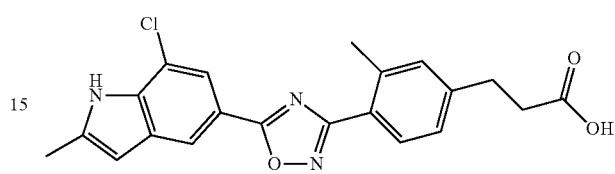

According to the method described in Example 1, 3-{4-[5-(7-chloro-2-methyl-1H-indol-5-yl)-[1,2,4]oxadiazol-3-yl]-3-methyl-phenyl}-propanoic acid ethyl ester (30 mg, 0.07 mmol) obtained from Preparation Example 64-5 was used to obtain the title compound (21 mg, 76%).

NMR: $^1$H-NMR (400 HMz, MeOD); δ 8.26 (s, 1H), 7.97 (d, 1H), 7.87 (d, 1H), 7.27 (s, 1H), 7.25 (d, 1H), 6.42 (d, 1H), 2.98 (t, 2H), 2.67 (t, 2H), 2.64 (s, 3H), 2.50 (s, 3H)

PREPARATION EXAMPLE 65-1

Synthesis of 5-[5-(3-cyano-1-isopropyl-1H-indol-5-yl)-[1,2,4]oxadiazol-3-yl]-3,4-dihydro-1H-isoquinoline-2-carboxylic acid t-butyl ester According to the method described in Preparation Example 1-4, 3-cyano-1-isopropyl-1H-indole-5-carboxylic acid (500 mg, 2.19 mmol) obtained from Preparation Example 4-4 and 5-(N-hydroxycarbimidoyl)-3,4-dihydro-1H-isoquinoline-2-carboxylic acid t-butyl ester (638 mg, 2.19 mmol) obtained from Preparation Example 27-1 were used to obtain the title compound (620 mg, 59%).

NMR: $^1$H-NMR (400 HMz, CDCl$_3$); δ 8.69 (s, 1H), 8.19 (dd, J=1.6 Hz, 1H), 8.01 (d, 1H), 7.84 (s, 1H), 7.61 (d, 1H), 7.37 (t, 1H), 7.29 (d, 1H), 4.82-4.76 (m, 1H), 4.68 (s, 2H), 3.70 (t, 2H), 3.29 (t, 2H), 1.63 (d, 6H), 1.51 (s, 9H)

EXAMPLE 65

Synthesis of 1-isopropyl-5-[3-(1,2,3,4-tetrahydro-isoquinolin-5-yl)-[1,2,4]oxadiazol-5-yl]-1H-indole-3-carbonitrile, hydrochloride

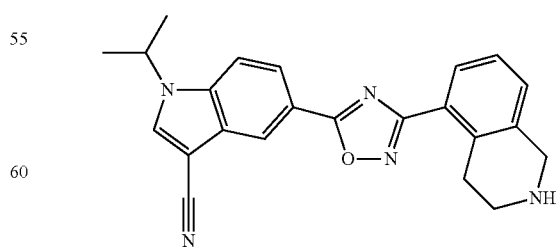

According to the method described in Example 27, 5-[5-(3-cyano-1-isopropyl-1H-indol-5-yl)-[1,2,4]oxadiazol-3-yl]-3,4-dihydro-1H-isoquinoline-2-carboxylic acid t-butyl ester (620 mg, 1.28 mmol) obtained from Preparation Example 65-1 was used to obtain the title compound (480 mg, 89%).

NMR: $^1$H-NMR (400 MHz, DMSO-d6) δ 8.72 (s, 1H), 8.46 (d, J=1.2 Hz, 1H), 8.14 (dd, J=1.6 Hz, s, 1H), 8.09-8.05 (m, 2H), 7.54-7.49 (m, 1H), 5.03-4.96 (m, 1H), 4.40 (br, s, 2H), 3.45 (br, s, 2H), 3.38 (t, 2H), 1.53 (d, 6H)

PREPARATION EXAMPLE 66-1

Synthesis of 4-amino-3-iodo-benzoic acid methyl ester

The title compound was obtained according to the method described in WO 2007103759 A2.

PREPARATION EXAMPLE 66-2

Synthesis of 4-amino-3-cyclopentylethynyl-benzoic acid methyl ester

According to the method described in Preparation Example 64-2, 4-amino-3-iodo-benzoic acid methyl ester (1.0 g, 3.61 mmol) obtained from Preparation Example 66-1 and cyclopentylacetylene (0.2 mL, 4.33 mmol) were used to obtain the title compound (1.0 g, 100%).

NMR: $^1$H-NMR (400 HMz, CDCl$_3$); δ 7.94 (d, 1H), 7.74 (dd, 1H), 6.64 (d, 1H), 4.57 (s, 2H), 3.84 (s, 3H), 2.88 (m, 1H), 2.03 (m, 2H), 1.73 (m, 6H)

PREPARATION EXAMPLE 66-3

Synthesis of 4-amino-3-cyclopentylethynyl-benzoic acid

According to the method described in Preparation Example 64-4, 4-amino-3-cyclopentylethynyl-benzoic acid methyl ester (1.0 g, 4.11 mmol) obtained from Preparation Example 66-2 was used to obtain the title compound (600 mg, 64%).

NMR: $^1$H-NMR (400 HMz, CDCl$_3$); δ 8.01 (s, 1H), 7.79 (d, 1H), 6.65 (d, 1H), 2.89 (m, 1H), 2.02 (m, 2H), 1.79 (m, 6H)

PREPARATION EXAMPLE 66-4

Synthesis of 2-cyclopentyl-1H-indole-5-carboxylic acid

4-Amino-3-cyclopentylethynyl-benzoic acid (600 mg, 2.62 mmol) obtained from Preparation Example 66-3 was dissolved in N-methylpyrrolidone, and a catalytic amount of bis(triphenylphosphine)palladium(II) dichloride (Pd(Ph$_3$P)$_2$Cl) was added dropwise thereto. The mixture was stirred for 2 hours under reflux at 150° C., added with water and extracted with ethyl acetate. The extract was washed with brine, dried with anhydrous magnesium sulfate and filtered. The filtrate was distilled under reduced pressure. The residue was separated by column chromatography to obtain the title compound (450 mg, 75%).

NMR: $^1$H-NMR (400 HMz, CDCl$_3$); δ 8.37 (s, 1H), 8.14 (s, 1H), 7.90 (dd, 1H), 7.31 (d, 1H), 6.35 (s, 1H), 3.17 (m, 1H), 2.12 (m, 2H), 1.76 (m, 6H)

PREPARATION EXAMPLE 66-5

Synthesis of 3-{4-[5-(2-cyclopentyl-1H-indol-5-yl)-[1,2,4]oxadiazol-3-yl]-3-methyl-phenyl}-propanoic acid ethyl ester According to the method described in Preparation Example 1-4, 2-cyclopentyl-1H-indole-5-carboxylic acid (30 mg, 0.13 mmol) obtained from Preparation Example 66-4 and 3-[4-(N-hydroxycarbimidoyl)-3-methyl-phenyl]-propanoic acid ethyl ester (33 mg, 0.13 mmol) obtained from Preparation Example 1-3 were used to obtain the title compound (50 mg, 68%).

EXAMPLE 66

Synthesis of 3-{4-[5-(2-cyclopentyl-1H-indol-5-yl)-[1,2,4]oxadiazol-3-yl]-3-methyl-phenyl}-propanoic acid

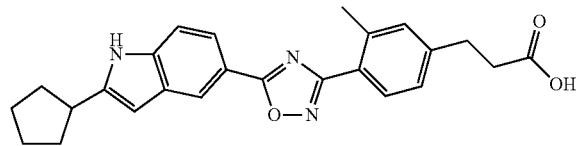 [SMILES: Cc1cc(CCC(=O)O)ccc1-c1noc(-c2ccc3[nH]c(C4CCCC4)cc3c2)n1]

According to the method described in Example 1, 3-{4-[5-(2-cyclopentyl-1H-indol-5-yl)-[1,2,4]oxadiazol-3-yl]-3-methyl-phenyl}-propanoic acid ethyl ester (50 mg, 0.11 mmol) obtained from Preparation Example 66-5 was used to obtain the title compound (38 mg, 83%).

NMR: $^1$H-NMR (400 HMz, DMSO$_{d6}$); δ 11.44 (s, 1H), 8.27 (s, 1H), 7.92 (d, 1H), 7.80 (d, 1H), 7.46 (d, 1H), 7.25 (s, 1H), 7.23 (d, 1H), 6.35 (s, 1H), 3.15 (m, 1H), 2.83 (t, 2H), 2.56 (m, 5H), 2.05 (m 2H), 1.65 (m, 6H)

PREPARATION EXAMPLE 67-1

Synthesis of {5-[5-(3-cyano-1-isopropyl-1H-indol-5-yl)-[1,2,4]oxadiazol-3-yl]-3,4-dihydro-1H-isoquinolin-2-yl}-acetic acid ethyl ester According to the method described in Preparation Example 28-1, 1-isopropyl-5-[3-(1,2,3,4-tetrahydro-isoquinolin-5-yl)-[1,2,4]oxadiazol-5-yl]-1H-indole-3-carbonitrile, hydrochloride (100 mg, 0.24 mmol) obtained from Example 65 and ethyl bromoacetate (0.048 mL, 0.43 mmol) were used to obtain the title compound (90 mg, 80%).

NMR: $^1$H-NMR (400 HMz, CDCl$_3$); δ 8.69 (d, J=1.2 Hz, 1H), 8.19 (dd, J=1.6 Hz, 1H), 8.05 (d, 1H), 7.84 (s, 1H), 7.60 (d, 1H), 7.32 (t, 1H), 7.19 (d, 1H), 4.81-4.76 (m, 1H), 4.24 (q, 2H), 3.91 (s, 2H), 3.45 (s, 2H), 3.37 (t, 2H), 2.98 (t, 2H), 1.62 (d, 6H), 1.32 (t, 3H)

EXAMPLE 67

Synthesis of {5-[5-(3-cyano-1-isopropyl-1H-indol-5-yl)-[1,2,4]oxadiazol-3-yl]-3,4-dihydro-1H-isoquinolin-2-yl}-acetic acid, hydrochloride

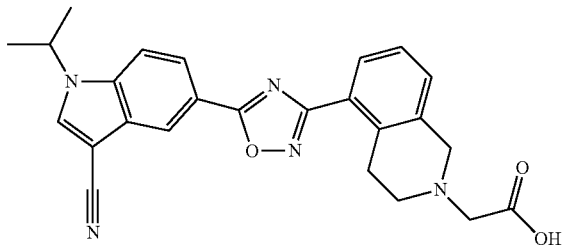 [SMILES: CC(C)n1cc(C#N)c2cc(-c3nc(-c4cccc5c4CCN(CC(=O)O)C5)no3)ccc21]

According to the method described in Example 1, {5-[5-(3-cyano-1-isopropyl-1H-indol-5-yl)-[1,2,4]oxadiazol-3-yl]-3,4-dihydro-1H-isoquinolin-2-yl}-acetic acid ethyl ester (90 mg, 0.19 mmol) obtained from Preparation Example 67-1 was used to obtain the title compound (70 mg, 83%).

NMR: $^1$H-NMR (400 MHz, CDCl$_3$) δ 8.56 (d, 1H), 8.12 (t, 2H), 7.82 (s, 1H), 7.59 (d, 1H), 7.38 (t, 1H), 7.26 (s, 1H), 4.80-4.76 (m, 1H), 4.40 (s, 2H), 3.73 (s, 2H), 3.51 (d, 5H), 1.62 (d, 6H)

PREPARATION EXAMPLE 68-1

Synthesis of 1-benzyl-1H-indole-5-carboxylic acid methyl ester

According to the method described in Preparation Example 1-1, 1H-indole-5-carboxylic acid methyl ester (72 mg, 0.41 mmol) and benzylbromide (84 mg, 0.49 mmol) were used to obtain the title compound (93 mg, 85%).

PREPARATION EXAMPLE 68-2

Synthesis of 1-benzyl-1H-indole-5-carboxylic acid

According to the method described in Preparation Example 1-2, 1-benzyl-1H-indole-5-carboxylic acid methyl ester (93 mg, 0.35 mmol) obtained from Preparation Example 68-1 was used to obtain the title compound (65 mg, 75%).

PREPARATION EXAMPLE 68-3

Synthesis of 3-{4-[5-(1-benzyl-1H-indol-5-yl)-[1,2,4]oxadiazol-3-yl]-3-methyl-phenyl}-propanoic acid ethyl ester According to the method described in Preparation Example 1-4, 1-benzyl-1H-indole-5-carboxylic acid (65 mg, 0.26 mmol) obtained from Preparation Example 68-2 and 3-[4-(N-hydroxycarbimidoyl)-3-methyl-phenyl]-propanoic acid ethyl ester (66 mg, 0.26 mmol) obtained from Preparation Example 1-3 were used to obtain the title compound (80 mg, 65%).

EXAMPLE 68

Synthesis of 3-{4-[5-(1-benzyl-1H-indol-5-yl)-[1,2,4]oxadiazol-3-yl]-3-methyl-phenyl}-propanoic acid

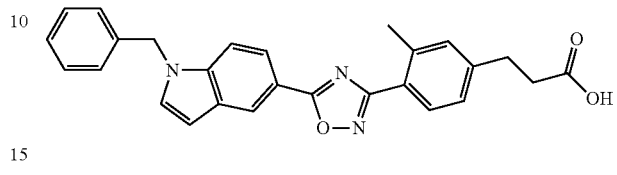

According to the method described in Example 1, 3-{4-[5-(1-benzyl-1H-indol-5-yl)-[1,2,4]oxadiazol-3-yl]-3-methyl-phenyl}-propanoic acid ethyl ester (80 mg, 0.17 mmol) obtained from Preparation Example 68-3 was used to obtain the title compound (65 mg, 87%).

NMR: $^1$H-NMR (400 HMz, DMSO$_{d6}$); δ 8.44 (s, 1H), 7.90 (m, 2H), 7.68 (m, 2H), 7.25 (m, 7H), 6.72 (d, 1H), 5.49 (s, 2H), 2.84 (t, 2H), 2.55 (m, 5H)

PREPARATION EXAMPLE 69-1

Synthesis of 1-cyclopentyl-1H-indole-5-carboxylic acid methyl ester

According to the method described in Preparation Example 1-1, 1H-indole-5-carboxylic acid methyl ester (42 mg, 0.24 mmol) and cyclopentylbromide (43 mg, 0.29 mmol) were used to obtain the title compound (50 mg, 83%).

PREPARATION EXAMPLE 69-2

Synthesis of 1-cyclopentyl-1H-indole-5-carboxylic acid

According to the method described in Preparation Example 1-2, 1-cyclopentyl-1H-indole-5-carboxylic acid methyl ester (50 mg, 0.20 mmol) obtained from Preparation Example 69-1 was used to obtain the title compound (39 mg, 83%).

PREPARATION EXAMPLE 69-3

Synthesis of 3-{4-[5-(1-cyclopentyl-1H-indol-5-yl)-[1,2,4]oxadiazol-3-yl]-3-methyl-phenyl}-propanoic acid ethyl ester According to the method described in Preparation Example 1-4, 1-cyclopentyl-1H-indole-5-carboxylic acid (39 mg, 0.17 mmol) obtained from Preparation Example 69-2 and 3-[4-(N-hydroxycarbimidoyl)-3-methyl-phenyl]-propanoic acid ethyl ester (43 mg, 0.17 mmol) obtained from Preparation Example 1-3 were used to obtain the title compound (50 mg, 65%).

EXAMPLE 69

Synthesis of 3-{4-[5-(1-cyclopentyl-1H-indol-5-yl)-[1,2,4]oxadiazol-3-yl]-3-methyl-phenyl}-propanoic acid

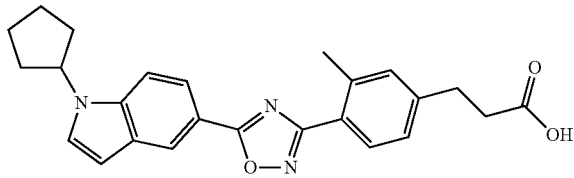 [SMILES: Cc1cc(CCC(=O)O)ccc1-c1noc(-c2ccc3c(ccn3C3CCCC3)c2)n1]

According to the method described in Example 1, 3-{4-[5-(1-cyclopentyl-1H-indol-5-yl)-[1,2,4]oxadiazol-3-yl]-3-methyl-phenyl}-propanoic acid ethyl ester (50 mg, 0.11 mmol) obtained from Preparation Example 69-3 was used to obtain the title compound (39 mg, 85%).

NMR: $^1$H-NMR (400 HMz, DMSO$_{d6}$); δ 8.41 (s, 1H), 7.92 (m, 2H), 7.74 (d, 1H), 7.62 (d, 1H), 7.26 (s, 1H), 7.24 (d, 1H), 6.67 (d, 1H), 4.94 (m, 1H), 2.84 (t, 2H), 2.58 (m, 5H), 2.14 (m, 2H), 1.83 (m, 4H), 1.69 (m, 2H)

PREPARATION EXAMPLE 70-1

Synthesis of 4-amino-3-cyano-5-iodo-benzoic acid methyl ester

4-Amino-3-cyano-benzoic acid methyl ester (1.4 g, 7.95 mmol) was dissolved in a mixed solution of tetrahydrofuran and methanol (1/1, 50 mL), and iodine (I$_2$, 2.2 g, 8.74 mmol) and silver nitrate (AgNO$_3$, 1.5 g, 8.74 mmol) were added dropwise thereto. The mixture was stirred for 6 hours at room temperature and filtered with celite. The filtrate was added with 10% sodium thiosulfate aqueous solution and extracted with ethyl acetate. The extract was washed with brine, dried with anhydrous magnesium sulfate and filtered. The filtrate was distilled under reduced pressure. The residue was separated by column chromatography to obtain the title compound (2.0 g, 84%).

PREPARATION EXAMPLE 70-2

Synthesis of 4-amino-3-cyano-5-prop-1-ynyl-benzoic acid methyl ester

According to the method described in Preparation Example 64-2, 4-amino-3-cyano-5-iodo-benzoic acid methyl ester (2.0 g, 6.62 mmol) obtained from Preparation Example 70-1 and methyl acetylene (530 mg, 13.24 mmol) were used to obtain the title compound (1.4 g, 99%).

NMR: $^1$H-NMR (400 HMz, CDCl$_3$); δ 8.06 (d, J=2.0 Hz, 1H), 8.02 (d, J=2.0 Hz, 1H), 5.32 (br, s, 2H), 3.87 (s, 3H), 2.14 (s, 3H)

PREPARATION EXAMPLE 70-3

Synthesis of 7-cyano-2-methyl-1H-indole-5-carboxylic acid methyl ester

According to the method described in Preparation Example 64-3, 4-amino-3-cyano-5-prop-1-ynyl-benzoic acid methyl ester (1.4 g, 6.54 mmol) obtained from Preparation Example 70-2 was used to obtain the title compound (1.0 g, 71%).

NMR: $^1$H-NMR (400 HMz, CDCl$_3$); δ 8.62 (br, s, 1H), 8.45 (s, 1H), 8.16 (d, J=1.6 Hz, 1H), 6.42 (s, 1H), 3.95 (s, 3H), 2.53 (s, 3H)

PREPARATION EXAMPLE 70-4

Synthesis of 7-cyano-2-methyl-1H-indole-5-carboxylic acid

According to the method described in Preparation Example 1-2, 7-cyano-2-methyl-1H-indole-5-carboxylic acid methyl ester (1.0 g, 4.67 mmol) obtained from Preparation Example 70-3 was used to obtain the title compound (880 mg, 83%).

NMR: $^1$H-NMR (400 HMz, DMSO-d$_6$); δ 12.86 (br, s, 1H), 12.19 (s, 1H), 8.36 (s, 1H), 8.00 (s, 1H), 6.48 (s, 1H), 2.44 (s, 3H)

PREPARATION EXAMPLE 70-5

Synthesis of 3-{4-[5-(7-cyano-2-methyl-1H-indol-5-yl)-[1,2,4]oxadiazol-3-yl]-3-methyl-phenyl}-propanoic acid ethyl ester According to the method described in Preparation Example 1-4, 7-cyano-2-methyl-1H-indole-5-carboxylic acid (200 mg, 0.99 mmol) obtained from Preparation Example 70-4 and 3-[4-(N-hydroxycarbimidoyl)-3-methyl-phenyl]-propanoic acid ethyl ester (250 mg, 0.99 mmol) obtained from Preparation Example 1-3 were used to obtain the title compound (220 mg, 68%).

NMR: $^1$H-NMR (400 HMz, CDCl$_3$); δ 8.69 (br, s, 1H), 8.58 (s, 1H), 8.30 (d, J=1.2 Hz, 1H), 8.03 (d, 1H), 7.19 (br, s, 2H), 6.49 (s, 1H), 4.15 (q, 2H), 3.00 (t, 2H), 2.67 (s, 3H), 2.66 (t, 2H), 2.56 (s, 3H), 1.24 (t, 3H)

EXAMPLE 70

Synthesis of 3-{4-[5-(7-cyano-2-methyl-1H-indol-5-yl)-[1,2,4]oxadiazol-3-yl]-3-methyl-phenyl}-propanoic acid

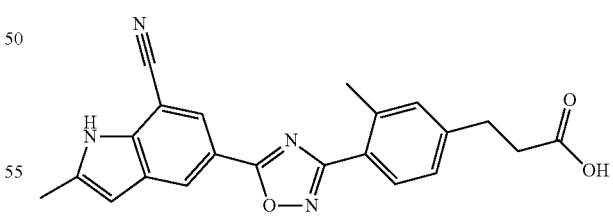

According to the method described in Example 1, 3-{4-[5-(7-cyano-2-methyl-1H-indol-5-yl)-[1,2,4]oxadiazol-3-yl]-3-methyl-phenyl}-propanoic acid ethyl ester (220 mg, 0.68 mmol) obtained from Preparation Example 70-5 was used to obtain the title compound (110 mg, 42%).

NMR: $^1$H-NMR (500 MHz, DMSO-d6) δ 8.57 (d, J=1.2 Hz, 1H), 8.22 (d, J=1.2 Hz, 1H), 7.93 (d, 1H), 7.27 (s, 1H), 7.25 (d, 1H), 6.54 (s, 1H), 2.85 (t, 2H), 2.58-2.55 (m, 5H), 2.44 (s, 3H)

PREPARATION EXAMPLE 71-1

Synthesis of 4-amino-3-cyano-5-cyclopropylethynyl-benzoic acid methyl ester

According to the method described in Preparation Example 64-2, 4-amino-3-cyano-5-iodo-benzoic acid methyl ester (2.0 g, 6.62 mmol) obtained from Preparation Example 70-1 and cyclopropylacetylene (1.12 mL, 13.24 mmol) were used to obtain the title compound (1.7 g, 100%).

NMR: $^1$H-NMR (400 HMz, CDCl$_3$); δ 8.05 (d, J=2.0 Hz, 1H), 8.01 (d, J=2.0 Hz, 1H), 5.31 (br, s, 2H), 3.87 (s, 3H), 1.57-1.48 (m, 1H), 0.98-0.94 (m, 2H), 0.87-0.83 (m, 2H)

PREPARATION EXAMPLE 71-2

Synthesis of 7-cyano-2-cyclopropyl-1H-indole-5-carboxylic acid methyl ester

According to the method described in Preparation Example 64-3, 4-amino-3-cyano-5-cyclopropylethynyl-benzoic acid methyl ester (1.7 g, 7.08 mmol) obtained from Preparation Example 71-1 was used to obtain the title compound (1.2 g, 70%).

NMR: $^1$H-NMR (400 HMz, CDCl$_3$); δ 8.87 (br, s, 1H), 8.42 (s, 1H), 8.15 (d, J=1.6 Hz, 1H), 6.32 (d, J=1.6 Hz, 1H), 3.94 (s, 3H), 2.06-2.00 (m, 1H), 1.12-1.07 (m, 2H), 0.89-0.85 (m, 2H)

PREPARATION EXAMPLE 71-3

Synthesis of 7-cyano-2-cyclopropyl-1H-indole-5-carboxylic acid

According to the method described in Preparation Example 1-2, 7-cyano-2-cyclopropyl-1H-indole-5-carboxylic acid methyl ester (1.2 g, 4.99 mmol) obtained from Preparation Example 71-2 was used to obtain the title compound (1.1 g, 97%).

NMR: $^1$H-NMR (400 HMz, DMSO-d$_6$); δ 12.85 (br, s, 1H), 12.23 (s, 1H), 8.31 (s, 1H), 7.97 (d, J=1.6 Hz, 1H), 6.36 (d, J=1.6 Hz, 1H), 2.13-2.07 (m, 1H), 1.06-0.97 (m, 2H), 0.88-0.84 (m, 2H)

PREPARATION EXAMPLE 71-4

Synthesis of 3-{4-[5-(7-cyano-2-cyclopropyl-1H-indol-5-yl)-[1,2,4]oxadiazol-3-yl]-3-methyl-phenyl}-propanoic acid ethyl ester According to the method described in Preparation Example 1-4, 7-cyano-2-cyclopropyl-1H-indole-5-carboxylic acid (226 mg, 1.0 mmol) obtained from Preparation Example 71-3 and 3-[4-(N-hydroxycarbimidoyl)-3-methyl-phenyl]-propanoic acid ethyl ester (250 mg, 1.0 mmol) obtained from Preparation Example 1-3 were used to obtain the title compound (200 mg, 45%).

NMR: $^1$H-NMR (400 HMz, CDCl$_3$); δ 8.80 (br, s, 1H), 8.55 (s, 1H), 8.29 (d, J=1.6 Hz, 1H), 8.03 (d, 1H), 7.19 (br, s, 2H), 6.38 (d, J=1.6 Hz, 1H), 4.15 (q, 2H), 3.00 (t, 2H), 2.67 (s, 3H), 2.66 (t, 2H), 2.08-2.02 (m, 1H), 1.25 (t, 3H), 1.15-1.10 (m, 2H), 0.92-0.88 (m, 2H)

EXAMPLE 71

Synthesis of 3-{4-[5-(7-cyano-2-cyclopropyl-1H-indol-5-yl)-[1,2,4]oxadiazol-3-yl]-3-methyl-phenyl}-propanoic acid

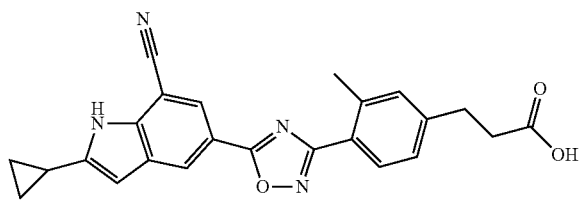 [SMILES: Cc1cc(CCC(=O)O)ccc1-c1noc(-c2cc(C#N)c3[nH]c(C4CC4)cc3c2)n1]

According to the method described in Example 1, 3-{4-[5-(7-cyano-2-cyclopropyl-1H-indol-5-yl)-[1,2,4]oxadiazol-3-yl]-3-methyl-phenyl}-propanoic acid ethyl ester (200 mg, 0.45 mmol) obtained from Preparation Example 71-4 was used to obtain the title compound (130 mg, 55%).

NMR: $^1$H-NMR (500 MHz, DMSO-d6) δ 8.51 (d, 1H), 8.20 (d, 1H), 7.93 (d, 1H), 7.27 (s, 1H), 7.24 (d, 1H), 6.43 (s, 1H), 2.85 (t, 2H), 2.58-2.55 (m, 5H), 2.46 (s, 3H), 2.12-2.09 (m, 1H), 1.04 (q, 2H), 0.87 (q, 2H)

PREPARATION EXAMPLE 72-1

Synthesis of 4-amino-3-cyano-5-trimethylsilanylethynyl-benzoic acid methyl ester According to the method described in Preparation Example 64-2, 4-amino-3-cyano-5-iodo-benzoic acid methyl ester (2.0 g, 6.62 mmol) obtained from Preparation Example 70-1 and trimethylsilylacetylene (1.0 mL, 7.28 mmol) were used to obtain the title compound (2.0 g, 100%).

NMR: $^1$H-NMR (400 HMz, CDCl$_3$); δ 7.94 (d, 1H), 7.87 (d, 1H), 5.18 (s, 2H), 3.69 (s, 3H), 0.15 (s, 9H)

PREPARATION EXAMPLE 72-2

Synthesis of 7-cyano-1H-indole-5-carboxylic acid methyl ester

According to the method described in Preparation Example 64-3, 4-amino-3-cyano-5-trimethylsilanylethynyl-benzoic acid methyl ester (1.3 g, 4.77 mmol) obtained from Preparation Example 72-1 was used to obtain the title compound (570 mg, 60%).

NMR: $^1$H-NMR (400 HMz, CDCl$_3$); δ 9.26 (s, 1H), 8.61 (s, 1H), 8.25 (d, 1H), 7.42 (m, 1H), 6.76 (m, 1H), 3.97 (s, 3H)

PREPARATION EXAMPLE 72-3

Synthesis of 7-cyano-1H-indole-5-carboxylic acid

According to the method described in Preparation Example 1-2, 7-cyano-1H-indole-5-carboxylic acid methyl ester (46 mg, 0.23 mmol) obtained from Preparation Example 72-2 was used to obtain the title compound (39 mg, 92%).

PREPARATION EXAMPLE 72-4

Synthesis of 3-{4-[5-(7-cyano-1H-indol-5-yl)-[1,2,4]oxadiazol-3-yl]-3-methyl-phenyl}-propanoic acid ethyl ester According to the method described in Preparation Example 1-4, 7-cyano-1H-indole-5-carboxylic acid (39 mg, 0.21 mmol) obtained from Preparation Example 72-3 and 3-[4-(N-hydroxycarbimidoyl)-3-methyl-phenyl]-propanoic acid ethyl ester (53 mg, 0.21 mmol) obtained from Preparation Example 1-3 were used to obtain the title compound (50 mg, 57%).

EXAMPLE 72

Synthesis of 3-{4-[5-(7-cyano-1H-indol-5-yl)-[1,2,4]oxadiazol-3-yl]-3-methyl-phenyl}-propanoic acid

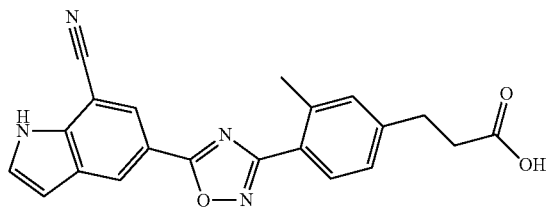 [SMILES: Cc1cc(CCC(=O)O)ccc1-c1noc(-c2cc(C#N)c3[nH]ccc3c2)n1]

According to the method described in Example 1, 3-{4-[5-(7-cyano-1H-indol-5-yl)-[1,2,4]oxadiazol-3-yl]-3-methyl-phenyl}-propanoic acid ethyl ester (50 mg, 0.12 mmol) obtained from Preparation Example 72-4 was used to obtain the title compound (30 mg, 65%).

NMR: $^1$H-NMR (400 HMz, $DMSO_{d6}$); δ 8.71 (s, 1H), 8.32 (s, 1H), 7.92 (d, 1H), 7.90 (d, 1H), 7.26 (s, 1H), 7.24 (d, 1H), 6.92 (d, 1H), 2.84 (t, 2H), 2.56 (m, 5H)

PREPARATION EXAMPLE 73-1

Synthesis of 3-{4-[5-(7-cyano-1-isopropyl-1H-indol-5-yl)-[1,2,4]oxadiazol-3-yl]-3-methyl-phenyl}-propanoic acid ethyl ester According to the method described in Preparation Example 1-1, 3-{4-[5-(7-cyano-1H-indol-5-yl)-[1,2,4]oxadiazol-3-yl]-3-methyl-phenyl}-propanoic acid ethyl ester (92 mg, 0.23 mmol) obtained from Preparation Example 72-4 and isopropyl iodide (46 mg, 0.27 mmol) were used to obtain the title compound (85 mg, 85%).

EXAMPLE 73

Synthesis of 3-{4-[5-(7-cyano-1-isopropyl-1H-indol-5-yl)-[1,2,4]oxadiazol-3-yl]-3-methyl-phenyl}-propanoic acid

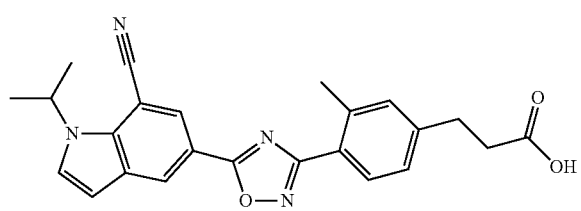 [SMILES: Cc1cc(CCC(=O)O)ccc1-c1noc(-c2cc(C#N)c3c(ccn3C(C)C)c2)n1]

According to the method described in Example 1, 3-{4-[5-(7-cyano-1-isopropyl-1H-indol-5-yl)-[1,2,4]oxadiazol-3-yl]-3-methyl-phenyl}-propanoic acid ethyl ester (50 mg, 0.11 mmol) obtained from Preparation Example 73-1 was used to obtain the title compound (33 mg, 71%).

NMR: $^1$H-NMR (400 HMz, $DMSO_{d6}$); δ 8.71 (s, 1H), 8.32 (s, 1H), 7.92 (d, 1H), 7.90 (d, 1H), 7.26 (s, 1H), 7.24 (d, 1H), 6.92 (d, 1H), 5.34 (m, 1H), 2.84 (t, 2H), 2.56 (m, 5H), 1.55 (d, 6H)

PREPARATION EXAMPLE 74-1

Synthesis of 3-{4-[5-(7-cyano-1-methyl-1H-indol-5-yl)-[1,2,4]oxadiazol-3-yl]-3-methyl-phenyl}-propanoic acid ethyl ester According to the method described in Preparation Example 1-1, 3-{4-[5-(7-cyano-1H-indol-5-yl)-[1,2,4]oxadiazol-3-yl]-3-methyl-phenyl}-propanoic acid ethyl ester (54 mg, 0.18 mmol) obtained from Preparation Example 72-4 and methyl iodide (31 mg, 0.22 mmol) were used to obtain the title compound (65 mg, 85%).

EXAMPLE 74

Synthesis of 3-{4-[5-(7-cyano-1-methyl-1H-indol-5-yl)-[1,2,4]oxadiazol-3-yl]-3-methyl-phenyl}-propanoic acid

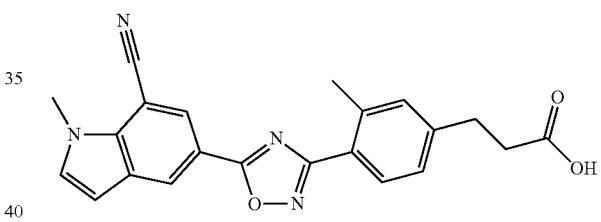

According to the method described in Example 1, 3-{4-[5-(7-cyano-1-methyl-1H-indol-5-yl)-[1,2,4]oxadiazol-3-yl]-3-methyl-phenyl}-propanoic acid ethyl ester (50 mg, 0.12 mmol) obtained from Preparation Example 74-1 was used to obtain the title compound (38 mg, 82%).

NMR: $^1$H-NMR (400 HMz, $DMSO_{d6}$); δ 8.70 (s, 1H), 8.31 (s, 1H), 7.93 (d, 1H), 7.66 (d, 1H), 7.27 (s, 1H), 7.25 (d, 1H), 6.83 (d, 1H), 4.12 (s, 3H), 2.84 (t, 2H), 2.56 (m, 5H)

PREPARATION EXAMPLE 75-1

Synthesis of 3-{5-[5-(3-chloro-1-isopropyl-1H-indol-5-yl)-[1,2,4]oxadiazol-3-yl]-3,4-dihydro-1H-isoquinolin-2-yl}-propanoic acid ethyl ester According to the method described in Preparation Example 29-1, 5-[5-(3-chloro-1-isopropyl-1H-indol-5-yl)-[1,2,4]oxadiazol-3-yl]-1,2,3,4-tetrahydro-isoquinoline, hydrochloride (200 mg, 0.47 mmol) obtained from Example 40 and ethyl acrylate (0.07 mL, 0.70 mmol) were used to obtain the title compound (190 mg, 82%).

NMR: $^1$H-NMR (400 HMz, $CDCl_3$); δ 8.53 (s, 1H), 8.08 (dd, J=1.6 Hz, 1H), 8.02 (d, 1H), 7.49 (d, 1H), 7.30 (t, 1H), 7.29 (s, 1H), 7.18 (d, 1H), 4.75-4.69 (m, 1H), 4.17 (q, 2H), 3.76 (s, 1H), 3.31 (t, 2H), 2.90 (t, 2H), 2.84 (t, 2H), 2.63 (t, 2H), 1.56 (d, 6H), 1.27 (t, 3H)

EXAMPLE 75

Synthesis of 3-{5-[5-(3-chloro-1-isopropyl-1H-indol-5-yl)-[1,2,4]oxadiazol-3-yl]-3,4-dihydro-1H-isoquinolin-2-yl}-propanoic acid, hydrochloride

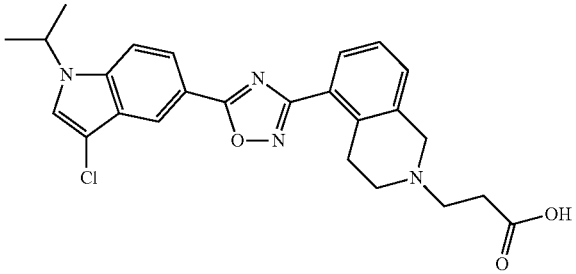 [SMILES: CC(C)n1cc(Cl)c2cc(-c3nc(-c4cccc5c4CCN(CCC(=O)O)C5)no3)ccc21]

According to the method described in Example 1, 3-{5-[5-(3-chloro-1-isopropyl-1H-indol-5-yl)-[1,2,4]oxadiazol-3-yl]-3,4-dihydro-1H-isoquinolin-2-yl}-propanoic acid ethyl ester (190 mg, 0.39 mmol) obtained from Preparation Example 75-1 was used to obtain the title compound (150 mg, 77%).

NMR: $^1$H-NMR (400 MHz, CDCl$_3$) δ 8.33 (d, 1H), 8.10 (d, 1H), 8.04 (d, 1H), 7.99 (s, 1H), 7.91 (d, 1H), 7.54 (t, 1H), 7.46 (d, 1H), 4.94-4.89 (m, 1H), 4.54 (br, s, 2H), 3.47 (d, 2H), 2.91 (t, 2H), 1.49 (d, 6H)

PREPARATION EXAMPLE 76-1

Synthesis of 3-{6-[5-(1-isopropyl-1H-indol-5-yl)-[1,2,4]oxadiazol-3-yl]-5-methyl-3,4-dihydro-1H-isoquinolin-2-yl}-propanoic acid ethyl ester According to the method described in Preparation Example 29-1, 6-[5-(1-isopropyl-1H-indol-5-yl)-[1,2,4]oxadiazol-3-yl]-5-methyl-1,2,3,4-tetrahydro-isoquinoline, hydrochloride (90 mg, 0.22 mmol) obtained from Example 61 and ethyl acrylate (0.036 mL, 0.33 mmol) were used to obtain the title compound (72 mg, 69%).

NMR: $^1$H-NMR (400 HMz, CDCl$_3$); δ 8.53 (s, 1H), 8.05 (dd, 1H), 7.75 (d, 1H), 7.49 (d, 1H), 7.33 (d, 1H), 7.02 (d, 1H), 6.66 (d, 1H), 4.76-4.72 (m, 1H), 4.17 (q, 2H), 3.72 (s, 2H), 2.91-2.83 (m, 6H), 2.63 (t, 2H), 2.51 (s, 3H), 1.57 (d, 6H), 1.27 (t, 3H)

EXAMPLE 76

Synthesis of 3-{6-[5-(1-isopropyl-1H-indol-5-yl)-[1,2,4]oxadiazol-3-yl]-5-methyl-3,4-dihydro-1H-isoquinolin-2-yl}-propanoic acid, hydrochloride

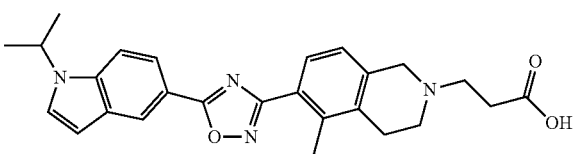 [SMILES: Cc1c(-c2noc(-c3ccc4c(ccn4C(C)C)c3)n2)ccc2c1CCN(CCC(=O)O)C2]

According to the method described in Example 1, 3-{6-[5-(1-isopropyl-1H-indol-5-yl)-[1,2,4]oxadiazol-3-yl]-5-methyl-3,4-dihydro-1H-isoquinolin-2-yl}-propanoic acid ethyl ester (72 mg, 0.15 mmol) obtained from Preparation Example 76-1 was used to obtain the title compound (50 mg, 69%).

NMR: $^1$H-NMR (400 MHz, DMSO-d6) δ 8.45 (s, 1H), 7.93 (d, 1H), 7.80 (q, 2H), 7.72 (d, 1H), 7.25 (d, 1H), 6.73 (d, 1H), 4.90-4.85 (m, 1H), 4.47 (br, s, 2H), 3.42 (br, s, 2H), 3.07 (br s, 2H), 2.87 (br s, 2H), 2.51 (br, s, 5H), 1.50 (d, 6H)

PREPARATION EXAMPLE 77-1

Synthesis of 3-{6-[5-(3-chloro-1-isopropyl-1H-indol-5-yl)-[1,2,4]oxadiazol-3-yl]-5-methyl-3,4-dihydro-1H-isoquinolin-2-yl}-propanoic acid ethyl ester According to the method described in Preparation Example 29-1, 6-[5-(3-chloro-1-isopropyl-1H-indol-5-yl)-[1,2,4]oxadiazol-3-yl]-5-methyl-1,2,3,4-tetrahydro-isoquinoline, hydrochloride (100 mg, 0.23 mmol) obtained from Example 56 and ethyl acrylate (0.04 mL, 0.34 mmol) were used to obtain the title compound (100 mg, 85%).

NMR: $^1$H-NMR (400 HMz, CDCl$_3$); δ 8.53 (s, 1H), 8.08 (dd, 1H), 7.76 (d, 1H), 7.48 (d, 1H), 7.29 (s, 1H), 7.03 (d, 1H), 4.74-4.70 (m, 1H), 4.17 (q, 2H), 3.72 (s, 2H), 2.91-2.83 (m, 6H), 2.63 (t, 2H), 2.52 (s, 3H), 1.56 (d, 6H), 1.27 (t, 3H)

EXAMPLE 77

Synthesis of 3-{6-[5-(3-chloro-1-isopropyl-1H-indol-5-yl)-[1,2,4]oxadiazol-3-yl]-5-methyl-3,4-dihydro-1H-isoquinolin-2-yl}-propanoic acid, hydrochloride

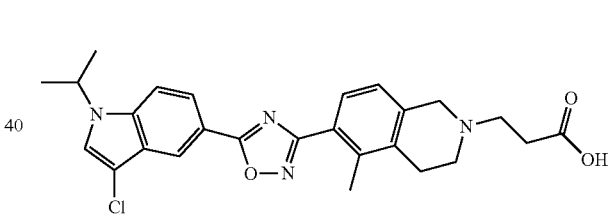

According to the method described in Example 1, 3-{6-[5-(3-chloro-1-isopropyl-1H-indol-5-yl)-[1,2,4]oxadiazol-3-yl]-5-methyl-3,4-dihydro-1H-isoquinolin-2-yl}-propanoic acid ethyl ester (100 mg, 0.20 mmol) obtained from Preparation Example 77-1 was used to obtain the title compound (69 mg, 67%).

NMR: $^1$H-NMR (400 MHz, DMSO-d6) δ 8.32 (d, J=1.6 Hz, 1H), 8.02 (dd, J=1.6 Hz, 1H), 7.99 (s, 1H), 7.90 (d, 1H), 7.84 (d, 1H), 7.25 (d, 1H), 4.94-4.89 (m, 1H), 4.48 (br, s, 2H), 3.42 (br, s, 2H), 3.09 (br s, 2H), 2.88 (t, 2H), 2.54 (br, s 2H), 2.50 (s, 3H), 1.49 (d, 6H)

PREPARATION EXAMPLE 78-1

Synthesis of 4-amino-3-iodo-5-methoxy-benzoic acid methyl ester

The title compound was obtained according to the method described in Tetrahedron, 63(2007), 347-355.

NMR: $^1$H-NMR (400 HMz, CDCl$_3$); δ 8.04 (d, 1H), 7.44 (d, 1H), 4.74 (s, 2H), 3.94 (s, 3H), 3.91 (s, 3H)

PREPARATION EXAMPLE 78-2

Synthesis of
4-amino-3-methoxy-5-prop-1-ynyl-benzoic acid
methyl ester

According to the method described in Preparation Example 64-2, 4-amino-3-iodo-5-methoxy-benzoic acid methyl ester (1.0 g, 3.26 mmol) obtained from Preparation Example 78-1 and methyl acetylene (260 mg, 6.51 mmol) were used to obtain the title compound (630 mg, 88%).
NMR: $^1$H-NMR (400 HMz, CDCl$_3$); δ 7.65 (s, 1H), 7.35 (s, 1H), 4.73 (s, 2H), 3.88 (s, 3H), 3.84 (s, 3H), 2.10 (s, 3H)

PREPARATION EXAMPLE 78-3

Synthesis of
7-methoxy-2-methyl-1H-indole-5-carboxylic acid
methyl ester

4-Amino-3-methoxy-5-prop-1-ynyl-benzoic acid methyl ester (480 mg, 2.19 mmol) obtained from Preparation Example 78-2 was dissolved in pyridine (6 mL) and then acetylchloride (0.31 mL, 4.38 mmol) was added dropwise thereto at 0° C. The mixture was heated slowly to room temperature and stirred for 3 hours. The solvent was removed by distillation under reduced pressure. The residue was added with 1N hydrochloric acid aqueous solution and extracted with ethyl acetate. The extract was washed with brine, dried with anhydrous magnesium sulfate and filtered. The filtrate was distilled under reduced pressure. The residue was dissolved in tetrahydrofuran (20 mL) and then 1.0 M tetrabutylammonium fluoride solution in tetrahydrofuran (2.6 mL, 2.62 mmol) was added dropwise thereto. The mixture was stirred for 18 hours under reflux, added with water and extracted with ethyl acetate. The extract was washed with brine, dried with anhydrous magnesium sulfate and filtered. The filtrate was distilled under reduced pressure. The residue was separated by column chromatography to obtain the title compound (110 mg, 23%).
NMR: $^1$H-NMR (400 HMz, CDCl$_3$); δ 8.26 (s, 1H), 7.94 (s, 1H), 7.28 (s, 1H), 6.27 (s, 1H), 3.98 (s, 3H), 3.92 (s, 3H), 2.45 (s, 3H)

PREPARATION EXAMPLE 78-4

Synthesis of
7-methoxy-2-methyl-1H-indole-5-carboxylic acid

According to the method described in Preparation Example 1-2, 7-methoxy-2-methyl-1H-indole-5-carboxylic acid methyl ester (110 mg, 0.50 mmol) obtained from Preparation Example 78-3 was used to obtain the title compound (93 mg, 90%).

PREPARATION EXAMPLE 78-5

Synthesis of 3-{4-[5-(7-methoxy-2-methyl-1H-indol-5-yl)-[1,2,4]oxadiazol-3-yl]-3-methyl-phenyl}-propanoic acid ethyl ester According to the method described in Preparation Example 1-4, 7-methoxy-2-methyl-1H-indole-5-carboxylic acid (93 mg, 0.45 mmol) obtained from Preparation Example 78-4 and 3-[4-(N-hydroxycarbimidoyl)-3-methyl-phenyl]-propanoic acid ethyl ester (113 mg, 0.45 mmol) obtained from Preparation Example 1-3 were used to obtain the title compound (119 mg, 63%).

EXAMPLE 78

Synthesis of 3-{4-[5-(7-methoxy-2-methyl-1H-indol-5-yl)-[1,2,4]oxadiazol-3-yl]-3-methyl-phenyl}-propanoic acid

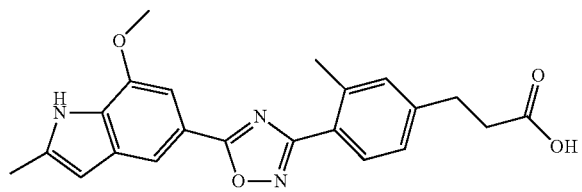 [SMILES: COc1cc(-c2nc(-c3ccc(CCC(=O)O)cc3C)no2)cc2cc(C)[nH]c12]

According to the method described in Example 1, 3-{4-[5-(7-methoxy-2-methyl-1H-indol-5-yl)-[1,2,4]oxadiazol-3-yl]-3-methyl-phenyl}-propanoic acid ethyl ester (50 mg, 0.12 mmol) obtained from Preparation Example 78-5 was used to obtain the title compound (34 mg, 72%).
NMR: $^1$H-NMR (400 HMz, DMSO$_{d6}$); δ 11.54 (s, 1H), 7.92 (m, 2H), 7.24 (m, 3H), 6.29 (s, 1H), 4.00 (s, 3H), 2.84 (t, 2H), 2.55 (m, 5H), 2.35 (s, 3H)

PREPARATION EXAMPLE 79-1

Synthesis of
4-amino-3-chloro-5-trimethylsilanylethynyl-benzoic
acid methyl ester According to the method described in Preparation Example 64-2, 4-amino-3-chloro-5-iodo-benzoic acid methyl ester (2.1 g, 6.74 mmol) obtained from Preparation Example 64-1 and trimethylsilylacetylene (1.0 mL, 7.41 mmol) were used to obtain the title compound the title compound (1.9 g, 100%).
NMR: $^1$H-NMR (400 HMz, CDCl$_3$); δ 7.73 (d, 1H), 7.72 (d, 1H), 4.85 (s, 2H), 3.67 (s, 3H), 0.08 (s, 9H)

PREPARATION EXAMPLE 79-2

Synthesis of 7-chloro-1H-indole-5-carboxylic acid
methyl ester

According to the method described in Preparation Example 64-3, 4-amino-3-chloro-5-trimethylsilanylethynyl-benzoic acid methyl ester (1.3 g, 4.61 mmol) obtained from Preparation Example 79-1 was used to obtain the title compound (800 mg, 83%).
NMR: $^1$H-NMR (400 HMz, DMSO$_{d6}$); δ 11.92 (s, 1H), 8.25 (s, 1H), 7.72 (s, 1H), 7.56 (d, 1H), 6.74 (d, 1H), 3.86 (s, 3H),

PREPARATION EXAMPLE 79-3

Synthesis of 7-chloro-1H-indole-5-carboxylic acid

According to the method described in Preparation Example 1-2, 7-chloro-1H-indole-5-carboxylic acid methyl ester (800 mg, 3.82 mmol) obtained from Preparation Example 79-2 was used to obtain the title compound (650 mg, 87%).

PREPARATION EXAMPLE 79-4

Synthesis of 3-{4-[5-(7-chloro-1H-indol-5-yl)-[1,2,4]oxadiazol-3-yl]-3-methyl-phenyl}-propanoic acid ethyl ester According to the method described in Preparation Example 1-4, 7-chloro-1H-indole-5-carboxylic acid (650 mg, 3.32 mmol) obtained from Preparation Example 79-3 and 3-[4-(N-hydroxycarbimidoyl)-3-methyl-phenyl]-propanoic acid ethyl ester (831 mg, 3.32 mmol) obtained from Preparation Example 1-3 were used to obtain the title compound (762 mg, 56%).

PREPARATION EXAMPLE 79-5

Synthesis of 3-{4-[5-(7-chloro-1-isopropyl-1H-indol-5-yl)-[1,2,4]oxadiazol-3-yl]-3-methyl-phenyl}-propanoic acid ethyl ester According to the method described in Preparation Example 1-1, 3-{4-[5-(7-chloro-1H-indol-5-yl)-[1,2,4]oxadiazol-3-yl]-3-methyl-phenyl}-propanoic acid ethyl ester (60 mg, 0.15 mmol) obtained from Preparation Example 79-4 and isopropyl iodide (29 mg, 0.17 mmol) were used to obtain the title compound (56 mg, 85%).

EXAMPLE 79

Synthesis of 3-{4-[5-(7-chloro-1-isopropyl-1H-indol-5-yl)-[1,2,4]oxadiazol-3-yl]-3-methyl-phenyl}-propanoic acid

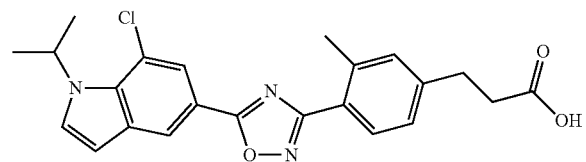 [SMILES: Cc1cc(CCC(=O)O)ccc1-c1noc(-c2cc(Cl)c3c(ccn3C(C)C)c2)n1]

According to the method described in Example 1, 3-{4-[5-(7-chloro-1-isopropyl-1H-indol-5-yl)-[1,2,4]oxadiazol-3-yl]-3-methyl-phenyl}-propanoic acid ethyl ester (56 mg, 0.12 mmol) obtained from Preparation Example 79-5 was used to obtain the title compound (34 mg, 83%).

NMR: $^1$H-NMR (400 HMz, MeOD); δ 8.22 (s, 1H), 7.93 (d, 1H), 7.80 (s, 1H), 7.55 (d, 1H), 7.17 (m, 2H), 6.66 (d, 1H), 5.69 (m, 1H), 2.92 (t, 2H), 2.63 (t, 2H), 2.59 (s, 3H), 1.54 (d, 6H)

PREPARATION EXAMPLE 80-1

Synthesis of 1H-indazole-5-carboxylic acid methyl ester

4-Amino-3-methyl-benzoic acid methyl ester (2.0 g, 12.03 mmol) was dissolved in chloroform (25 mL) and then acetic anhydride (2.12 g, 30.07 mmol) was slowly added dropwise thereto at 0° C. The mixture was stirred for 1 hour at room temperature, and potassium acetate (250 mg, 3.61 mmol) and isoamyl nitrite (2.23 mL, 24.06 mmol) were added thereto. The mixture was stirred under reflux for 18 hours at 70° C. and added with excess dichloromethane. The mixture was washed with saturated sodium hydrogen carbonate aqueous solution, dried with anhydrous magnesium sulfate and filtered. The filtrate was distilled under reduced pressure. The residue was separated by column chromatography to obtain the intermediate acetyl indazole (1.2 g, 5.50 mmol).

The obtained acetyl indazole (1.2 g, 5.50 mmol) was dissolved in a mixed solution of tetrahydrofuran and methanol (1/1, 20 mL) and then 6N sodium hydroxide aqueous solution (1.8 mL) was added dropwise thereto. The mixture was stirred for 10 minutes at room temperature and acidified with 6N hydrochloric acid aqueous solution. The mixture was extracted with dichloromethane. The extract was dried with anhydrous magnesium sulfate and distilled under reduced pressure to obtain the title compound (1.0 g, 47%).

NMR: $^1$H-NMR (400 HMz, CDCl$_3$); δ 9.72 (br, s, 1H), 8.59 (s, 1H), 8.27 (s, 1H), 8.14 (dd, J=1.2 Hz, 1H), 7.60 (d, 1H), 3.97 (s, 3H)

PREPARATION EXAMPLE 80-2

Synthesis of 1-isopropyl-1H-indazole-5-carboxylic acid methyl ester and 2-isopropyl-2H-indazole-5-carboxylic acid methyl ester According to the method described in Preparation Example 1-1, 1H-indazole-5-carboxylic acid methyl ester (1.0 g, 5.68 mmol) obtained from Preparation Example 80-1 and isopropyl iodide (1.7 mL, 17.03 mmol) were used to obtain 1-isopropyl-1H-indazole-5-carboxylic acid methyl ester (680 mg, 55%) which passed firstly through column chromatography and 2-isopropyl-2H-indazole-5-carboxylic acid methyl ester (320 mg, 26%) which passed secondly through column chromatography.

NMR: $^1$H-NMR (400 HMz, CDCl$_3$); δ 8.51 (s, 1H), 8.11 (s, 1H), 8.02 (dd, J=1.6 Hz, 1H), 7.45 (d, 1H), 4.90-4.84 (m, 1H), 3.95 (s, 3H), 1.61 (d, 6H)

NMR: $^1$H-NMR (400 HMz, CDCl$_3$); δ 8.50 (s, 1H), 8.10 (s, 1H), 7.90 (d, 1H), 7.71 (d, 1H), 4.85-4.79 (m, 1H), 3.94 (s, 3H), 1.68 (d, 6H)

Preparation Example 80-3

Synthesis of 1-isopropyl-1H-indazole-5-carboxylic acid

According to the method described in Preparation Example 1-2, 1-isopropyl-1H-indazole-5-carboxylic acid methyl ester (680 mg, 3.12 mmol) obtained from Preparation Example 80-2 was used to obtain the title compound (610 mg, 96%).

NMR: $^1$H-NMR (400 HMz, CDCl$_3$); δ 8.62 (s, 1H), 8.16 (s, 1H), 8.11 (dd, J=1.2, 1.6 Hz, 1H), 7.49 (d, 1H), 4.93-4.86 (m, 1H), 1.63 (d, 6H)

Preparation Example 80-4

Synthesis of 3-{4-[5-(1-isopropyl-1H-indazol-5-yl)-[1,2,4]oxadiazol-3-yl]-3-methyl-phenyl}-propanoic acid ethyl ester According to the method described in Preparation Example 1-4, 1-isopropyl-1H-indazole-5-carboxylic acid (100 mg, 0.49 mmol) obtained from Preparation Example 80-3 and 3-[4-(N-hydroxycarbimidoyl)-3-methyl-phenyl]-propanoic acid ethyl ester (123 mg, 0.49 mmol) obtained from Preparation Example 1-3 were used to obtain the title compound (180 mg, 88%).

NMR: ¹H-NMR (400 HMz, CDCl₃); δ 8.66 (s, 1H), 8.20 (dd, J=1.6 Hz, 1H), 8.17 (s, 1H), 8.04 (d, 1H), 7.58 (d, 1H), 7.19 (br, s, 2H), 4.94-4.88 (m, 1H), 4.15 (q, 2H), 3.00 (t, 2H), 2.68 (s, 3H), 2.66 (t, 2H), 1.64 (d, 6H), 1.25 (t, 3H)

Example 80

Synthesis of 3-{4-[5-(1-isopropyl-1H-indazol-5-yl)-[1,2,4]oxadiazol-3-yl]-3-methyl-phenyl}-propanoic acid

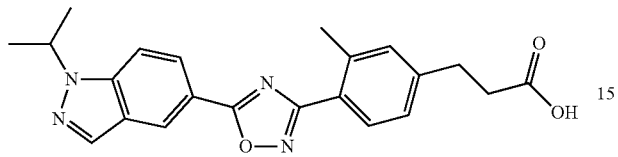

According to the method described in Example 1, 3-{4-[5-(1-isopropyl-1H-indazol-5-yl)-[1,2,4]oxadiazol-3-yl]-3-methyl-phenyl}-propanoic acid ethyl ester (180 mg, 0.43 mmol) obtained from Preparation Example 80-4 was used to obtain the title compound (145 mg, 86%).

NMR: ¹H-NMR (400 MHz, CDCl₃) δ 8.66 (s, 1H), 8.20 (d, 1H), 8.17 (s, 1H), 8.05 (d, 1H), 7.57 (d, 1H), 7.21 (d, 2H), 4.93-4.88 (m, 1H), 3.02 (t, 2H), 2.74 (t, 2H), 2.68 (s, 3H), 1.64 (d, 6H)

Preparation Example 81-1

Synthesis of 5-(N-hydroxycarbimidoyl)-1,3-dihydro-isoindole-2-carboxylic acid t-butyl ester The title compound was obtained according to the method described in WO 2010042998 A1.

Preparation Example 81-2

Synthesis of 5-[5-(1-isopropyl-1H-indol-5-yl)-[1,2,4]oxadiazol-3-yl]-1,3-dihydro-isoindole-2-carboxylic acid t-butyl ester According to the method described in Preparation Example 1-4, 1-isopropyl-1H-indole-5-carboxylic acid (100 mg, 0.49 mmol) obtained from Preparation Example 1-2 and 5-(N-hydroxycarbimidoyl)-1,3-dihydro-isoindole-2-carboxylic acid t-butyl ester (135 mg, 0.49 mmol) obtained from Preparation Example 81-1 were used to obtain the title compound (163 mg, 75%).

Preparation Example 81-3

Synthesis of 5-[3-(2,3-dihydro-1H-isoindol-5-yl)-[1,2,4]oxadiazol-5-yl]-1-isopropyl-1H-indole, hydrochloride According to the method described in Example 27, 5-[5-(1-isopropyl-1H-indol-5-yl)-[1,2,4]oxadiazol-3-yl]-1,3-dihydro-isoindole-2-carboxylic acid t-butyl ester (163 mg, 0.37 mmol) obtained from Preparation Example 81-2 was used to obtain the title compound (113 mg, 89%).

Preparation Example 81-4

Synthesis of {5-[5-(1-isopropyl-1H-indol-5-yl)-[1,2,4]oxadiazol-3-yl]-1,3-dihydro-isoindol-2-yl}-acetic acid ethyl ester According to the method described in Preparation Example 28-1, 5-[3-(2,3-dihydro-1H-isoindol-5-yl)-[1,2,4] oxadiazol-5-yl]-1-isopropyl-1H-indole, hydrochloride (113 mg, 0.33 mmol) obtained from Preparation Example 81-3 and ethyl bromoacetate (0.07 mL, 0.66 mmol) were used to obtain the title compound (112 mg, 79%).

NMR: ¹H-NMR (400 HMz, CDCl₃); δ 8.53 (s, 1H), 8.05 (m, 3H), 7.48 (d, 1H), 7.33 (m, 2H), 6.66 (d, 1H), 4.73 (m, 1H), 4.23 (m, 6H), 3.64 (s, 2H), 1.56 (d, 6H), 1.32 (t, 3H)

Example 81

Synthesis of {5-[5-(1-isopropyl-1H-indol-5-yl)-[1,2,4]oxadiazol-3-yl]-1,3-dihydro-isoindol-2-yl}-acetic acid

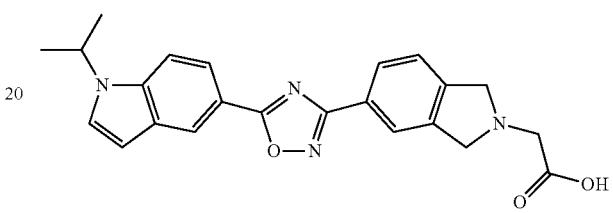

According to the method described in Example 1, {5-[5-(1-isopropyl-1H-indol-5-yl)-[1,2,4]oxadiazol-3-yl]-1,3-dihydro-isoindol-2-yl}-acetic acid ethyl ester (50 mg, 0.12 mmol) obtained from Preparation Example 81-4 was used to obtain the title compound (42 mg, 86%).

NMR: ¹H-NMR (400 HMz, DMSO_{d6}); δ 8.45 (s, 1H), 7.95 (m, 3H), 7.77 (d, 1H), 7.72 (d, 1H), 7.48 (d, 1H), 6.72 (d, 1H), 4.87 (m, 1H), 4.19 (m, 4H), 3.52 (s, 2H), 1.50 (d, 6H)

Preparation Example 82-1

Synthesis of 2-isopropyl-2H-indazole-5-carboxylic acid

According to the method described in Preparation Example 1-2, 2-isopropyl-2H-indazole-5-carboxylic acid methyl ester (320 mg, 1.47 mmol) obtained from Preparation Example 80-2 was used to obtain the title compound (310 mg, 100%).

NMR: ¹H-NMR (400 HMz, CDCl₃); δ 8.61 (s, 1H), 8.15 (s, 1H), 7.96 (dd, J=1.6 Hz, 1H), 7.76 (d, 1H), 4.89-4.82 (m, 1H), 1.70 (d, 6H)

Preparation Example 82-2

Synthesis of 3-{4-[5-(2-isopropyl-2H-indazol-5-yl)-[1,2,4]oxadiazol-3-yl]-3-methyl-phenyl}-propanoic acid ethyl ester According to the method described in Preparation Example 1-4, 2-isopropyl-2H-indazole-5-carboxylic acid (100 mg, 0.49 mmol) obtained from Preparation Example 82-1 and 3-[4-(N-hydroxycarbimidoyl)-3-methyl-phenyl]-propanoic acid ethyl ester (123 mg, 0.49 mmol) obtained from Preparation Example 1-3 were used to obtain the title compound (60 mg, 29%).

NMR: ¹H-NMR (400 HMz, CDCl₃); δ 8.64 (s, 1H), 8.16 (s, 1H), 8.07 (dd, J=1.6 Hz, 1H), 8.04 (d, 1H), 7.85 (d, 1H), 7.19 (br, s, 2H), 4.88-4.82 (m, 1H), 4.15 (q, 2H), 2.99 (t, 2H), 2.68 (s, 3H), 2.66 (t, 2H), 1.70 (d, 6H), 1.25 (t, 3H)

Example 82

Synthesis of 3-{4-[5-(2-isopropyl-2H-indazol-5-yl)-[1,2,4]oxadiazol-3-yl]-3-methyl-phenyl}-propanoic acid

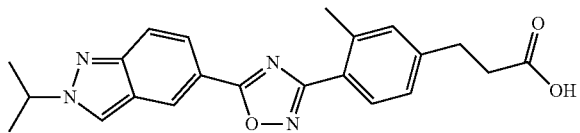 [SMILES: Cc1cc(CCC(=O)O)ccc1-c1noc(-c2ccc3nn(C(C)C)cc3c2)n1]

According to the method described in Example 1, 3-{4-[5-(2-isopropyl-2H-indazol-5-yl)-[1,2,4]oxadiazol-3-yl]-3-methyl-phenyl}-propanoic acid ethyl ester (60 mg, 0.14 mmol) obtained from Preparation Example 82-2 was used to obtain the title compound (37 mg, 68%).

NMR: $^1$H-NMR (400 MHz, CDCl$_3$) δ 8.64 (s, 1H), 8.16 (s, 1H), 8.08 (dd, J=1.2 Hz, 1H), 8.05 (d, 1H), 7.85 (d, 1H), 7.21 (d, 2H), 4.89-4.82 (m, 1H), 3.02 (t, 2H), 2.74 (t, 2H), 2.68 (s, 3H), 1.71 (d, 6H)

Preparation Example 83-1

Synthesis of {5-[5-(1-isopropyl-1H-indazol-5-yl)-[1,2,4]oxadiazol-3-yl]-3,4-dihydro-1H-isoquinolin-2-yl}-acetic acid ethyl ester According to the method described in Preparation Example 28-1, 5-[5-(1-isopropyl-1H-indazol-5-yl)-[1,2,4]oxadiazol-3-yl]-1,2,3,4-tetrahydro-isoquinoline, hydrochloride (100 mg, 0.25 mmol) obtained from Example 96 and ethyl bromoacetate (0.04 mL, 0.38 mmol) were used to obtain the title compound (107 mg, 95%).

NMR: $^1$H-NMR (400 HMz, CDCl$_3$); δ 8.65 (s, 1H), 8.19 (dd, 1H), 8.17 (s, 1H), 8.02 (d, 1H), 7.57 (d, 1H), 7.29 (d, 1H), 7.19 (d, 1H), 4.95-4.90 (m, 1H), 4.24 (q, 2H), 3.91 (s, 2H), 3.45 (s, 2H), 3.36 (t, 2H), 2.96 (t, 2H), 1.64 (d, 6H), 1.31 (t, 3H)

Example 83

Synthesis of {5-[5-(1-isopropyl-1H-indazol-5-yl)-[1,2,4]oxadiazol-3-yl]-3,4-dihydro-1H-isoquinolin-2-yl}-acetic acid

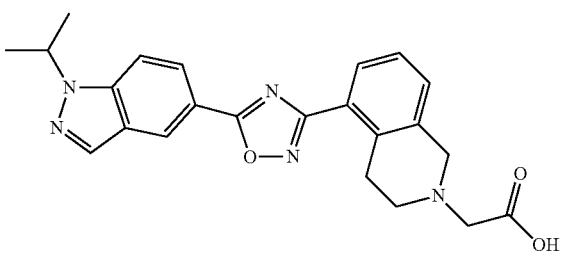 [SMILES: CC(C)n1ncc2cc(-c3nc(-c4cccc5c4CCN(CC(=O)O)C5)no3)ccc21]

According to the method described in Example 1, {5-[5-(1-isopropyl-1H-indazol-5-yl)-[1,2,4]oxadiazol-3-yl]-3,4-dihydro-1H-isoquinolin-2-yl}-acetic acid ethyl ester (97 mg, 0.22 mmol) obtained from Preparation Example 83-1 was used to obtain the title compound (30 mg, 33%).

NMR: $^1$H-NMR (400 MHz, DMSO-d6) δ 8.71 (s, 1H), 8.35 (s, 1H), 8.15 (d, 2H), 7.99 (t, 2H), 7.46-7.38 (m, 2H), 5.13-5.08 (m, 1H), 4.14 (br, s, 2H), 3.72 (br, s, 2H), 3.30 (br s, 4H), 1.53 (d, 6H)

Preparation Example 84-1

Synthesis of 3-{5-[5-(1-isopropyl-1H-indazol-5-yl)-[1,2,4]oxadiazol-3-yl]-3,4-dihydro-1H-isoquinolin-2-yl}-propanoic acid ethyl ester According to the method described in Preparation Example 29-1, 5-[5-(1-isopropyl-1H-indazol-5-yl)-[1,2,4]oxadiazol-3-yl]-1,2,3,4-tetrahydro-isoquinoline, hydrochloride (100 mg, 0.25 mmol) obtained from Example 96 and ethyl acrylate (0.04 mL, 0.38 mmol) were used to obtain the title compound (100 mg, 86%).

NMR: $^1$H-NMR (400 HMz, CDCl$_3$); δ 8.65 (s, 1H), 8.20 (dd, J=1.6 Hz, 1H), 8.17 (s, 1H), 8.01 (d, 1H), 7.58 (d, 1H), 7.30 (t, 1H), 7.19 (d, 1H), 4.94-4.88 (m, 1H), 4.17 (q, 2H), 3.76 (s, 2H), 3.31 (t, 2H), 2.90 (t, 2H), 2.83 (t, 2H), 2.63 (t, 2H), 1.64 (d, 6H), 1.27 (t, 3H)

Example 84

Synthesis of 3-{5-[5-(1-isopropyl-1H-indazol-5-yl)-[1,2,4]oxadiazol-3-yl]-3,4-dihydro-1H-isoquinolin-2-yl}-propanoic acid

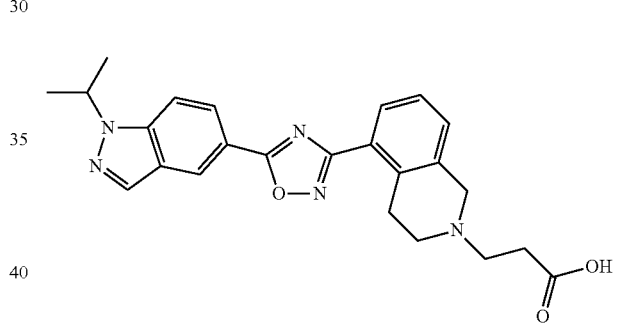

According to the method described in Example 1, 3-{5-[5-(1-isopropyl-1H-indazol-5-yl)-[1,2,4]oxadiazol-3-yl]-3,4-dihydro-1H-isoquinolin-2-yl}-propanoic acid ethyl ester (111 mg, 0.24 mmol) obtained from Preparation Example 84-1 was used to obtain the title compound (62 mg, 59%).

NMR: $^1$H-NMR (400 MHz, DMSO-d6) δ 8.71 (s, 1H), 8.35 (s, 1H), 8.14 (dd, 2H), 7.97 (d, 2H), 7.42 (t, 1H), 7.36 (d, 1H), 5.14-5.08 (m, 1H), 3.93 (br, s, 2H), 3.32 (br, s, 2H), 3.22 (br s, 2H), 2.94 (br, s, 2H), 2.61 (t, 2H), 1.52 (d, 6H)

Preparation Example 85-1

Synthesis of {6-[5-(1-isopropyl-1H-indazol-5-yl)-[1,2,4]oxadiazol-3-yl]-5-methyl-3,4-dihydro-1H-isoquinolin-2-yl}-acetic acid t-butyl ester According to the method described in Preparation Example 28-1, 6-[5-(1-isopropyl-1H-indazol-5-yl)-[1,2,4]oxadiazol-3-yl]-5-methyl-1,2,3,4-tetrahydro-isoquinoline, hydrochloride (104 mg, 0.25 mmol) obtained from Example 89 and t-butyl bromoacetate (0.06 mL, 0.38 mmol) were used to obtain the title compound (110 mg, 89%).

NMR: $^1$H-NMR (400 HMz, CDCl$_3$); δ 8.66 (s, 1H), 8.20 (dd, 1H), 8.16 (s, 1H), 7.75 (d, 1H), 7.57 (d, 1H), 7.02 (d,

1H), 4.93-4.89 (m, 1H), 3.86 (s, 2H), 3.34 (s, 2H), 2.95 (t, 2H), 2.90 (t, 2H), 2.52 (s, 3H), 1.64 (d, 6H), 1.51 (s, 9H)

Example 85

Synthesis of {6-[5-(1-isopropyl-1H-indazol-5-yl)-[1,2,4]oxadiazol-3-yl]-5-methyl-3,4-dihydro-1H-isoquinolin-2-yl}-acetic acid, trifluoroacetate

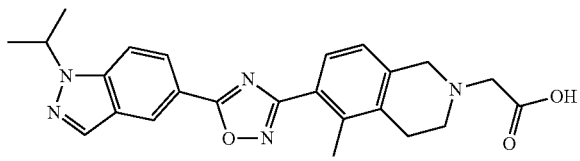

According to the method described in Example 5, {6-[5-(1-isopropyl-1H-indazol-5-yl)-[1,2,4]oxadiazol-3-yl]-5-methyl-3,4-dihydro-1H-isoquinolin-2-yl}-acetic acid t-butyl ester (110 mg, 0.23 mmol) obtained from Preparation Example 85-1 was used to obtain the title compound (76 mg, 62%).

NMR: $^1$H-NMR (500 MHz, DMSO-d6) δ 8.66 (s, 1H), 8.31 (s, 1H), 8.09 (d, 1H), 7.94 (d, 1H), 7.71 (d, 1H), 7.16 (d, 1H), 5.09-5.05 (m, 1H), 4.12 (br, s, 2H), 3.74 (br, s, 2H), 3.21 (br s, 2H), 2.92 (br s, 2H), 2.44 (s, 3H), 1.48 (d, 6H)

Preparation Example 86-1

Synthesis of 3-{6-[5-(1-isopropyl-1H-indazol-5-yl)-[1,2,4]oxadiazol-3-yl]-5-methyl-3,4-dihydro-1H-isoquinolin-2-yl}-propanoic acid t-butyl ester According to the method described in Preparation Example 29-1, 6-[5-(1-isopropyl-1H-indazol-5-yl)-[1,2,4]oxadiazol-3-yl]-5-methyl-1,2,3,4-tetrahydro-isoquinoline, hydrochloride (104 mg, 0.25 mmol) obtained from Example 89 and t-butyl acrylate (0.06 mL, 0.38 mmol) were used to obtain the title compound (79 mg, 62%).

NMR: $^1$H-NMR (400 HMz, CDCl$_3$); δ 8.65 (s, 1H), 8.19 (dd, J=1.6 Hz, 1H), 8.16 (s, 1H), 7.75 (d, 1H), 7.57 (d, 1H), 7.02 (d, 1H), 4.93-4.89 (m, 1H), 3.71 (s, 2H), 2.87-2.82 (m, 6H), 2.55 (t, 2H), 2.52 (s, 3H), 1.64 (d, 6H), 1.46 (s, 9H)

Example 86

Synthesis of 3-{6-[5-(1-isopropyl-1H-indazol-5-yl)-[1,2,4]oxadiazol-3-yl]-5-methyl-3,4-dihydro-1H-isoquinolin-2-yl}-propanoic acid, trifluoroacetate

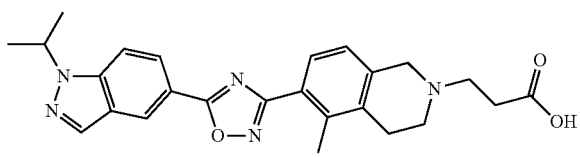

According to the method described in Example 5, 3-{6-[5-(1-isopropyl-1H-indazol-5-yl)-[1,2,4]oxadiazol-3-yl]-5-methyl-3,4-dihydro-1H-isoquinolin-2-yl}-propanoic acid t-butyl ester (79 mg, 0.16 mmol) obtained from Preparation Example 86-1 was used to obtain the title compound (85 mg, 96%).

NMR: $^1$H-NMR (500 MHz, DMSO-d6) δ 8.66 (s, 1H), 8.31 (s, 1H), 8.09 (d, 1H), 7.94 (d, 1H), 7.79 (d, 1H), 7.22 (d, 1H), 5.09-5.05 (m, 1H), 4.48 (br, s, 2H), 3.42 (br, s, 2H), 3.34 (br, d, 2H), 3.05 (br, s, 2H), 2.83 (t, 2H), 2.46 (s, 3H), 1.48 (d, 6H)

Preparation Example 87-1

Synthesis of {5-[5-(2-isopropyl-2H-indazol-5-yl)-[1,2,4]oxadiazol-3-yl]-3,4-dihydro-1H-isoquinolin-2-yl}-acetic acid t-butyl ester According to the method described in Preparation Example 28-1, 5-[5-(2-isopropyl-2H-indazol-5-yl)-[1,2,4]oxadiazol-3-yl]-1,2,3,4-tetrahydro-isoquinoline, hydrochloride (100 mg, 0.25 mmol) obtained from Example 90 and t-butyl bromoacetate (0.06 mL, 0.38 mmol) were used to obtain the title compound (100 mg, 84%).

NMR: $^1$H-NMR (400 HMz, CDCl$_3$); δ 8.64 (s, 1H), 8.16 (s, 1H), 8.07 (dd, J=1.6 Hz, 1H), 8.01 (d, 1H), 7.84 (d, 1H), 7.29 (t, 1H), 7.18 (d, 1H), 4.87-4.82 (m, 1H), 3.90 (s, 2H), 3.35 (t, 4H) 2.96 (t, 2H), 1.71 (d, 6H), 1.50 (s, 9H)

Example 87

Synthesis of {5-[5-(2-isopropyl-2H-indazol-5-yl)-[1,2,4]oxadiazol-3-yl]-3,4-dihydro-1H-isoquinolin-2-yl}-acetic acid, trifluoroacetate

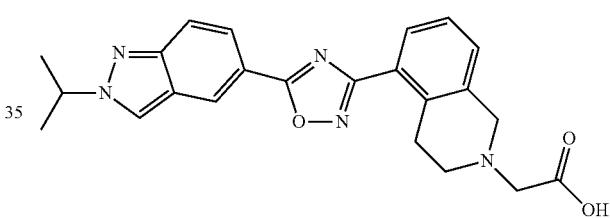

According to the method described in Example 5, {5-[5-(2-isopropyl-2H-indazol-5-yl)-[1,2,4]oxadiazol-3-yl]-3,4-dihydro-1H-isoquinolin-2-yl}-acetic acid t-butyl ester (100 mg, 0.21 mmol) obtained from Preparation Example 87-1 was used to obtain the title compound (88 mg, 78%).

NMR: $^1$H-NMR (400 MHz, DMSO-d6) δ 8.73 (d, 2H), 8.04 (d, 1H), 7.97 (dd, J=1.2 Hz, 1H), 7.86 (d, 1H), 7.51-7.44 (m, 2H), 4.96-4.90 (m, 1H), 4.40 (br, s, 2H), 4.03 (br, s, 2H), 3.41 (br, s, 4H), 1.60 (d, 6H)

Preparation Example 88-1

Synthesis of 3-{5-[5-(2-isopropyl-2H-indazol-5-yl)-[1,2,4]oxadiazol-3-yl]-3,4-dihydro-1H-isoquinolin-2-yl}-propanoic acid t-butyl ester According to the method described in Preparation Example 29-1, 5-[5-(2-isopropyl-2H-indazol-5-yl)-[1,2,4]oxadiazol-3-yl]-1,2,3,4-tetrahydro-isoquinoline, hydrochloride (100 mg, 0.24 mmol) obtained from Example 90 and t-butyl acrylate (0.05 mL, 0.37 mmol) were used to obtain the title compound (85 mg, 71%).

NMR: $^1$H-NMR (400 HMz, CDCl$_3$); δ 8.63 (s, 1H), 8.16 (s, 1H), 8.07 (dd, J=1.2, 1.6 Hz, 1H), 8.00 (d, 1H), 7.85 (d, 1H), 7.30 (t, 1H), 7.18 (d, 1H), 4.87-4.82 (m, 1H), 3.75 (s, 2H), 3.31 (t, 2H), 2.88-2.80 (m, 4H), 2.55 (t, 2H), 1.71 (d, 6H), 1.46 (s, 9H)

Example 88

Synthesis of 3-{5-[5-(2-isopropyl-2H-indazol-5-yl)-[1,2,4]oxadiazol-3-yl]-3,4-dihydro-1H-isoquinolin-2-yl}-propanoic acid, trifluoroacetate

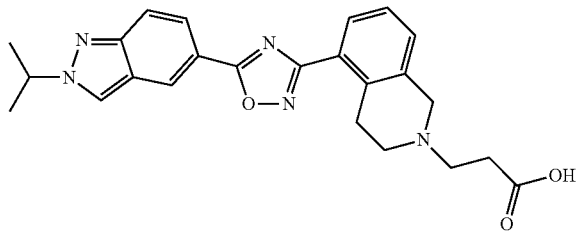 [SMILES: CC(C)n1cc2cc(-c3nc(-c4cccc5c4CCN(CCC(=O)O)C5)no3)ccc2n1]

According to the method described in Example 5, 3-{5-[5-(2-isopropyl-2H-indazol-5-yl)-[1,2,4]oxadiazol-3-yl]-3,4-dihydro-1H-isoquinolin-2-yl}-propanoic acid t-butyl ester (85 mg, 0.17 mmol) obtained from Preparation Example 88-1 was used to obtain the title compound (60 mg, 63%).

NMR: $^1$H-NMR (400 MHz, DMSO-d6) δ 8.74 (d, 1H), 8.08 (d, 1H), 7.97 (d, 1H), 7.86 (d, 1H), 7.54 (t, 1H), 7.46 (d, 1H), 4.95-4.90 (m, 1H), 4.54 (br, s, 2H), 3.57 (br, s, 2H), 3.45 (br, s, 4H), 2.86 (t, 2H), 1.60 (d, 6H)

Preparation Example 88-1

Synthesis of 6-[5-(1-isopropyl-1H-indazol-5-yl)-[1,2,4]oxadiazol-3-yl]-5-methyl-3,4-dihydro-1H-isoquinoline-2-carboxylic acid t-butyl ester According to the method described in Preparation Example 1-4, 1-isopropyl-1H-indazol-5-carboxylic acid (235 mg, 1.15 mmol) obtained from Preparation Example 80-3 and 6-(N-hydroxycarbimidoyl)-5-methyl-3,4-dihydro-1H-isoquinoline-2-carboxylic acid t-butyl ester (352 mg, 1.15 mmol) obtained from Preparation Example 56-1 were used to obtain the title compound (521 mg, 96%).

NMR: $^1$H-NMR (400 HMz, CDCl$_3$); δ 8.66 (s, 1H), 8.20 (dd, J=1.2 Hz, 1H), 8.17 (s, 1H), 7.80 (d, 1H), 7.57 (d, 1H), 7.11 (d, 1H), 4.93-4.88 (m, 1H), 4.64 (s, 2H), 3.72 (t, 2H), 2.85 (t, 2H), 2.55 (s, 3H), 1.64 (d, 6H), 1.51 (s, 9H)

Example 89

Synthesis of 6-[5-(1-isopropyl-1H-indazol-5-yl)-[1,2,4]oxadiazol-3-yl]-5-methyl-1,2,3,4-tetrahydro-isoquinoline, hydrochloride

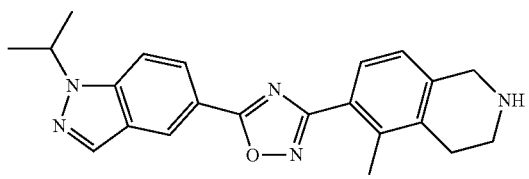 [SMILES: Cc1c(-c2noc(-c3ccc4c(cnn4C(C)C)c3)n2)ccc2c1CCNC2]

According to the method described in Example 27, 6-[5-(1-isopropyl-1H-indazol-5-yl)-[1,2,4]oxadiazol-3-yl]-5-methyl-3,4-dihydro-1H-isoquinoline-2-carboxylic acid t-butyl ester (521 mg, 1.10 mmol) obtained from Preparation Example 89-1 was used to obtain the title compound (450 mg, 100%).

NMR: $^1$H-NMR (400 MHz, DMSO-d6) δ 8.70 (s, 1H), 8.35 (s, 1H), 8.13 (dd, J=1.6 Hz, 1H), 7.98 (d, 1H), 7.81 (d, 1H), 7.30 (d, 1H), 5.13-5.07 (m, 1H), 4.37 (br, s, 2H), 3.48 (br, s, 2H), 3.00 (t, 2H), 2.50 (s, 3H), 1.52 (d, 6H)

Preparation Example 90-1

Synthesis of 5-[5-(2-isopropyl-2H-indazol-5-yl)-[1,2,4]oxadiazol-3-yl]-3,4-dihydro-1H-isoquinoline-2-carboxylic acid t-butyl ester According to the method described in Preparation Example 1-4, 2-isopropyl-2H-indazole-5-carboxylic acid (319 mg, 1.56 mmol) obtained from Preparation Example 82-1 and 5-(N-hydroxycarbimidoyl)-3,4-dihydro-1H-isoquinoline-2-carboxylic acid t-butyl ester (453 mg, 1.56 mmol) obtained from Preparation Example 27-1 were used to obtain the title compound (620 mg, 87%).

NMR: $^1$H-NMR (400 HMz, CDCl$_3$); δ 8.64 (s, 1H), 8.16 (s, 1H), 8.07 (dd, J=1.6 Hz, 1H), 7.98 (d, 1H), 7.85 (d, 1H), 7.35 (t, 1H), 7.28 (d, 1H), 4.88-4.82 (m, 1H), 4.67 (s, 2H), 3.68 (t, 2H), 3.28 (t, 2H), 1.71 (d, 6H), 1.51 (s, 9H)

Example 90

Synthesis of 5-[5-(2-isopropyl-2H-indazol-5-yl)-[1,2,4]oxadiazol-3-yl]-1,2,3,4-tetrahydro-isoquinoline, hydrochloride

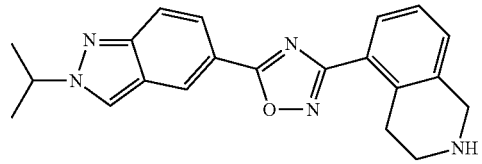 [SMILES: CC(C)n1cc2cc(-c3nc(-c4cccc5c4CCNC5)no3)ccc2n1]

According to the method described in Example 27, 5-[5-(2-isopropyl-2H-indazol-5-yl)-[1,2,4]oxadiazol-3-yl]-3,4-dihydro-1H-isoquinoline-2-carboxylic acid t-butyl ester (620 mg, 1.35 mmol) obtained from Preparation Example 90-1 was used to obtain the title compound (590 mg, 100%).

NMR: $^1$H-NMR (400 MHz, DMSO-d6) δ 8.75 (s, 1H), 8.72 (s, 1H). 8.04 (dd, J=2.4 Hz, 1H), 7.96 (dd, J=1.6, 2.0 Hz, 1H), 7.86 (d, 1H), 7.54-7.48 (m, 2H), 4.96-4.90 (m, 1H), 4.40 (br, s, 2H), 3.45 (br, s, 2H), 3.36 (br, s, 2H), 1.60 (d, 6H)

Preparation Example 91-1

Synthesis of 6-[5-(2-isopropyl-2H-indazol-5-yl)-[1,2,4]oxadiazol-3-yl]-5-methyl-3,4-dihydro-1H-isoquinoline-2-carboxylic acid t-butyl ester According to the method described in Preparation Example 1-4, 2-isopropyl-2H-indazole-5-carboxylic acid (319 mg, 1.56 mmol) obtained from Preparation Example 82-1 and 6-(N-hydroxycarbimidoyl)-5-methyl-3,4-dihydro-1H-isoquinoline-2-carboxylic acid t-butyl ester (475 mg, 1.56 mmol) obtained from Preparation Example 56-1 were used to obtain the title compound (672 mg, 91%).

NMR: $^1$H-NMR (400 HMz, CDCl$_3$); δ 8.64 (s, 1H), 8.16 (s, 1H), 8.07 (dd, J=1.6, 1.2 Hz, 1H), 7.85 (d, 1H), 7.79 (d, 1H), 7.11 (d, 1H), 4.88-4.82 (m, 1H), 4.64 (s, 2H), 3.72 (t, 2H), 2.85 (t, 2H), 2.55 (s, 3H), 1.71 (d, 6H), 1.51 (s, 9H)

Example 91

Synthesis of 6-[5-(2-isopropyl-2H-indazol-5-yl)-[1,2,4]oxadiazol-3-yl]-5-methyl-1,2,3,4-tetrahydro-isoquinoline, hydrochloride

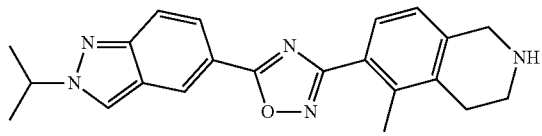 [SMILES: Cc1c(-c2noc(-c3ccc4nn(C(C)C)cc4c3)n2)ccc2c1CCNC2]

According to the method described in Example 27, 6-[5-(2-isopropyl-2H-indazol-5-yl)-[1,2,4]oxadiazol-3-yl]-5-methyl-3,4-dihydro-1H-isoquinoline-2-carboxylic acid t-butyl ester (672 mg, 1.46 mmol) obtained from Preparation Example 91-1 was used to obtain the title compound (630 mg, 100%).

NMR: $^1$H-NMR (400 MHz, DMSO-d6) δ 8.74 (s, 1H), 8.71 (s, 1H). 7.95 (dd, J=1.2, 1.6 Hz, 1H), 7.85 (d, 1H), 7.79 (d, 1H), 7.29 (d, 1H), 4.96-4.89 (m, 1H), 4.35 (br, s, 2H), 3.46 (br, s, 2H), 3.01 (t, 2H), 2.50 (s, 3H), 1.60 (d, 6H)

Preparation Example 92-1

Synthesis of 3-chloro-1-isopropyl-1H-indazole-5-carboxylic acid methyl ester

According to the method described in Preparation Example 3-1, 1-isopropyl-1H-indazole-5-carboxylic acid methyl ester (500 mg, 2.29 mmol) obtained from Preparation Example 80-2 was used to obtain the title compound (420 mg, 72%).

NMR: $^1$H-NMR (400 HMz, CDCl$_3$); δ 8.43 (s, 1H), 8.07 (dd, 1H), 7.41 (d, 1H), 4.79 (m, 1H), 3.95 (s, 3H), 1.58 (d, 6H)

Preparation Example 92-2

Synthesis of 3-chloro-1-isopropyl-1H-indazole-5-carboxylic acid

According to the method described in Preparation Example 1-2, 3-chloro-1-isopropyl-1H-indazole-5-carboxylic acid methyl ester (420 mg, 1.66 mmol) obtained from Preparation Example 92-1 was used to obtain the title compound (390 mg, 98%).

NMR: $^1$H-NMR (400 HMz, CDCl$_3$); δ 8.55 (s, 1H), 8.13 (dd, J=1.2, 1.6 Hz, 1H), 7.46 (d, 1H), 4.86-4.80 (m, 1H), 1.60 (d, 6H)

Preparation Example 92-3

Synthesis of 6-[5-(3-chloro-1-isopropyl-1H-indazol-5-yl)-[1,2,4]oxadiazol-3-yl]-5-methyl-3,4-dihydro-1H-isoquinoline-2-carboxylic acid t-butyl ester According to the method described in Preparation Example 1-4, 3-chloro-1-isopropyl-1H-indazole-5-carboxylic acid (390 mg, 1.63 mmol) obtained from Preparation Example 92-2 and 6-(N-hydroxycarbimidoyl)-5-methyl-3,4-dihydro-1H-isoquinoline-2-carboxylic acid t-butyl ester (500 mg, 1.63 mmol) obtained from Preparation Example 56-1 were used to obtain the title compound (450 mg, 62%).

NMR: $^1$H-NMR (400 HMz, CDCl$_3$); δ 8.60 (s, 1H), 8.23 (dd, J=1.6 Hz, 1H), 7.80 (d, 1H), 7.56 (d, 1H), 7.12 (d, 1H), 4.88-4.82 (m, 1H), 4.65 (s, 2H), 3.72 (t, 2H), 2.85 (t, 2H), 2.55 (s, 3H), 1.62 (d, 6H), 1.51 (s, 9H)

Example 92

Synthesis of 6-[5-(3-chloro-1-isopropyl-1H-indazol-5-yl)-[1,2,4]oxadiazol-3-yl]-5-methyl-1,2,3,4-tetrahydro-isoquinoline, hydrochloride

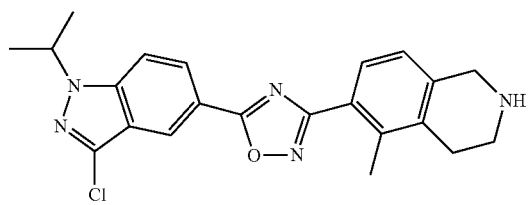 [SMILES: Cc1c(-c2noc(-c3ccc4c(c3)c(Cl)nn4C(C)C)n2)ccc2c1CCNC2]

According to the method described in Example 27, 6-[5-(3-chloro-1-isopropyl-1H-indazol-5-yl)-[1,2,4]oxadiazol-3-yl]-5-methyl-3,4-dihydro-1H-isoquinoline-2-carboxylic acid t-butyl ester (450 mg, 1.01 mmol) obtained from Preparation Example 92-3 was used to obtain the title compound (380 mg, 97%).

NMR: $^1$H-NMR (400 MHz, DMSO-d6) δ 8.48 (s, 1H), 8.23 (dd, J=1.6 Hz, 1H). 8.08 (d, 1H), 7.83 (d, 1H), 7.30 (d, 1H), 5.17-5.10 (m, 1H), 4.37 (s, 2H), 3.47 (br, s, 2H), 3.01 (t, 2H), 2.50 (s, 3H), 1.51 (d, 6H)

Preparation Example 93-1

Synthesis of {6-[5-(3-chloro-1-isopropyl-1H-indazol-5-yl)-[1,2,4]oxadiazol-3-yl]-5-methyl-3,4-dihydro-1H-isoquinolin-2-yl}-acetic acid t-butyl ester According to the method described in Preparation Example 28-1, 6-[5-(3-chloro-1-isopropyl-1H-indazol-5-yl)-[1,2,4]oxadiazol-3-yl]-5-methyl-1,2,3,4-tetrahydro-isoquinoline, hydrochloride (100 mg, 0.23 mmol) obtained from Example 92 and t-butyl bromoacetate (0.05 mL, 0.34 mmol) were used to obtain the title compound (100 mg, 81%).

NMR: $^1$H-NMR (400 HMz, CDCl$_3$); δ 8.60 (s, 1H), 8.23 (d, H), 7.75 (d, 1H), 7.55 (d, 1H), 7.02 (s, 1H), 4.86-4.82 (m, 1H), 3.86 (s, 2H), 3.34 (s, 2H), 2.97-2.91 (m, 4H), 2.53 (s, 3H), 1.62 (d, 6H), 1.51 (s, 9H)

Example 93

Synthesis of {6-[5-(3-chloro-1-isopropyl-1H-indazol-5-yl)-[1,2,4]oxadiazol-3-yl]-5-methyl-3,4-dihydro-1H-isoquinolin-2-yl}-acetic acid, trifluoroacetate

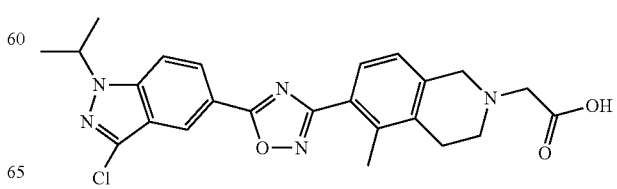

According to the method described in Example 5, {6-[5-(3-chloro-1-isopropyl-1H-indazol-5-yl)-[1,2,4]oxadiazol-3-yl]-5-methyl-3,4-dihydro-1H-isoquinolin-2-yl}-acetic acid t-butyl ester (100 mg, 0.18 mmol) obtained from Preparation Example 93-1 was used to obtain the title compound (73 mg, 69%).

NMR: ¹H-NMR (400 MHz, DMSO-d6) δ 8.48 (s, 1H), 8.23 (dd, J=1.2, 1.6 Hz, 1H). 8.07 (d, 1H), 7.76 (d, 1H), 7.19 (d, 1H), 5.16-5.10 (m, 1H), 4.12 (s, 2H), 3.72 (br, s, 2H), 3.21 (br, s, 2H), 2.94 (br, s, 2H), 2.50 (s, 3H), 1.51 (d, 6H)

Preparation Example 94-1

Synthesis of 3-{6-[5-(3-chloro-1-isopropyl-1H-indazol-5-yl)-[1,2,4]oxadiazol-3-yl]-5-methyl-3,4-dihydro-1H-isoquinolin-2-yl}-propanoic acid t-butyl ester According to the method described in Preparation Example 29-1, 6-[5-(3-chloro-1-isopropyl-1H-indazol-5-yl)-[1,2,4]oxadiazol-3-yl]-5-methyl-1,2,3,4-tetrahydro-isoquinoline, hydrochloride (100 mg, 0.23 mmol) obtained from Example 92 and t-butyl acrylate (0.05 mL, 0.34 mmol) were used to obtain the title compound (45 mg, 38%).

NMR: ¹H-NMR (400 HMz, CDCl₃); δ 8.50 (s, 1H), 8.23 (dd, J=1.2 Hz, 1H), 7.76 (d, 1H), 7.55 (d, 1H), 7.03 (d, 1H), 4.88-4.81 (m, 1H), 3.71 (s, 2H), 2.88-2.84 (m, 6H), 2.55 (t, 2H), 2.52 (s, 3H), 1.62 (d, 6H), 1.46 (s, 9H)

Example 94

Synthesis of 3-{6-[5-(3-chloro-1-isopropyl-1H-indazol-5-yl)-[1,2,4]oxadiazol-3-yl]-5-methyl-3,4-dihydro-1H-isoquinolin-2-yl}-propanoic acid, trifluoroacetate

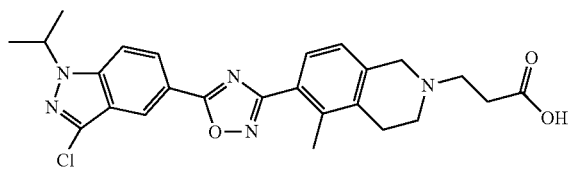 [SMILES: Cc1c(-c2noc(-c3ccc4c(c3)c(Cl)nn4C(C)C)n2)ccc2c1CCN(CCC(=O)O)C2]

According to the method described in Example 5, 3-{6-[5-(3-chloro-1-isopropyl-1H-indazol-5-yl)-[1,2,4]oxadiazol-3-yl]-5-methyl-3,4-dihydro-1H-isoquinolin-2-yl}-propanoic acid t-butyl ester (45 mg, 0.08 mmol) obtained from Preparation Example 94-1 was used to obtain the title compound (40 mg, 80%).

NMR: ¹H-NMR (400 MHz, DMSO-d6) δ 8.49 (s, 1H), 8.23 (dd, J=1.6, 1.2 Hz, 1H). 8.08 (d, 1H), 7.85 (d, 1H), 7.26 (d, 1H), 5.17-5.10 (m, 1H), 4.50 (s, 2H), 3.59 (br, s, 2H), 3.42 (br, s, 2H), 3.08 (br, s, 2H), 2.86 (t, 3H), 2.51 (s, 3H), 1.51 (d, 6H)

Preparation Example 95-1

Synthesis of 5-bromo-1H-pyrazolo[3,4-b]pyridine

The title compound was obtained according to the method described in WO 2009016460 A2.

NMR: ¹H-NMR (400 HMz, CDCl₃); δ 8.56 (d, 1H), 8.29 (d, 1H), 8.03 (s, 1H)

Preparation Example 95-2

Synthesis of 5-bromo-1-isopropyl-1H-pyrazolo[3,4-b]pyridine and 5-bromo-2-isopropyl-2H-pyrazolo[3,4-b]pyridine According to the method described in Preparation Example 1-1, 5-bromo-1H-pyrazolo[3,4-b]pyridine (1.8 g, 9.09 mmol) obtained from Preparation Example 95-1 and isopropyl iodide (1.4 mL, 13.64 mmol) were used to obtain 5-bromo-1-isopropyl-1H-pyrazolo[3,4-b]pyridine (1.7 g, 78%) which passed firstly through column chromatography and 5-bromo-2-isopropyl-2H-pyrazolo[3,4-b]pyridine (350 mg, 16%) which passed secondly through column chromatography.

NMR: ¹H-NMR (400 HMz, CDCl₃); δ 8.53 (d, 1H), 8.17 (d, 1H), 7.96 (s, 1H), 5.26 (m, 1H), 1.58 (d, 6H) (5-bromo-1-isopropyl-1H-pyrazolo[3,4-b]pyridine)

Preparation Example 95-3

Synthesis of 1-isopropyl-1H-pyrazolo[3,4-b]pyridine-5-carbonitrile

5-Bromo-1-isopropyl-1H-pyrazolo[3,4-b]pyridine (1.7 g, 7.08 mmol) obtained from Preparation Example 95-2 was dissolved in N-methylpyrrolidone, and then zinc cyanide (ZnCN₂, 1.9 g, 14.16 mmol) and palladium tetrakis triphenylphosphine ([Pd(Ph₃P)₄], 1.0 g, 0.71 mmol) were added dropwise thereto. The mixture was stirred for 4 hours at 100° C., added with water and extracted with ethyl acetate. The extract was washed with brine, dried with anhydrous magnesium sulfate and filtered. The filtrate was distilled under reduced pressure. The residue was separated by column chromatography to obtain the title compound (750 mg, 58%).

NMR: ¹H-NMR (400 HMz, CDCl₃); δ 8.72 (d, 1H), 8.40 (d, 1H), 8.14 (s, 1H), 5.33 (m, 1H), 1.61 (d, 6H)

Preparation Example 95-4

Synthesis of 1-isopropyl-1H-pyrazolo[3,4-b]pyridine-5-carboxylic acid

1-Isopropyl-1H-pyrazolo[3,4-b]pyridine-5-carbonitrile (750 mg, 4.02 mmol) obtained from Preparation Example 95-3 was dissolved in ethanol (100 mL), and 6N sodium hydroxide aqueous solution (6.7 mL, 40.20 mmol) was added dropwise thereto. The mixture was stirred under reflux for 18 hours and the solvent was removed by distillation under reduced pressure. The residue was added with 1N hydrochloric acid aqueous solution and extracted with ethyl acetate. The extract was washed with brine, dried with anhydrous magnesium sulfate and filtered. The filtrate was distilled under reduced pressure to obtain the title compound (800 mg, 97%).

NMR: ¹H-NMR (400 HMz, DMSO_d6); δ 9.06 (d, 1H), 8.80 (d, 1H), 8.33 (s, 1H), 5.26 (m, 1H), 1.53 (d, 6H)

Preparation Example 95-5

Synthesis of 6-[5-(1-isopropyl-1H-pyrazolo[3,4-b]pyridin-5-yl)-[1,2,4]oxadiazol-3-yl]-5-methyl-3,4-dihydro-1H-isoquinoline-2-carboxylic acid t-butyl ester According to the method described in Preparation Example 1-4, 1-isopropyl-1H-pyrazolo[3,4-b]pyridine-5- carboxylic acid (335 mg, 1.63 mmol) obtained from Preparation Example 95-4 and 6-(N-hydroxycarbimidoyl)-5-methyl-3,4-dihydro-1H-isoquinoline-2-carboxylic acid t-butyl ester (500 mg, 1.63 mmol) obtained from Preparation Example 56-1 were used to obtain the title compound (503 mg, 65%).

Preparation Example 95-6

Synthesis of 6-[5-(1-isopropyl-1H-pyrazolo[3,4-b]pyridin-5-yl)-[1,2,4]oxadiazol-3-yl]-5-methyl-1,2,3,4-tetrahydro-isoquinoline, hydrochloride According to the method described in Example 27, 6-[5-(1-isopropyl-1H-pyrazolo[3,4-b]pyridin-5-yl)-[1,2,4]oxadiazol-3-yl]-5-methyl-3,4-dihydro-1H-isoquinoline-2-carboxylic acid t-butyl ester (503 mg, 1.06 mmol) obtained from Preparation Example 95-5 was used to obtain the title compound (374 mg, 81%).

Preparation Example 95-7

Synthesis of {6-[5-(1-isopropyl-1H-pyrazolo[3,4-b]pyridin-5-yl)-[1,2,4]oxadiazol-3-yl]-5-methyl-3,4-dihydro-1H-isoquinolin-2-yl}-acetic acid t-butyl ester According to the method described in Preparation Example 28-1, 6-[5-(1-isopropyl-1H-pyrazolo[3,4-b]pyridin-5-yl)-[1,2,4]oxadiazol-3-yl]-5-methyl-1,2,3,4-tetrahydro-isoquinoline, hydrochloride (100 mg, 0.24 mmol) obtained from Preparation Example 95-6 and t-butyl bromoacetate (0.05 mL, 0.35 mmol) were used to obtain the title compound (85 mg, 72%).

Example 95

Synthesis of {6-[5-(1-isopropyl-1H-pyrazolo[3,4-b]pyridin-5-yl)-[1,2,4]oxadiazol-3-yl]-5-methyl-3,4-dihydro-1H-isoquinolin-2-yl}-acetic acid

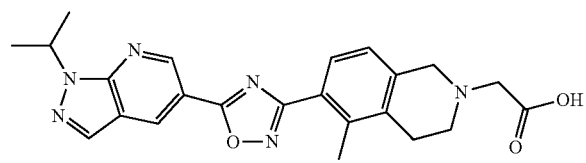

According to the method described in Example 5, {6-[5-(1-isopropyl-1H-pyrazolo[3,4-b]pyridin-5-yl)-[1,2,4]oxadiazol-3-yl]-5-methyl-3,4-dihydro-1H-isoquinolin-2-yl}-acetic acid t-butyl ester (85 mg, 0.17 mmol) obtained from Preparation Example 95-7 was used to obtain the title compound (68 mg, 92%).

NMR: $^1$H-NMR (400 HMz, DMSO$_{d6}$); δ 9.21 (s, 1H), 9.01 (s, 1H), 8.35 (s, 1H), 7.69 (s, 1H), 7.14 (s, 1H), 5.23 (m, 1H), 4.10 (s, 2H), 3.69 (s, 2H), 3.19 (s, 2H), 2.90 (s, 2H), 2.42 (s, 3H), 1.50 (d, 6H)

Preparation Example 96-1

Synthesis of 5-[5-(1-isopropyl-1H-indazol-5-yl)-[1,2,4]oxadiazol-3-yl]-3,4-dihydro-1H-isoquinoline-2-carboxylic acid t-butyl ester According to the method described in Preparation Example 1-4, 1-isopropyl-1H-indazole-5-carboxylic acid (253 mg, 1.24 mmol) obtained from Preparation Example 80-3 and 5-(N-hydroxycarbimidoyl)-3,4-dihydro-1H-isoquinoline-2-carboxylic acid t-butyl ester (362 mg, 1.24 mmol) obtained from Preparation Example 27-1 were used to obtain the title compound (490 mg, 86%).

NMR: $^1$H-NMR (400 HMz, CDCl$_3$); δ 8.66 (s, 1H), 8.20 (dd, J=1.6 Hz, 1H), 8.18 (s, 1H), 7.99 (d, 1H), 7.58 (d, 1H), 7.36 (t, 1H), 7.28 (d, 1H), 4.95-4.88 (m, 1H), 4.67 (s, 1H), 3.69 (t, 2H), 3.28 (t, 2H), 1.64 (d, 6H), 1.51 (s, 9H)

Example 96

Synthesis of 5-[5-(1-isopropyl-1H-indazol-5-yl)-[1,2,4]oxadiazol-3-yl]-1,2,3,4-tetrahydro-isoquinoline, hydrochloride

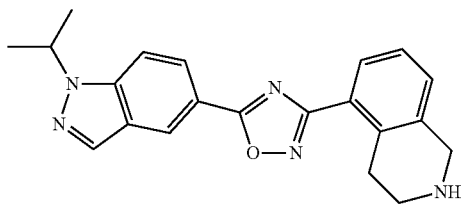 [SMILES: CC(C)n1ncc2cc(-c3nc(-c4cccc5c4CCNC5)no3)ccc21]

According to the method described in Example 27, 5-[5-(1-isopropyl-1H-indazol-5-yl)-[1,2,4]oxadiazol-3-yl]-3,4-dihydro-1H-isoquinoline-2-carboxylic acid t-butyl ester (490 mg, 1.07 mmol) obtained from Preparation Example 96-1 was used to obtain the title compound (340 mg, 81%).

NMR: $^1$H-NMR (400 MHz, DMSO-d6) δ 8.72 (s, 1H), 8.36 (s, 1H), 8.15 (dd, J=1.6, 1.2 Hz, 1H). 8.05 (dd, J=2.4 Hz, 1H), 7.99 (d, 1H), 7.52 (d, 1H), 7.50 (s, 1H), 5.15-5.08 (m, 1H), 4.99 (br, s, 2H), 4.39 (br, s, 2H), 3.41 (br, s, 2H), 1.53 (d, 6H)

Preparation Example 97-1

Synthesis of {6-[5-(2-isopropyl-2H-indazol-5-yl)-[1,2,4]oxadiazol-3-yl]-5-methyl-3,4-dihydro-1H-isoquinolin-2-yl}-acetic acid t-butyl ester According to the method described in Preparation Example 28-1, 6-[5-(2-isopropyl-2H-indazol-5-yl)-[1,2,4]oxadiazol-3-yl]-5-methyl-1,2,3,4-tetrahydro-isoquinoline, hydrochloride (104 mg, 0.25 mmol) obtained from Example 91 and t-butyl bromoacetate (0.06 mL, 0.38 mmol) were used to obtain the title compound (100 mg, 81%).

NMR: $^1$H-NMR (400 HMz, CDCl$_3$); δ 8.64 (s, 1H), 8.15 (s, 1H), 8.07 (dd, J=1.6 Hz, 1H), 7.84 (d, 1H), 7.74 (d, 1H), 7.02 (d, 1H), 4.88 (m, 1H), 3.86 (s, 2H), 3.34 (s, 2H), 2.96-2.90 (m, 4H), 2.52 (s, 2H), 1.70 (d, 6H), 1.51 (s, 9H)

Example 97

Synthesis of {6-[5-(2-isopropyl-2H-indazol-5-yl)-[1,2,4]oxadiazol-3-yl]-5-methyl-3,4-dihydro-1H-isoquinolin-2-yl}-acetic acid, trifluoroacetate

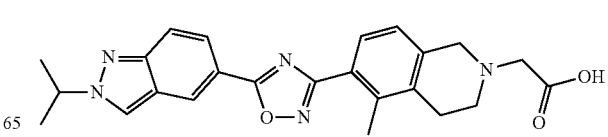

According to the method described in Example 5, {6-[5-(2-isopropyl-2H-indazol-5-yl)-[1,2,4]oxadiazol-3-yl]-5-methyl-3,4-dihydro-1H-isoquinolin-2-yl}-acetic acid t-butyl ester (100 mg, 0.21 mmol) obtained from Preparation Example 97-1 was used to obtain the title compound (60 mg, 54%).

NMR: $^1$H-NMR (400 MHz, DMSO-d6) δ 8.73 (s, 1H), 8.70 (s, 1H), 7.95 (dd, J=1.6 Hz, 1H). 7.85 (d, 1H), 7.75 (d, 1H), 7.22 (d, 1H), 4.95-4.91 (m, 1H), 4.25 (br, s, 2H), 3.87 (br, s, 2H), 3.32 (br, s, 2H), 2.99 (br, s, 2H), 1.60 (d, 6H)

Preparation Example 98-1

Synthesis of 3-{6-[5-(2-isopropyl-2H-indazol-5-yl)-[1,2,4]oxadiazol-3-yl]-5-methyl-3,4-dihydro-1H-isoquinolin-2-yl}-propanoic acid t-butyl ester According to the method described in Preparation Example 29-1, 6-[5-(2-isopropyl-2H-indazol-5-yl)-[1,2,4]oxadiazol-3-yl]-5-methyl-1,2,3,4-tetrahydro-isoquinoline, hydrochloride (104 mg, 0.25 mmol) obtained from Example 91 and t-butyl acrylate (0.05 mL, 0.38 mmol) were used to obtain the title compound (60 mg, 48%).

NMR: $^1$H-NMR (400 HMz, CDCl$_3$); δ 8.64 (s, 1H), 8.15 (s, 1H), 8.07 (dd, J=1.6 Hz, 1H), 7.84 (d, 1H), 7.75 (d, 1H), 7.02 (d, 1H), 4.88-4.82 (m, 1H), 3.71 (s, 2H), 2.73-2.83 (m, 6H), 2.55 (t, 2H), 2.52 (s, 3H), 1.71 (d, 6H), 1.46 (s, 9H)

Example 98

Synthesis of 3-{6-[5-(2-isopropyl-2H-indazol-5-yl)-[1,2,4]oxadiazol-3-yl]-5-methyl-3,4-dihydro-1H-isoquinolin-2-yl}-propanoic acid, trifluoroacetate

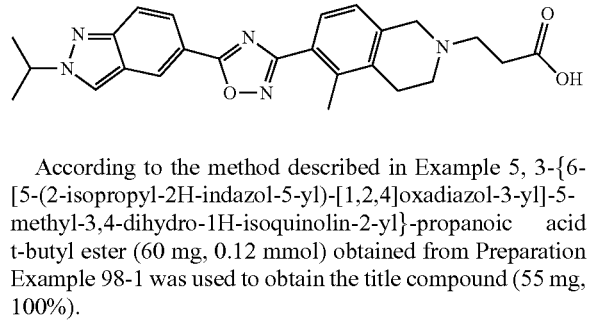

According to the method described in Example 5, 3-{6-[5-(2-isopropyl-2H-indazol-5-yl)-[1,2,4]oxadiazol-3-yl]-5-methyl-3,4-dihydro-1H-isoquinolin-2-yl}-propanoic acid t-butyl ester (60 mg, 0.12 mmol) obtained from Preparation Example 98-1 was used to obtain the title compound (55 mg, 100%).

NMR: $^1$H-NMR (400 MHz, DMSO-d6) δ 8.74 (s, 1H), 8.71 (s, 1H), 7.95 (dd, J=1.6, 1.2 Hz, 1H). 7.85 (d, 1H), 7.83 (d, 1H), 7.26 (d, 1H), 4.94-4.89 (m, 1H), 4.53 (br, s, 2H), 3.62 (br, s, 2H), 3.47 (t, 2H), 3.09 (br, s, 2H), 2.87 (t, 2H), 2.50 (s, 3H), 1.59 (d, 6H)

Preparation Example 99-1

Synthesis of 5-[5-(1-isopropyl-1H-pyrazolo[3,4-b]pyridin-5-yl)-[1,2,4]oxadiazol-3-yl]-3,4-dihydro-1H-isoquinoline-2-carboxylic acid t-butyl ester 1-Isopropyl-1H-pyrazolo[3,4-b]pyridine-5-carboxylic acid (335 mg, 1.63 mmol) obtained in Preparation Example 95-4 and 5-(N-hydroxycarbamimidoyl)-3,4-dihydro-1H-isoquinoline-2-carboxylic acid t-butyl ester (500 mg, 1.63 mmol) obtained in Preparation Example 27-1 were reacted according to the method described in Preparation Example 1-4 to obtain the title compound (562 mg, 75%).

Preparation Example 99-2

Synthesis of 5-[5-(1-isopropyl-1H-pyrazolo[3,4-b]pyridin-5-yl)-[1,2,4]oxadiazol-3-yl]-1,2,3,4-tetrahydro-isoquinoline 5-[5-(1-Isopropyl-1H-pyrazolo[3,4-b]pyridin-5-yl)-[1,2,4]oxadiazol-3-yl]-3,4-dihydro-1H-isoquinoline-2-carboxylic acid t-butyl ester (562 mg, 1.22 mmol) obtained in Preparation Example 99-1 was reacted according to the method described in Example 27 to obtain the title compound (343 mg, 78%).

Preparation Example 99-3

Synthesis of {5-[5-(1-isopropyl-1H-pyrazolo[3,4-b]pyridin-5-yl)-[1,2,4]oxadiazol-3-yl]-3,4-dihydro-1H-isoquinolin-2-yl}-acetic acid t-butyl ester 6-[5-(1-Isopropyl-1H-pyrazolo[3,4-b]pyridin-5-yl)-[1,2,4]oxadiazol-3-yl]-5-methyl-1,2,3,4-tetrahydro-isoquinoline, hydrochloride (100 mg, 0.24 mmol) obtained in Example 95-6 and t-butylbromoacetate (0.05 mL, 0.35 mmol) were reacted according to the method described in Preparation Example 28-1 to obtain the title compound (92 mg, 81%).

Example 99

Synthesis of {5-[5-(1-isopropyl-1H-pyrazolo[3,4-b]pyridin-5-yl)-[1,2,4]oxadiazol-3-yl]-3,4-dihydro-1H-isoquinolin-2-yl}-acetic acid

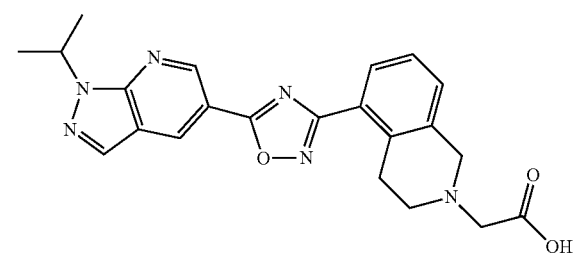 [SMILES: CC(C)n1ncc2cc(-c3nc(-c4cccc5c4CCN(CC(=O)O)C5)no3)cnc21]

{5-[5-(1-Isopropyl-1H-pyrazolo[3,4-b]pyridin-5-yl)-[1,2,4]oxadiazol-3-yl]-3,4-dihydro-1H-isoquinolin-2-yl}-acetic acid t-butyl ester (92 mg, 0.19 mmol) obtained in Preparation Example 99-3 was reacted according to the method described in Example 5 to obtain the title compound (73 mg, 92%).

NMR: $^1$H-NMR (400 HMz, DMSO-d6); δ 9.30 (d, 1H), 9.09 (d, 1H), 8.41 (s, 1H), 7.95 (m, 1H), 7.38 (m, 2H), 5.30 (m, 1H), 3.93 (s, 2H), 3.45 (s, 2H), 3.20 (m, 2H), 2.99 (m, 2H), 1.56 (d, 6H)

Preparation Example 100-1

Synthesis of 4-[5-(1-isopropyl-1H-indazol-5-yl)-[1,2,4]oxadiazol-3-yl]-3-methyl-phenyl}-methanol 1-Isopropyl-1H-indazole-5-carboxylic acid (1.13 g, 5.55 mmol) obtained in Preparation Example 80-3 and N-hydroxy-4-hydroxymethyl-2-methyl-benzamidine (1.0 g, 5.55 mmol) obtained in Preparation Example 14-1 were reacted according to the method described in Preparation Example 1-4 to obtain the title compound (1.25 g, 65%).

NMR: $^1$H-NMR (400 HMz, CDCl$_3$); δ 8.66 (s, 1H), 8.18 (dd, J=8.8, 9.2 Hz, 2H), 8.12 (d, J=7.6 Hz, 1H), 7.58 (d, J=8.8 Hz, 1H), 7.34-7.36 (m, 2H), 4.89-4.92 (m, 1H), 4.77 (br s, 2H), 2.72 (s, 3H), 1.64 (d, J=6.8 Hz, 6H)

Preparation Example 100-2

Synthesis of 4-[5-(1-isopropyl-1H-indazol-5-yl)-[1,2,4]oxadiazol-3-yl]-3-methyl-benzaldehyde 4-[5-(1-Isopropyl-1H-indazol-5-yl)-[1,2,4]oxadiazol-3-yl]-3-methyl-phenyl}-methanol (1.25 g, 3.59 mmol) obtained in Preparation Example 100-1 was reacted according to the method described in Preparation Example 14-3 to obtain the title compound (1.1 g, 89%).

NMR: $^1$H-NMR (400 HMz, CDCl$_3$); δ 10.09 (s, 1H), 8.68 (s, 1H), 8.32 (d, J=8.0 Hz, 1H), 8.19-8.22 (m, 2H), 7.87 (br s, 2H), 7.60 (d, J=12.0 Hz, 1H), 4.90-4.94 (m, 2H), 2.80 (s, 3H), 1.65 (d, J=4.0 Hz, 6H)

Preparation Example 100-3

Synthesis of ({4-[5-(1-isopropyl-1H-indazol-5-yl)-[1,2,4]oxadiazol-3-yl]-3-methyl-benzyl}-methyl-amino)-acetic acid t-butyl ester 4-[5-(1-Isopropyl-1H-indazol-5-yl)-[1,2,4]oxadiazol-3-yl]-3-methyl-benzaldehyde (100 mg, 0.29 mmol) obtained in Preparation Example 100-2 and sarcosine t-butyl ester hydrochloride (79 mg, 0.43 mmol) were reacted according to the method described in Preparation Example 14-4 to obtain the title compound (120 mg, 87%).

NMR: $^1$H-NMR (400 HMz, CDCl$_3$); δ 8.85 (s, 1H), 8.23 (d, J=8.0 Hz, 1H), 8.11 (s, 1H), 8.06 (d, J=8.0 Hz, 1H), 7.56 (d, J=8.0 Hz, 1H), 7.33 (d, J=8.0 Hz, 1H), 7.30 (s, 1H), 4.86-4.94 (m, 1H), 3.72 (s, 2H), 3.24 (s, 2H), 2.73 (s, 3H), 2.45 (s, 3H), 1.55 (d, J=8.0 Hz, 6H), 1.49 (s, 9H)

Example 100

Synthesis of ({4-[5-(1-isopropyl-1H-indazol-5-yl)-[1,2,4]oxadiazol-3-yl]-3-methyl-benzyl}-methyl-amino)-acetic acid, trifluoroacetate

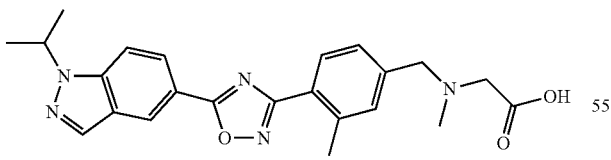

({4-[5-(1-Isopropyl-1H-indazol-5-yl)-[1,2,4]oxadiazol-3-yl]-3-methyl-benzyl}-methyl-amino)-acetic acid t-butyl ester (120 mg, 0.25 mmol) obtained in Preparation Example 100-3 was reacted according to the method described in Example 5 to obtain the title compound (76 mg, 72%).

NMR: $^1$H-NMR (400 MHz, DMSO-d6) δ 8.71 (s, 1H), 8.36 (s, 1H), 8.10-8.16 (m, 2H), 7.99 (d, 1H), 7.52 (d, 2H), 5.10-5.13 (m, 1H), 4.21 (s, 2H), 3.87 (s, 2H), 2.66 (s, 6H), 1.53 (d, 6H)

Preparation Example 101-1

Synthesis of 5-[5-(3-chloro-1-isopropyl-1H-indazol-5-yl)-[1,2,4]oxadiazol-3-yl]-3,4-dihydro-1H-isoquinoline-2-carboxylic acid t-butyl ester 3-Chloro-1-isopropyl-1H-indazole-5-carboxylic acid (172 mg, 0.84 mmol) obtained in Preparation Example 92-2 and 5-(N-hydroxycarbamimidoyl)-3,4-dihydro-1H-isoquinoline-2-carboxylic acid t-butyl ester (246 mg, 0.84 mmol) obtained in Preparation Example 27-1 were reacted according to the method described in Preparation Example 1-4 to obtain the title compound (220 mg, 56%).

NMR: $^1$H-NMR (400 HMz, CDCl$_3$); δ 8.58 (s, 1H), 8.22 (d, J=8.0 Hz, 1H), 8.00 (d, J=4.0 Hz, 1H), 7.56 (d, J=4.0 Hz, 1H), 7.35 (dd, J=4.0, 8.0 Hz, 1H), 7.29 (d, J=4.0 Hz, 1H), 4.80-4.90 (m, 1H), 4.67 (s, 2H), 3.69 (dd, J=4.0, 8.0 Hz, 2H), 3.28 (dd, J=2.0, 4.0 Hz, 2H), 1.62 (d, J=8.0 Hz, 6H), 1.51 (s, 9H)

Example 101

Synthesis of 5-[5-(3-chloro-1-isopropyl-1H-indazol-5-yl)-[1,2,4]oxadiazol-3-yl]-1,2,3,4-tetrahydro-iso-quinoline, hydrochloride

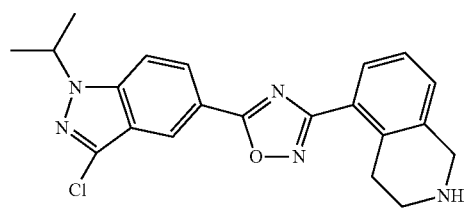 [SMILES: CC(C)n1nc(Cl)c2cc(-c3nc(-c4cccc5c4CCNC5)no3)ccc21]

5-[5-(3-Chloro-1-isopropyl-1H-indazol-5-yl)-[1,2,4]oxadiazol-3-yl]-3,4-dihydro-1H-isoquinoline-2-carboxylic acid t-butyl ester (220 mg, 0.45 mmol) obtained in Preparation Example 101-1 was reacted according to the method described in Example 27 to obtain the title compound (193 mg, 100%).

NMR: $^1$H-NMR (400 MHz, DMSO-d6) δ 8.50 (s, 1H), 8.23-8.25 (m, 1H), 8.07-8.09 (m, 2H), 7.51-7.53 (m, 2H), 5.12-5.15 (m, 1H), 4.41 (s, 2H), 3.46 (br s, 2H), 3.37 (br s, 2H), 1.51 (d, 6H)

Preparation Example 102-1

Synthesis of {5-[5-(3-chloro-1-isopropyl-1H-indazol-5-yl)-[1,2,4]oxadiazol-3-yl]-3,4-dihydro-1H-isoquinolin-2-yl}-acetic acid t-butyl ester 5-[5-(3-chloro-1-isopropyl-1H-indazol-5-yl)-[1,2,4]oxadiazol-3-yl]-1,2,3,4-tetrahydro-isoquinoline, hydrochloride (93 mg, 0.24 mmol) obtained in Example 101 and t-butylbromoacetate (0.05 mL, 0.31 mmol) were reacted according to the method described in Preparation Example 28-1 to obtain the title compound (95 mg, 78%).

NMR: $^1$H-NMR (400 HMz, CDCl$_3$); δ 8.55 (s, 1H), 8.19 (d, J=8.0 Hz, 1H), 8.02 (d, J=8.0 Hz, 1H), 7.50 (dd, J=8.0, 20.0 Hz, 1H), 7.28-7.30 (m, 1H), 7.17-7.23 (m, 1H), 4.79-4.89 (m, 1H), 4.11 (s, 2H), 3.18-3.33 (m, 4H), 2.94 (t, J=8.0 Hz, 2H), 1.56 (d, J=8.0 Hz, 6H), 1.49 (s, 9H)

Example 102

Synthesis of {5-[5-(3-chloro-1-isopropyl-1H-indazol-5-yl)-[1,2,4]oxadiazol-3-yl]-3,4-dihydro-1H-isoquinolin-2-yl}-acetic acid, trifluoroacetate

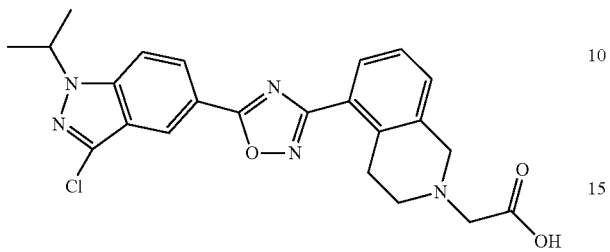

{5-[5-(3-chloro-1-isopropyl-1H-indazol-5-yl)-[1,2,4]oxadiazol-3-yl]-3,4-dihydro-1H-isoquinolin-2-yl}-acetic acid t-butyl ester (95 mg, 0.19 mmol) obtained in Preparation Example 102-1 was reacted according to the method described in Example 5 to obtain the title compound (77 mg, 89%).

NMR: $^1$H-NMR (400 MHz, DMSO-d6) δ 8.50 (s, 1H), 8.25 (dd, 1H), 8.04-8.09 (m, 2H), 7.43-7.50 (m, 2H), 5.10-5.16 (m, 1H), 4.33 (br s, 2H), 3.95 (br s, 2H), 3.37 (br s, 4H), 1.51 (d, 6H)

Preparation Example 103-1

Synthesis of 3-{5-[5-(3-chloro-1-isopropyl-1H-indazol-5-yl)-[1,2,4]oxadiazol-3-yl]-3,4-dihydro-1H-isoquinolin-2-yl}-propanoic acid t-butyl ester 5-[5-(3-chloro-1-isopropyl-1H-indazol-5-yl)-[1,2,4]oxadiazol-3-yl]-1,2,3,4-tetrahydro-isoquinoline, hydrochloride (93 mg, 0.24 mmol) obtained in Example 101 and t-butyl acrylate (0.05 mL, 0.35 mmol) were reacted according to the method described in Preparation Example 29-1 to obtain the title compound (75 mg, 60%).

NMR: $^1$H-NMR (400 HMz, CDCl$_3$); δ 8.78 (s, 1H), 8.21 (d, J=8.0 Hz, 1H), 8.02 (d, J=8.0 Hz, 1H), 7.45-7.53 (m, 1H), 7.28-7.35 (m, 1H), 7.19 (d, J=8.0 Hz, 1H), 4.81-4.89 (m, 1H), 3.65 (s, 2H), 3.31 (t, J=8.0 Hz, 2H), 2.59-2.89 (m, 4H), 2.53-2.57 (m, 2H), 1.55 (d, J=8.0 Hz, 6H), 1.49 (s, 9H)

Example 103

Synthesis of 3-{5-[5-(3-chloro-1-isopropyl-1H-indazol-5-yl)-[1,2,4]oxadiazol-3-yl]-3,4-dihydro-1H-isoquinolin-2-yl}-propanoic acid, trifluoroacetate

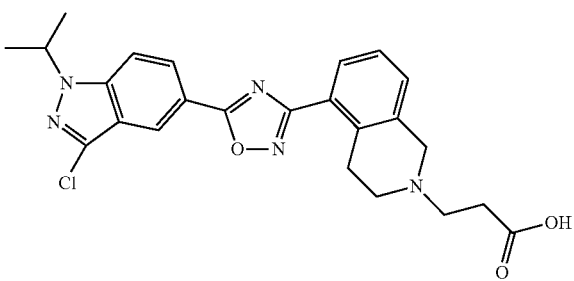 [SMILES: CC(C)n1nc(Cl)c2cc(-c3nc(-c4cccc5c4CCN(CCC(=O)O)C5)no3)ccc21]

3-{5-[5-(3-chloro-1-isopropyl-1H-indazol-5-yl)-[1,2,4]oxadiazol-3-yl]-3,4-dihydro-1H-isoquinolin-2-yl}-propanoic acid t-butyl ester (75 mg, 0.14 mmol) obtained in Preparation Example 103-1 was reacted according to the method described in Example 5 to obtain the title compound (48 mg, 73%).

NMR: $^1$H-NMR (400 MHz, DMSO-d6) δ 8.49 (s, 1H), 8.23 (dd, J=1.6, 8.0 Hz, 1H), 8.07-8.11 (m, 2H), 7.51-7.55 (m, 1H), 7.46 (d, 1H), 5.10-5.16 (m, 1H), 4.51 (br s, 2H), 3.37-3.56 (m, 6H), 2.85 (t, 4H), 1.67 (d, 6H)

Preparation Example 104-1

Synthesis of 1-isopropyl-1H-pyrrolo[2,3-b]pyridine-5-carboxylic acid methyl ester 1H-Pyrrolo[2,3-b]pyridine-5-carboxylic acid methyl ester (1.2 g, 6.81 mmol) and isopropyl iodide (1.02 mL, 10.22 mmol) were reacted to obtain the title compound (1.2 g, 85%).

Preparation Example 104-2

Synthesis of 1-isopropyl-1H-pyrrolo[2,3-b]pyridine-5-carboxylic acid

1-Isopropyl-1H-pyrrolo[2,3-b]pyridine-5-carboxylic acid methyl ester (1.2 g, 5.79 mmol) obtained in Preparation Example 104-1 was reacted according to the method described in Preparation Example 1-2 to obtain the title compound (922 mg, 78%).

NMR: $^1$H-NMR (400 HMz, CDCl$_3$); δ 9.08 (d, 1H), 8.64 (d, 1H), 7.41 (d, 1H), 6.61 (d, 1H), 5.28 (m, 1H), 1.55 (d, 6H)

Preparation Example 104-3

Synthesis of 5-[5-(1-isopropyl-1H-pyrrolo[2,3-b]pyridin-5-yl)-[1,2,4]oxadiazol-3-yl]-3,4-dihydro-1H-isoquinoline-2-carboxylic acid t-butyl ester 1-Isopropyl-1H-pyrrolo[2,3-b]pyridine-5-carboxylic acid (460 mg, 2.26 mmol) obtained in Preparation Example 104-2 and 5-(N-hydroxycarbamimidoyl)-3,4-dihydro-1H-isoquinoline-2-carboxylic acid t-butyl ester (490 mg, 2.26 mmol) obtained in Preparation Example 27-1 were reacted according to the method described in Preparation Example 1-4 to obtain the title compound (650 mg, 62%).

Preparation Example 104-4

Synthesis of 5-[5-(1-isopropyl-1H-pyrrolo[2,3-b]pyridin-5-yl)-[1,2,4]oxadiazol-3-yl]-1,2,3,4-tetrahydro-isoquinoline, hydrochloride 5-[5-(1-Isopropyl-1H-pyrrolo[2,3-b]pyridin-5-yl)-[1,2,4]oxadiazol-3-yl]-3,4-dihydro-1H-isoquinoline-2-carboxylic acid t-butyl ester (650 mg, 2.80 mmol) obtained in Preparation Example 104-3 was reacted according to the method described in Example 27 to obtain the title compound (463 mg, 92%).

Preparation Example 104-5

Synthesis of {5-[5-(1-isopropyl-1H-pyrrolo[2,3-b]pyridin-5-yl)-[1,2,4]oxadiazol-3-yl]-3,4-dihydro-1H-isoquinolin-2-yl}-acetic acid t-butyl ester 5-[5-(1-isopropyl-1H-pyrrolo[2,3-b]pyridin-5-yl)-[1,2,4]oxadiazol-3-yl]-1,2,3,4-tetrahydro-isoquinoline, hydrochloride (100 mg, 0.25 mmol) obtained in Preparation Example 104-4 and t-butylbromoacetate (0.04 mL, 0.38 mmol) were reacted according to the method described in Preparation Example 28-1 to obtain the title compound (89 mg, 75%).

Example 104

Synthesis of {5-[5-(1-isopropyl-1H-pyrrolo[2,3-b]pyridin-5-yl)-[1,2,4]oxadiazol-3-yl]-3,4-dihydro-1H-isoquinolin-2-yl}-acetic acid

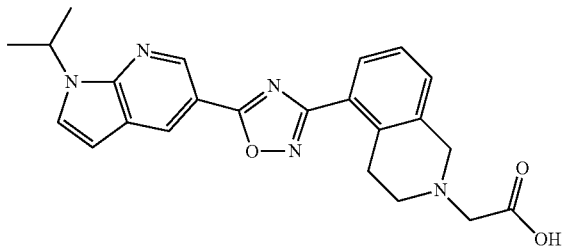 [SMILES: CC(C)n1ccc2cc(-c3nc(-c4cccc5c4CCN(CC(=O)O)C5)no3)cnc21]

{5-[5-(1-isopropyl-1H-pyrrolo[2,3-b]pyridin-5-yl)-[1,2,4]oxadiazol-3-yl]-3,4-dihydro-1H-isoquinolin-2-yl}-acetic acid t-butyl ester (89 mg, 0.19 mmol) obtained in Preparation Example 104-5 was reacted according to the method described in Example 5 to obtain the title compound (59 mg, 75%).

NMR: $^1$H-NMR (400 HMz, DMSO$_{d6}$); δ 9.04 (s, 1H), 8.77 (s, 1H), 7.92 (m, 2H), 7.37 (m, 2H), 6.74 (d, 1H), 5.18 (m, 1H), 3.89 (s, 2H), 3.42 (s, 2H), 3.18 (m, 2H), 2.94 (m, 2H), 1.52 (d, 6H)

Example 105

Synthesis of 6-[5-(3-chloro-1-isopropyl-1H-indazol-5-yl)-[1,2,4]oxadiazol-3-yl]-5-methyl-3,4-dihydro-1H-isoquinoline-2-sulfonic acid amide

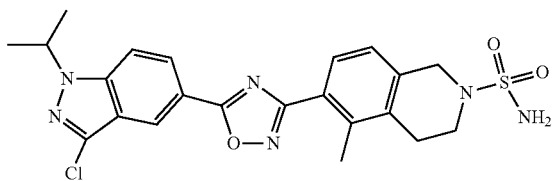 [SMILES: Cc1c(-c2noc(-c3ccc4c(c3)c(Cl)nn4C(C)C)n2)ccc2c1CCN(S(N)(=O)=O)C2]

6-[5-(3-Chloro-1-isopropyl-1H-indazol-5-yl)-[1,2,4]oxadiazol-3-yl]-5-methyl-1,2,3,4-tetrahydro-isoquinoline, hydrochloride (80 mg, 0.18 mmol) obtained in Example 92 was dissolved in 1,4-dioxane (10 mL), and diisopropylethylamine (0.09 mL, 0.54 mmol) and sulfamide (21 mg, 0.22 mmol) were added dropwise thereto. The mixture was stirred at 110° C. for 18 hours and then distilled under reduced pressure to remove the solvent. To the residue was added water and was extracted with ethylacetate. The extract was washed with brine, dried with anhydrous magnesium sulfate and filtered. The filtrate was distilled under reduced pressure to obtain the title compound (31 mg, 35%).

NMR: $^1$H-NMR (400 MHz, DMSO-d6) δ 8.48 (s, 1H), 8.22 (d, J=1H), 8.07 (d, 1H), 7.75 (d, J=8.0 Hz, 1H), 7.23 (d, 1H), 5.11-5.15 (m, 1H), 4.27 (s, 2H), 3.34 (s, 3H), 2.92 (br s, 2H), 2.48 (br s, 2H), 1.51 (d, 6H)

Preparation Example 106-1

Synthesis of 6-[5-(1-isopropyl-1H-pyrrolo[2,3-b]pyridin-5-yl)-[1,2,4]oxadiazol-3-yl]-5-methyl-3,4-dihydro-1H-isoquinoline-2-carboxylic acid t-butyl ester 1-Isopropyl-1H-pyrrolo[2,3-b]pyridine-5-carboxylic acid (460 mg, 2.26 mmol) obtained in Preparation Example 104-2 and 6-(N-hydroxycarbamimidoyl)-5-methyl-3,4-dihydro-1H-isoquinoline-2-carboxylic acid t-butyl ester (490 mg, 2.26 mmol) obtained in Preparation Example 56-1 were reacted according to the method described in Preparation Example 1-4 to obtain the title compound (696 mg, 65%).

Preparation Example 106-2

Synthesis of 6-[5-(1-isopropyl-1H-pyrrolo[2,3-b]pyridin-5-yl)-[1,2,4]oxadiazol-3-yl]-5-methyl-1,2,3,4-tetrahydro-isoquinoline, hydrochloride 6-[5-(1-isopropyl-1H-pyrrolo[2,3-b]pyridin-5-yl)-[1,2,4]oxadiazol-3-yl]-5-methyl-3,4-dihydro-1H-isoquinoline-2-carboxylic acid t-butyl ester (696 mg, 1.47 mmol) obtained in Preparation Example 106-1 was reacted according to the method described in Example 27 to obtain the title compound (467 mg, 85%).

Preparation Example 106-3

Synthesis of {6-[5-(1-isopropyl-1H-pyrrolo[2,3-b]pyridin-5-yl)-[1,2,4]oxadiazol-3-yl]-5-methyl-3,4-dihydro-1H-isoquinolin-2-yl}-acetic acid ethyl ester 6-[5-(1-isopropyl-1H-pyrrolo[2,3-b]pyridin-5-yl)-[1,2,4]oxadiazol-3-yl]-5-methyl-1,2,3,4-tetrahydro-isoquinoline, hydrochloride (100 mg, 0.25 mmol) obtained in Preparation Example 106-2 and t-butylbromoacetate (0.04 mL, 0.38 mmol) were reacted according to the method described in Preparation Example 28-1 to obtain the title compound (94 mg, 82%).

Example 106

Synthesis of {6-[5-(1-isopropyl-1H-pyrrolo[2,3-b]pyridin-5-yl)-[1,2,4]oxadiazol-3-yl]-5-methyl-3,4-dihydro-1H-isoquinoin-2-yl}-acetic acid

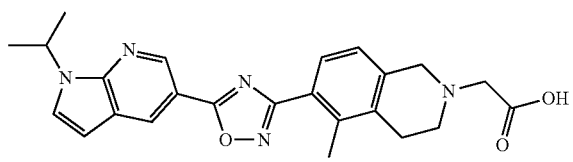 [SMILES: Cc1c(-c2noc(-c3cnc4c(ccn4C(C)C)c3)n2)ccc2c1CCN(CC(=O)O)C2]

{6-[5-(1-Isopropyl-1H-pyrrolo[2,3-b]pyridin-5-yl)-[1,2,4]oxadiazol-3-yl]-5-methyl-3,4-dihydro-1H-isoquinolin-2-yl}-acetic acid ethyl ester (94 mg, 0.20 mmol) obtained in Preparation Example 106-3 was reacted according to the method described in Example 5 to obtain the title compound (72 mg, 84%).

NMR: $^1$H-NMR (400 HMz, DMSO$_{d6}$); δ 9.03 (s, 1H), 8.76 (s, 1H), 7.91 (d, 1H), 7.71 (d, 1H), 6.75 (d, 1H), 5.17 (m, 1H), 3.96 (s, 2H), 3.44 (s, 2H), 3.06 (m, 2H), 2.88 (m, 2H), 2.47 (s, 3H), 1.51 (d, 6H)

Example 107

Synthesis of 1-{4-[5-(1-isopropyl-1H-indazol-5-yl)-[1,2,4]oxadiazol-3-yl]-3-methyl-benzyl}-azetidine-3-carboxylic acid

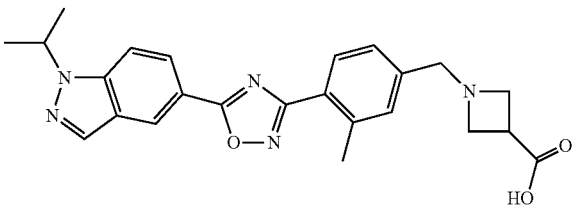 [SMILES: Cc1cc(CN2CC(C(=O)O)C2)ccc1-c1noc(-c2ccc3c(cnn3C(C)C)c2)n1]

4-[5-(1-Isopropyl-1H-indazol-5-yl)-[1,2,4]oxadiazol-3-yl]-3-methyl-benzaldehyde (100 mg, 0.29 mmol) obtained in Preparation Example 100-2 and azetidine-3-carboxylic acid (32 mg, 0.32 mmol) were reacted according to the method described in Example 3 to obtain the title compound (44 mg, 35%).

NMR: $^1$H-NMR (400 MHz, CDCl$_3$) δ 8.62 (s, 1H), 8.11-8.17 (m, 3H), 7.55 (d, J=8.8 Hz, 1H), 7.39-7.41 (m, 2H), 4.87-4.90 (m, 1H), 4.11 (br s, 4H), 3.93 (br s, 2H), 3.49 (br s, 1H), 2.69 (s, 3H), 1.62 (d, J=6.8 Hz, 6H)

Example 108

Synthesis of 5-[5-(3-chloro-1-isopropyl-1H-indazol-5-yl)-[1,2,4]oxadiazol-3-yl]-3,4-dihydro-1H-isoquinoline-2-sulfonic acid amide

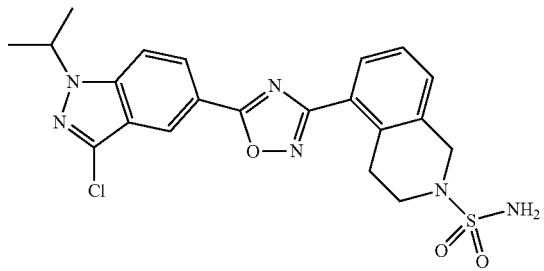 [SMILES: CC(C)n1nc(Cl)c2cc(-c3nc(-c4cccc5c4CCN(S(N)(=O)=O)C5)no3)ccc21]

5-[5-(3-chloro-1-isopropyl-1H-indazol-5-yl)-[1,2,4]oxadiazol-3-yl]-1,2,3,4-tetrahydro-isoquinoline, hydrochloride (120 mg, 0.28 mmol) obtained in Example 101 was reacted according to the method described in Example 105 to obtain the title compound (40 mg, 34%).

NMR: $^1$H-NMR (400 MHz, CDCl$_3$) δ 8.60 (s, 1H), 8.23 (d, 1H), 8.07 (d, 1H), 7.56 (d, 1H), 7.39 (dd, 1H), 7.28 (d, 1H), 4.84-4.87 (m, 1H), 4.52 (s, 2H), 4.45 (br s, 2H), 3.58 (dd, 2H), 3.46 (dd, 2H), 1.62 (d, 6H)

Preparation Example 109-1

Synthesis of 6-(N-hydroxycarbamimidoyl)-3,4-dihydro-1H-isoquinoline-2-carboxylic acid t-butyl ester The title compound was obtained according to the method described in WO 2010/146105 A1.

NMR: $^1$H-NMR (400 HMz, CDCl$_3$); δ 7.43 (d, 1H), 7.41 (s, 1H), 7.13 (d, 1H), 6.96 (br, s, 1H), 4.83 (s, 2H), 4.59 (s, 2H), 3.65 (t, 2H), 2.85 (t, 2H), 1.49 (s, 9H)

Preparation Example 109-2

Synthesis of 6-[5-(1-isopropyl-1H-indazol-5-yl)-[1,2,4]oxadiazol-3-yl]-3,4-dihydro-1H-isoquinoline-2-carboxylic acid t-butyl ester 1-Isopropyl-1H-indazole-5-carboxylic acid (318 mg, 1.56 mmol) obtained in Preparation Example 80-3 and 6-(N-hydroxycarbamimidoyl)-3,4-dihydro-1H-isoquinoline-2-carboxylic acid t-butyl ester (453 mg, 1.56 mmol) obtained in Preparation Example 109-1 were reacted according to the method described in Preparation Example 1-4 to obtain the title compound (640 mg, 90%).

NMR: $^1$H-NMR (400 HMz, CDCl$_3$); δ 8.67 (s, 1H), 8.20 (dd, J=1.6 Hz, 1H), 8.17 (s, 1H), 8.05 (d, 2H), 7.58 (d, 1H), 7.25 (d, 1H), 4.95-4.88 (m, 1H), 4.65 (s, 2H), 3.70 (br, s, 2H), 2.95 (br, s, 2H), 1.64 (d, 6H), 1.51 (s, 9H)

Preparation Example 109-3

Synthesis of 6-[5-(1-isopropyl-1H-indazol-5-yl)-[1,2,4]oxadiazol-3-yl]-1,2,3,4-tetrahydro-isoquinoline, hydrochloride 6-[5-(1-Isopropyl-1H-indazol-5-yl)-[1,2,4]oxadiazol-3-yl]-3,4-dihydro-1H-isoquinoline-2-carboxylic acid t-butyl ester (640 mg, 1.39 mmol) obtained in Preparation Example 109-2 was reacted according to the method described in Example 27 to obtain the title compound (480 mg, 87%).

NMR: $^1$H-NMR (400 HMz, DMSO$_{d6}$); δ 9.52 (br, s, 1H), 8.71 (s, 1H), 8.35 (s, 1H), 8.14 (dd, J=1.6 Hz, 1H), 7.99 (s, 2H), 7.97 (s, 1H), 7.46 (d, 1H), 5.14-5.18 (m, 1H), 4.37 (br, s, 2H), 3.44 (br, s, 2H), 3.16 (t, 2H), 1.52 (d, 6H)

Preparation Example 109-4

Synthesis of {6-[5-(1-isopropyl-1H-indazol-5-yl)-[1,2,4]oxadiazol-3-yl]-3,4-dihydro-1H-isoquinolin-2-yl}-acetic acid t-butyl ester 6-[5-(1-Isopropyl-1H-indazol-5-yl)-[1,2,4]oxadiazol-3-yl]-1,2,3,4-tetrahydro-isoquinoline, hydrochloride (100 mg, 0.25 mmol) obtained in Preparation Example 109-3 and t-butylbromoacetate (0.06 mL, 0.38 mmol) were reacted according to the method described in Preparation Example 28-1 to obtain the title compound (67 mg, 56%).

NMR: $^1$H-NMR (400 HMz, CDCl$_3$); δ 8.67 (s, 1H), 8.20 (dd, 1H), 8.17 (s, 1H), 7.95 (d, 2H), 7.57 (d, 1H), 7.16 (d, 1H), 4.94-4.88 (m, 1H), 3.88 (s, 2H), 3.36 (s, 2H), 3.03 (t, 2H), 2.94 (t, 2H), 1.64 (d, 2H), 1.50 (s, 9H)

Example 109

Synthesis of {6-[5-(1-isopropyl-1H-indazol-5-yl)-[1,2,4]oxadiazol-3-yl]-3,4-dihydro-1H-isoquinolin-2-yl}-acetic acid, trifluoroacetate

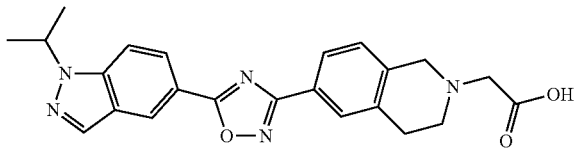 [SMILES: CC(C)n1ncc2cc(-c3nc(-c4ccc5c(c4)CCN(CC(=O)O)C5)no3)ccc21]

{6-[5-(1-Isopropyl-1H-indazol-5-yl)-[1,2,4]oxadiazol-3-yl]-3,4-dihydro-1H-isoquinolin-2-yl}-acetic acid t-butyl ester (67 mg, 0.14 mmol) obtained in Preparation Example 109-4 was reacted according to the method described in Example 5 to obtain the title compound (6 mg, 8%).

NMR: ¹H-NMR (400 MHz, DMSO-d6) δ 8.71 (s, 1H), 8.35 (s, 1H), 8.14 (d, 1H). 7.98 (d, 1H), 7.93 (s, 1H), 7.91 (d, 1H), 7.36 (d, 1H), 5.13-5.09 (m, 1H), 4.12 (br, s, 2H), 3.71 (br, s, 2H), 3.17 (br, s, 2H), 3.08 (br, s, 2H), 1.52 (d, 6H)

Preparation Example 110-1

Synthesis of (4-bromo-indan-1-yl)-methyl-amine

4-Bromo-indan-1-one (320 mg, 1.52 mmol) and methyl-amine hydrochloride (123 mg, 1.82 mmol) were reacted according to the method described in Example 3 to obtain the title compound (258 mg, 75%).

Preparation Example 110-2

Synthesis of (4-bromo-indan-1-yl)-methyl-carbamic acid t-butyl ester (4-Bromo-indan-1-yl)-methyl-amine (258 mg, 1.14 mmol) obtained in Preparation Example 110-1 was dissolved in tetrahydrofuran (10 mL), and Boc₂O (298 mg, 1.37 mmol) and triethylamine (0.31 mL, 2.28 mmol) were added dropwise thereto. The mixture was stirred at room temperature for 18 hours and then water was added thereto. The solution was extracted with ethylacetate. The extract was washed with brine, dried with anhydrous magnesium sulfate and filtered. The filtrate was distilled under reduced pressure. The residue was separated by column chromatography to obtain the title compound (279 mg, 75%).

NMR: ¹H-NMR (400 HMz, CDCl₃); δ 7.38 (m, 1H), 7.08 (m, 2H), 5.80 (m, 1H), 3.0 (m, 1H), 2.81 (m, 1H), 2.58 (m, 3H), 2.38 (m, 1H), 1.95 (m, 1H), 1.54 (s, 9H)

Preparation Example 110-3

Synthesis of (4-cyano-indan-1-yl)-methyl-carbamic acid t-butyl ester (4-Bromo-indan-1-yl)-methyl-carbamic acid t-butyl ester (279 mg, 0.86 mmol) obtained in Preparation Example 110-2 was reacted according to the method described in Preparation Example 95-3 to obtain the title compound (187 mg, 80%).

Preparation Example 110-4

Synthesis of [4-(N-hydroxycarbamimidoyl)-indan-1-yl]-methyl-carbamic acid t-butyl ester (4-Cyano-indan-1-yl)-methyl-carbamic acid t-butyl ester (187 mg, 0.69 mmol) obtained in Preparation Example 110-3 was reacted according to the method described in Preparation Example 9-2 to obtain the title compound (164 mg, 78%).

Preparation Example 110-5

Synthesis of {4-[5-(1-isopropyl-1H-indazol-5-yl)-[1,2,4]oxadiazol-3-yl]-indan-1-yl}-methyl-carbamic acid t-butyl ester 1-Isopropyl-1H-indazole-5-carboxylic acid (110 mg, 0.54 mmol) obtained in Preparation Example 80-3 and [4-(N-hydroxycarbamimidoyl)-indan-1-yl]-methyl-carbamic acid t-butyl ester (164 mg, 0.54 mmol) obtained in Preparation Example 110-4 were reacted according to the method described in Preparation Example 1-4 to obtain the title compound (166 mg, 65%).

Preparation Example 110-6

Synthesis of {4-[5-(1-isopropyl-1H-indazol-5-yl)-[1,2,4]oxadiazol-3-yl]-indan-1-yl}-methyl-amine, hydrochloride {4-[5-(1-Isopropyl-1H-indazol-5-yl)-[1,2,4]oxadiazol-3-yl]-indan-1-yl}-methyl-carbamic acid t-butyl ester (166 mg, 0.35 mmol) obtained in Preparation Example 110-5 was reacted according to the method described in Example 27 to obtain the title compound (123 mg, 87%).

Preparation Example 110-7

Synthesis of ({4-[5-(1-isopropyl-1H-indazol-5-yl)-[1,2,4]oxadiazol-3-yl]-indan-1-yl}-methyl-amino)-acetic acid ethyl ester {4-[5-(1-Isopropyl-1H-indazol-5-yl)-[1,2,4]oxadiazol-3-yl]-indan-1-yl}-methyl-amine, hydrochloride (123 mg, 0.30 mmol) obtained in Preparation Example 110-6 and ethyl-bromoacetate (0.07 mL, 0.60 mmol) were reacted according to the method described in Preparation Example 28-1 to obtain the title compound (98 mg, 71%).

Example 110

Synthesis of ({4-[5-(1-isopropyl-1H-indazol-5-yl)-[1,2,4]oxadiazol-3-yl]-indan-1-yl}-methyl-amino)-acetic acid

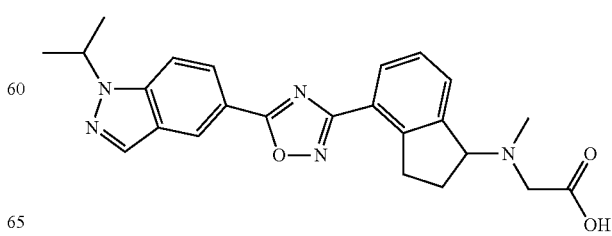

({4-[5-(1-Isopropyl-1H-indazol-5-yl)-[1,2,4]oxadiazol-3-yl]-indan-1-yl}-methyl-amino)-acetic acid ethyl ester (98 mg, 0.21 mmol) obtained in Preparation Example 110-7 was reacted according to the method described in Example 1 to obtain the title compound (68 mg, 75%).

NMR: $^1$H-NMR (400 HMz, DMSO$_{d6}$); δ 8.61 (s, 1H), 8.28 (s, 1H), 8.05 (m, 2H), 7.89 (d, 1H), 7.61 (d, 1H), 7.44 (m, 1H), 5.03 (m, 1H), 4.68 (m, 1H), 3.3 (m, 3H), 3.1 (m, 1H), 2.36 (s, 3H), 2.18 (m, 2H), 1.46 (d, 6H)

Preparation Example 111-1

Synthesis of 3-{6-[5-(1-isopropyl-1H-indazol-5-yl)-[1,2,4]oxadiazol-3-yl]-3,4-dihydro-1H-isoquinolin-2-yl}-propanoic acid t-butyl ester 6-[5-(1-Isopropyl-1H-indazol-5-yl)-[1,2,4]oxadiazol-3-yl]-1,2,3,4-tetrahydro-isoquinoline, hydrochloride (100 mg, 0.25 mmol) obtained in Preparation Example 109-3 and t-butyl acrylate (0.06 mL, 0.38 mmol) were reacted according to the method described in Preparation Example 29-1 to obtain the title compound (88 mg, 71%).

NMR: $^1$H-NMR (400 HMz, CDCl$_3$); δ 8.66 (s, 1H), 8.20 (dd, J=1.6 Hz, 1H), 8.17 (s, 1H), 7.93 (d, 2H), 7.57 (d, 1H), 7.16 (d, 1H), 4.92 (m, 1H), 3.73 (s, 2H), 3.00 (t, 2H), 2.87 (t, 2H), 2.81 (t, 2H), 2.55 (t, 2H), 1.64 (d, 6H), 1.46 (s, 9H)

Example 111

Synthesis of 3-{6-[5-(1-isopropyl-1H-indazol-5-yl)-[1,2,4]oxadiazol-3-yl]-3,4-dihydro-1H-isoquinolin-2-yl}-propanoic acid, trifluoroacetate

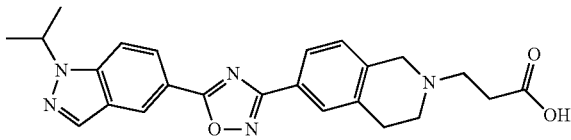 [SMILES: CC(C)n1ncc2cc(-c3nc(-c4ccc5c(c4)CCN(CCC(=O)O)C5)no3)ccc21]

3-{6-[5-(1-Isopropyl-1H-indazol-5-yl)-[1,2,4]oxadiazol-3-yl]-3,4-dihydro-1H-isoquinolin-2-yl}-propanoic acid t-butyl ester (88 mg, 0.18 mmol) obtained in Preparation Example 111-1 was reacted according to the method described in Example 5 to obtain the title compound (86 mg, 87%).

NMR: $^1$H-NMR (400 MHz, DMSO-d6) δ 8.72 (s, 1H), 8.36 (s, 1H), 8.14 (d, 1H). 8.01 (d, 2H), 7.98 (d, 1H), 7.44 (d, 1H), 5.13-5.09 (m, 1H), 4.52 (br, s, 2H), 3.61 (br, s, 2H), 3.45 (br, s, 2H), 3.24 (br, s, 2H), 2.86 (t, 2H), 1.52 (d, 6H)

Example 112

Synthesis of (R)-2-{4-[5-(1-isopropyl-1H-indazol-5-yl)-[1,2,4]oxadiazol-3-yl]-3-methyl-benzylamino}-propanoic acid

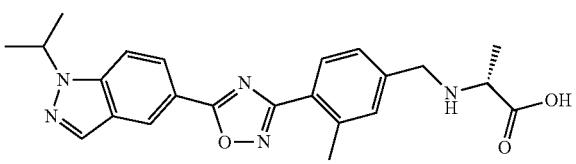 [SMILES: Cc1cc(CN[C@H](C)C(=O)O)ccc1-c1noc(-c2ccc3c(cnn3C(C)C)c2)n1]

4-[5-(1-Isopropyl-1H-indazol-5-yl)-[1,2,4]oxadiazol-3-yl]-3-methyl-benzaldehyde (100 mg, 0.29 mmol) obtained in Preparation Example 100-2 and D-alanine (29 mg, 0.32 mmol) were reacted according to the method described in Example 3 to obtain the title compound (100 mg, 82%).

NMR: $^1$H-NMR (400 MHz, DMSO-d6) δ 8.71 (s, 1H), 8.35 (s, 1H), 8.14 (d, 1H), 8.04 (d, 1H), 7.97 (d, 1H), 7.44-7.47 (m, 2H), 5.09-5.12 (m, 1H), 3.99 (d, 1H), 3.87 (d, 1H), 3.19-3.21 (m, 1H), 2.63 (s, 3H), 2.49 (d, 3H), 1.52 (d, 6H)

Preparation Example 113-1

Synthesis of {4-[5-(1-isopropyl-1H-indazol-5-yl)-[1,2,4]oxadiazol-3-yl]-3-methyl-benzylamino}-acetic acid t-butyl ester 4-[5-(1-Isopropyl-1H-indazol-5-yl)-[1,2,4]oxadiazol-3-yl]-3-methyl-benzaldehyde (100 mg, 0.29 mmol) obtained in Preparation Example 100-2 and glycine t-butyl ester (72 mg, 0.43 mmol) were reacted according to the method described in Preparation Example 14-4 to obtain the title compound (93 mg, 69%).

NMR: $^1$H-NMR (400 HMz, CDCl$_3$); δ 8.56 (s, 1H), 8.07-8.11 (m, 2H), 8.01 (dd, J=4.0, 8.0 Hz, 1H), 7.48 (d, J=8.0 Hz, 1H), 7.20-7.25 (m, 2H), 4.77-4.84 (m, 1H), 3.37 (s, 2H), 3.26 (s, 2H), 2.61 (s, 3H), 1.54 (d, J=8.0 Hz, 6H), 1.40 (s, 9H)

Example 113

Synthesis of {4-[5-(1-isopropyl-1H-indazol-5-yl)-[1,2,4]oxadiazol-3-yl]-3-methyl-benzylamino}-acetic acid, trifluoroacetate

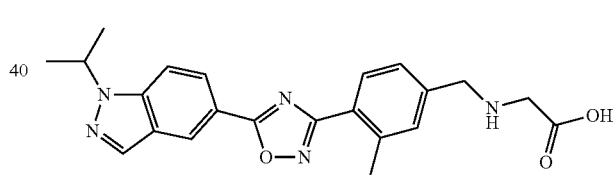

{4-[5-(1-Isopropyl-1H-indazol-5-yl)-[1,2,4]oxadiazol-3-yl]-3-methyl-benzylamino}-acetic acid t-butyl ester (93 mg, 0.20 mmol) obtained in Preparation Example 113-1 was reacted according to the method described in Example 5 to obtain the title compound (51 mg, 63%).

NMR: $^1$H-NMR (400 MHz, DMSO-d6) δ 8.71 (s, 1H), 8.35 (s, 1H), 8.14 (d, 1H), 8.09 (d, 1H), 7.98 (d, 1H), 7.52 (m, 2H), 5.11-5.13 (m, 1H), 4.13 (br s, 2H), 3.61 (br s, 2H), 2.65 (s, 3H), 1.52 (d, 6H)

Preparation Example 114-1

Synthesis of (ethyl-{4-[5-(1-isopropyl-1H-indazol-5-yl)-[1,2,4]oxadiazol-3-yl]-3-methyl-benzyl}-amino)-acetic acid t-butyl ester 4-[5-(1-Isopropyl-1H-indazol-5-yl)-[1,2,4]oxadiazol-3-yl]-3-methyl-benzaldehyde (80 mg, 0.23 mmol) obtained in Preparation Example 100-2 and N-ethylglycine t-butyl ester (61 mg, 0.35 mmol) were reacted according to the method described in Preparation Example 14-4 to obtain the title compound (87 mg, 78%).

NMR: ¹H-NMR (400 HMz, CDCl₃); δ 8.86 (s, 1H), 8.17-8.21 (m, 2H), 8.06 (d, J=8.0 Hz, 1H), 7.58 (d, J=12.0 Hz, 1H), 7.27-7.36 (m, 2H), 4.85-4.95 (m, 1H), 3.98 (s, 2H), 3.65 (s, 2H), 2.73 (q, J=4.0 Hz, 2H), 2.53 (s, 3H), 1.64 (d, J=4.0 Hz, 6H), 1.52 (s, 9H), 1.11 (t, J=8.0 Hz, 3H)

Example 114

Synthesis of (ethyl-{4-[5-(1-isopropyl-1H-indazol-5-yl)-[1,2,4]oxadiazol-3-yl]-3-methyl-benzyl}-amino)-acetic acid, trifluoroacetate

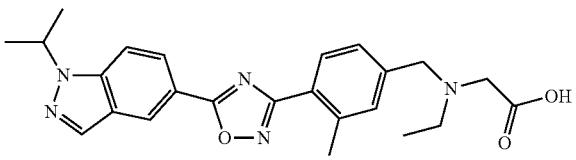 [SMILES: CCN(CC(=O)O)Cc1ccc(-c2noc(-c3ccc4c(cnn4C(C)C)c3)n2)c(C)c1]

(Ethyl-{4-[5-(1-isopropyl-1H-indazol-5-yl)-[1,2,4]oxadiazol-3-yl]-3-methyl-benzyl}-amino)-acetic acid t-butyl ester (87 mg, 0.18 mmol) obtained in Preparation Example 114-1 was reacted according to the method described in Example 5 to obtain the title compound (24 mg, 31%).

NMR: ¹H-NMR (400 MHz, CDCl₃) δ 8.59 (s, 1H), 8.12-8.14 (m, 3H), 7.55 (d, 1H), 7.44 (br s, 2H), 4.87-4.90 (m, 1H), 4.46 (br s, 2H), 3.81 (br s, 2H), 3.35 (q, 2H), 2.68 (s, 3H), 1.62 (d, 6H), 1.40 (t, 3H)

Example 115

Synthesis of (R)-2-({4-[5-(1-isopropyl-1H-indazol-5-yl)-[1,2,4]oxadiazol-3-yl]-3-methyl-benzyl}-methyl-amino)-propanoic acid

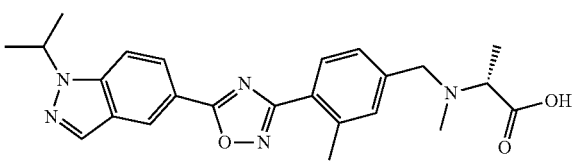 [SMILES: Cc1cc(CN(C)[C@H](C)C(=O)O)ccc1-c1noc(-c2ccc3c(cnn3C(C)C)c2)n1]

{4-[5-(1-Isopropyl-1H-indazol-5-yl)-[1,2,4]oxadiazol-3-yl]-3-methyl-benzylamino}-acetic acid, trifluoroacetate (25 mg, 0.06 mmol) obtained in Example 113 and 37 wt % formaldehyde solution (3 mg, 0.05 mmol) were reacted according to the method described in Example 3 to obtain the title compound (15 mg, 82%).

NMR: ¹H-NMR (400 MHz, CDCl₃) δ 8.43 (s, 1H), 7.99-8.06 (m, 3H), 7.40-7.46 (m, 3H), 4.80-4.83 (m, 1H), 4.30 (d, 1H), 3.89 (d, 1H), 2.70 (s, 3H), 2.59 (d, 3H), 1.58 (d, 6H), 1.52 (s, 3H)

Preparation Example 116-1

Synthesis of {4-[5-(1-isopropyl-1H-indazol-5-yl)-[1,2,4]oxadiazol-3-yl]-phenyl}-methanol 1-Isopropyl-1H-indaozle-5-carboxylic acid (1.26 g, 6.22 mmol) obtained in Preparation Example 80-3 and N-hydroxy-4-hydroxymethyl-benzamidine (1.0 g, 6.22 mmol) obtained in Preparation Example 10-1 were reacted according to the method described in Preparation Example 1-4 to obtain the title compound (1.33 g, 64%).

NMR: ¹H-NMR (500 HMz, CDCl₃); δ 8.66 (s, 1H), 8.20-8.17 (m, 4H), 7.57 (d, 1H), 7.52 (d, 2H), 4.92-4.88 (m, 1H), 4.80 (d, 2H), 1.76 (t, 1H), 1.63 (d, 6H)

Preparation Example 116-2

Synthesis of 4-[5-(1-isopropyl-1H-indazol-5-yl)-[1,2,4]oxadiazol-3-yl]-benzaldehyde {4-[5-(1-Isopropyl-1H-indazol-5-yl)-[1,2,4]oxadiazol-3-yl]-phenyl}-methanol (1.33 g, 4.0 mmol) obtained in Preparation Example 116-1 was reacted according to the method described in Preparation Example 14-3 to obtain the title compound (1.28 g, 97%).

NMR: ¹H-NMR (400 HMz, CDCl₃); δ 10.12 (s, 1H), 8.69 (s, 1H), 8.38 (d, 2H), 8.21 (dd, J=1.2 Hz, 1H), 8.19 (s, 1H), 8.04 (d, 1H), 7.60 (d, 1H), 4.95-4.89 (m, 1H), 1.65 (d, 6H)

Preparation Example 116-3

Synthesis of ({4-[5-(1-isopropyl-1H-indazol-5-yl)-[1,2,4]oxadiazol-3-yl]-benzyl}-methyl-amino)-acetic acid t-butyl ester 4-[5-(1-Isopropyl-1H-indazol-5-yl)-[1,2,4]oxadiazol-3-yl]-benzaldehyde (200 mg, 0.60 mmol) obtained in Preparation Example 116-2 and N-methylglycine t-butyl ester (131 mg, 0.90 mmol) were reacted according to the method described in Preparation Example 14-4 to obtain the title compound (150 mg, 54%).

NMR: ¹H-NMR (400 HMz, CDCl₃); δ 8.68 (s, 1H), 8.21 (dd, 1H), 8.18 (s, 1H), 8.15 (d, 2H), 7.58 (d, 1H), 7.52 (d, 2H), 4.94-4.90 (m, 1H), 3.76 (s, 2H), 3.21 (s, 2H), 2.40 (s, 3H), 1.64 (d, 6H), 1.49 (s, 9H)

Example 116

Synthesis of ({4-[5-(1-isopropyl-1H-indazol-5-yl)-[1,2,4]oxadiazol-3-yl]-benzyl}-methyl-amino)-acetic acid, trifluoroacetate

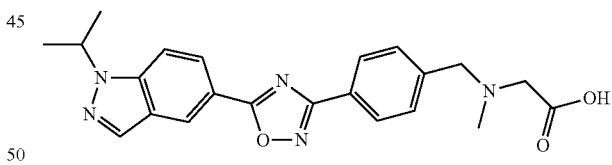

({4-[5-(1-Isopropyl-1H-indazol-5-yl)-[1,2,4]oxadiazol-3-yl]-benzyl}-methyl-amino)-acetic acid t-butyl ester (150 mg, 0.32 mmol) obtained in Preparation Example 116-3 was reacted according to the method described in Example 5 to obtain the title compound (180 mg, 100%).

NMR: ¹H-NMR (400 MHz, DMSO-d6) δ 8.72 (s, 1H), 8.36 (s, 1H), 8.19 (d, 2H). 8.15 (d, 1H), 7.99 (d, 1H), 7.73 (d, 2H), 5.14-5.09 (m, 1H), 4.34 (br, s, 2H), 3.98 (br, s, 2H), 2.73 (s, 3H), 1.53 (d, 6H)

Preparation Example 117-1

Synthesis of 5-bromo-3-methyl-1H-indazole

The title compound was obtained according to the method described in WO 2009/011880 A2.

NMR: $^1$H-NMR (400 HMz, CDCl$_3$); δ 10.20 (s, 1H), 7.83 (d, 1H), 7.48 (dd, 1H), 7.32 (d, 1H), 2.57 (s, 3H)

Preparation Example 117-2

Synthesis of 5-bromo-1-isopropyl-3-methyl-1H-indazole

5-Bromo-3-methyl-1H-indazole (750 mg, 3.55 mmol) obtained in Preparation Example 117-1 and isopropyliodide (0.43 mL, 4.26 mmol) were reacted according to the method described in Preparation Example 1-1 to obtain the title compound (670 mg, 74%).
NMR: $^1$H-NMR (400 HMz, CDCl$_3$); δ 7.78 (d, 1H), 7.41 (dd, 1H), 7.26 (d, 1H), 4.73 (m, 1H), 2.54 (s, 3H), 1.55 (d, 6H)

Preparation Example 117-3

Synthesis of 1-isopropyl-3-methyl-1H-indazole-5-carbonitrile

5-Bromo-1-isopropyl-3-methyl-1H-indazole (670 mg, 2.64 mmol) obtained in Preparation Example 117-2 was reacted according to the method described in Preparation Example 95-3 to obtain the title compound (500 mg, 95%).
NMR: $^1$H-NMR (400 HMz, CDCl$_3$); δ 8.02 (s, 1H), 7.52 (dd, 1H), 7.41 (d, 1H), 4.77 (m, 1H), 2.58 (s, 3H), 1.56 (d, 6H)

Preparation Example 117-4

Synthesis of 1-isopropyl-3-methyl-1H-indazole-5-carboxylic acid

1-Isopropyl-3-methyl-1H-indazole-5-carbonitrile (500 mg, 2.51 mmol) obtained in Preparation Example 117-3 was reacted according to the method described in Preparation Example 95-4 to obtain the title compound (455 mg, 83%).

Preparation Example 117-5

Synthesis of 6-[5-(1-isopropyl-3-methyl-1H-indazol-5-yl)-[1,2,4]oxadiazol-3-yl]-5-methyl-3,4-dihydro-1H-isoquinoline-2-carboxylic acid t-butyl ester 1-Isopropyl-3-methyl-1H-indazole-5-carboxylic acid (100 mg, 0.46 mmol) obtained in Preparation Example 117-4 and 6-(N-hydroxycarbamimidoyl)-5-methyl-3,4-dihydro-1H-isoquinoline-2-carboxylic acid t-butyl ester (139 mg, 0.46 mmol) obtained in Preparation Example 56-1 were reacted according to the method described in Preparation Example 1-4 to obtain the title compound (106 mg, 48%).

Preparation Example 117-6

Synthesis of 6-[5-(1-isopropyl-3-methyl-1H-indazol-5-yl)-[1,2,4]oxadiazol-3-yl]-5-methyl-1,2,3,4-tetrahydro-isoquinoline, hydrochloride 6-[5-(1-Isopropyl-3-methyl-1H-indazol-5-yl)-[1,2,4]oxadiazol-3-yl]-5-methyl-3,4-dihydro-1H-isoquinoline-2-carboxylic acid t-butyl ester (106 mg, 0.22 mmol) obtained in Preparation Example 117-5 was reacted according to the method described in Example 27 to obtain the title compound (80 mg, 87%).

Preparation Example 117-7

Synthesis of {6-[5-(1-isopropyl-3-methyl-1H-indazol-5-yl)-[1,2,4]oxadiazol-3-yl]-5-methyl-3,4-dihydro-1H-isoquinolin-2-yl}-acetic acid t-butyl ester 6-[5-(1-Isopropyl-3-methyl-1H-indazol-5-yl)-[1,2,4]oxadiazol-3-yl]-5-methyl-1,2,3,4-tetrahydro-isoquinoline, hydrochloride (80 mg, 0.19 mmol) obtained in Preparation Example 117-6 and t-butylbromoacetate (0.08 mL, 0.57 mmol) were reacted according to the method described in Preparation Example 28-1 to obtain the title compound (82 mg, 85%).

Example 117

Synthesis of {6-[5-(1-isopropyl-3-methyl-1H-indazol-5-yl)-[1,2,4]oxadiazol-3-yl]-5-methyl-3,4-dihydro-1H-isoquinolin-2-yl}-acetic acid, trifluoroacetate

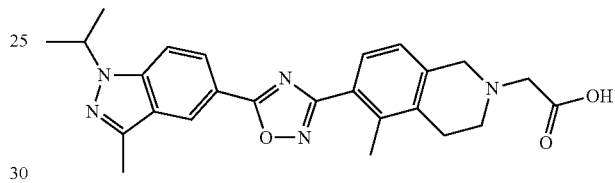

{6-[5-(1-Isopropyl-3-methyl-1H-indazol-5-yl)-[1,2,4]oxadiazol-3-yl]-5-methyl-3,4-dihydro-1H-isoquinolin-2-yl}-acetic acid t-butyl ester (82 mg, 0.16 mmol) obtained in Preparation Example 117-7 was reacted according to the method described in Example 5 to obtain the title compound (87 mg, 95%).
NMR: $^1$H-NMR (400 HMz, MeOD); δ 8.60 (s, 1H), 8.15 (m, 1H), 7.86 (d, 1H), 7.72 (d, 1H), 7.23 (d, 1H), 4.96 (m, 1H), 4.61 (s, 2H), 4.21 (s, 2H), 3.75 (m, 2H), 3.28 (m, 2H), 2.62 (s, 3H), 2.56 (s, 3H), 1.54 (d, 6H)

Preparation Example 118-1

Synthesis of {3-[5-(3-chloro-1-isopropyl-1H-indol-5-yl)-[1,2,4]oxadiazol-3-yl]-phenyl}-methanol 3-Chloro-1-isopropyl-1H-indole-5-carboxylic acid (133 mg, 0.56 mmol) obtained in Preparation Example 3-2 and N-hydroxy-3-hyddroxymethyl-benzamidine (94 mg, 0.56 mmol) obtained in Preparation Example 21-1 were reacted according to the method described in Preparation Example 1-4 to obtain the title compound (170 mg, 82%).
NMR: $^1$H-NMR (400 HMz, CDCl$_3$); δ 8.55 (s, 1H), 8.22 (s, 1H), 8.15 (d, 1H), 8.10 (d, 1H), 7.55-7.49 (m, 3H), 7.30 (s, 1H), 4.82 (d, 2H), 4.27-4.20 (m, 1H), 1.55 (d, 6H)

Preparation Example 118-2

Synthesis of 3-[5-(3-chloro-1-isopropyl-1H-indol-5-yl)-[1,2,4]oxadiazol-3-yl]-benzaldehyde {3-[5-(3-Chloro-1-isopropyl-1H-indol-5-yl)-[1,2,4]oxadiazol-3-yl]-phenyl}-methanol (170 mg, 0.46 mmol) obtained in Preparation Example 118-1 was reacted according to the method described in Preparation Example 14-3 to obtain the title compound (150 mg, 89%).

NMR: ¹H-NMR (400 HMz, CDCl₃); δ 10.11 (s, 1H), 8.68 (s, 1H), 8.50 (s, 1H), 8.44 (d, 1H), 8.07-8.01 (m, 2H), 7.67 (t, 1H), 7.47 (d, 1H), 7.29 (s, 1H), 4.75-4.66 (m, 1H), 1.55 (d, 6H)

Preparation Example 118-3

Synthesis of ({3-[5-(3-chloro-1-isopropyl-1H-indol-5-yl)-[1,2,4]oxadiazol-3-yl]-benzyl}-methyl-amino)-acetic acid t-butyl ester 3-[5-(3-Chloro-1-isopropyl-1H-indol-5-yl)-[1,2,4]oxadiazol-3-yl]-benzaldehyde (150 mg, 0.41 mmol) obtained in Preparation Example 118-2 and N-methylglycine t-butyl ester hydrochloride (112 mg, 0.62 mmol) were reacted according to the method described in Preparation Example 14-4 to obtain the title compound (150 mg, 74%).

NMR: ¹H-NMR (400 HMz, CDCl₃); δ 8.55 (s, 1H), 8.16 (s, 1H), 8.10 (dd, J=1.6 Hz, 1H), 7.57 (d, 1H), 7.49 (d, 2H), 7.30 (s, 1H), 4.76-4.70 (m, 1H), 3.80 (s, 2H), 3.23 (s, 2H), 2.42 (s, 3H), 1.56 (d, 6H), 1.51 (s, 9H)

Example 118

Synthesis of ({3-[5-(3-chloro-1-isopropyl-1H-indol-5-yl)-[1,2,4]oxadiazol-3-yl]-benzyl}-methyl-amino)-acetic acid, trifluoroacetate

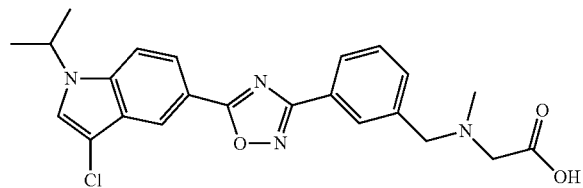 [SMILES: CC(C)n1cc(Cl)c2cc(-c3nc(-c4cccc(CN(C)CC(=O)O)c4)no3)ccc21]

({3-[5-(3-Chloro-1-isopropyl-1H-indol-5-yl)-[1,2,4]oxadiazol-3-yl]-benzyl}-methyl-amino)-acetic acid t-butyl ester (150 mg, 0.30 mmol) obtained in Preparation Example 118-3 was reacted according to the method described in Example 5 to obtain the title compound (133 mg, 80%).

NMR: ¹H-NMR (400 MHz, DMSO-d6) δ 8.38 (s, 1H), 8.24 (d, 1H), 8.05 (d, 1H), 8.01 (s, 1H), 7.93 (d, 1H), 7.77-7.72 (m, 2H), 4.96-4.92 (m, 1H), 4.51 (br, s, 2H), 3.50 (br, s, 2H), 2.83 (t, 2H), 2.75 (s, 3H), 1.51 (d, 6H)

Preparation Example 119-1

Synthesis of 3-({3-[5-(3-chloro-1-isopropyl-1H-indol-5-yl)-[1,2,4]oxadiazol-3-yl]-benzyl}-methyl-amino)-propanoic acid t-butyl ester 4-[5-(1-Isopropyl-1H-indazol-5-yl)-[1,2,4]oxadiazol-3-yl]-benzaldehyde (158 mg, 0.43 mmol) obtained in Preparation Example 116-2 and 3-methylaminopropanoic acid t-butyl ester hydrochloride (93 mg, 0.48 mmol) were reacted according to the method described in Preparation Example 14-4 to obtain the title compound (65 mg, 30%).

NMR: ¹H-NMR (400 HMz, CDCl₃); δ 8.54 (s, 1H), 8.13-8.04 (m, 3H), 7.51-7.44 (m, 3H), 7.29 (s, 1H), 4.77- 4.69 (m 1H), 3.62 (s, 2H), 2.79 (t, 2H), 2.48 (t, 2H), 2.24 (s, 3H), 1.55 (d, 6H), 1.46 (s, 9H)

Example 119

Synthesis of 3-({3-[5-(3-chloro-1-isopropyl-1H-indol-5-yl)-[1,2,4]oxadiazol-3-yl]-benzyl}-methyl-amino)-propanoic acid, trifluoroacetate

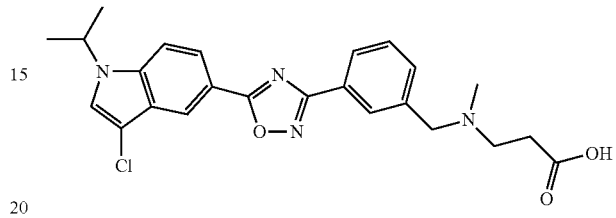

3-({3-[5-(3-Chloro-1-isopropyl-1H-indol-5-yl)-[1,2,4]oxadiazol-3-yl]-benzyl}-methyl-amino)-propanoic acid t-butyl ester (65 mg, 0.13 mmol) obtained in Preparation Example 119-1 was reacted according to the method described in Example 5 to obtain the title compound (54 mg, 73%).

NMR: ¹H-NMR (400 MHz, CDCl₃) δ 8.50 (s, 1H), 8.29 (d, 1H), 8.23 (s, 1H), 8.07 (d, 1H), 7.65-7.60 (m, 2H), 7.48 (d, 1H), 7.29 (s, 1H), 4.73-4.70 (m, 1H), 4.37 (s, 2H), 3.46 (m, 2H), 2.95 (m, 2H), 2.82 (s, 3H), 1.55 (d, 6H)

Preparation Example 120-1

Synthesis of {3-[5-(3-chloro-1-isopropyl-1H-indol-5-yl)-[1,2,4]oxadiazol-3-yl]-2-methyl-phenyl}-methanol 3-Chloro-1-isopropyl-1H-indol-5-carboxylic acid (435 mg, 1.83 mmol) obtained in Preparation Example 3-2 and N-hydroxy-3-hydroxymethyl-2-methyl-benzamidine (330 mg, 1.83 mmol) obtained in Preparation Example 26-1 were reacted according to the method described in Preparation Example 1-4 to obtain the title compound (598 mg, 86%).

NMR: ¹H-NMR (400 HMz, CDCl₃); δ 8.54 (s, 1H), 8.09 (dd, 1H), 7.92 (d, 1H), 7.56 (d, 1H), 7.49 (d, 1H), 7.36 (t, 1H), 7.29 (s, 1H), 4.83 (s, 2H), 4.76-4.69 (m, 1H), 2.63 (s, 3H), 1.65 (br, s, 1H), 1.56 (d, 6H)

Preparation Example 120-2

Synthesis of 3-[5-(3-chloro-1-isopropyl-1H-indol-5-yl)-[1,2,4]oxadiazol-3-yl]-2-methyl-benzaldehyde {3-[5-(3-Chloro-1-isopropyl-1H-indol-5-yl)-[1,2,4]oxadiazol-3-yl]-2-methyl-phenyl}-methanol (598 mg, 1.57 mmol) obtained in Preparation Example 120-1 was reacted according to the method described in Preparation Example 14-3 to obtain the title compound (533 mg, 89%).

NMR: ¹H-NMR (400 HMz, CDCl₃); δ 10.46 (s, 1H), 8.52 (s, 1H), 8.19 (d, 1H), 8.07 (d, 1H), 7.98 (d, 1H), 7.51 (t, 1H), 7.49 (d, 1H), 7.30 (s, 1H), 4.76-4.69 (m, 1H), 2.97 (s, 3H), 1.55 (d, 6H)

Preparation Example 120-3

Synthesis of ({3-[5-(3-chloro-1-isopropyl-1H-indol-5-yl)-[1,2,4]oxadiazol-3-yl]-2-methyl-benzyl}-methyl-amino)-acetic acid t-butyl ester 3-[5-(3-Chloro-1-isopropyl-1H-indol-5-yl)-[1,2,4]oxadiazol-3-yl]-2-methyl-benzaldehyde (139 mg, 0.37 mmol) obtained in Preparation Example 120-2 and N-methylglycine t-butyl ester hydrochloride (100 mg, 0.55 mmol) were reacted according to the method described in Preparation Example 14-4 to obtain the title compound (128 mg, 68%).

NMR: $^1$H-NMR (400 HMz, CDCl$_3$); δ 8.54 (s, 1H), 8.08 (d, 1H), 7.84 (d, 1H), 7.50-7.47 (m, 2H), 7.32-7.26 (m, 2H), 4.75-4.68 (m, 1H), 3.79 (s, 2H), 3.21 (s, 2H), 2.64 (s, 3H), 2.42 (s, 3H), 1.54 (d, 6H), 1.49 (s, 9H)

Example 120

Synthesis of ({3-[5-(3-chloro-1-isopropyl-1H-indol-5-yl)-[1,2,4]oxadiazol-3-yl]-2-methyl-benzyl}-methyl-amino)-acetic acid, trifluoroacetate

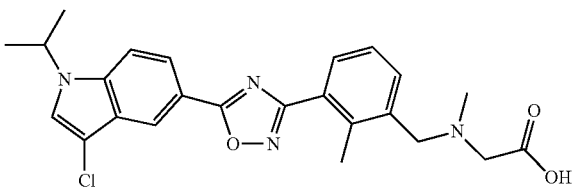 [SMILES: Cc1c(CN(C)CC(=O)O)cccc1-c1noc(-c2ccc3c(c2)c(Cl)cn3C(C)C)n1]

({3-[5-(3-Chloro-1-isopropyl-1H-indol-5-yl)-[1,2,4]oxadiazol-3-yl]-2-methyl-benzyl}-methyl-amino)-acetic acid t-butyl ester (128 mg, 0.25 mmol) obtained in Preparation Example 120-3 was reacted according to the method described in Example 5 to obtain the title compound (72 mg, 51%).

NMR: $^1$H-NMR (400 MHz, DMSO-d6) δ 8.33 (s, 1H), 8.02 (d, 2H), 7.98 (s, 1H), 7.89 (d, 1H), 7.73 (s, 1H), 7.52 (d, 1H), 4.92 (br, s, 1H), 4.50 (d, 2H), 4.16 (d, 2H), 2.81 (s, 3H), 2.68 (s, 3H), 1.49 (d, 6H)

Preparation Example 121-1

Synthesis of 3-{3-[5-(3-chloro-1-isopropyl-1H-indol-5-yl)-[1,2,4]oxadiazol-3-yl]-2-methyl-benzylamino}-propanoic acid t-butyl ester 3-[5-(3-Chloro-1-isopropyl-1H-indol-5-yl)-[1,2,4]oxadiazol-3-yl]-2-methyl-benzaldehyde (186 mg, 0.49 mmol) obtained in Preparation Example 120-2 and 3-methylaminopropanoic acid t-butyl ester hydrochloride (178 mg, 0.98 mmol) were reacted according to the method described in Preparation Example 14-4 to obtain the title compound (130 mg, 52%).

NMR: $^1$H-NMR (400 HMz, CDCl$_3$); δ 8.53 (s, 1H), 8.07 (d, 1H), 7.86 (d, 1H), 7.49 (d, 1H), 7.47 (t, 1H), 7.31 (t, 1H), 7.28 (s, 1H), 4.75-4.67 (m, 1H), 3.89 (s, 2H), 2.94 (t, 2H), 2.63 (s, 3H), 2.50 (t, 2H), 2.16 (s, 1H), 1.54 (d, 6H), 1.45 (s, 9H)

Example 121

Synthesis of 3-{3-[5-(3-chloro-1-isopropyl-1H-indol-5-yl)-[1,2,4]oxadiazol-3-yl]-2-methyl-benzylamino}-propanoic acid, trifluoroacetate

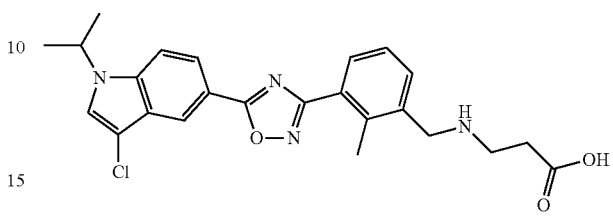

3-{3-[5-(3-Chloro-1-isopropyl-1H-indol-5-yl)-[1,2,4]oxadiazol-3-yl]-2-methyl-benzylamino}-propanoic acid t-butyl ester (40 mg, 0.08 mmol) obtained in Preparation Example 121-1 was reacted according to the method described in Example 5 to obtain the title compound (34 mg, 75%).

NMR: $^1$H-NMR (400 MHz, CDCl$_3$) δ 8.53 (s, 1H), 8.00 (t, 2H), 7.56 (d, 1H), 7.49 (d, 1H), 7.37 (t, 1H), 7.27 (d, 1H), 4.73-4.66 (m, 1H), 4.39 (s, 2H), 3.27 (br, s, 2H), 2.81 (br, s, 2H), 2.66 (s, 3H), 1.54 (d, 6H)

Preparation Example 122-1

Synthesis of 3-({3-[5-(3-chloro-1-isopropyl-1H-indol-5-yl)-[1,2,4]oxadiazol-3-yl]-2-methyl-benzyl}-methyl-amino)-propanoic acid t-butyl ester 3-{3-[5-(3-Chloro-1-isopropyl-1H-indol-5-yl)-[1,2,4]oxadiazol-3-yl]-2-methyl-benzylamino}-propanoic acid t-butyl ester (91 mg, 0.18 mmol) obtained in Preparation Example 121-1 and 37 wt % formaldehyde solution were reacted according to the method described in Example 3 to obtain the title compound (57 mg, 61%).

NMR: $^1$H-NMR (400 HMz, CDCl$_3$); δ 8.54 (s, 1H), 8.08 (dd, J=1.2 Hz, 1H), 7.83 (d, 1H), 7.48 (d, 1H), 7.44 (d, 1H), 7.28 (d, 2H), 4.75-4.69 (m, 1H), 3.57 (s, 2H), 2.77 (t, 2H), 2.62 (s, 3H), 2.45 (t, 2H), 2.20 (s, 3H), 1.55 (d, 6H), 1.44 (s, 9H),

Example 122

Synthesis of 3-({3-[5-(3-chloro-1-isopropyl-1H-indol-5-yl)-[1,2,4]oxadiazol-3-yl]-2-methyl-benzyl}-methyl-amino)-propanoic acid, trifluoroacetate

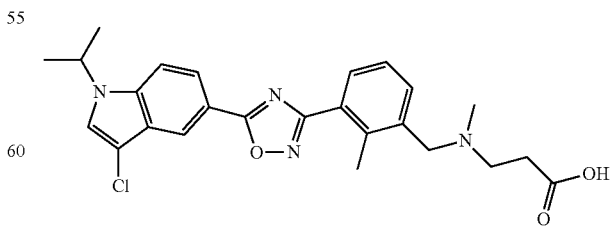

3-({3-[5-(3-Chloro-1-isopropyl-1H-indol-5-yl)-[1,2,4] oxadiazol-3-yl]-2-methyl-benzyl}-methyl-amino)-propanoic acid t-butyl ester (57 mg, 0.11 mmol) obtained in Preparation Example 122-1 was reacted according to the method described in Example 5 to obtain the title compound (54 mg, 84%).

NMR: $^1$H-NMR (400 MHz, DMSO-d6) δ 8.33 (s, 1H), 8.04-7.97 (m, 3H), 7.90 (d, 1H), 7.73 (d, 1H), 7.53 (t, 1H), 4.94-4.90 (m, 1H), 4.53 (br, s, 2H), 3.43 (br, s, 2H), 2.85 (br s, 2H), 2.76 (s, 3H), 2.64 (s, 3H), 1.50 (d, 6H)

Preparation Example 123-1

Synthesis of 3-{4-[5-(3-chloro-1-isopropyl-1H-indazol-5-yl)-[1,2,4]oxadiazol-3-yl]-3-methyl-phenyl}-propanoic acid ethyl ester 3-Chloro-1-isopropyl-1H-indazol-5-carboxylic acid (234 mg, 0.98 mmol) obtained in Preparation Example 92-2 and 3-[4-(N-hydroxycarbamimidoyl)-3-methyl-phenyl]-propanoic acid ethyl ester (246 mg, 0.98 mmol) obtained in Preparation Example 1-3 were reacted according to the method described in Preparation Example 1-4 to obtain the title compound (122 mg, 27%).

NMR: $^1$H-NMR (400 HMz, CDCl$_3$); δ 8.58 (s, 1H), 8.22 (dd, J=1.2 Hz, 1H), 8.04 (d, 1H), 7.55 (d, 1H), 7.19 (br, s, 2H), 4.89-4.80 (m, 1H), 4.15 (q, 2H), 3.00 (t, 2H), 2.68 (br, s, 5H), 1.61 (d, 6H), 1.26 (t, 3H)

Example 123

Synthesis of 3-{4-[5-(3-chloro-1-isopropyl-1H-indazol-5-yl)-[1,2,4]oxadiazol-3-yl]-3-methyl-phenyl}-propanoic acid

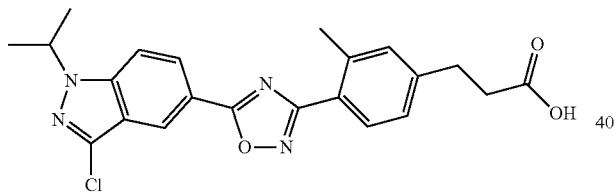

3-{4-[5-(3-Chloro-1-isopropyl-1H-indazol-5-yl)-[1,2,4] oxadiazol-3-yl]-3-methyl-phenyl}-propanoic acid ethyl ester (122 mg, 0.27 mmol) obtained in Preparation Example 123-1 was reacted according to the method described in Example 1 to obtain the title compound (79 mg, 69%).

NMR: $^1$H-NMR (400 MHz, CDCl$_3$) δ 8.59 (s, 1H), 8.24 (d, 1H), 8.06 (d, 1H), 7.55 (d, 1H), 7.21 (br, s, 1H), 4.85 (br, s, 1H), 3.02 (br, s, 2H), 2.74 (br, s, 2H), 2.68 (s, 3H), 1.62 (d, 6H)

Preparation Example 124-1

Synthesis of {3-[5-(3-chloro-1-isopropyl-1H-indazol-5-yl)-[1,2,4]oxadiazol-3-yl]-2-methyl-phenyl}-methanol 3-Chloro-1-isopropyl-1H-indazole-5-carboxylic acid (404 mg, 1.69 mmol) obtained in Preparation Example 92-2 and N-hydroxy-3-hydroxymethyl-2-methyl-benzamidine (304 mg, 1.69 mmol) obtained in Preparation Example 26-1 were reacted according to the method described in Preparation Example 1-4 to obtain the title compound (479 mg, 74%).

NMR: $^1$H-NMR (400 HMz, CDCl$_3$); δ 8.62 (s, 1H), 8.26 (dd, J=1.6, 1.2 Hz, 1H), 7.93 (d, 1H), 7.59 (d, 2H), 7.38 (t, 1H), 4.93-4.86 (m, 1H), 4.84 (s, 2H), 2.64 (s, 3H), 1.65 (d, 6H)

Preparation Example 124-2

Synthesis of 3-[5-(3-chloro-1-isopropyl-1H-indazol-5-yl)-[1,2,4]oxadiazol-3-yl]-2-methyl-benzaldehyde {3-[5-(3-Chloro-1-isopropyl-1H-indazol-5-yl)-[1,2,4]oxadiazol-3-yl]-2-methyl-phen yl}-methanol (479 mg, 1.25 mmol) obtained in Preparation Example 124-1 was reacted according to the method described in Preparation Example 14-3 to obtain the title compound (400 mg, 84%).

NMR: $^1$H-NMR (400 HMz, CDCl$_3$); δ 10.46 (s, 1H), 8.57 (s, 1H), 8.20 (t, 2H), 7.98 (d, 1H), 7.58-7.49 (m, 2H), 4.91-4.82 (m, 1H), 2.96 (s, 3H), 1.62 (d, 6H)

Preparation Example 124-3

Synthesis of ({3-[5-(3-chloro-1-isopropyl-1H-indazol-5-yl)-[1,2,4]oxadiazol-3-yl]-2-methyl-benzyl}-methyl-amino)-acetic acid t-butyl ester 3-[5-(3-Chloro-1-isopropyl-1H-indazol-5-yl)-[1,2,4]oxadiazol-3-yl]-2-methyl-benzaldehyde (136 mg, 0.36 mmol) obtained in Preparation Example 124-2 and N-methylglycine t-butyl ester hydrochloride (98 mg, 0.54 mmol) were reacted according to the method described in Preparation Example 14-4 to obtain the title compound (74 mg, 40%).

NMR: $^1$H-NMR (400 HMz, CDCl$_3$); δ 8.60 (s, 1H), 8.23 (dd, J=1.6 Hz, 1H), 7.85 (d, 1H), 7.56 (d, 1H), 7.50 (d, 1H), 7.32-7.27 (m, 1H), 4.90-4.81 (m, 1H), 3.79 (s, 2H), 3.21 (s, 2H), 2.64 (s, 3H), 2.42 (s, 3H), 1.62 (d, 6H), 1.49 (s, 9H)

Example 124

Synthesis of ({3-[5-(3-chloro-1-isopropyl-1H-indazol-5-yl)-[1,2,4]oxadiazol-3-yl]-2-methyl-benzyl}-methyl-amino)-acetic acid, trifluoroacetate

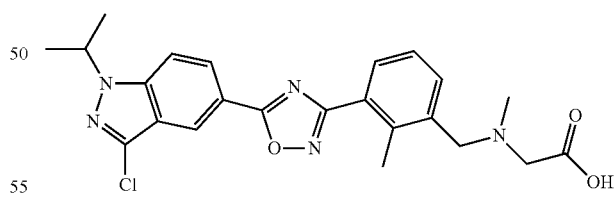

({3-[5-(3-Chloro-1-isopropyl-1H-indazol-5-yl)-[1,2,4] oxadiazol-3-yl]-2-methyl-benzyl}-methyl-amino)-acetic acid t-butyl ester (74 mg, 0.15 mmol) obtained in Preparation Example 124-3 was reacted according to the method described in Example 5 to obtain the title compound (64 mg, 75%).

NMR: $^1$H-NMR (400 MHz, DMSO-d6) δ 8.49 (s, 1H), 8.23 (d, 1H), 8.08 (d, 1H), 8.00 (d, 1H), 7.72 (d, 1H), 7.51 (d, 1H), 5.17-5.10 (m, 1H), 4.48 (br, s, 2H), 4.14 (br, s, 2H), 2.77 (s, 3H), 2.67 (s, 3H), 1.51 (d, 6H)

Preparation Example 125-1

Synthesis of 1-{3-[5-(3-chloro-1-isopropyl-1H-indazol-5-yl)-[1,2,4]oxadiazol-3-yl]-2-methyl-benzyl}-azetidine-3-carboxylic acid methyl ester 3-[5-(3-Chloro-1-isopropyl-1H-indazol-5-yl)-[1,2,4]oxadiazol-3-yl]-2-methyl-benzaldehyde (160 mg, 0.42 mmol) obtained in Preparation Example 124-2 and azetidine-3-carboxylic acid methyl ester (145 mg, 1.26 mmol) were reacted according to the method described in Preparation Example 14-4 to obtain the title compound (110 mg, 55%).

NMR: $^1$H-NMR (400 HMz, CDCl$_3$); δ 8.58 (s, 1H), 8.21 (dd, J=1.2 Hz, 1H), 7.84 (d, 1H), 7.55 (d, 1H), 7.45 (d, 1H), 7.31 (t, 1H), 4.89-4.81 (m, 1H), 3.73 (br, s, 4H), 3.60 (br, s, 2H), 3.38 (br, s, 3H), 2.59 (s, 3H), 1.61 (d, 6H)

Example 125

Synthesis of 1-{3-[5-(3-chloro-1-isopropyl-1H-indazol-5-yl)-[1,2,4]oxadiazol-3-yl]-2-methyl-benzyl}-azetidine-3-carboxylic acid

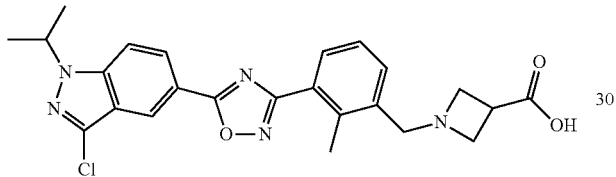

1-{3-[5-(3-chloro-1-isopropyl-1H-indazol-5-yl)-[1,2,4]oxadiazol-3-yl]-2-methyl-benzyl}-azetidine-3-carboxylic acid methyl ester (110 mg, 0.23 mmol) obtained in Preparation Example 125-1 was reacted according to the method described in Example 1 to obtain the title compound (25 mg, 23%).

NMR: $^1$H-NMR (400 MHz, CDCl$_3$) δ 8.54 (s, 1H), 8.18 (d, 1H), 8.00 (d, 1H), 7.70 (d, 1H), 7.56 (d, 1H), 7.44 (t, 1H), 4.89-4.82 (m, 1H), 4.56 (br, s, 2H), 4.48 (br, s, 2H), 4.22 (br, s, 1H), 3.07 (br, s, 4H), 2.71 (s, 3H), 1.61 (d, 6H)

Preparation Example 126-1

Synthesis of 3-chloro-1-isopropyl-5-{3-[3-((E)-2-methoxy-vinyl)-phenyl]-[1,2,4]oxadiazol-5-yl}-1H-indole Methoxymethyltriphenylphosphonium chloride (234 mg, 0.68 mmol) was dissolved in tetrahydrofuran (7 mL), and 1.0M NaHMDS tetrahydrofuran solution (0.68 mL, 0.68 mmol) was slowly added dropwise thereto at 0° C. The mixture was stirred at 0° C. for 30 minutes, and then 3-[5-(3-chloro-1-isopropyl-1H-indol-5-yl)-[1,2,4]oxadiazol-3-yl]-benzaldehyde (100 mg, 0.27 mmol) obtained in Preparation Example 118-2 dissolved in tetrahydrofuran solution (5 mL) was slowly added thereto. The mixture was stirred at room temperature for 2 hours, and then water was added thereto. The solution was extracted with dichloromethane. The extract was washed with brine, dried with anhydrous magnesium sulfate and filtered. The filtrate was distilled under reduced pressure. The residue was separated by column chromatography to obtain the title compound (69 mg, 65%).

NMR: $^1$H-NMR (400 HMz, CDCl$_3$); δ 8.54 (s, 1H), 8.08 (s, 1H), 7.98-7.95 (m, 1H), 7.55 (d, 1H), 7.37 (d, 1H), 7.28 (s, 1H), 7.19 (d, 1H), 4.75-4.67 (m, 1H), 3.77 (s, 3H), 1.54 (d, 6H)

Preparation Example 126-2

Synthesis of {3-[5-(3-chloro-1-isopropyl-1H-indol-5-yl)-[1,2,4]oxadiazol-3-yl]-phenyl}-acetaldehyde 3-Chloro-1-isopropyl-5-{3-[3-((E)-2-methoxy-vinyl)-phenyl]-[1,2,4]oxadiazol-5-yl}-1H-indole (69 mg, 0.18 mmol) obtained in Preparation Example 126-1 was dissolved in acetone (4 mL), and 6N hydrochloric acid solution (0.18 mL) was added dropwise thereto. The mixture was stirred at room temperature for 18 hours, and then water was added thereto. The solution was extracted with dichloromethane. The extract was washed with brine, dried with anhydrous magnesium sulfate and filtered. The filtrate was distilled under reduced pressure to obtain the title compound (62 mg, 91%).

NMR: $^1$H-NMR (400 HMz, CDCl$_3$); δ 9.83 (t, 1H), 8.53 (s, 1H), 8.17 (d, 1H), 8.08 (d, 2H), 7.55-7.48 (m, 2H), 7.38 (d, 1H), 7.29 (s, 1H), 4.76-4.68 (m, 1H), 3.82 (s, 2H), 1.55 (d, 6H)

Preparation Example 126-3

Synthesis of [(2-{3-[5-(3-chloro-1-isopropyl-1H-indol-5-yl)-[1,2,4]oxadiazol-3-yl]-phenyl}-ethyl)-methyl-amino]-acetic acid t-butyl ester {3-[5-(3-Chloro-1-isopropyl-1H-indol-5-yl)-[1,2,4]oxadiazol-3-yl]-phenyl}-acetaldehyde (62 mg, 0.16 mmol) obtained in Preparation Example 126-2 and N-methylglycine t-butyl ester hydrochloride (59 mg, 0.33 mmol) were reacted according to the method described in Preparation Example 14-4 to obtain the title compound (58 mg, 71%).

NMR: $^1$H-NMR (400 HMz, CDCl$_3$); δ 8.54 (s, 1H), 8.09 (dd, J=1.6 Hz, 1H), 8.04 (d, 2H), 7.48 (d, 1H), 7.42 (d, 1H), 7.37 (d, 1H), 7.29 (s, 1H), 476-4.67 (m, 1H), 3.26 (s, 2H), 2.94-2.83 (m, 4H), 2.49 (s, 3H), 1.55 (d, 6H), 1.49 (s, 9H)

Example 126

Synthesis of [(2-{3-[5-(3-chloro-1-isopropyl-1H-indol-5-yl)-[1,2,4]oxadiazol-3-yl]-phenyl}-ethyl)-methyl-amino]-acetic acid, trifluoroacetate

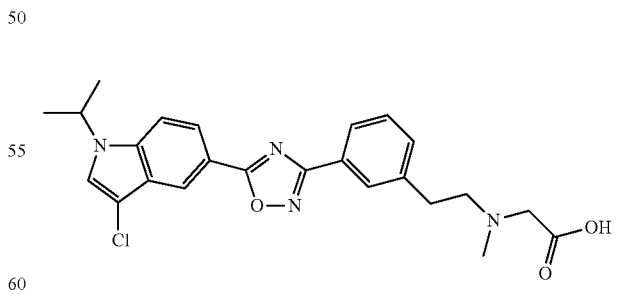

[(2-{3-[5-(3-Chloro-1-isopropyl-1H-indol-5-yl)-[1,2,4]oxadiazol-3-yl]-phenyl}-ethyl)-methyl-amino]-acetic acid t-butyl ester (58 mg, 0.11 mmol) obtained in Preparation Example 126-3 was reacted according to the method described in Example 5 to obtain the title compound (55 mg, 88%).

NMR: $^1$H-NMR (400 MHz, DMSO-d6) δ 8.35 (d, J=1.2 Hz, 1H), 8.09 (s, 1H), 8.06-8.02 (m, 2H), 8.00 (s, 1H), 7.91 (d, 1H), 7.60 (t, 1H), 7.54 (d, 1H), 4.95-4.89 (m, 1H), 4.20 (s, 2H), 3.44 (br, s, 2H), 3.17 (br s, 2H), 2.95 (s, 3H), 1.50 (d, 6H)

Preparation Example 127-1

Synthesis of 1-(2-{3-[5-(3-chloro-1-isopropyl-1H-indol-5-yl)-[1,2,4]oxadiazol-3-yl]-phenyl}-ethyl)-piperidine-4-carboxylic acid ethyl ester {3-[5-(3-Chloro-1-isopropyl-1H-indol-5-yl)-[1,2,4]oxadiazol-3-yl]-phenyl}-acetaldehyde (67 mg, 0.18 mmol) obtained in Preparation Example 126-2 and piperidine-4-carboxylic acid ethyl ester (0.05 mL, 0.35 mmol) were reacted according to the method described in OPreparation Example 14-4 to obtain the title compound (50 mg, 54%).

NMR: $^1$H-NMR (400 HMz, CDCl$_3$); δ 8.54 (s, 1H), 8.09 (dd, J=1.6 Hz, 1H), 8.04 (d, 2H), 7.49 (d, 1H), 7.43 (d, 1H), 7.37 (d, 1H), 7.29 (s, 1H), 4.75-4.67 (m, 1H), 4.14 (q, 2H), 3.00 (d, 2H), 2.92 (t, 2H), 2.68 (t, 2H), 2.34-2.28 (m, 1H), 2.16 (t, 2H), 1.96 (d, 2H), 1.87-1.79 (m, 2H), 1.55 (d, 6H), 1.26 (t, 3H)

Example 127

Synthesis of 1-(2-{3-[5-(3-chloro-1-isopropyl-1H-indol-5-yl)-[1,2,4]oxadiazol-3-yl]-phenyl}-ethyl)-piperidine-4-carboxylic acid

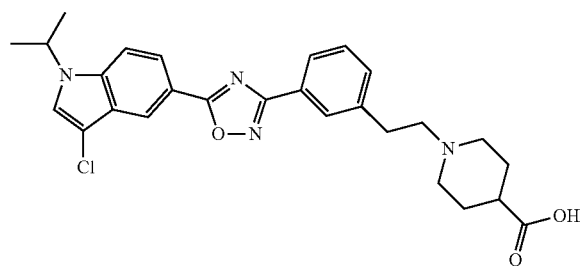 [SMILES: CC(C)n1cc(Cl)c2cc(-c3nc(-c4cccc(CCN5CCC(C(=O)O)CC5)c4)no3)ccc21]

1-(2-{3-[5-(3-Chloro-1-isopropyl-1H-indol-5-yl)-[1,2,4]oxadiazol-3-yl]-phenyl}-ethyl)-piperidine-4-carboxylic acid ethyl ester (50 mg, 0.10 mmol) obtained in Preparation Example 127-1 was reacted according to the method described in Example 1 to obtain the title compound (41 mg, 83%).

NMR: $^1$H-NMR (400 MHz, DMSO-d6) δ 8.37 (s, 1H), 8.07 (s, 1H, 8.03 (d, 2H), 8.00 (s, 1H), 7.90 (d, 1H), 7.61-7.54 (m, 2H), 4.93-4.90 (m, 1H), 3.62 (br, s, 1H), 3.35-3.00 (m, 8H), 2.06 (br s, 2H), 1.92 (br s, 2H), 1.49 (d, 6H)

Preparation Example 128-1

Synthesis of 5-bromo-3-cyclopropyl-1H-indazole

The title compound was obtained according to the method described in WO 2006/081230 A2.

Preparation Example 128-2

Synthesis of 5-bromo-3-cyclopropyl-1-isopropyl-1H-indazole

5-Bromo-3-cyclopropyl-1H-indazole (394 mg, 1.66 mmol) obtained in Preparation Example 128-1 and isopropyliodide (0.20 mL, 1.99 mmol) were reacted according to the method described in Preparation Example 1-1 to obtain the title compound (323 mg, 70%).

Preparation Example 128-3

Synthesis of 3-cyclopropyl-1-isopropyl-1H-indazole-5-carbonitrile

5-Bromo-3-cyclopropyl-1-isopropyl-1H-indazole (323 mg, 1.16 mmol) obtained in Preparation Example 128-2 was reacted according to the method described in Preparation Example 95-3 to obtain the title compound (233 mg, 90%).

Preparation Example 128-4

Synthesis of 3-cyclopropyl-1-isopropyl-1H-indazole-5-carboxylic acid

3-Cyclopropyl-1-isopropyl-1H-indazole-5-carbonitrile (233 mg, 1.04 mmol) obtained in Preparation Example 128-3 was reacted according to the method described in Preparation Example 95-4 to obtain the title compound (214 mg, 85%).

Preparation Example 128-5

Synthesis of 6-[5-(3-cyclopropyl-1-isopropyl-1H-indazol-5-yl)-[1,2,4]oxadiazol-3-yl]-5-methyl-3,4-dihydro-1H-isoquinoline-2-carboxylic acid t-butyl ester 3-Cyclopropyl-1-isopropyl-1H-indazole-5-carboxylic acid (214 mg, 0.88 mmol) obtained in Preparation Example 128-4 and 6-(N-hydroxycarbamimidoyl)-5-methyl-3,4-dihydro-1H-isoquinoline-2-carboxylic acid t-butyl ester (290 mg, 0.88 mmol) obtained in Preparation Example 56-1 were reacted according to the method described in Preparation Example 1-4 to obtain the title compound (250 mg, 56%).

Preparation Example 128-6

Synthesis of 6-[5-(3-cyclopropyl-1-isopropyl-1H-indazol-5-yl)-[1,2,4]oxadiazol-3-yl]-5-methyl-1,2,3,4-tetrahydro-isoquinoline, hydrochloride 6-[5-(3-Cyclopropyl-1-isopropyl-1H-indazol-5-yl)-[1,2,4]oxadiazol-3-yl]-5-methyl-3,4-dihydro-1H-isoquinoline-2-carboxylic acid t-butyl ester (250 mg, 0.49 mmol) obtained in Preparation Example 128-5 was reacted according to the method described in Example 27 to obtain the title compound (170 mg, 78%).

Preparation Example 128-7

Synthesis of 3-{6-[5-(3-cyclopropyl-1-isopropyl-1H-indazol-5-yl)-[1,2,4]oxadiazol-3-yl]-5-methyl-3,4-dihydro-1H-isoquinolin-2-yl}-propanoic acid t-butyl ester 6-[5-(3-cyclopropyl-1-isopropyl-1H-indazol-5-yl)-[1,2,4]oxadiazol-3-yl]-5-methyl-1,2,3,4-tetrahydro-isoquinoline, hydrochloride (170 mg, 0.38 mmol) obtained in Preparation Example 128-6 and t-butyl acrylate (0.16 mL, 1.14 mmol) were reacted according to the method described in Preparation Example 29-1 to obtain the title compound (170 mg, 81%).

Example 128

3-{6-[5-(3-cyclopropyl-1-isopropyl-1H-indazol-5-yl)-[1,2,4]oxadiazol-3-yl]-5-methyl-3,4-dihydro-1H-isoquinolin-2-yl}-propanoic acid, trifluoroacetate

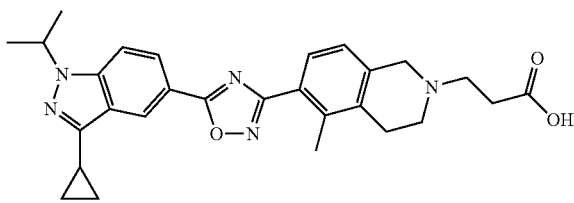 [SMILES: Cc1c(-c2noc(-c3ccc4c(c3)c(C3CC3)nn4C(C)C)n2)ccc2c1CCN(CCC(=O)O)C2]

3-{6-[5-(3-Cyclopropyl-1-isopropyl-1H-indazol-5-yl)-[1,2,4]oxadiazol-3-yl]-5-methyl-3,4-dihydro-1H-isoquinolin-2-yl}-propanoic acid t-butyl ester (170 mg, 0.31 mmol) obtained in Preparation Example 128-7 was reacted according to the method described in Example 5 to obtain the title compound (160 mg, 85%).

NMR: $^1$H-NMR (400 HMz, CDCl$_3$); δ 8.41 (s, 1H), 8.02 (d, 1H), 7.84 (d, 1H), 7.41 (d, 1H), 7.12 (m, 1H), 4.74 (m, 1H), 4.35 (m, 4H), 3.52 (m, 2H), 3.05 (m, 4H), 2.49 (s, 3H), 2.21 (m, 1H), 1.51 (d, 6H), 1.04 (m, 4H)

Preparation Example 129-1

Synthesis of 3-[4-(N-hydroxycarbamimidoyl)-3-methyl-phenyl]-butyric acid t-butyl ester The title compound was obtained according to the method described in Bioorganic & Medicinal Chemistry Letters, 2007(17), 828-831.

NMR: $^1$H-NMR (400 HMz, CDCl$_3$); δ 7.30 (d, 1H), 7.06 (s, 1H), 7.04 (d, 1H), 4.80 (br, s, 2H), 3.19 (q, 1H), 2.47 (s, 2H), 2.41 (s, 3H), 1.37 (s, 9H), 1.26 (d, 3H),

Preparation Example 129-2

Synthesis of 3-{4-[5-(3-chloro-1-isopropyl-1H-indazol-5-yl)-[1,2,4]oxadiazol-3-yl]-3-methyl-phenyl}-butyric acid t-butyl ester 3-Chloro-1-isopropyl-1H-indazole-5-carboxylic acid (81 mg, 0.34 mmol) obtained in Preparation Example 92-2 and 3-[4-(N-hydroxycarbamimidoyl)-3-methyl-phenyl]-butyric acid t-butyl ester (99 mg, 0.34 mmol) obtained in Preparation Example 129-1 were reacted according to the method described in Preparation Example 1-4 to obtain the title compound (157 mg, 94%).

NMR: $^1$H-NMR (400 HMz, CDCl$_3$); δ 8.58 (s, 1H), 8.23 (dd, J=1.6, 1.2 Hz, 1H), 8.06 (d, 1H), 7.55 (d, 1H), 7.22 (d, 2H), 4.89-4.82 (m, 1H), 3.32-3.24 (m, 1H), 2.69 (s, 3H), 2.60-2.47 (m, 2H), 1.62 (d, 6H), 1.38 (s, 9H), 1.33 (d, 3H)

Example 129

Synthesis of 3-{4-[5-(3-chloro-1-isopropyl-1H-indazol-5-yl)-[1,2,4]oxadiazol-3-yl]-3-methyl-phenyl}-butyric acid, trifluoroacetate

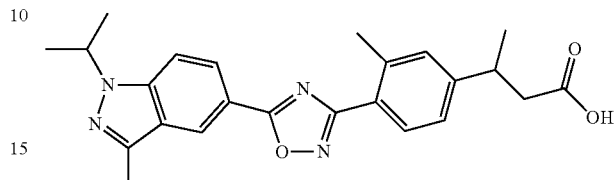

3-{4-[5-(3-Chloro-1-isopropyl-1H-indazol-5-yl)-[1,2,4]oxadiazol-3-yl]-3-methyl-phenyl}-butyric acid t-butyl ester (157 mg, 0.32 mmol) obtained in Preparation Example 129-2 was reacted according to the method described in Example 5 to obtain the title compound (128 mg, 72%).

NMR: $^1$H-NMR (400 MHz, CDCl$_3$) δ 8.94 (br, s, 1H), 8.57 (s, 1H), 8.21 (d, 1H), 8.04 (d, 1H), 7.54 (d, 1H), 7.21 (d, 2H), 4.89-4.79 (m, 1H), 3.33 (q, 1H), 2.76-2.61 (m, 5H), 1.61 (d, 6H), 1.36 (d, 3H)

Preparation Example 130-1

Synthesis of 3-{4-[5-(3-chloro-1-isopropyl-1H-indol-5-yl)-[1,2,4]oxadiazol-3-yl]-3-methyl-phenyl}-butyric acid t-butyl ester 3-Chloro-1-isopropyl-1H-indole-5-carboxylic acid (81 mg, 0.34 mmol) obtained in Preparation Example 3-2 and 3-[4-(N-hydroxycarbamimidoyl)-3-methyl-phenyl]-butyric acid t-butyl ester (99 mg, 0.34 mmol) obtained in Preparation Example 129-1 were reacted according to the method described in Preparation Example 1-4 to obtain the title compound (158 mg, 94%).

NMR: $^1$H-NMR (400 HMz, CDCl$_3$); δ 8.52 (s, 1H), 8.07 (dd, J=1.6, 2.0 Hz, 1H), 8.06 (d, 1H), 7.47 (d, 1H), 7.27 (s, 1H), 7.21 (d, 2H), 4.75-4.68 (m, 1H), 3.29-3.23 (m, 1H), 2.69 (s, 3H), 2.60-2.49 (m, 2H), 1.53 (d, 6H), 1.38 (s, 9H), 1.31 (d, 3H)

Example 130

Synthesis of 3-{4-[5-(3-chloro-1-isopropyl-1H-indol-5-yl)-[1,2,4]oxadiazol-3-yl]-3-methyl-phenyl}-butyric acid, trifluoroacetate

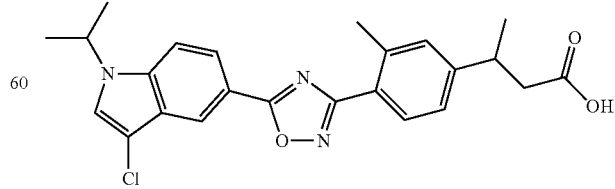

3-{4-[5-(3-Chloro-1-isopropyl-1H-indol-5-yl)-[1,2,4]oxadiazol-3-yl]-3-methyl-phenyl }-butyric acid t-butyl ester (157 mg, 0.32 mmol) obtained in Preparation Example 130-1 was reacted according to the method described in Example 5 to obtain the title compound (126 mg, 72%).

NMR: $^1$H-NMR (400 MHz, CDCl$_3$) δ 8.67 (br, s, 1H), 8.51 (s, 1H), 8.05 (t, 2H), 7.47 (d, 1H), 7.28 (s, 1H), 7.21 (d, 2H), 4.75-4.65 (m, 1H), 3.33 (q, 1H), 2.76-2.60 (m, 5H), 1.54 (d, 6H), 1.36 (d, 3H)

Preparation Example 131-1

Synthesis of 1-isopropyl-1H-indole-5-carbaldehyde

1H-Indole-5-carbaldehyde (300 mg, 2.07 mmol) and isopropyliodide (108 mg, 2.48 mmol) were reacted according to the method described in Preparation Example 1-1 to obtain the title compound (320 mg, 83%).

NMR: $^1$H-NMR (400 HMz, CDCl$_3$); δ 10.02 (s, 1H), 8.15 (s, 1H), 7.77 (d, 1H), 7.45 (d, 1H), 7.32 (d, 1H), 6.67 (d, 1H), 4.72 (m, 1H), 1.55 (d, 6H)

Preparation Example 131-2

Synthesis of (1-isopropyl-1H-indol-5-yl)-methanol

1-Isopropyl-1H-indole-5-carbaldehyde (320 mg, 1.71 mmol) obtained in Preparation Example 131-1 was dissolved in methanol (10 mL), and then sodium borohydride (97 mg, 2.56 mmol) was added dropwise thereto at 0° C. The mixture was stirred at 0° C. for 1 hour, and then water was added thereto. The solution was extracted with ethylacetate. The extract was washed with brine, dried with anhydrous magnesium sulfate and filtered. The filtrate was distilled under reduced pressure to obtain the title compound (300 mg, 93%).

NMR: $^1$H-NMR (400 HMz, CDCl$_3$); δ 7.61 (s, 1H), 7.37 (d, 1H), 7.23 (m, 2H), 6.50 (d, 1H), 4.75 (d, 2H), 4.67 (m, 1H), 1.53 (d, 6H)

Preparation Example 131-3

Synthesis of 4-(1-isopropyl-1H-indol-5-ylmethoxy)-benzaldehyde (1-Isopropyl-1H-indol-5-yl)-methanol (300 mg, 1.59 mmol) obtained in Preparation Example 131-2 and 4-hydroxybenzaldehyde (314 mg, 2.57 mmol) were dissolved in tetrahydrofuran, and then triphenylphosphin (PhP$_3$, 897 mg, 3.42 mmol) and diethyl azodicarboxylate (DEAD, 0.62 mL, 3.42 mmol) were added dropwise thereto. The mixture was stirred at room temperature for 18 hours and distilled under reduced pressure to remove the solvent. The residue was purified by column chromatography to obtain the title compound (150 mg, 20%).

NMR: $^1$H-NMR (400 HMz, CDCl$_3$); δ 9.87 (s, 1H), 7.82 (d, 2H), 7.69 (d, J=1.2 Hz, 1H), 7.41 (d, 1H), 7.28-7.25 (m, 2H), 7.11 (d, 2H), 6.52 (d, 1H), 5.24 (s, 2H), 4.73-7.65 (m, 1H), 1.53 (d, 6H)

Example 131

Synthesis of 1-[4-(1-isopropyl-1H-indol-5-ylmethoxy)-benzyl]-azetidine-3-carboxylic acid

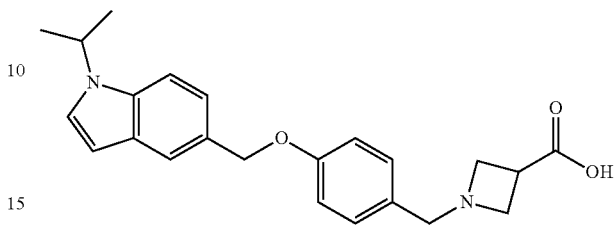

4-(1-Isopropyl-1H-indol-5-ylmethoxy)-benzaldehyde (150 mg, 0.51 mmol) obtained in Preparation Example 131-3 and azetidine-3-carboxylic acid (57 mg, 0.56 mmol) were reacted according to the method described in Example 3 to obtain the title compound (65 mg, 34%).

NMR: $^1$H NMR (400 MHz, MeOD-d$_4$); δ 7.62 (s, 1H), 7.44 (d, 1H), 7.39-7.35 (m, 3H), 7.23 (dd, J=1.2 1.6 Hz, 1H), 7.09 (d, 2H), 6.47 (d, 1H), 5.19 (s, 2H), 4.79-4.75 (m, 1H), 4.28 (s, 2H), 4.17 (d, 4H), 3.46-3.37 (m, 1H), 1.52 (d, 6H)

Preparation Example 132-1

Synthesis of 6-(1-isopropyl-1H-indol-5-ylmethoxy)-naphthalene-2-carbaldehyde (1-Isopropyl-1H-indol-5-yl)-methanol (200 mg, 1.06 mmol) obtained in Preparation Example 131-2 and 6-hydroxynaphthalene-2-carbaldehyde (182 mg, 1.06 mmol) were reacted according to the method described in Preparation Example 131-3 to obtain the title compound (90 mg, 25%).

NMR: $^1$H-NMR (400 HMz, CDCl$_3$); δ 10.09 (s, 1H), 8.25 (s, 1H), 7.91 (dd, J=1.6 Hz, 1H), 7.89 (d, 1H), 7.81 (d, 1H), 7.75 (s, 1H), 7.42 (d, 1H), 7.33-7.30 (m, 3H), 7.27 (s, 1H), 6.54 (d, 1H), 5.30 (s, 2H), 4.73-4.65 (m, 1H), 1.56 (d, 6H)

Example 132

Synthesis of 1-[4-(1-isopropyl-1H-indol-5-ylmethoxy)-benzyl]-azetidine-3-carboxylic acid

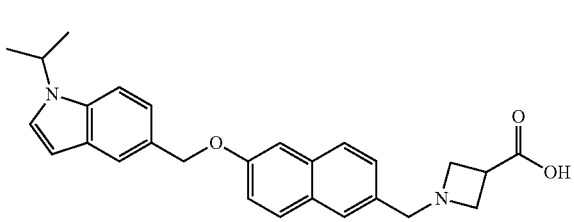 [SMILES: CC(C)n1ccc2cc(COc3ccc4cc(CN5CC(C(=O)O)C5)ccc4c3)ccc21]

6-(1-Isopropyl-1H-indol-5-ylmethoxy)-naphthalene-2-carbaldehyde (90 mg, 0.26 mmol) obtained in Preparation Example 132-1 and azetidine-3-carboxylic acid (30 mg, 0.29 mmol) were reacted according to the method described in Example 3 to obtain the title compound (1 mg, 1%).

NMR: $^1$H-NMR (400 MHz, MeOD-d4) δ 7.89-7.83 (m, 3H), 7.69 (s, 1H), 7.89-7.43 (m, 3H), 7.38 (d, 1H), 7.32-7.27

(m, 2H), 6.49 (d, 1H), 5.29 (s, 2H), 4.79-4.75 (m, 1H), 4.39 (s, 2H), 4.13 (d, 4H), 3.46-3.37 (m, 1H), 1.54 (d, 6H)

Preparation Example 133-1

Synthesis of 3-(4-hydroxy-phenyl)-propanoic acid ethyl ester

The title compound was obtained according to the method described in Journal of Medicinal Chemistry, 2007(50), 1495~1503.
NMR: $^1$H-NMR (400 HMz, CDCl$_3$); δ 7.06 (d, 2H), 6.74 (d, 2H), 4.12 (q, 2H), 2.87 (t, 2H), 2.57 (t, 2H), 1.22 (t, 3H)

Preparation Example 133-2

Synthesis of 3-[4-(1-isopropyl-1H-indol-5-yl-methoxy)-phenyl]-propanoic acid ethyl ester (1-Isopropyl-1H-indol-5-yl)-methanol (195 mg, 1.03 mmol) obtained in Preparation Example 131-2 and 3-(4-hydroxyphenyl)-propanoic acid ethyl ester (200 mg, 1.03 mmol) obtained in Preparation Example 133-1 were reacted according to the method described in Preparation Example 131-3 to obtain the title compound (160 mg, 43%).
NMR: $^1$H-NMR (400 HMz, CDCl$_3$); δ 7.77 (s, 1H), 7.43 (d, 1H), 7.38 (dd, 1H), 7.32 (d, 1H), 7.20 (d, 2H), 7.03 (d, 2H), 5.21 (s, 2H), 4.75 (m, 2H), 4.20 (q, 2H), 2.99 (t, 2H), 2.66 (t, 2H), 1.60 (d, 6H), 1.30 (t, 3H)

Example 133

Synthesis of 3-[4-(1-isopropyl-1H-indol-5-yl-methoxy)-phenyl]-propanoic acid

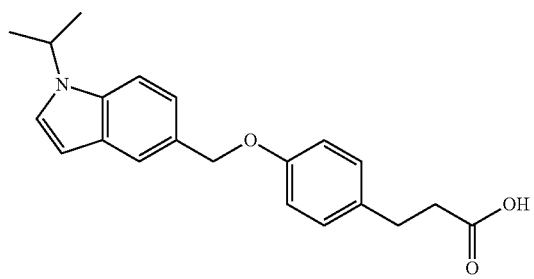 [SMILES: CC(C)n1ccc2cc(COc3ccc(CCC(=O)O)cc3)ccc21]

3-[4-(1-Isopropyl-1H-indol-5-ylmethoxy)-phenyl]-propanoic acid ethyl ester (160 mg, 0.44 mmol) obtained in Preparation Example 133-2 was reacted according to the method described in Example 1 to obtain the title compound (130 mg, 88%).
NMR: $^1$H-NMR (400 HMz, MeOD); δ 7.61 (d, 1H), 7.43 (d, 1H), 7.35 (d, 1H), 7.23 (dd, 1H), 7.13 (d, 2H), 6.94 (d, 2H), 6.46 (d, 1H), 5.10 (s, 2H), 4.73 (m, 1H), 2.84 (t, 2H), 2.53 (t, 2H), 1.54 (d, 6H)

Preparation Example 134-1

Synthesis of 3-chloro-1-isopropyl-1H-indole-5-carbaldehyde

1-Isopropyl-1H-indole-5-carbaldehyde (490 mg, 2.62 mmol) obtained in Preparation Example 131-1 was reacted according to the method described in Preparation Example 3-1 to obtain the title compound (220 mg, 38%).
NMR: $^1$H-NMR (400 HMz, CDCl$_3$); δ 10.05 (s, 1H), 8.14 (s, 1H), 7.81 (dd, 1H), 7.44 (d, 1H), 7.27 (s, 1H), 4.70 (m, 1H), 1.53 (d, 6H)

Preparation Example 134-2

Synthesis of (3-chloro-1-isopropyl-1H-indol-5-yl)-methanol

3-Chloro-1-isopropyl-1H-indole-5-carbaldehyde (220 mg, 0.99 mmol) obtained in Preparation Example 134-1 was reacted according to the method described in Preparation Example 131-2 to obtain the title compound (190 mg, 86%).
NMR: $^1$H-NMR (400 HMz, CDCl$_3$); δ 7.60 (s, 1H), 7.35 (d, 1H), 7.27 (d, 1H), 7.20 (s, 1H), 4.79 (d, 2H), 4.65 (m, 1H), 1.50 (d, 6H)

Preparation Example 134-3

Synthesis of 3-chloro-5-chloromethyl-1-isopropyl-1H-indole (3-Chloro-1-isopropyl-1H-indol-5-yl)-methanol (190 mg, 0.85 mmol) obtained in Preparation Example 134-2 was dissolved in dichloromethane (3 mL), and then thionylchloride (0.18 mL, 2.54 mmol) and a catalytic amount of dimethylformamide were added dropwise thereto. The mixture was stirred at room temperature for 1 hour, and the solvent was removed by distillation under reduced pressure to obtain the title compound (180 mg, 87%).

Preparation Example 134-4

Synthesis of 4-(3-chloro-1-isopropyl-1H-indol-5-ylmethoxy)-3-methyl-benzaldehyde 3-Chloro-5-chloromethyl-1-isopropyl-1H-indole (180 mg, 0.74 mmol) obtained in Preparation Example 134-3 was dissolved in dimethylformamide (3 mL), and then potassium carbonate (235 mg, 1.70 mmol) and 4-hydroxy-3-methyl-benzaldehyde (122 mg, 0.89 mmol) were added dropwise. The mixture was stirred at 70° C. for 18 hours and distilled under reduced pressure to remove the solvent. After adding water, the solution was extracted with ethylacetate. The extract was washed with brine, dried with anhydrous magnesium sulfate and filtered. The filtrate was distilled under reduced pressure. The residue was purified by column chromatography to obtain the title compound (150 mg, 59%).
NMR: $^1$H-NMR (400 HMz, CDCl$_3$); δ 9.90 (s, 1H), 7.73 (m, 3H), 7.45 (d, 1H), 7.35 (dd, 1H), 7.27 (s, 1H), 7.11 (d, 1H), 5.32 (s, 2H), 4.70 (m, 1H), 2.36 (s, 3H), 1.54 (d, 6H)

Example 134

Synthesis of 1-[4-(3-chloro-1-isopropyl-1H-indol-5-ylmethoxy)-3-methyl-benzyl]-azetidine-3-carboxylic acid

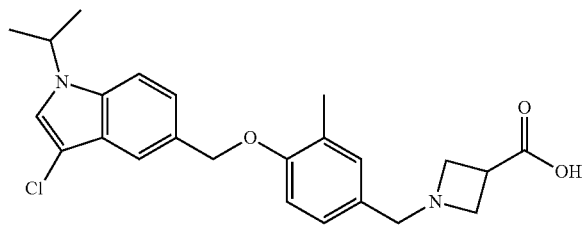 [SMILES: Cc1cc(CN2CC(C(=O)O)C2)ccc1OCc1ccc2c(c1)c(Cl)cn2C(C)C]

4-(3-Chloro-1-isopropyl-1H-indol-5-ylmethoxy)-3-methyl-benzaldehyde (150 mg, 0.44 mmol) obtained in Preparation Example 134-4 and azetidine-3-carboxylic acid (44 mg, 0.44 mmol) were reacted according to the method described in Example 3 to obtain the title compound (95 mg, 51%).

NMR: $^1$H-NMR (400 HMz, MeOD); δ 7.59 (s, 1H), 7.49 (d, 1H), 7.42 (s, 1H), 7.34 (dd, 1H), 7.16 (dd, 2H), 7.04 (d, 1H), 5.22 (s, 2H), 4.77 (m, 1H), 3.92 (s, 2H), 3.85 (t, 2H), 3.76 (t, 2H), 3.28 (m, 1H), 2.27 (s, 3H), 1.52 (d, 6H)

Preparation Example 135-1

Synthesis of (1-isopropyl-1H-indazol-5-yl)-methanol

1-Isopropyl-1H-indazole-5-carboxylic acid methyl ester (2.0 g, 9.16 mmol) obtained in Preparation Example 80-2 was reacted according to the method described in Example 44 to obtain the title compound (1.76 g, 100%).

NMR: $^1$H-NMR (400 HMz, CDCl$_3$); δ 7.99 (s, 1H), 7.70 (s, 1H), 7.45 (d, J=8.0 Hz, 1H), 7.40 (d, J=8.0 Hz, 1H), 4.82-4.90 (m, 1H), 4.79 (d, J=4.0 Hz, 2H), 1.65 (t, J=4.0 Hz, 1H), 1.60 (d, J=4.0 Hz, 6H)

Preparation Example 135-2

Synthesis of 5-hydroxy-3,4-dihydro-1H-isoquinoline-2-carboxylic acid t-butyl ester The title compound was obtained according to the method described in WO 2005/051945 A1.

NMR: $^1$H-NMR (400 HMz, CDCl$_3$); δ 7.05 (t, 1H), 6.70 (d, 1H), 6.64 (d, 1H), 4.95 (s, 1H), 4.56 (s, 2H), 3.67 (t, 2H), 2.75 (t, 2H), 1.49 (s, 9H)

Preparation Example 135-3

Synthesis of 5-(1-isopropyl-1H-indazol-5-yl-methoxy)-3,4-dihydro-1H-isoquinoline-2-carboxylic acid t-butyl ester (1-Isopropyl-1H-indazol-5-yl)-methanol (215 mg, 1.13 mmol) obtained in Preparation Example 135-1 and 5-hydroxy-3,4-dihydro-1H-isoquinoline-2-carboxylic acid t-butyl ester (254 mg, 1.02 mmol) were reacted according to the method described in Preparation Example 131-3 to obtain the title compound (139 mg, 32%).

NMR: $^1$H-NMR (400 HMz, CDCl$_3$); δ 8.00 (s, 1H), 7.76 (s, 1H), 7.47-7.38 (m, 2H), 7.15-7.10 (m, 1H), 6.81 (d, 1H), 6.73 (d, 1H), 5.15 (s, 2H), 4.90-4.82 (m, 1H), 4.57 (br, s, 2H), 3.64 (br, t, 2H), 2.82 (br, t, 2H), 1.63 (d, 6H), 1.48 (s, 9H)

Preparation Example 135-4

Synthesis of 5-(1-isopropyl-1H-indazol-5-yl-methoxy)-1,2,3,4-tetrahydro-isoquinoline, hydrochloride 5-(1-Isopropyl-1H-indazol-5-ylmethoxy)-3,4-dihydro-1H-isoquinoline-2-carboxylic acid t-butyl ester (139 mg, 0.33 mmol) obtained in Preparation Example 135-3 was reacted according to the method described in Example 27 to obtain the title compound (101 mg, 95%).

NMR: $^1$H-NMR (400 HMz, CDCl$_3$); δ 8.08 (s, 1H), 7.78 (s, 1H), 7.52 (s, 1H), 7.48 (d, 2H), 6.88 (d, 1H), 6.76 (d, 1H), 5.16 (s, 2H), 4.94-4.87 (m, 1H), 4.36 (br, s, 2H), 3.48 (br, s, 2H), 3.16 (br, s, 2H), 1.64 (d, 6H)

Preparation Example 135-5

Synthesis of [5-(1-isopropyl-1H-indazol-5-yl-methoxy)-3,4-dihydro-1H-isoquinolin-2-yl]-acetic acid t-butyl ester 5-(1-Isopropyl-1H-indazol-5-ylmethoxy)-1,2,3,4-tetrahydro-isoquinoline, hydrochloride (101 mg, 0.31 mmol) obtained in Preparation Example 135-4 and t-butylbromoacetate (0.06 mL, 0.43 mmol) were reacted according to the method described in Preparation Example 28-1 to obtain the title compound (80 mg, 56%).

NMR: $^1$H-NMR (400 HMz, CDCl$_3$); δ 8.23 (s, 1H), 8.05 (s, 1H), 7.40-7.46 (m, 2H), 7.05-7.09 (m, 1H), 6.76 (d, J=8.0 Hz, 1H), 6.65 (d, J=8.00 Hz, 1H), 5.14 (s, 2H), 4.81-4.89 (m, 1H), 3.95 (s, 2H), 3.44 (s, 2H), 2.93 (s, 4H), 1.64 (d, J=4.0 Hz, 6H), 1.58 (s, 9H)

Example 135

Synthesis of [5-(1-isopropyl-1H-indazol-5-yl-methoxy)-3,4-dihydro-1H-isoquinolin-2-yl]-acetic acid, trifluoroacetate

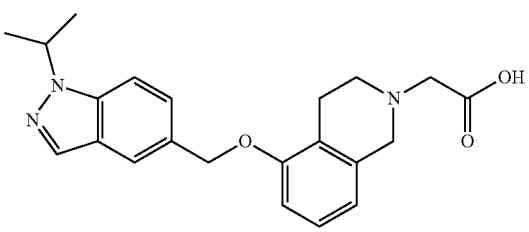 [SMILES: CC(C)n1ncc2cc(COc3cccc4c3CCN(CC(=O)O)C4)ccc21]

[5-(1-Isopropyl-1H-indazol-5-ylmethoxy)-3,4-dihydro-1H-isoquinolin-2-yl]-acetic acid t-butyl ester (80 mg, 0.18 mmol) obtained in Preparation Example 135-5 was reacted according to the method described in Example 5 to obtain the title compound (30 mg, 34%).

NMR: $^1$H-NMR (400 MHz, DMSO-d6) δ 8.07 (s, 1H), 7.83 (s, 1H), 7.71 (d, 1H), 7.46 (d, 1H), 7.13 (dd, 1H), 6.98

(d, 1H), 6.71 (d, 1H), 5.21 (s, 2H), 4.97-5.00 (m, 1H), 3.99 (br s, 2H), 3.33 (s, 2H), 2.81 (br s, 2H), 2.32 (br s, 2H), 1.48 (d, 6H)

Preparation Example 136-1

Synthesis of 5-hydroxy-3,4-dihydro-1H-isoquinoline-2-carboxylic acid t-butyl ester The title compound was obtained according to the method described in WO 2009/080724 A1.
NMR: $^1$H-NMR (400 HMz, CDCl$_3$); δ 6.83 (d, 1H), 6.65 (d, 1H), 4.74 (s, 1H), 4.49 (s, 2H), 3.64 (t, 2H), 2.73 (t, 2H), 2.14 (s, 3H), 1.48 (s, 9H)

Preparation Example 136-2

Synthesis of 6-(1-isopropyl-1H-indazol-5-yl-methoxy)-5-methyl-3,4-dihydro-1H-isoquinoline-2-carboxylic acid t-butyl ester (1-Isopropyl-1H-indazol-5-yl)-methanol (215 mg, 1.13 mmol) obtained in Preparation Example 135-1 and 5-hydroxy-3,4-dihydro-1H-isoquinoline-2-carboxylic acid t-butyl ester (268 mg, 1.02 mmol) obtained in Preparation Example 136-1 were reacted according to the method described in Preparation Example 131-3 to obtain the title compound (180 mg, 40%).
NMR: $^1$H-NMR (400 HMz, CDCl$_3$); δ 8.23 (s, 1H), 8.00 (s, 1H), 7.43-7.47 (m, 2H), 6.91 (d, J=8.0 Hz, 1H), 6.84 (d, J=8.0 Hz, 1H), 5.28 (s, 2H), 4.83-4.88 (m, 1H), 4.52 (br s, 2H), 3.65 (br t, J=4.0 Hz, 2H), 2.75 (br t, J=8.0 Hz, 2H), 2.32 (s, 3H), 1.60 (d, J=8.0 Hz, 6H), 1.48 (s, 9H)

Preparation Example 136-3

Synthesis of 6-(1-isopropyl-1H-indazol-5-yl-methoxy)-5-methyl-1,2,3,4-tetrahydro-isoquinoline, hydrochloride 6-(1-Isopropyl-1H-indazol-5-ylmethoxy)-5-methyl-3,4-dihydro-1H-isoquinoline-2-carboxylic acid t-butyl ester (180 mg, 0.41 mmol) obtained in Preparation Example 136-2 was reacted according to the method described in Example 27 to obtain the title compound (131 mg, 95%).
NMR: $^1$H-NMR (400 HMz, CDCl$_3$); δ 8.01 (s, 1H), 7.76 (s, 1H), 7.46-7.52 (m, 2H), 6.88-6.92 (m, 2H), 5.16 (s, 2H), 4.93-4.97 (m, 1H), 4.28 (br s, 2H), 3.47 (br t, J=4.0 Hz, 2H), 3.03 (br t, J=8.0 Hz, 2H), 2.17 (s, 3H), 1.61 (d, J=4.0 Hz, 6H)

Preparation Example 136-4

Synthesis of [6-(1-isopropyl-1H-indazol-5-yl-methoxy)-5-methyl-3,4-dihydro-1H-isoquinolin-2-yl]-acetic acid t-butyl ester 6-(1-Isopropyl-1H-indazol-5-ylmethoxy)-5-methyl-1,2,3,4-tetrahydro-isoquinoline, hydrochloride (131 mg, 0.39 mmol) obtained in Preparation Example 136-3 and t-butyl-bromoacetate (0.08 mL, 0.53 mmol) were reacted according to the method described in Preparation Example 28-1 to obtain the title compound (124 mg, 67%).
NMR: $^1$H-NMR (400 HMz, CDCl$_3$); δ 8.00 (s, 1H), 7.77 (s, 1H), 7.43-7.47 (m, 2H), 6.78-6.84 (m, 2H), 5.12 (s, 2H), 4.82-4.91 (m, 1H), 3.73 (br s, 2H), 3.29 (s, 2H), 2.87-2.91 (m, 2H), 2.79-2.82 (m, 2H), 2.31 (s, 3H), 1.60 (d, J=8.0 Hz, 6H), 1.49 (s, 9H)

Example 136

Synthesis of [6-(1-isopropyl-1H-indazol-5-yl-methoxy)-5-methyl-3,4-dihydro-1H-isoquinolin-2-yl]-acetic acid, trifluoroacetate

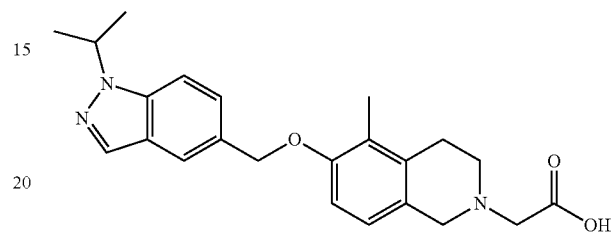

[6-(1-Isopropyl-1H-indazol-5-ylmethoxy)-5-methyl-3,4-dihydro-1H-isoquinolin-2-yl]-acetic acid t-butyl ester (124 mg, 0.28 mmol) obtained in Preparation Example 136-4 was reacted according to the method described in Example 5 to obtain the title compound (52 mg, 37%).
NMR: $^1$H-NMR (400 MHz, DMSO-d6) δ 8.05 (s, 1H), 7.81 (s, 1H), 7.70 (d, 1H), 7.44 (d, 1H), 6.92-6.98 (m, 2H), 5.17 (s, 2H), 4.97-5.00 (m, 1H), 3.22 (br s, 2H), 2.78 (s, 2H), 2.54 (br s, 2H), 2.33 (br s, 2H), 2.08 (s, 3H), 1.48 (d, 6H)

Preparation Example 137-1

Synthesis of (2-isopropyl-2H-indazol-5-yl)-methanol

2-Isopropyl-2H-indazole-5-carboxylic acid methyl ester (2.0 g, 9.16 mmol) obtained in Preparation Example 80-2 was reacted according to the method described in Example 44 to obtain the title compound (1.65 g, 95%).
NMR: $^1$H-NMR (400 HMz, CDCl$_3$); δ 7.99 (s, 1H), 7.72 (d, J=8.0 Hz, 1H), 7.60-7.62 (m, 1H), 7.29 (dd, J=4.0, 8.0 Hz, 1H), 4.78-4.83 (m, 1H), 4.75 (d, J=4.0 Hz, 2H), 1.66 (d, J=4.0 Hz, 6H)

Preparation Example 137-2

Synthesis of 6-(2-isopropyl-2H-indazol-5-yl-methoxy)-5-methyl-3,4-dihydro-1H-isoquinoline-2-carboxylic acid t-butyl ester (2-Isopropyl-2H-indazol-5-yl)-methanol (500 mg, 2.63 mmol) obtained in Preparation Example 137-1 and 5-hydroxy-3,4-dihydro-1H-isoquinoline-2-carboxylic acid t-butyl ester (623 mg, 2.37 mmol) obtained in Preparation Example 136-1 were reacted according to the method described din Preparation Example 131-3 to obtain the title compound (470 mg, 46%).
NMR: $^1$H-NMR (400 HMz, CDCl$_3$); δ 7.94 (s, 1H), 7.74 (d, J=8.0 Hz, 1H), 7.69 (s, 1H), 7.34 (d, J=12.0 Hz, 1H), 6.99 (d, J=8.0 Hz, 1H), 6.83 (d, J=8.0 Hz, 1H), 5.11 (s, 2H), 4.78-4.81 (m, 1H), 4.51 (br s, 2H), 3.65 (br s, 2H), 2.75 (br s, 2H), 1.66 (d, J=8.0 Hz, 6H), 1.48 (s, 9H)

Preparation Example 137-3

Synthesis of 6-(2-isopropyl-2H-indazol-5-yl-methoxy)-5-methyl-1,2,3,4-tetrahydro-isoquinoline, hydrochloride 6-(2-Isopropyl-2H-indazol-5-ylmethoxy)-5-methyl-3,4-dihydro-1H-isoquinoline-2-carboxylic acid t-butyl ester (470 mg, 1.08 mmol) obtained in Preparation Example 137-2 was reacted according to the method described in Example 27 to obtain the title compound (484 mg, 100%).

NMR: $^1$H-NMR (400 HMz, DMSO-$d_6$) δ 8.40 (s, 1H), 7.73 (s, 1H), 7.62 (d, J=8.0 Hz, 1H), 7.28 (d, J=8.0 Hz, 1H), 6.99-7.04 (m, 2H), 5.16 (s, 2H), 4.78-4.83 (m, 1H), 3.35 (br s, 2H), 2.87 (br t, J=4.0 Hz, 2H), 2.11 (s, 3H), 1.54 (d, J=4.0 Hz, 6H)

Preparation Example 137-4

Synthesis of [6-(2-isopropyl-2H-indazol-5-yl-methoxy)-5-methyl-3,4-dihydro-1H-isoquinolin-2-yl]-acetic acid t-butyl ester 6-(2-Isopropyl-2H-indazol-5-ylmethoxy)-5-methyl-1,2,3,4-tetrahydro-isoquinoline, hydrochloride (400 mg, 1.08 mmol) obtained in Preparation Example 137-3 and t-butylbromoacetate (0.27 mL, 1.40 mmol) were reacted according to the method described in Preparation Example 28-1 to obtain the title compound (242 mg, 50%).

NMR: $^1$H-NMR (400 HMz, CDCl$_3$); δ 8.10 (s, 1H), 7.99 (d, J=8.0 Hz, 1H), 7.74 (s, 1H), 7.68 (d, J=8.0 Hz, 1H), 6.76-6.82 (m, 2H), 5.26 (s, 2H), 4.76-4.82 (m, 1H), 3.78 (s, 2H), 3.29 (s, 2H), 2.90 (br t, J=4.0 Hz, 2H), 2.80 (br t, J=8.0 Hz, 2H), 2.15 (s, 3H), 1.65 (d, J=4.0 Hz, 6H), 1.48 (s, 9H)

Example 137

Synthesis of [6-(2-isopropyl-2H-indazol-5-yl-methoxy)-5-methyl-3,4-dihydro-1H-isoquinolin-2-yl]-acetic acid, trifluoroacetate

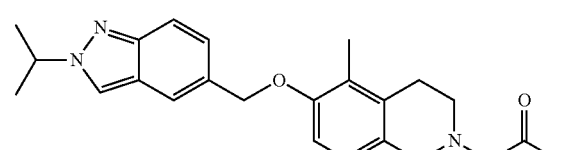

[6-(2-Isopropyl-2H-indazol-5-ylmethoxy)-5-methyl-3,4-dihydro-1H-isoquinolin-2-yl]-acetic acid t-butyl ester (100 mg, 0.22 mmol) obtained in Preparation Example 137-4 was reacted according to the method described in Example 5 to obtain the title compound (27 mg, 24%).

NMR: $^1$H-NMR (400 MHz, DMSO-d6) δ 8.40 (s, 1H), 7.74 (s, 1H), 7.62 (d, 1H). 7.28 (d, 1H), 6.98 (q, 2H), 5.15 (s, 2H), 4.83-4.79 (m, 1H), 4.18 (br, s, 2H), 3.94 (br, s, 2H), 3.34 (br, s, 2H), 2.90 (br, s, 2H), 2.50 (s, 3H), 1.54 (d, 6H)

Preparation Example 138-1

Synthesis of 5-(2-isopropyl-2H-indazol-5-yl-methoxy)-3,4-dihydro-1H-isoquinoline-2-carboxylic acid t-butyl ester (2-Isopropyl-2H-indazol-5-yl)-methanol (500 mg, 2.63 mmol) obtained in Preparation Example 137-1 and 5-hydroxy-3,4-dihydro-1H-isoquinoline-2-carboxylic acid t-butyl ester (590 mg, 2.37 mmol) obtained in Preparation Example 135-2 were reacted according to the method described in Preparation Example 131-3 to obtain the title compound (500 mg, 50%).

Preparation Example 138-2

Synthesis of 5-(2-isopropyl-2H-indazol-5-yl-methoxy)-1,2,3,4-tetrahydro-isoquinoline, hydrochloride 5-(2-Isopropyl-2H-indazol-5-ylmethoxy)-3,4-dihydro-1H-isoquinoline-2-carboxylic acid t-butyl ester (500 mg, 1.19 mmol) obtained in Preparation Example 138-1 was reacted according to the method described in Example 27 to obtain the title compound (384 mg, 100%).

Preparation Example 138-3

Synthesis of [5-(2-isopropyl-2H-indazol-5-yl-methoxy)-3,4-dihydro-1H-isoquinolin-2-yl]-acetic acid t-butyl ester 5-(2-Isopropyl-2H-indazol-5-ylmethoxy)-1,2,3,4-tetrahydro-isoquinoline, hydrochloride (383 mg, 1.19 mmol) obtained in Preparation Example 138-2 and t-butylbromoacetate (0.23 mL, 1.55 mmol) were reacted according to the method described in Preparation Example 28-1 to obtain the title compound (260 mg, 50%).

Example 138

Synthesis of [5-(2-isopropyl-2H-indazol-5-yl-methoxy)-3,4-dihydro-1H-isoquinolin-2-yl]-acetic acid, trifluoroacetate

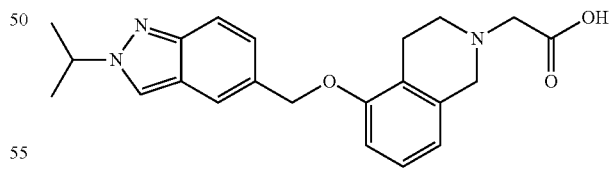

[5-(2-Isopropyl-2H-indazol-5-ylmethoxy)-3,4-dihydro-1H-isoquinolin-2-yl]-acetic acid t-butyl ester (100 mg, 0.23 mmol) obtained in Preparation Example 138-3 was reacted according to the method described in Example 5 to obtain the title compound (34 mg, 30%).

NMR: $^1$H-NMR (400 MHz, DMSO-d6) δ 8.41 (s, 1H), 7.76 (s, 1H), 7.63 (d, 1H). 7.30 (d, 1H), 7.18 (t, 1H), 7.02 (d, 1H), 6.75 (d, 1H), 5.18 (s, 2H), 4.84-4.79 (m, 1H), 4.20 (br, s, 2H), 3.91 (br, s, 2H), 3.31 (br, s, 2H), 2.89 (br, s, 2H), 1.55 (d, 6H)

Preparation Example 139-1

Synthesis of 3-(2-fluoro-4-hydroxy-phenyl)-propanoic acid ethyl ester

The title compound was obtained according to the method described in WO 2004/063155 A1.

Preparation Example 139-2

Synthesis of 3-[4-(3-chloro-1-isopropyl-1H-indol-5-ylmethoxy)-2-fluoro-phenyl]-propanoic acid ethyl ester (3-Chloro-1-isopropyl-1H-indol-5-yl)-methanol (160 mg, 0.72 mmol) obtained in Preparation Example 134-2 and 3-(2-fluoro-4-hydroxy-phenyl)-propanoic acid ethyl ester (152 mg, 0.72 mmol) obtained in Preparation Example 139-1 were dissolved in toluene (10 mL), and then tributylphosphine (BuP3, 291 mg, 1.44 mmol) and 1,1'-(azodicarbonyl)dipiperidine (ADD, 363 mg, 1.44 mmol) were added dropwise thereto. After stirring the mixture at room temperature for 18 hours, an excess amount of hexane was added thereto. The mixture was filtered, and the filtrate was distilled under reduced pressure. The residue was purified by column chromatography to obtain the title compound (169 mg, 56%).

Example 139

Synthesis of 3-[4-(3-chloro-1-isopropyl-1H-indol-5-ylmethoxy)-2-fluoro-phenyl]-propanoic acid

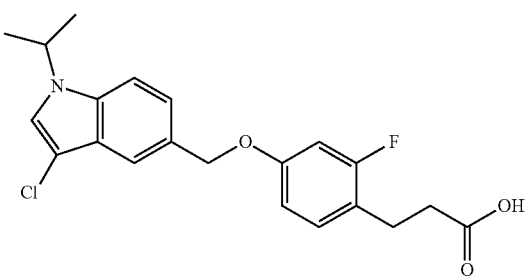 [SMILES: CC(C)n1cc(Cl)c2cc(COc3ccc(CCC(=O)O)c(F)c3)ccc21]

3-[4-(3-hloro-1-isopropyl-1H-indol-5-ylmethoxy)-2-fluoro-phenyl]-propanoic acid ethyl ester (169 mg, 0.40 mmol) obtained in Preparation Example 139-2 was reacted according to the method described in Example 1 to obtain the title compound (105 mg, 67%).

NMR: $^1$H-NMR (400 HMz, CDCl$_3$); δ 7.66 (s, 1H), 7.38 (d, 1H), 7.30 (d, 1H), 7.20 (s, 1H), 7.10 (m, 1H), 6.72 (m, 2H), 5.11 (s, 2H), 4.65 (m, 1H), 2.91 (t, 2H), 2.65 (t, 2H), 1.50 (d, 6H)

Preparation Example 140-1

Synthesis of 3-[5-(1-isopropyl-1H-indazol-5-ylmethoxy)-3,4-dihydro-1H-isoquinolin-2-yl]-propanoic acid t-butyl ester 5-(1-Isopropyl-1H-indazol-5-ylmethoxy)-1,2,3,4-tetrahydro-isoquinoline, hydrochloride (150 mg, 0.36 mmol) obtained in Preparation Example 135-4 and t-butyl acrylate (0.16 mL, 1.14 mmol) were reacted according to the method described in Preparation Example 29-1 to obtain the title compound (123 mg, 75%).

Example 140

Synthesis of 3-[5-(1-isopropyl-1H-indazol-5-ylmethoxy)-3,4-dihydro-1H-isoquinolin-2-yl]-propanoic acid, trifluoroacetate

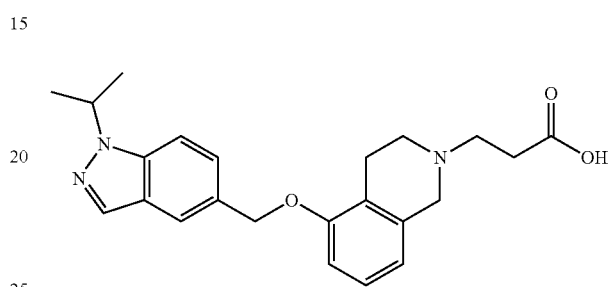

3-[5-(1-Isopropyl-1H-indazol-5-ylmethoxy)-3,4-dihydro-1H-isoquinolin-2-yl]-propanoic acid t-butyl ester (100 mg, 0.22 mmol) obtained in Preparation Example 140-1 was reacted according to the method described in Example 5 to obtain the title compound (64 mg, 57%).

NMR: $^1$H-NMR (400 HMz, CDCl$_3$); δ 8.00 (s, 1H), 7.72 (s, 1H), 7.46 (d, 1H), 7.39 (d, 1H), 7.17 (m, 1H), 6.86 (d, 1H), 6.68 (d, 1H), 5.12 (s, 2H), 4.85 (m, 1H), 4.43 (m, 2H), 4.17 (m, 2H), 3.43 (m, 2H), 3.03 (2H), 2.89 (m, 2H) 1.53 (d, 6H)

Preparation Example 141-1

Synthesis of 3-(6-hydroxy-naphthalen-2-yl)-propanoic acid ethyl ester

The title compound was obtained according to the method described in EP 1535915 A1.

Preparation Example 141-2

Synthesis of 3-[6-(3-chloro-1-isopropyl-1H-indol-5-ylmethoxy)-naphthalen-2-yl]-propanoic acid ethyl ester (3-Chloro-1-isopropyl-1H-indol-5-yl)-methanol (380 mg, 1.71 mmol) obtained in Preparation Example 134-2 and 3-(6-hydroxy-naphthalen-2-yl)-propanoic acid ethyl ester (417 mg, 1.71 mmol) obtained in Preparation Example 141-1 were reacted according to the method described in Preparation Example 139-2 to obtain the title compound (500 mg, 65%).

Example 141

Synthesis of 3-[6-(3-chloro-1-isopropyl-1H-indol-5-ylmethoxy)-naphthalen-2-yl]-propanoic acid

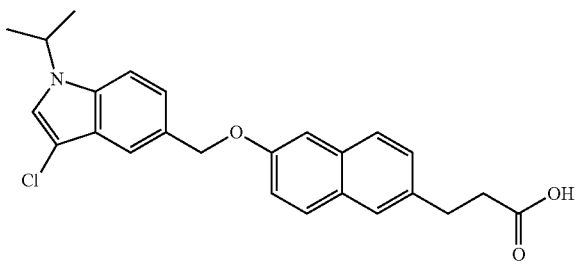 [SMILES: CC(C)n1cc(Cl)c2cc(COc3ccc4cc(CCC(=O)O)ccc4c3)ccc21]

3-[4-(3-Chloro-1-isopropyl-1H-indol-5-ylmethoxy)-2-fluoro-phenyl]-propanoic acid ethyl ester (500 mg, 1.11 mmol) obtained in Preparation Example 141-2 was reacted according to the method described in Example 1 to obtain the title compound (333 mg, 71%).

NMR: $^1$H-NMR (400 HMz, CDCl$_3$); δ 7.72 (s, 1H), 7.68 (m, 2H), 7.57 (s, 1H), 7.37 (s, 2H), 7.23 (m, 4H), 5.26 (s, 2H), 4.65 (m, 1H), 3.08 (t, 2H), 2.75 (t, 2H), 1.50 (d, 6H)

Preparation Example 142-1

Synthesis of (3-chloro-1-isopropyl-1H-indazol-5-yl)-methanol

3-Chloro-1-isopropyl-1H-indazole-5-carboxylic acid methyl ester (200 mg, 0.79 mmol) obtained in, Preparation Example 92-1 was reacted according to the method described in Example 44 to obtain the title compound (163 mg, 92%).

NMR: $^1$H-NMR (400 HMz, CDCl$_3$); δ 7.64 (s, 1H), 7.43 (m, 2H), 4.79 (m, 3H), 1.83 (br s, 1H), 1.56 (d, 6H)

Preparation Example 142-2

Synthesis of 6-(3-chloro-1-isopropyl-1H-indazol-5-ylmethoxy)-naphthalene-2-carbaldehyde (3-Chloro-1-isopropyl-1H-indazol-5-yl)-methanol (163 mg, 0.73 mmol) obtained in Preparation Example 142-1 and 6-hydroxynaphthalene-2-carbaldehyde (178 mg, 0.73 mmol) were reacted according to the method described in Preparation Example 139-2 to obtain the title compound (174 mg, 63%).

NMR: $^1$H-NMR (400 HMz, CDCl$_3$); δ 10.08 (s, 1H), 8.25 (s, 1H), 7.90 (m, 2H), 7.79 (m, 2H), 7.52 (d, 1H), 7.45 (d, 1H), 7.31 (m, 2H), 5.29 (s, 2H), 4.79 (m, 1H), 1.56 (d, 6H)

Example 142

Synthesis of 1-[6-(3-chloro-1-isopropyl-1H-indazol-5-ylmethoxy)-naphthalen-2-ylmethyl]-azetidine-3-carboxylic acid

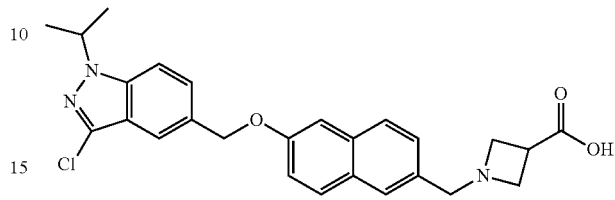

6-(3-Chloro-1-isopropyl-1H-indazol-5-ylmethoxy)-naphthalene-2-carbaldehyde (174 mg, 0.46 mmol) obtained in Preparation Example 142-2 and azetidine-3-carboxylic acid (93 mg, 0.92 mmol) were reacted according to the method described in Example 3 to obtain the title compound (90 mg, 42%).

NMR: $^1$H-NMR (400 HMz, DMSO$_{d6}$); δ 8.78 (s, 1H), 8.32 (s, 1H), 7.78 (d, 1H), 7.73 (d, 1H), 7.67 (s, 1H), 7.44 (s, 1H), 7.35 (m, 1H), 7.20 (m, 1H), 5.35 (s 2H), 5.18 (m, 1H), 3.64 (s, 2H), 3.39 (m 2H), 3.21 (m, 3H), 1.46 (d, 6H)

Preparation Example 143-1

Synthesis of 3-chloro-1-isopropyl-1H-pyrrolo[2,3-b]pyridine-5-carboxylic acid methyl ester 1-Isopropyl-1H-pyrrolo[2,3-b]pyridine-5-carboxylic acid methyl ester (451 mg, 2.07 mmol) obtained in Preparation Example 104-1 was reacted according to the method described in Preparation Example 3-1 to obtain the title compound (392 mg, 75%).

Preparation Example 143-2

Synthesis of (3-chloro-1-isopropyl-1H-pyrrolo[2,3-b]pyridin-5-yl)-methanol

3-Chloro-1-isopropyl-1H-pyrrolo[2,3-b]pyridine-5-carboxylic acid methyl ester (392 mg, 1.55 mmol) obtained in Preparation Example 143-1 was reacted according to the method described in Example 44 to obtain the title compound (297 mg, 85%).

Preparation Example 143-3

Synthesis of 6-(3-chloro-1-isopropyl-1H-pyrrolo[2,3-b]pyridin-5-ylmethoxy)-naphthalene-2-carbaldehyde (3-Chloro-1-isopropyl-1H-pyrrolo[2,3-b]pyridin-5-yl)-methanol (297 mg, 1.32 mmol) obtained in Preparation Example 143-2 and 6-hydroxynaphthalene-2-carbaldehyde (322 mg, 1.32 mmol) were reacted according to the method described in Preparation Example 139-2 to obtain the title compound (314 mg, 63%).

Preparation Example 143-4

Synthesis of {[6-(3-chloro-1-isopropyl-1H-pyrrolo[2,3-b]pyridin-5-ylmethoxy)-naphthalen-2-ylmethyl]-methyl-amino}-acetic acid ethyl ester 6-(3-Chloro-1-isopropyl-1H-pyrrolo[2,3-b]pyridin-5-ylmethoxy)-naphthalene-2-carbaldehyde (314 mg, 0.83 mmol) obtained in Preparation Example 143-3 and sarcosine ethylester hydrochloride (152 mg, 0.83 mmol) were reacted according to the method described in Preparation Example 14-4 to obtain the title compound (300 mg, 75%).

NMR: $^1$H-NMR (400 HMz, CDCl$_3$); δ 8.46 (s, 1H), 8.03 (d, 1H), 7.70 (m, 3H), 7.48 (1H), 7.25 (m, 2H), 7.21 (dd, 1H), 5.25 (s, 2H), 5.19 (m, 1H), 4.17 (q, 1H), 3.78 (s, 2H), 3.27 (s, 2H), 2.41 (s, 3H), 1.49 (d, 6H), 1.25 (t, 3H)

Example 143

Synthesis of {[6-(3-chloro-1-isopropyl-1H-pyrrolo[2,3-b]pyridin-5-ylmethoxy)-naphthalen-2-ylmethyl]-methyl-amino}-acetic acid

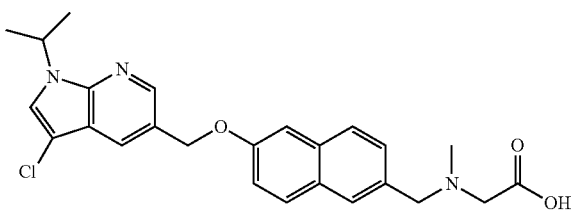 [SMILES: CC(C)n1cc(Cl)c2cc(COc3ccc4cc(CN(C)CC(=O)O)ccc4c3)cnc21]

{[6-(3-Chloro-1-isopropyl-1H-pyrrolo[2,3-b]pyridin-5-ylmethoxy)-naphthalen-2-ylmethyl]-methyl-amino}-acetic acid ethyl ester (300 mg, 0.62 mmol) obtained in Preparation Example 143-4 was reacted according to the method described in Example 1 to obtain the title compound (219 mg, 78%).

NMR: $^1$H-NMR (400 HMz, DMSO$_{d6}$); δ 8.46 (s, 1H), 8.04 (s, 1H), 7.89 (s, 1H), 7.56 (m, 3H), 7.45 (m, 2H), 7.20 (m, 1H), 5.31 (s, 2H), 5.06 (m, 1H), 3.85 (s, 2H), 3.24 (s, 2H), 2.33 (s, 3H), 1.42 (d, 6H)

Preparation Example 144-1

Synthesis of{[6-(3-chloro-1-isopropyl-1H-indazol-5-ylmethoxy)-naphthalen-2-ylmethyl]-methyl-amino}-acetic acid ethyl ester 6-(3-Chloro-1-isopropyl-1H-indazol-5-ylmethoxy)-naphthalene-2-carbaldehyde (224 mg, 0.59 mmol) obtained in Preparation Example 142-2 and sarcosine ethylester hydrochloride (129 mg, 0.59 mmol) were reacted according to the method described in Preparation Example 14-4 to obtain the title compound (220 mg, 78%).

Example 144

Synthesis of {[6-(3-chloro-1-isopropyl-1H-indazol-5-ylmethoxy)-naphthalen-2-ylmethyl]-methyl-amino}-acetic acid

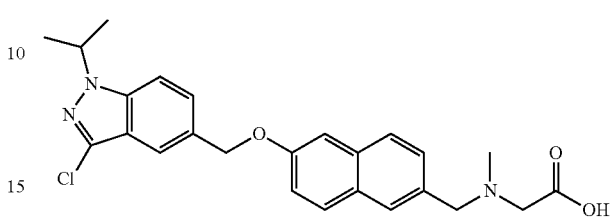

{[6-(3-Chloro-1-isopropyl-1H-indazol-5-ylmethoxy)-naphthalen-2-ylmethyl]-methyl-amino}-acetic acid ethyl ester (220 mg, 0.46 mmol) obtained in Preparation Example 144-1 was reacted according to the method described in Example 1 to obtain the title compound (141 mg, 68%).

NMR: $^1$H-NMR (400 HMz, DMSO$_{d6}$); δ 7.76 (m, 5H), 7.57 (m, 1H), 7.45 (m, 2H), 7.22 (m, 1H), 5.30 (s, 2H), 4.96 (m, 1H), 3.95 (s, 2H), 3.39 (s, 2H), 2.42 (s, 3H), 1.42 (d, 6H)

Preparation Example 145-1

Synthesis of 6-hydroxy-1-methyl-3,4-dihydro-naphthalene-2-carbaldehyde

The title compound was obtained according to the method described in WO 2006/064757 A1.

NMR: $^1$H-NMR (400 HMz, CDCl$_3$); δ 10.25 (s, 1H), 9.95 (br, s, 1H), 7.49 (d, 1H), 6.72 (dd, J=2.4 Hz, 1H), 6.67 (d, 1H), 2.63 (t, 2H), 2.47 (s, 3H), 2.35 (t, 2H)

Preparation Example 145-2

Synthesis of 6-(3-chloro-1-isopropyl-1H-indazol-5-ylmethoxy)-1-methyl-3,4-dihydro-naphthalene-2-carbaldehyde (3-Chloro-1-isopropyl-1H-indazol-5-yl)-methanol (300 mg, 1.34 mmol) obtained in Preparation Example 142-1 and 6-hydroxy-1-methyl-3,4-dihydro-naphthalene-2-carbaldehyde (252 mg, 1.34 mmol) obtained in Preparation Example 145-1 were reacted according to the method described in Preparation Example 139-2 to obtain the title compound (360 mg, 68%).

NMR: $^1$H-NMR (500 HMz, CDCl$_3$); δ 10.31 (s, 1H), 7.72 (s, 1H), 7.50-7.48 (m, 2H), 7.44 (d, 1H), 6.90 (dd, J=2.45 Hz, 1H), 6.85 (d, 1H), 5.19 (s, 2H), 4.81-4.76 (m, 1H), 2.73 (t, 2H), 2.51 (t, 2H), 2.48 (s, 3H), 1.57 (d, 6H)

Preparation Example 145-3

Synthesis of {[6-(3-chloro-1-isopropyl-1H-indazol-5-ylmethoxy)-1-methyl-3,4-dihydro-naphthalen-2-ylmethyl]-methyl-amino}-acetic acid ethyl ester 6-(3-Chloro-1-isopropyl-1H-indazol-5-ylmethoxy)-1-methyl-3,4-dihydro-naphthalene-2-carbaldehyde (180 mg, 0.46 mmol) obtained in Preparation Example 145-2 and sarcosine ethylester hydrochloride (139 mg, 0.91 mmol)

were reacted according to the method described in Preparation Example 14-4 to obtain the title compound (120 mg, 52%).

NMR: $^1$H-NMR (400 HMz, CDCl$_3$); δ 7.72 (s, 1H), 7.49 (d, 1H), 7.42 (d, 1H), 7.21 (d, 1H), 6.84 (d, 1H), 6.81 (s, 1H), 5.16 (s, 2H), 4.82-4.76 (m, 1H), 4.17 (q, 2H), 3.29 (s, 2H), 3.26 (s, 2H), 2.72 (t, 2H), 2.41 (s, 3H), 2.35 (t, 2H), 2.06 (s, 3H), 1.57 (d, 6H), 1.27 (t, 3H)

Example 145

Synthesis of {[6-(3-chloro-1-isopropyl-1H-indazol-5-ylmethoxy)-1-methyl-3,4-dihydro-naphthalen-2-ylmethyl]-methyl-amino}-acetic acid

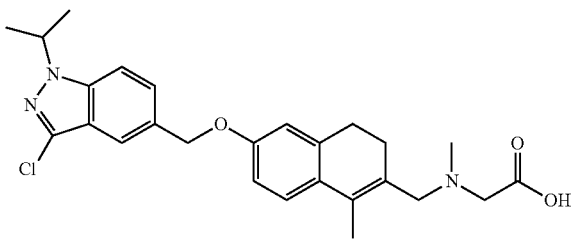 [SMILES: CC1=C(CN(C)CC(=O)O)CCc2cc(OCc3ccc4c(c3)c(Cl)nn4C(C)C)ccc21]

{[6-(3-Chloro-1-isopropyl-1H-indazol-5-ylmethoxy)-1-methyl-3,4-dihydro-naphthalen-2-ylmethyl]-methyl-amino}-acetic acid ethyl ester (120 mg, 0.24 mmol) obtained in Preparation Example 145-3 was reacted according to the method described in Example 1 to obtain the title compound (40 mg, 36%).

NMR: $^1$H-NMR (500 MHz, CDCl$_3$) δ 7.71 (s, 1H), 7.48 (d, 1H), 7.41 (d, 1H), 7.23 (d, 1H), 6.84 (d, 1H), 6.80 (s, 2H), 5.15 (s, 2H), 4.79-4.76 (m, 1H), 3.66 (s, 2H), 3.37 (s, 2H), 2.73 (t, 2H). 2.64 (s, 3H), 2.36 (t, 2H), 2.10 (s, 3H), 1.56 (d, 6H)

Preparation Example 146-1

Synthesis of 1-[6-(3-chloro-1-isopropyl-1H-indazol-5-ylmethoxy)-1-methyl-3,4-dihydro-naphthalen-2-ylmethyl]-azetidine-3-carboxylic acid methyl ester 6-(3-Chloro-1-isopropyl-1H-indazol-5-ylmethoxy)-1-methyl-3,4-dihydro-naphthalene-2-carbaldehyde (180 mg, 0.46 mmol) obtained in Preparation Example 145-2 and azetidine-3-carboxylic acid methylester hydrochloride (137 mg, 0.91 mmol) were reacted according to the method described in Preparation Example 14-4 to obtain the title compound (180 mg, 78%).

NMR: $^1$H-NMR (400 HMz, CDCl$_3$); δ 7.72 (s, 1H), 7.49 (dd, J=1.6 Hz, 1H), 7.42 (d, 1H), 7.21 (d, 1H), 6.82 (d, 1H), 6.78 (s, 1H), 5.15 (s, 2H), 4.82-4.76 (m, 1H), 3.70 (s, 3H), 3.54 (t, 2H), 3.36-3.27 (m 5H), 2.69 (t, 2H), 2.27 (t, 2H), 2.09 (s, 3H), 1.57 (d, 6H)

Example 146

Synthesis of 1-[6-(3-chloro-1-isopropyl-1H-indazol-5-ylmethoxy)-1-methyl-3,4-dihydro-naphthalen-2-ylmethyl]-azetidine-3-carboxylic acid

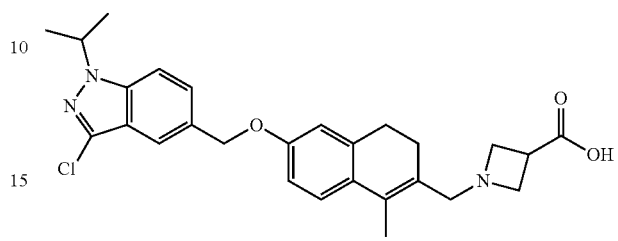

1-[6-(3-Chloro-1-isopropyl-1H-indazol-5-ylmethoxy)-1-methyl-3,4-dihydro-naphthalen-2-ylmethyl]-azetidine-3-carboxylic acid methyl ester (180 mg, 0.36 mmol) obtained in Preparation Example 146-1 was reacted according to the method described in Example 1 to obtain the title compound (90 mg, 52%).

NMR: $^1$H-NMR (400 MHz, DMSO-d6) δ 7.81 (d, 1H), 7.74 (s, 1H), 7.57 (dd, 1H), 7.27 (d, 1H), 6.90 (d, 1H), 6.88 (s, 1H), 5.24 (s, 2H), 5.04-5.00 (m, 1H), 3.98-3.74 (m, 4H), 3.46 (br, s, 2H), 2.66 (t, 2H), 2.21 (t, 2H), 2.11 (s, 3H), 1.48 (d, 6H)

Preparation Example 147-1

Synthesis of 1-isopropyl-1H-pyrazolo[3,4-b]pyridine-5-carboxylic acid methyl ester 1-Isopropyl-1H-pyrazolo[3,4-b]pyridine-5-carboxylic acid (300 mg, 1.46 mmol) obtained in Preparation Example 95-4 was dissolved in tetrahydrofuran (10 mL), and then 0.25M diazomethane diethylether solution (7 mL, 1.75 mmol) was slowly added dropwise thereto. The mixtures was stirred at room temperature for 30 minutes and distilled under reduced pressure to obtain the title compound (260 mg, 81%).

Preparation Example 147-2

Synthesis of 3-chloro-1-isopropyl-1H-pyrazolo[3,4-b]pyridine-5-carboxylic acid methyl ester 1-Isopropyl-1H-pyrazolo[3,4-b]pyridine-5-carboxylic acid methyl ester (260 mg, 1.18 mmol) obtained in Preparation Example 147-1 was reacted according to the method described in Preparation Example 3-1 to obtain the title compound (204 mg, 68%).

Preparation Example 147-3

Synthesis of (3-chloro-1-isopropyl-1H-pyrazolo[3,4-b]pyridin-5-yl)-methanol

3-Chloro-1-isopropyl-1H-pyrrolo[2,3-b]pyridine-5-carboxylic acid methyl ester (204 mg, 0.80 mmol) obtained in Preparation Example 147-2 was reacted according to the method described in Example 44 to obtain the title compound (153 mg, 85%).

Preparation Example 147-4

Synthesis of 6-(3-chloro-1-isopropyl-1H-pyrazolo[3,4-b]pyridin-5-ylmethoxy)-naphthalene-2-carbaldehyde (3-Chloroo-1-isopropyl-1H-pyrazolo[3,4-b]pyridin-5-yl)-methanol (153 mg, 0.68 mmol) obtained in Preparation Example 147-3 and 6-hydroxynaphthalene-2-carbaldehyde (166 mg, 0.68 mmol) were reacted according to the method described in Preparation Example 139-2 to obtain the title compound (152 mg, 59%).

Preparation Example 147-5

Synthesis of 1-[6-(3-chloro-1-isopropyl-1H-pyrazolo[3,4-b]pyridin-5-ylmethoxy)-naphthalen-2-ylmethyl]-azetidine-3-carboxylic acid methyl ester 6-(3-Chloro-1-isopropyl-1H-pyrazolo[3,4-b]pyridin-5-ylmethoxy)-naphthalene-2-carbaldehyde (152 mg, 0.40 mmol) obtained in Preparation Example 147-4 and azetidine-3-carboxylic acid methylester hydrochloride (121 mg, 0.80 mmol) were reacted according to the method described in Preparation Example 14-4 to obtain the title compound (157 mg, 82%).

Example 147

Synthesis of 1-[6-(3-chloro-1-isopropyl-1H-pyrazolo[3,4-b]pyridin-5-ylmethoxy)-naphthalen-2-ylmethyl]-azetidine-3-carboxylic acid

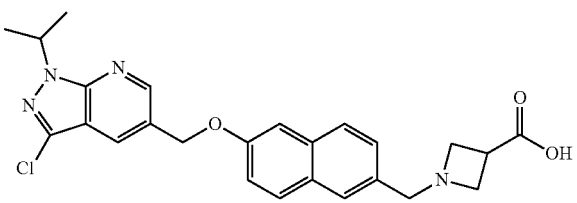

1-[6-(3-Chloro-1-isopropyl-1H-pyrazolo[3,4-b]pyridin-5-ylmethoxy)-naphthalen-2-ylmethyl]-azetidine-3-carboxylic acid methyl ester (157 mg, 0.33 mmol) obtained in Preparation Example 147-5 was reacted according to the method described in Example 1 to obtain the title compound (86 mg, 56%).

NMR: $^1$H-NMR (400 HMz, DMSO$_{d6}$); δ 8.81 (s, 1H), 8.35 (s, 1H), 7.77 (m, 3H), 7.48 (s, 1H), 7.38 (d, 1H), 7.24 (m, 1H), 5.40 (s, 2H), 5.22 (m, 1H), 3.68 (s, 2H), 3.43 (m, 2H), 3.23 (m, 2H), 1.50 (d, 6H)

Preparation Example 148-1

Synthesis of 1-[6-(3-chloro-1-isopropyl-1H-indazol-5-ylmethoxy)-1-methyl-3,4-dihydro-naphthalen-2-ylmethyl]-piperidine-4-carboxylic acid ethyl ester 6-(3-Chloro-1-isopropyl-1H-indazol-5-ylmethoxy)-1-methyl-3,4-dihydro-naphthalene-2-carbaldehyde (2.5 g, 6.33 mmol) obtained in Preparation Example 145-2 and piperidine-4-carboxylic acid ethyl ester (2.0 mL, 12.66 mmol) were reacted according to the method described in Preparation Example 14-4 to obtain the title compound (3.0 g, 88%).

NMR: $^1$H-NMR (500 HMz, CDCl$_3$); 7.71 (s, 1H), 7.48 (d, 1H), 7.41 (d, 1H), 7.19 (d, 1H), 6.81 (m, 2H), 5.15 (s, 2H), 4.78 (m, 1H), 4.12 (q 2H), 3.09 (s, 2H), 2.85 (m, 2H), 2.68 (t, 2H), 2.30 (t, 2H), 2.26 (m, 1H), 2.03 (s, 3H), 1.99 (m, 2H), 1.85 (m, 2H), 1.73 (m, 2H), 1.57 (d, 6H), 1.24 (t, 3H)

Example 148

Synthesis of 1-[6-(3-chloro-1-isopropyl-1H-indazol-5-ylmethoxy)-1-methyl-3,4-dihydro-naphthalen-2-ylmethyl]-piperidine-4-carboxylic acid

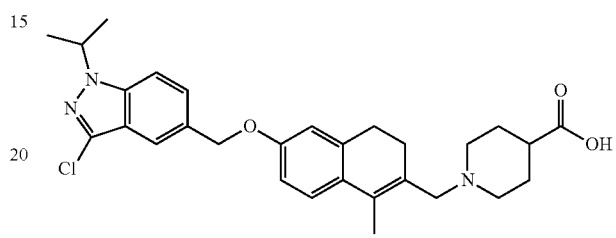

1-[6-(3-Chloro-1-isopropyl-1H-indazol-5-ylmethoxy)-1-methyl-3,4-dihydro-naphthalen-2-ylmethyl]-piperidine-4-carboxylic acid ethyl ester (3.0 g, 5.60 mmol) obtained in Preparation Example 148-1 was reacted according to the method described in Example 1 to obtain the title compound (996 mg, 35%).

NMR: $^1$H-NMR (500 MHz, CDCl$_3$) δ 7.70 (s, 1H), 7.47 (d, 1H), 7.41 (d, 1H), 7.24 (d, 1H), 6.82 (m, 2H), 5.15 (s, 2H), 4.78 (m, 1H), 3.84 (s 2H), 3.38 (m, 2H), 2.78 (t, 2H), 2.61 (m, 2H), 2.19 (m, 2H), 2.08 (s, 3H), 2.07 (m, 3H), 1.84 (m, 2H), 1.57 (d, 6H)

Preparation Example 149-1

Synthesis of azepane-4-carboxylic acid ethyl ester, hydrochloride

The title compound was obtained according to the method described in US2007/0225275.

NMR: $^1$H-NMR (500 HMz, CDCl$_3$); δ 9.55 (br, s, 2H), 4.09 (m, 2H), 3.41-2.95 (m, 4H), 2.68 (br, s, 1H), 2.41-1.73 (m, 6H), 1.22-1.10 (m, 3H)

Preparation Example 149-2

Synthesis of 1-[6-(3-chloro-1-isopropyl-1H-indazol-5-ylmethoxy)-1-methyl-3,4-dihydro-naphthalen-2-ylmethyl]-azepane-4-carboxylic acid ethyl ester 6-(3-Chloro-1-isopropyl-1H-indazol-5-ylmethoxy)-1-methyl-3,4-dihydro-naphthalene-2-carbaldehyde (180 mg, 0.46 mmol) obtained in Preparation Example 145-2 and azepane-4-carboxylic acid ethyl ester hydrochloride (142 mg, 0.69 mmol) obtained in Preparation Example 149-1 were reacted according to the method described in Preparation Example 14-4 to obtain the title compound (270 mg, 100%).

NMR: $^1$H-NMR (500 HMz, CDCl$_3$); 7.71 (s, 1H), 7.48 (d, 1H), 7.41 (d, 1H), 7.19 (d, 1H), 6.81 (m, 2H), 5.14 (s, 2H), 4.78 (m, 1H), 4.12 (q 2H), 3.19 (s, 2H), 2.69 (m, 2H), 2.59 (m, 4H), 2.31 (t, 2H), 2.03 (s, 3H), 1.94 (m, 2H), 1.80 (m, 3H), 1.73 (m, 2H), 1.57 (d, 6H), 1.24 (t, 3H)

Example 149

Synthesis of 1-[6-(3-chloro-1-isopropyl-1H-indazol-5-ylmethoxy)-1-methyl-3,4-dihydro-naphthalen-2-ylmethyl]-azepane-4-carboxylic acid

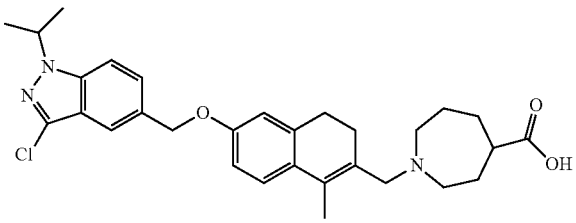 [SMILES: CC1=C(CN2CCCC(C(=O)O)CC2)CCc2cc(OCc3ccc4c(c3)c(Cl)nn4C(C)C)ccc21]

1-[6-(3-Chloro-1-isopropyl-1H-indazol-5-ylmethoxy)-1-methyl-3,4-dihydro-naphthalen-2-ylmethyl]-azepane-4-carboxylic acid ethyl ester (270 mg, 0.49 mmol) obtained in Preparation Example 149-2 was reacted according to the method described in Example 1 to obtain the title compound (225 mg, 88%).

NMR: $^1$H-NMR (500 MHz, CDCl$_3$) δ 7.71 (s, 1H), 7.48 (d, 1H), 7.42 (d, 1H), 7.24 (d, 1H), 6.82 (m, 2H), 5.15 (s, 2H), 4.78 (m, 1H), 3.83 (m, 2H), 2.91 (m, 2H), 2.78 (t, 2H), 2.61 (m, 2H), 2.19 (m, 2H), 2.08 (s, 3H), 2.07 (m, 3H), 1.84 (m, 2H), 1.73 (m, 2H), 1.57 (d, 6H)

Preparation Example 150-1

Synthesis of 1-chloro-6-hydroxy-3,4-dihydro-naphthalene-2-carbaldehyde

The title compound was obtained according to the method described in EP 1760071 A1.

NMR: $^1$H-NMR (500 HMz, CDCl$_3$); δ 10.30 (s, 1H), 7.76 (d, 1H), 7.78 (dd, 1H), 6.70 (d, 1H), 5.50 (s, 1H), 2.79 (t, 2H), 2.62 (t, 2H)

Preparation Example 150-2

Synthesis of 1-chloro-6-(3-chloro-1-isopropyl-1H-indazol-5-ylmethoxy)-3,4-dihydro-naphthalene-2-carbaldehyde (3-Chloro-1-isopropyl-1H-indazol-5-yl)-methanol (300 mg, 1.34 mmol) obtained in Preparation Example 142-1 and 1-chloro-6-hydroxy-3,4-dihydro-naphthalene-2-carbaldehyde (252 mg, 1.34 mmol) obtained in Preparation Example 150-1 were reacted according to the method described in Preparation Example 139-2 to obtain the title compound (360 mg, 68%).

NMR: $^1$H-NMR (500 HMz, CDCl$_3$); δ 10.31 (s, 1H), 7.72 (s, 1H), 7.50-7.48 (m, 2H), 7.44 (d, 1H), 6.90 (dd, J=2.45 Hz, 1H), 6.85 (d, 1H), 5.19 (s, 2H), 4.81-4.76 (m, 1H), 2.73 (t, 2H), 2.51 (t, 2H), 2.48 (s, 3H), 1.57 (d, 6H)

Preparation Example 150-3

Synthesis of 1-[1-chloro-6-(3-chloro-1-isopropyl-1H-indazol-5-ylmethoxy)-3,4-dihydro-naphthalen-2-ylmethyl]-pyrrolidine-3-carboxylic acid methyl ester 1-Chloro-6-(3-chloro-1-isopropyl-1H-indazol-5-ylmethoxy)-3,4-dihydro-naphthalene-2-carbaldehyde (190 mg, 0.45 mmol) obtained in Preparation Example 150-2 and pyrrolidine carboxylic acid methyl ester hydrochloride (150 mg, 0.90 mmol) were reacted according to the method described in Preparation Example 14-4 to obtain the title compound (80 mg, 33%).

NMR: $^1$H-NMR (500 HMz, CDCl$_3$); 7.71 (s, 1H), 7.54 (d, 1H), 7.47 (d, 1H), 7.42 (d, 1H), 6.85 (dd, 1H), 6.79 (d, 1H), 5.16 (s, 2H), 4.78 (m, 1H), 3.70 (s 3H), 3.44 (s, 2H), 3.03 (m, 1H), 2.89 (t, 1H), 2.78 (m, 2H), 2.70 (m, 2H), 2.63 (m, 1H), 2.49 (m, 2H), 2.09 (m, 2H), 1.57 (d, 6H)

Example 150

Synthesis of 1-[1-chloro-6-(3-chloro-1-isopropyl-1H-indazol-5-ylmethoxy)-3,4-dihydro-naphthalen-2-ylmethyl]-pyrrolidine-3-carboxylic acid

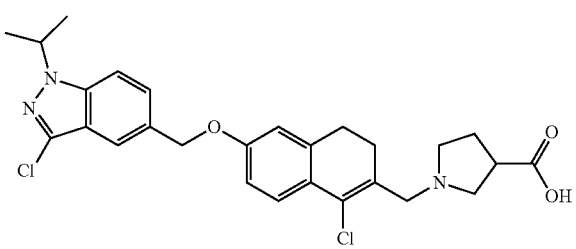 [SMILES: CC(C)n1nc(Cl)c2cc(COc3ccc4c(c3)CCC(CN3CCC(C(=O)O)C3)=C4Cl)ccc21]

1-[1-Chloro-6-(3-chloro-1-isopropyl-1H-indazol-5-ylmethoxy)-3,4-dihydro-naphthalen-2-ylmethyl]-pyrrolidine-3-carboxylic acid methyl ester (80 mg, 0.15 mmol) obtained in Preparation Example 150-3 was reacted according to the method described in Example 1 to obtain the title compound (43 mg, 56%).

NMR: $^1$H-NMR (500 MHz, CDCl$_3$) δ 7.70 (s, 1H), 7.53 (d, 1H), 7.46 (d, 1H), 7.41 (d, 1H), 6.84 (dd, 1H), 6.78 (d, 1H), 5.15 (s, 2H), 4.78 (m, 1H), 3.93 (m, 2H), 3.75 (m, 1H), 3.42 (m, 1H), 3.12 (m, 1H), 3.02-2.54 (m, 6H), 2.32 (m, 2H), 1.57 (d, 6H)

Preparation Example 151-1

Synthesis of (R)-1-[1-chloro-6-(3-chloro-1-isopropyl-1H-indazol-5-ylmethoxy)-3,4-dihydro-naphthalen-2-ylmethyl]-pyrrolidine-3-carboxylic acid methyl ester 1-Chloro-6-(3-chloro-1-isopropyl-1H-indazol-5-ylmethoxy)-3,4-dihydro-naphthalene-2-carbaldehyde (100 mg, 0.24 mmol) obtained in Preparation Example 150-2 and (R)-pyrrolidine carboxylic acid methylester hydrochloride (80 mg, 0.48 mmol) were reacted according to the method described in Preparation Example 14-4 to obtain the title compound (56 mg, 42%).

NMR: $^1$H-NMR (500 HMz, CDCl$_3$); δ 7.71 (s, 1H), 7.53 (d, 1H), 7.48 (d, 1H), 7.42 (d, 1H), 6.84 (dd, 1H), 6.78 (d, 1H), 5.15 (s, 2H), 4.78 (m, 1H), 3.68 (s 3H), 3.43 (s, 2H), 3.03 (m, 1H), 2.89 (t, 1H), 2.78 (m, 2H), 2.70 (m, 2H), 2.63 (m, 1H), 2.49 (m, 2H), 2.09 (m, 2H), 1.57 (d, 6H)

Example 151

Synthesis of (R)-1-[1-chloro-6-(3-chloro-1-isopropyl-1H-indazol-5-ylmethoxy)-3,4-dihydro-naphthalen-2-ylmethyl]-pyrrolidine-3-carboxylic acid

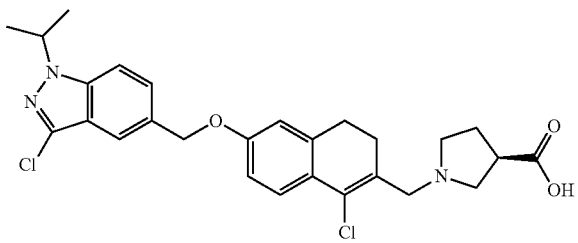 [SMILES: CC(C)n1nc(Cl)c2cc(COc3ccc4c(c3)CCC(CN3CC[C@@H](C(=O)O)C3)=C4Cl)ccc21]

(R)-1-[1-Chloro-6-(3-chloro-1-isopropyl-1H-indazol-5-ylmethoxy)-3,4-dihydro-naphthalen-2-ylmethyl]-pyrrolidine-3-carboxylic acid methyl ester (56 mg, 0.10 mmol) obtained in Preparation Example 151-1 was reacted according to the method described in Example 1 to obtain the title compound (22 mg, 42%).

NMR: $^1$H-NMR (500 MHz, CDCl$_3$); δ 7.70 (s, 1H), 7.53 (d, 1H), 7.46 (d, 1H), 7.41 (d, 1H), 6.84 (dd, 1H), 6.78 (d, 1H), 5.15 (s, 2H), 4.78 (m, 1H), 3.80 (m, 2H), 3.67 (m, 1H), 3.39 (m, 1H), 3.03 (m, 1H), 2.81 (t, 2H), 2.74-2.18 (m, 6H), 1.57 (d, 6H)

Preparation Example 152-1

Synthesis of 1-[1-chloro-6-(3-chloro-1-isopropyl-1H-indazol-5-ylmethoxy)-3,4-dihydro-naphthalen-2-ylmethyl]-3-methyl-pyrrolidine-3-carboxylic acid methyl ester 1-Chloro-6-(3-chloro-1-isopropyl-1H-indazol-5-ylmethoxy)-3,4-dihydro-naphthalene-2-carbaldehyde (79 mg, 0.19 mmol) obtained in Preparation Example 150-2 and 3-methyl-pyrrolidine carboxylic acid methylester hydrochloride (70 mg, 0.39 mmol) were reacted according to the method described in Preparation Example 14-4 to obtain the title compound (90 mg, 89%).

NMR: $^1$H-NMR (500 HMz, CDCl$_3$); δ 7.71 (s, 1H), 7.52 (d, 1H), 7.48 (d, 1H), 7.42 (d, 1H), 6.84 (dd, 1H), 6.78 (d, 1H), 5.15 (s, 2H), 4.78 (m, 1H), 3.68 (s 3H), 3.41 (s, 2H), 3.03 (d, 1H), 2.77 (t, 2H), 2.68 (m, 2H), 2.49 (m, 2H), 2.41 (m, 2H), 1.64 (m, 1H), 1.57 (d, 6H), 1.33 (s, 3H)

Example 152

Synthesis of 1-[1-chloro-6-(3-chloro-1-isopropyl-1H-indazol-5-ylmethoxy)-3,4-dihydro-naphthalen-2-ylmethyl]-3-methyl-pyrrolidine-3-carboxylic acid

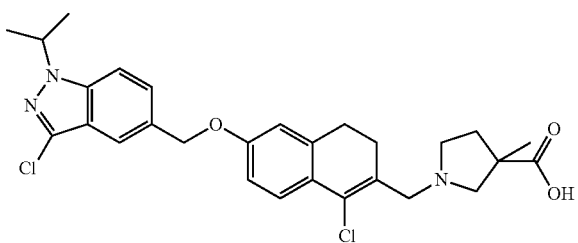 [SMILES: CC(C)n1nc(Cl)c2cc(COc3ccc4c(c3)CCC(CN3CCC(C)(C(=O)O)C3)=C4Cl)ccc21]

1-[1-Chloro-6-(3-chloro-1-isopropyl-1H-indazol-5-ylmethoxy)-3,4-dihydro-naphthalen-2-ylmethyl]-3-methyl-pyrrolidine-3-carboxylic acid methyl ester (90 mg, 0.17 mmol) obtained in Preparation Example 152-1 was reacted according to the method described in Example 1 to obtain the title compound (32 mg, 36%).

NMR: $^1$H-NMR (500 MHz, CDCl$_3$); δ 7.71 (s, 1H), 7.54 (d, 1H), 7.47 (d, 1H), 7.42 (d, 1H), 6.86 (dd, 1H), 6.79 (d, 1H), 5.16 (s, 2H), 4.78 (m, 1H), 3.22 (m, 2H), 2.82 (t, 2H), 2.63 (m, 1H), 2.48 (m, 2H), 2.28 (m, 4H), 1.81 (m, 1H), 1.57 (d, 6H), 1.33 (s, 3H)

Preparation Example 153-1

Synthesis of 1-[1-chloro-6-(3-chloro-1-isopropyl-1H-indazol-5-ylmethoxy)-3,4-dihydro-naphthalen-2-ylmethyl]-piperidine-4-carboxylic acid ethyl ester 1-Chloro-6-(3-chloro-1-isopropyl-1H-indazol-5-ylmethoxy)-3,4-dihydro-naphthalene-2-carbaldehyde (2.1 g, 5.06 mmol) obtained in Preparation Example 150-2 and piperidine-4-carboxylic acid ethyl ester (1.6 mL, 10.11 mmol) were reacted according to the method described in Preparation Example 14-4 to obtain the title compound (2.0 g, 71%).

NMR: $^1$H-NMR (400 HMz, CDCl$_3$); δ 7.71 (s, 1H), 7.52 (d, 1H), 7.47 (dd, 1H), 7.41 (d, 1H), 6.83 (dd, 1H), 6.78 (d, 1H), 5.14 (s, 2H), 4.78 (m, 1H), 4.11 (q, 2H), 3.29 (s, 2H), 2.86 (m, 2H), 2.76 (t, 2H), 2.47 (t, 2H), 2.27 (m, 1H), 2.10 (m, 2H), 1.87 (m, 2H), 1.74 (m, 2H), 1.56 (d, 6H), 1.25 (t, 3H)

Example 153

Synthesis of 1-[1-chloro-6-(3-chloro-1-isopropyl-1H-indazol-5-ylmethoxy)-3,4-dihydro-naphthalen-2-ylmethyl]-piperidine-4-carboxylic acid

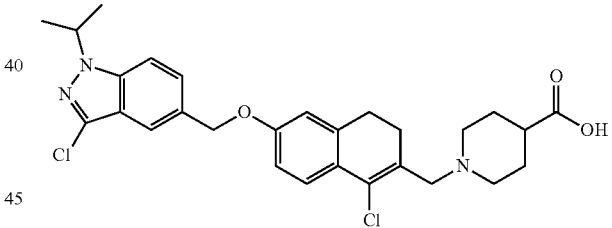

1-[1-Chloro-6-(3-chloro-1-isopropyl-1H-indazol-5-ylmethoxy)-3,4-dihydro-naphthalen-2-ylmethyl]-piperidine-4-carboxylic acid ethyl ester (2.0 g, 3.59 mmol) obtained in Preparation Example 153-1 was reacted according to the method described in Example 1 to obtain the title compound (1.1 g, 58%).

NMR: $^1$H-NMR (500 MHz, CDCl$_3$); δ 7.71 (s, 1H), 7.54 (d, 1H), 7.47 (d, 1H), 7.42 (d, 1H), 6.86 (dd, 1H), 6.79 (d, 1H), 5.16 (s, 2H), 4.78 (m, 1H), 3.22 (m, 2H), 2.82 (t, 2H), 2.63 (m, 1H), 2.48 (m, 2H), 2.28 (m, 4H), 1.81 (m, 1H), 1.57 (d, 6H)

Preparation Example 154-1

Synthesis of 1-[1-chloro-6-(3-chloro-1-isopropyl-1H-indazol-5-ylmethoxy)-3,4-dihydro-naphthalen-2-ylmethyl]-fluoro-piperidine-4-carboxylic acid ethyl ester 1-Chloro-6-(3-chloro-1-isopropyl-1H-indazol-5-ylmethoxy)-3,4-dihydro-naphthalene-2-carbaldehyde (50 mg, 0.12 mmol) obtained in Preparation Example 150-2 and 4-fluoro-piperidine-4-carboxylic acid ethyl ester (50 mg, 0.24 mmol) were reacted according to the method described in Preparation Example 14-4 to obtain the title compound (53 mg, 75%).

NMR: $^1$H-NMR (500 HMz, CDCl$_3$); δ 7.71 (s, 1H), 7.53 (d, 1H), 7.48 (d, 1H), 7.42 (d, 1H), 6.84 (dd, 1H), 6.79 (d, 1H), 5.15 (s, 2H), 4.78 (m, 1H), 4.23 (q 2H), 3.34 (s, 2H), 2.77 (m, 4H), 2.48 (m, 2H), 2.42 (m, 2H), 2.11 (m, 2H), 1.93 (m, 2H), 1.57 (d, 6H), 1.31 (t, 3H)

Example 154

Synthesis of 1-[1-chloro-6-(3-chloro-1-isopropyl-1H-indazol-5-ylmethoxy)-3,4-dihydro-naphthalen-2-ylmethyl]-4-fluoro-piperidine-4-carboxylic acid

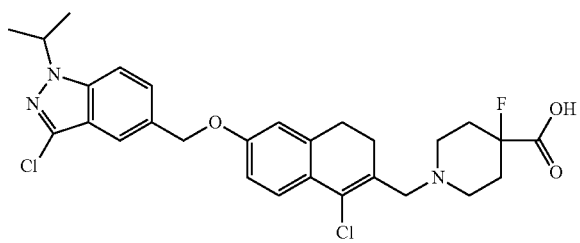 [SMILES: CC(C)n1nc(Cl)c2cc(COc3ccc4c(c3)CCC(CN3CCC(F)(C(=O)O)CC3)=C4Cl)ccc21]

1-[1-Chloro-6-(3-chloro-1-isopropyl-1H-indazol-5-yl-methoxy)-3,4-dihydro-naphthalen-2-ylmethyl]-fluoro-piperidine-4-carboxylic acid ethyl ester (53 mg, 0.09 mmol) obtained in Preparation Example 154-1 was reacted according to the method described in Example 1 to obtain the title compound (27 mg, 56%).

NMR: $^1$H-NMR (500 MHz, CDCl$_3$); δ 7.70 (s, 1H), 7.52 (d, 1H), 7.46 (d, 1H), 7.42 (d, 1H), 6.84 (dd, 1H), 6.78 (d, 1H), 5.15 (s, 2H), 4.77 (m, 1H), 3.99 (m, 2H), 3.39 (m, 2H), 2.93 (m, 2H), 2.77 (m, 2H), 2.60 (m, 2H), 2.51 (m, 2H), 2.11 (m, 2H), 1.57 (d, 6H)

Preparation Example 155-1

Synthesis of 1-[1-chloro-6-(3-chloro-1-isopropyl-1H-indazol-5-ylmethoxy)-3,4-dihydro-naphthalen-2-ylmethyl]-piperidine-3-carboxylic acid ethyl ester 1-Chloro-6-(3-chloro-1-isopropyl-1H-indazol-5-yl-methoxy)-3,4-dihydro-naphthalene-2-carbaldehyde (100 mg, 0.24 mmol) obtained in Preparation Example 150-2 and piperidine-3-carboxylic acid ethyl ester (0.07 mL, 0.48 mmol) were reacted according to the method described in Preparation Example 14-4 to obtain the title compound (100 mg, 75%).

NMR: $^1$H-NMR (500 HMz, CDCl$_3$); δ 7.71 (s, 1H), 7.52 (d, 1H), 7.46 (d, 1H), 7.42 (d, 1H), 6.84 (dd, 1H), 6.78 (d, 1H), 5.15 (s, 2H), 4.78 (m, 1H), 4.11 (q 2H), 3.48 (m, 2H), 3.30 (m, 2H), 2.87 (m, 4H), 2.76 (t, 2H), 2.67 (m, 2H), 2.54 (m, 1H), 2.45 (m, 2H), 2.35 (m, 1H), 2.14 (m, 1H), 1.85 (m, 1H), 1.70 (m, 1H), 1.57 (s, 6H), 1.23 (t, 3H)

Example 155

Synthesis of 1-[1-chloro-6-(3-chloro-1-isopropyl-1H-indazol-5-ylmethoxy)-3,4-dihydro-naphthalen-2-ylmethyl]-piperidine-3-carboxylic acid

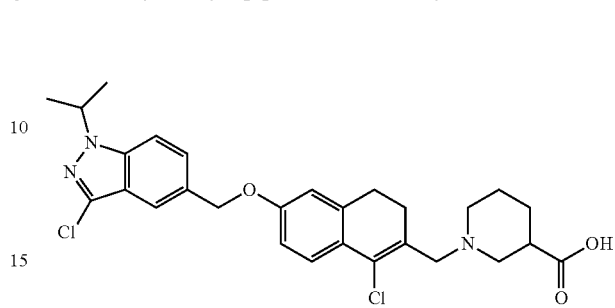

1-[1-Chloro-6-(3-chloro-1-isopropyl-1H-indazol-5-yl-methoxy)-3,4-dihydro-naphthalen-2-ylmethyl]-piperidine-3-carboxylic acid ethyl ester (100 mg, 0.18 mmol) obtained in Preparation Example 155-1 was reacted according to the method described in Example 1 to obtain the title compound (37 mg, 39%).

NMR: $^1$H-NMR (500 MHz, CDCl$_3$); δ 7.71 (s, 1H), 7.54 (d, 1H), 7.47 (d, 1H), 7.42 (d, 1H), 6.85 (dd, 1H), 6.80 (d, 1H), 5.16 (s, 2H), 4.78 (m, 1H), 3.53 (m, 2H), 3.27 (m, 2H), 3.14 (m, 1H), 2.89-2.73 (m, 3H), 2.58-2.32 (m, 4H), 2.07 (m, 1H), 1.91 (m, 1H), 1.88 (m, 1H), 1.74 (m, 1H), 1.57 (d, 6H)

Preparation Example 156-1

Synthesis of (S)-1-[1-chloro-6-(3-chloro-1-isopropyl-1H-indazol-5-ylmethoxy)-3,4-dihydro-naphthalen-2-ylmethyl]-piperidine-3-carboxylic acid ethyl ester 1-Chloro-6-(3-chloro-1-isopropyl-1H-indazol-5-yl-methoxy)-3,4-dihydro-naphthalene-2-carbaldehyde (300 mg, 0.72 mmol) obtained in Preparation Example 150-2 and (S)-piperidine-3-carboxylic acid ethyl ester (0.21 mL, 1.44 mmol) were reacted according to the method described in Preparation Example 14-4 to obtain the title compound (263 mg, 65%).

NMR: $^1$H-NMR (400 HMz, CDCl$_3$); δ 7.71 (s, 1H), 7.52 (d, 1H), 7.47 (dd, 1H), 7.41 (d, 1H), 6.83 (dd, 1H), 6.78 (d, 1H), 5.15 (s, 2H), 4.78 (m, 1H), 4.12 (m, 2H), 3.30 (m, 2H), 2.88 (m, 1H), 2.76 (t, 2H), 2.68 (m, 1H), 2.47 (m, 4H), 1.86 (m, 1H), 1.70 (m, 2H), 1.56 (m, 8H), 1.23 (t, 3H)

Example 156

Synthesis of (S)-1-[1-chloro-6-(3-chloro-1-isopropyl-1H-indazol-5-ylmethoxy)-3,4-dihydro-naphthalen-2-ylmethyl]-piperidine-3-carboxylic acid

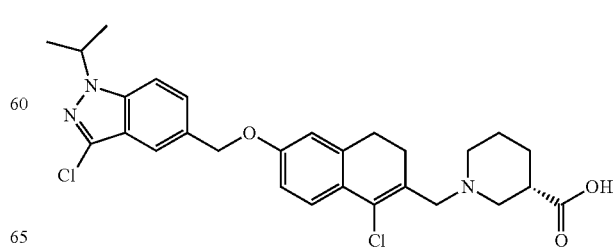

(S)-1-[1-Chloro-6-(3-chloro-1-isopropyl-1H-indazol-5-ylmethoxy)-3,4-dihydro-naphthalen-2-ylmethyl]-piperidine-3-carboxylic acid ethyl ester (263 mg, 0.47 mmol) was obtained in Preparation Example 156-1 reacted according to the method described in Example 1 to obtain the title compound (120 mg, 48%).

NMR: $^1$H-NMR (400 MHz, CDCl$_3$); δ 7.70 (s, 1H), 7.53 (d, 1H), 7.46 (dd, 1H), 7.41 (d, 1H), 6.85 (dd, 1H), 6.79 (d, 1H), 5.15 (s, 2H), 4.78 (m, 1H), 3.50 (m, 2H), 3.18 (m, 1H), 3.03 (m, 1H), 2.80 (m, 3H), 2.46 (m, 4H), 2.03 (m, 1H), 1.85 (m, 1H), 1.66 (m, 2H), 1.55 (d, 6H)

Preparation Example 157-1

Synthesis of (R)-1-[1-chloro-6-(3-chloro-1-isopropyl-1H-indazol-5-ylmethoxy)-3,4-dihydro-naphthalen-2-ylmethyl]-piperidine-3-carboxylic acid ethyl ester 1-Chloro-6-(3-chloro-1-isopropyl-1H-indazol-5-ylmethoxy)-3,4-dihydro-naphthalene-2-carbaldehyde (212 mg, 0.51 mmol) obtained in Preparation Example 150-2 and (R)-piperidine-3-carboxylic acid ethyl ester (0.15 mL, 1.01 mmol) were reacted according to the method described in Preparation Example 14-4 to obtain the title compound (213 mg, 75%).

NMR: $^1$H-NMR (400 HMz, CDCl$_3$); δ 7.71 (s, 1H), 7.52 (d, 1H), 7.47 (dd, 1H), 7.41 (d, 1H), 6.83 (dd, 1H), 6.78 (d, 1H), 5.15 (s, 2H), 4.78 (m, 1H), 4.12 (m, 2H), 3.30 (m, 2H), 2.88 (m, 1H), 2.76 (t, 2H), 2.68 (m, 1H), 2.47 (m, 4H), 1.86 (m, 1H), 1.70 (m, 2H), 1.56 (m, 8H), 1.23 (t, 3H)

Example 157

Synthesis of (R)-1-[1-chloro-6-(3-chloro-1-isopropyl-1H-indazol-5-ylmethoxy)-3,4-dihydro-naphthalen-2-ylmethyl]-piperidine-3-carboxylic acid

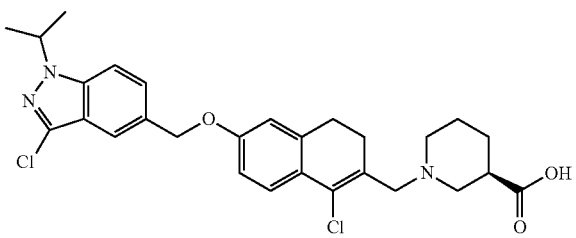 [SMILES: CC(C)n1nc(Cl)c2cc(COc3ccc4c(c3)CCC(CN3CCC[C@@H](C(=O)O)C3)=C4Cl)ccc21]

(R)-1-[1-Chloro-6-(3-chloro-1-isopropyl-1H-indazol-5-ylmethoxy)-3,4-dihydro-naphthalen-2-ylmethyl]-piperidine-3-carboxylic acid ethyl ester (213 mg, 0.38 mmol) obtained in Preparation Example 157-1 was reacted according to the method described in Example 1 to obtain the title compound (109 mg, 54%).

NMR: $^1$H-NMR (400 MHz, CDCl$_3$); δ 7.70 (s, 1H), 7.53 (d, 1H), 7.46 (dd, 1H), 7.41 (d, 1H), 6.84 (dd, 1H), 6.78 (d, 1H), 5.15 (s, 2H), 4.77 (m, 1H), 3.50 (m, 2H), 3.16 (m, 1H), 3.01 (m, 1H), 2.80 (m, 3H), 2.46 (m, 4H), 2.01 (m, 1H), 1.85 (m, 1H), 1.69 (m, 2H), 1.55 (d, 6H)

Preparation Example 158-1

Synthesis of 1-[I-chloro-6-(3-chloro-1-isopropyl-1H-indazol-5-ylmethoxy)-3,4-dihydro-naphthalen-2-ylmethyl]-3-fluoro-piperidine-3-carboxylic acid ethyl ester 1-Chloro-6-(3-chloro-1-isopropyl-1H-indazol-5-ylmethoxy)-3,4-dihydro-naphthalene-2-carbaldehyde (70 mg, 0.17 mmol) obtained in Preparation Example 150-2 and 3-fluoro-piperidine-3-carboxylic acid ethyl ester (72 mg, 0.34 mmol) were reacted according to the method described in Preparation Example 14-4 to obtain the title compound (60 mg, 59%).

NMR: $^1$H-NMR (500 HMz, CDCl$_3$); δ 7.71 (s, 1H), 7.52 (d, 1H), 7.48 (d, 1H), 7.42 (d, 1H), 6.84 (dd, 1H), 6.78 (d, 1H), 5.15 (s, 2H), 4.78 (m, 1H), 4.21 (m 2H), 3.48 (d, 2H), 3.36 (m, 2H), 2.85 (m, 1H), 2.78 (m, 4H), 2.48 (m, 2H), 2.31 (m, 1H), 1.57 (d, 6H), 1.28 (t, 3H)

Example 158

Synthesis of 1-[1-chloro-6-(3-chloro-1-isopropyl-1H-indazol-5-ylmethoxy)-3,4-dihydro-naphthalen-2-ylmethyl]-3-fluoro-piperidine-3-carboxylic acid

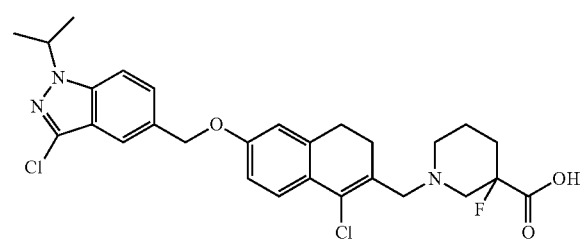 [SMILES: CC(C)n1nc(Cl)c2cc(COc3ccc4c(c3)CCC(CN3CCCC(F)(C(=O)O)C3)=C4Cl)ccc21]

1-[1-Chloro-6-(3-chloro-1-isopropyl-1H-indazol-5-ylmethoxy)-3,4-dihydro-naphthalen-2-ylmethyl]-3-fluoro-piperidine-3-carboxylic acid ethyl ester (60 mg, 0.10 mmol) obtained in Preparation Example 158-1 was reacted according to the method described in Example 1 to obtain the title compound (29 mg, 53%).

NMR: $^1$H-NMR (500 MHz, CDCl$_3$); δ 7.70 (s, 1H), 7.55 (d, 1H), 7.48 (d, 1H), 7.42 (d, 1H), 6.86 (dd, 1H), 6.79 (d, 1H), 5.16 (s, 2H), 4.78 (m, 1H), 3.58 (m, 2H), 3.31 (m, 1H), 3.08 (m, 1H), 2.82 (m, 2H), 2.55-2.25 (m, 5H), 1.86 (m, 3H), 1.57 (d, 6H)

Preparation Example 159-1

Synthesis of 1-[1-chloro-6-(3-chloro-1-isopropyl-1H-pyrazolo[3,4-b]pyridin-5-ylmethoxy)-3,4-dihydro-naphthalene-2-carbaldehyde (3-Chloro-1-isopropyl-1H-pyrazolo[3,4-b]pyridin-5-yl)-methanol (3.7 g, 16.39 mmol) obtained in Preparation Example 147-3 and 1-chloro-6-hydroxy-3,4-dihydro-naphthalene-2-carbaldehyde (2.3 g, 10.92 mmol) obtained in Preparation Example 150-1 were reacted according to the method described in Preparation Example 139-2 to obtain the title compound (1.0 g, 15%).

NMR: $^1$H-NMR (500 MHz, CDCl$_3$); δ 10.33 (s, 1H), 8.62 (d, 1H), 8.07 (d, 1H), 7.82 (d, 1H), 6.93 (dd, 1H), 6.85 (d, 1H), 5.28 (m, 2H), 5.23 (s, 2H), 2.83 (t, 2H), 2.64 (t, 2H), 1.57 (d, 6H)

Preparation Example 159-2

Synthesis of 1-[1-chloro-6-(3-chloro-1-isopropyl-1H-pyrazolo[3,4-b]pyridin-5-ylmethoxy)-3,4-dihydro-naphthalen-2-ylmethyl]-piperidine-4-carboxylic acid ethyl ester 1-[1-Chloro-6-(3-chloro-1-isopropyl-1H-pyrazolo[3,4-b]pyridin-5-ylmethoxy)-3,4-dihydro-naphthalene-2-carbaldehyde (1.0 g, 2.40 mmol) obtained in Preparation Example 159-1 and piperidine-4-carboxylic acid ethyl ester (0.73 mL, 4.80 mmol) were reacted according to the method described in Preparation Example 14-4 to obtain the title compound (1.0 g, 75%).

NMR: $^1$H-NMR (400 MHz, CDCl$_3$); δ 8.61 (d, 1H), 8.06 (s, 1H), 7.53 (d, 1H), 6.84 (dd, 1H), 6.78 (s, 1H), 5.26 (m, 1H), 5.18 (s, 2H), 4.12 (q, 2H), 3.30 (s, 2H), 2.86 (m, 2H), 2.77 (t, 2H), 2.48 (t, 2H), 2.28 (m, 1H), 2.10 (m, 2H), 1.87 (m, 2H), 1.74 (m, 2H), 1.56 (d, 6H), 1.23 (t, 3H)

Example 159

Synthesis of 1-[1-chloro-6-(3-chloro-1-isopropyl-1H-pyrazolo[3,4-b]pyridin-5-ylmethoxy)-3,4-dihydro-naphthalen-2-ylmethyl]-piperidine-4-carboxylic acid

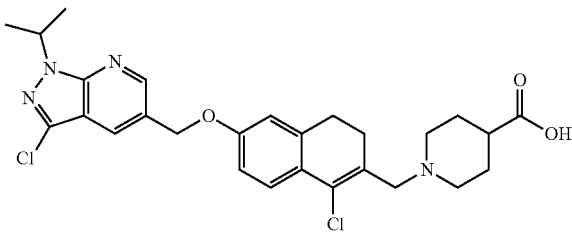 [SMILES: CC(C)n1nc(Cl)c2cc(COc3ccc4c(c3)CCC(CN3CCC(C(=O)O)CC3)=C4Cl)cnc21]

1-[1-Chloro-6-(3-chloro-1-isopropyl-1H-pyrazolo[3,4-b]pyridin-5-ylmethoxy)-3,4-dihydro-naphthalen-2-ylmethyl]-piperidine-4-carboxylic acid ethyl ester (1.0 g, 1.79 mmol) obtained in Preparation Example 159-2 was reacted according to the method described in Example 1 to obtain the title compound (890 mg, 94%).

NMR: $^1$H-NMR (400 HMz, CDCl$_3$); δ 8.60 (d, 1H), 8.05 (s, 1H), 7.53 (d, 1H), 6.82 (dd, 1H), 6.76 (d, 1H), 5.25 (m, 1H), 5.16 (s, 2H), 3.69 (s, 2H), 3.27 (m, 2H), 2.77 (t, 2H), 2.56 (t, 2H), 2.45 (m, 2H), 2.29 (m, 1H), 2.02 (m, 2H), 1.88 (m, 2H), 1.56 (d, 6H)

Preparation Example 160-1

Synthesis of 5-bromo-1-sec-butyl-1H-pyrazolo[3,4-b]pyridine and 5-bromo-2-isopropyl-2H-pyrazolo[3,4-b]pyridine 5-Bromo-1H-pyrazolo[3,4-b]pyridine (1.25 g, 6.31 mmol) obtained in Preparation Example 95-1 and sec-butyl iodide (2.2 mL, 13.64 mmol) were reacted according to the method described in Preparation Example 1-1 to obtain 5-bromo-1-sec-butyl-1H-pyrazolo[3,4-b]pyridine (715 mg, 48%) which primarily passed a column chromatography and subsequently to obtain 5-bromo-2-isopropyl-2H-pyrazolo[3,4-b]pyridine (150 mg, 10%) which secondarily passed a column chromatography.

NMR: $^1$H-NMR (500 HMz, CDCl$_3$); δ 8.51 (s, 1H), 8.16 (s, 1H), 8.00 (s, 1H), 4.99 (m, 1H), 2.06 (m, 1H), 1.90 (m, 1H), 1.56 (d, 3H), 0.75 (t, 3H) (5-bromo-1-sec-butyl-1H-pyrazolo[3,4-b]pyridine)

Preparation Example 160-2

Synthesis of 5-bromo-1-sec-butyl-3-chloro-1H-pyrazolo[3,4-b]pyridine

5-Bromo-1-sec-butyl-1H-pyrazolo[3,4-b]pyridine (370 mg, 1.46 mmol) obtained in Preparation Example 160-1 was reacted according to the method described in Preparation Example 3-1 to obtain the title compound (320 mg, 76%).

NMR: $^1$H-NMR (500 HMz, CDCl$_3$); δ 8.59 (s, 1H), 8.18 (s, 1H), 5.02 (m, 1H), 2.14 (m, 1H), 1.94 (m, 1H), 1.58 (d, 3H), 0.81 (t, 3H)

Preparation Example 160-3

Synthesis of 1-sec-butyl-3-chloro-1H-pyrazolo[3,4-b]pyridine-5-carbonitrile

5-Bromo-1-sec-butyl-3-chloro-1H-pyrazolo[3,4-b]pyridine (320 mg, 1.11 mmol) obtained in Preparation Example 160-2 was reacted according to the method described in Preparation Example 95-3 to obtain the title compound (115 mg, 44%).

NMR: $^1$H-NMR (500 HMz, CDCl$_3$); δ 8.78 (d, 1H), 8.40 (d, 1H), 5.08 (m, 1H), 2.11 (m, 1H), 1.96 (m, 1H), 1.61 (d, 3H), 0.81 (t, 3H)

Preparation Example 160-4

Synthesis of 1-sec-butyl-3-chloro-1H-pyrazolo[3,4-b]pyridine-5-carboxylic acid 1-sec-Butyl-3-chloro-1H-pyrazolo[3,4-b]pyridine-5-carbonitrile (115 mg, 0.49 mmol) obtained in Preparation Example 160-3 was reacted according to the method described in Preparation Example 95-4 to obtain the title compound (124 mg, 100%).

Preparation Example 160-5

Synthesis of 1-sec-butyl-3-chloro-1H-pyrazolo[3,4-b]pyridine-5-carboxylic acid methyl ester 1-sec-Butyl-3-chloro-1H-pyrazolo[3,4-b]pyridine-5-carboxylic acid (124 mg, 0.49 mmol) obtained in Preparation Example 160-4 was reacted according to the method described in Preparation Example 147-1 to obtain the title compound (70 mg, 53%).

Preparation Example 160-6

Synthesis of (1-sec-butyl-3-chloro-1H-pyrazolo[3,4-b]pyridin-5-yl)-methanol 1-sec-Butyl-3-chloro-1H-pyrazolo[3,4-b]pyridine-5-carboxylic acid methyl ester (70 mg, 0.26 mmol) obtained in Preparation Example 160-5 was reacted according to the method described in Example 44 to obtain the title compound (50 mg, 80%).

NMR: $^1$H-NMR (500 HMz, CDCl$_3$); δ 8.57 (d, 1H), 8.02 (d, 1H), 5.01 (m, 1H), 4.86 (s, 2H), 2.08 (m, 1H), 1.90 (m, 1H), 1.56 (d, 3H), 0.78 (t, 3H)

Preparation Example 160-7

Synthesis of 6-(1-sec-butyl-3-chloro-1H-pyrazolo[3,4-b]pyridin-5-ylmethoxy)-1-chloro-3,4-dihydro-naphthalene-2-carbaldehyde (1-sec-Butyl-3-chloro-1H-pyrazolo[3,4-b]pyridin-5-yl)-methanol (80 mg, 0.33 mmol) obtained in Preparation Example 160-6 and 1-chloro-6-hydroxy-3,4-dihydro-naphthalene-2-carbaldehyde (68 mg, 0.33 mmol) obtained in Preparation Example 150-1 were reacted according to the method described in Preparation Example 139-2 to obtain the title compound (50 mg, 36%).

NMR: $^1$H-NMR (500 MHz, CDCl$_3$); δ 10.32 (s, 1H), 8.61 (d, 1H), 8.08 (d, 1H), 7.82 (d, 1H), 6.94 (dd, 1H), 6.85 (d, 1H), 5.23 (s, 2H), 5.02 (m, 1H), 2.83 (t, 2H), 2.63 (t, 2H), 2.07 (m, 1H), 1.90 (m, 1H), 1.55 (d, 3H), 0.78 (t, 3H)

Preparation Example 160-8

Synthesis of 1-[6-(1-sec-butyl-3-chloro-1H-pyrazolo[3,4-b]pyridin-5-ylmethoxy)-1-chloro-3,4-dihydro-naphthalen-2-ylmethyl]-piperidine-4-carboxylic acid ethyl ester 6-(1-sec-Butyl-3-chloro-1H-pyrazolo[3,4-b]pyridin-5-ylmethoxy)-1-chloro-3,4-dihydro-naphthalene-2-carbaldehyde (140 mg, 0.33 mmol) obtained in Preparation Example 160-7 and piperidine-4-carboxylic acid ethyl ester (0.1 mL, 0.65 mmol) were reacted according to the method described in Preparation Example 14-4 to obtain the title compound (200 mg, 100%).

NMR: $^1$H-NMR (500 MHz, CDCl$_3$); δ 8.61 (d, 1H), 8.07 (d, 1H), 7.55 (d, 1H), 6.84 (dd, 1H), 6.79 (d, 1H), 5.18 (s, 2H), 5.01 (m, 1H), 4.11 (q 2H), 3.30 (s, 2H), 2.85 (m, 2H), 2.77 (t, 2H), 2.48 (t, 2H), 2.27 (m, 1H), 2.09 (m, 3H), 1.88 (m, 3H), 1.73 (m, 2H), 1.54 (d, 3H), 1.24 (t, 3H), 0.78 (t, 3H)

Example 160

Synthesis of 1-[6-(1-sec-butyl-3-chloro-1H-pyrazolo[3,4-b]pyridin-5-ylmethoxy)-1-chloro-3,4-dihydro-naphthalen-2-ylmethyl]-piperidine-4-carboxylic acid

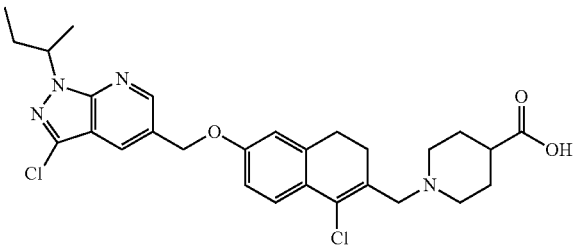 [SMILES: CCC(C)n1nc(Cl)c2cc(COc3ccc4c(c3)CCC(CN3CCC(C(=O)O)CC3)=C4Cl)cnc21]

1-[6-(1-sec-Butyl-3-chloro-1H-pyrazolo[3,4-b]pyridin-5-ylmethoxy)-1-chloro-3,4-dihydro-naphthalen-2-ylmethyl]-piperidine-4-carboxylic acid ethyl ester (200 mg, 0.35 mmol) obtained in Preparation Example 160-8 was reacted according to the method described in Example 1 to obtain the title compound (106 mg, 56%).

NMR: $^1$H-NMR (500 HMz, CDCl$_3$); δ 8.60 (d, 1H), 8.07 (d, 1H), 7.55 (d, 1H), 6.85 (dd, 1H), 6.79 (d, 1H), 5.18 (s, 2H), 5.01 (m, 1H), 3.65 (s 2H), 3.20 (m, 2H), 2.80 (t, 2H), 2.59 (t, 2H), 2.40 (m, 2H), 2.07 (m, 3H), 1.90 (m, 3H), 1.55 (d, 3H), 0.78 (t, 3H)

Preparation Example 161-1

Synthesis of 1-[1-chloro-6-(3-chloro-1-isopropyl-1H-indazol-5-ylmethoxy)-3,4-dihydro-naphthalen-2-ylmethyl]-3-fluoro-pyrrolidine-3-carboxylic acid methyl ester 1-Chloro-6-(3-chloro-1-isopropyl-1H-indazol-5-ylmethoxy)-3,4-dihydro-naphthalene-2-carbaldehyde (204 mg, 0.49 mmol) obtained in Preparation Example 150-2 and 3-fluoro-pyrrolidine carboxylic acid methyl ester hydrochloride (180 mg, 0.98 mmol) were reacted according to the method described in Preparation Example 14-4 to obtain the title compound (163 mg, 61%).

NMR: $^1$H-NMR (400 HMz, CDCl$_3$); δ 7.71 (s, 1H), 7.53 (d, 1H), 7.47 (dd, 1H), 7.41 (d, 1H), 6.84 (dd, 1H), 6.78 (d, 1H), 5.15 (s, 2H), 4.78 (m, 1H), 3.80 (s, 3H), 3.50 (s, 2H), 3.05 (m, 3H), 2.78 (t, 2H), 2.72 (m, 1H), 2.51 (t, 2H), 2.47 (m, 1H), 2.26 (m, 1H), 1.57 (d, 6H)

Example 161

Synthesis of 1-[1-chloro-6-(3-chloro-1-isopropyl-1H-indazol-5-ylmethoxy)-3,4-dihydro-naphthalen-2-ylmethyl]-3-fluoro-pyrrolidine-3-carboxylic acid

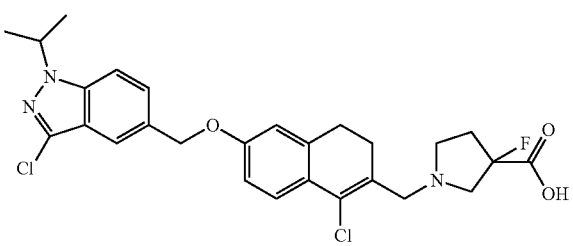 [SMILES: CC(C)n1nc(Cl)c2cc(COc3ccc4c(c3)CCC(CN3CCC(F)(C(=O)O)C3)=C4Cl)ccc21]

1-[1-Chloro-6-(3-chloro-1-isopropyl-1H-indazol-5-ylmethoxy)-3,4-dihydro-naphthalen-2-ylmethyl]-3-fluoro-pyrrolidine-3-carboxylic acid methyl ester (163 mg, 0.30 mmol) obtained in Preparation Example 161-1 was reacted according to the method described in Example 1 to obtain the title compound (78 mg, 49%).

NMR: $^1$H-NMR (500 MHz, CDCl$_3$); δ 7.71 (s, 1H), 7.54 (d, 1H), 7.47 (d, 1H), 7.42 (d, 1H), 6.86 (dd, 1H), 6.79 (d, 1H), 5.16 (s, 2H), 4.78 (m, 1H), 3.22 (m, 2H), 2.82 (t, 2H), 2.60 (m, 1H), 2.41 (m, 2H), 2.18 (m, 4H), 1.81 (m, 1H), 1.57 (d, 6H)

Experimental Example 1

Evaluation of $Ca^{2+}$ inducing ability of test compound using a cell line expressing human sphingosine-1-phosphate (1) Test Method CHO (Chinese hamster ovary) cells which overexpress human sphingosine-1-phosphate 1 receptor (S1P1 receptor) that react with sphingosine-1-phosphate (S1P) are used for a functional test method wherein an increase of calcium indicates a therapeutic efficacy of an agonist compound. CHO-K1 cells, which are used for preparing a stable cell line, show no change in the calcium concentration by S1P, and thus they are good for checking signals from human S1P receptors after transfecting each subtype of the cells with the receptors.

To prepare CHO cells which overexpress human S1P1~S1P5, human clones for each subtype having HA at the N terminal residue (S1P1: EDG010TN00, S1P2: EDG020TN00, S1P3: EDG030TN00, S1P4: EDG060TN00, S1P5: EDG080TN00) were purchased from the Missouri S&T cDNA Resource Center and co-transfected with G-protein alpha subunit (G-alpha-16) into CHO-K1 cells. After separating cells by FACS (fluorescence-activated cell sorting, LK BioScience, JSAN) using HA-antibodies (MACS, Anti-HA-PE), they were selectively cultured in the medium with 10% FBS (Gibco, USA), 0.5 mg/mL Geneticin (Gibco) and 0.2 mg/mL Hygromycin B F12 (Gibco) to obtain the desired cells.

A calcium measurement kit (Calcium 5 assay kit, Molecular Devices) was used to select an agonist compound. The principle of calcium measurement is that calcium-sensitive dyes are applied to cells, they enter into the cytoplasm of the cells during incubation, and when a ligand binds to a certain receptor to release calcium into the cytoplasm, the dyes bind to said calcium to induce fluorescence which is measured. This test method can sensitively measure only the intracellular calcium concentration change because any change that may occur outside the cells is masked by a masking dye.

The experimental procedure was as follows. One day before calcium measurement, CHO cells overexpressing hS1P1~hS1P5 were dispensed into a 96-well plate (bottom clear black well) in $3\times10^4$ cells per well and cultured at 37° C. under 5% carbon dioxide condition for one day. 100 µl of calcium dyes mixed with Assay Buffer (1×HBSS, 20 mM HEPES, 2.5 mM probenecid, pH 7.4) were dispensed into culture solution in well and cultured at 37° C. for one hour. Test compounds were dissolved in 100% DMSO to prepare 1 µl solution per each concentration, and each solution was mixed with 199 µl Assay Buffer such that the concentrations were 50, 5, 0.5, 0.05, 0.005 and 0.0005 µM. The plate cultured with the calcium dyes was put into FlaxstationII (Molecular Devices), and the prepared test compounds (the final concentrations of the test compounds: 10, 1, 0.1, 0.01, 0.001 and 0.0001 µM) were programmed to be automatically inoculated in 50 µl per each well. For a total of 90 seconds, RFU (relative fluorescence unit) values were measured. The value of Reference (S1P substance 1 µM) deducting the blank value was set as 100%, and $EC_{50}$ values of the test compounds were calculated by prism.

(2) Results

The results are shown by $EC_{50}$ (µM) in Table 1 below. In the table, FTY-720 as Reference refers to an S1P agonist compound, Fingolimod (trade name: Gilenya).

TABLE 1

| Example | $EC_{50}$ |
|---|---|
| 1 | 0.005 |
| 2 | 0.025 |
| 3 | 0.023 |
| 4 | 0.023 |
| 5 | 0.014 |
| 26 | 0.002 |
| 38 | 0.05 |
| 52 | 0.01 |
| 58 | 0.02 |
| 85 | 0.01 |
| 94 | 0.006 |
| 97 | 0.05 |
| 108 | 0.02 |
| 117 | 0.003 |
| 129 | 0.05 |
| 142 | 0.007 |
| 145 | 0.009 |
| 146 | 0.005 |
| 148 | 0.019 |
| 149 | 0.019 |
| 150 | 0.008 |
| 151 | 0.011 |
| 153 | 0.011 |
| 154 | 0.017 |
| 155 | 0.027 |
| 158 | 0.014 |
| 159 | 0.012 |
| 160 | 0.019 |
| 161 | 0.003 |
| FTY-720 | 0.003 |

As shown in Table 1 above, it can be understood that the S1P receptor agonist compounds according to the present invention exhibit an activity similar to that of the comparative substance, Fingolimod.

Experimental Example 2

Evaluation of beta-arrestin inducing ability of test compound using a cell line expressing human sphingosine-1-phosphate (1) Test Method This experiment is intended to measure an activity of beta-arrestin which is another signal transduction pathway of GPCR.

The experimental procedure was as follows. One day before activity measurement, after dissolving S1P1 PathHunter eXpress cells, the cell culture solution was put thereto and inoculated into a 96-well plate in 100 µl per each well. The next day, test compounds were dissolved in 100% DMSO to prepare 1 µl solution per each concentration, and each solution was mixed with 9 µl of the cell culture solution such that the concentrations were 100, 10, 1, 0.1, 0.01, 0.001 and 0.0001 µM. Each 10 µl of the test compounds with different concentrations was put into the plate which had been prepared the day before and cultured at 37° C. for 90 minutes. During culturing of the test compounds with the cells, PathHunter Detection Reagents were prepared, and after 90 minutes 55 µl of the reagents was put into each well of the plate. After culturing at room temperature for 60 minutes, values of each well of the plate were measured using a standard luminescence plate reader device.

Activity levels of the test compounds were analyzed by a statistical analysis program, GraphPad Prism. S1P compound was used as a positive control, and DMSO solvent was used as a negative control.

(2) Results

The results are shown by $EC_{50}$ (M) in Table 2 below. In the table, FTY-720 as Reference refers to an S1P agonist compound, Fingolimod (trade name: Gilenya).

TABLE 2

| Example | $EC_{50}$ |
|---|---|
| 148 | 0.001 |
| 153 | 0.001 |
| 159 | 0.0028 |
| FTY-720 | 0.0047 |

As a result of conducting this experiment, the S1P receptor agonist compounds according to the present invention show higher beta-arrestin binding activity than FTY-720. This means that the present compounds can activate S1P1 in vitro at a smaller concentration than FTY-720, indicating relatively higher efficacy than FTY-720.

Experimental Example 3

Evaluation of Rat Peripheral Blood Lymphocyte Decrease (1) Test Method

Lymphocyte decrease in blood by S1P1 agonist was evaluated using a male SD rat. After adapting a rat weighing about 250 g to a breeding facility for one week, a test compound was administered to it once. At 3 hours, 6 hours, 24 hours and 48 hours after administration, blood was taken from a tail caudal vein, and about 200 μl of the blood was put into an EDTA tube while preventing it from clotting, followed by measurement of the number of lymphocytes in blood. The number of lymphocytes was analyzed by a hematological examination device, Hemoanalyzer. The doses of the test compounds were 3 mg/kg for Example 52, 94, 108, 117, 142, 145, 146, 148 and 149 compounds, and 1 mg/kg for Example 150, 151, 153, 154, 155, 158, 159 and 161 compounds.

(2) Results

The results are shown in Table 3 below which represents the degree of decrease in lymphocyte number at 6 hours after administration (%). In the table, FTY-720 as Reference refers to an S1P agonist compound, Fingolimod (trade name: Gilenya).

TABLE 3

| Example | Lymphocyte count |
|---------|------------------|
| 52      | −80%             |
| 94      | −82%             |
| 108     | −70%             |
| 117     | −80%             |
| 142     | −80%             |
| 145     | −48%             |
| 146     | −78%             |
| 148     | −81%             |
| 149     | −80%             |
| 150     | −82%             |
| 151     | −80%             |
| 153     | −80%             |
| 154     | −65%             |
| 155     | −75%             |
| 158     | −30%             |
| 159     | −80%             |
| 161     | −65%             |
| FTY-720 | −80%             |

As shown in Table 3 above, the compounds according to the present invention exhibit a strong lymphocyte number decreasing activity at 6 hours after administration in the pharmacological test using a rat.

The invention claimed is:

1. A compound of Formula 1, or a pharmaceutically acceptable salt or stereoisomer thereof:

[Formula 1]

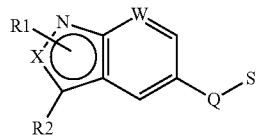

wherein
X represents C or N,
R1 represents optionally substituted alkyl,
  wherein the optional substituent of the optionally substituted alkyl is one or more selected from halo(gen), cyano, hydroxyl, $C_1$-$C_6$-alkyloxy, oxo or sulfonyl unsubstituted or substituted by alkyl,
R2 represents H, optionally substituted alkyl, halogen, CN, $CF_3$ or $COCF_3$,
  wherein the optional substituent of the optionally substituted alkyl is one or more selected from halo(gen), cyano, hydroxyl, $C_1$-$C_6$-alkyloxy, oxo or sulfonyl unsubstituted or substituted by alkyl, W represents C, N, C-alkoxy, C-halogen or C—CN,
Q represents $CH_2O$ or

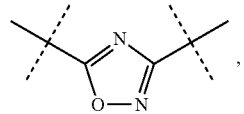

and
S is selected from the following residues:

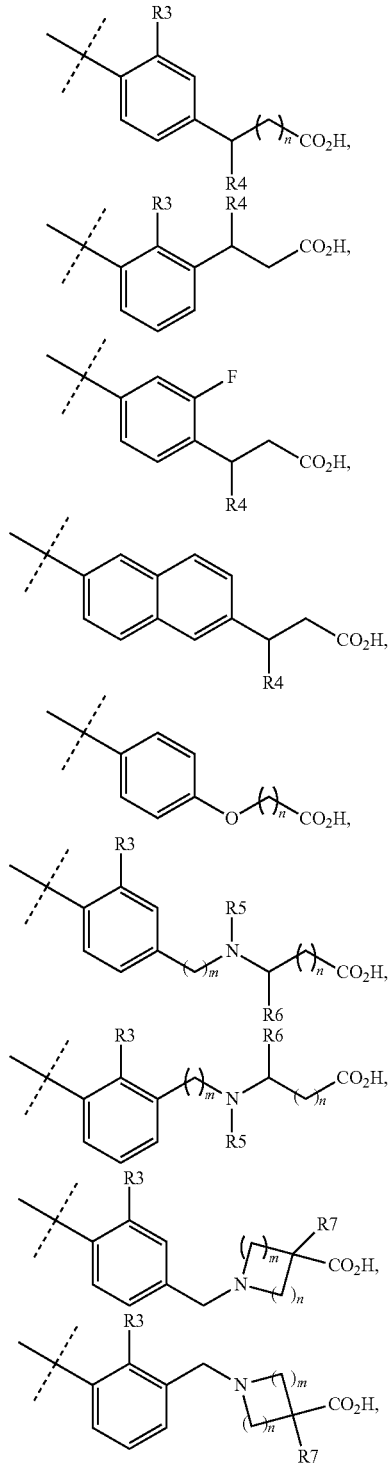

-continued
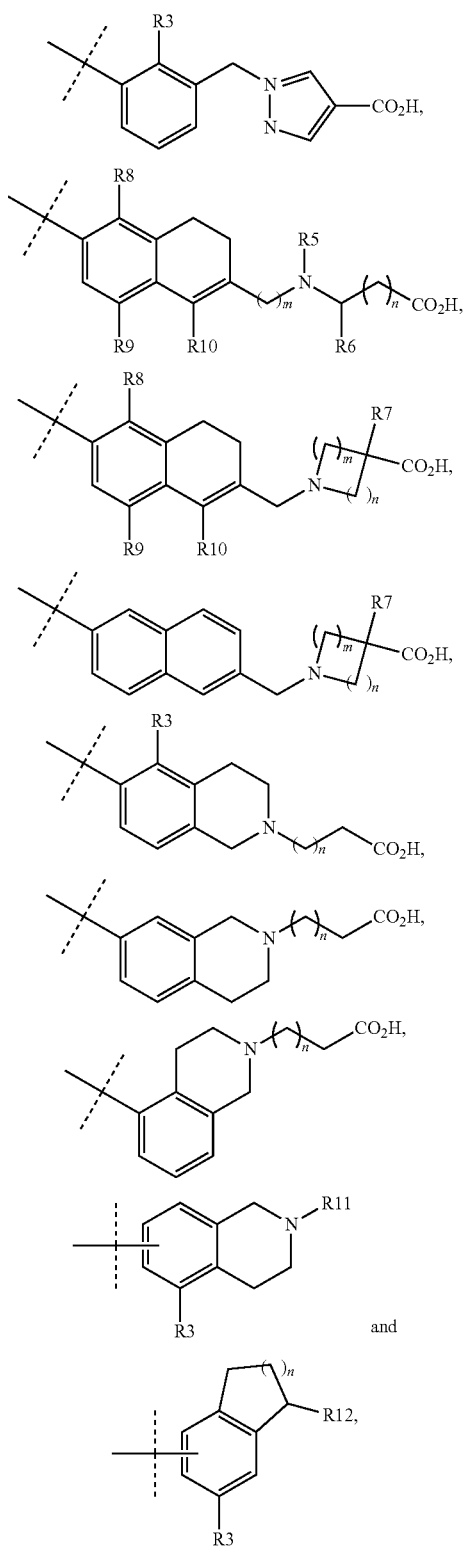
wherein
m and n represent independently 0, 1, 2 or 3,
R3-R10 represent independently H, alkyl, halogen, halogenoalkyl or alkoxyalkyl,
R11 represents H,
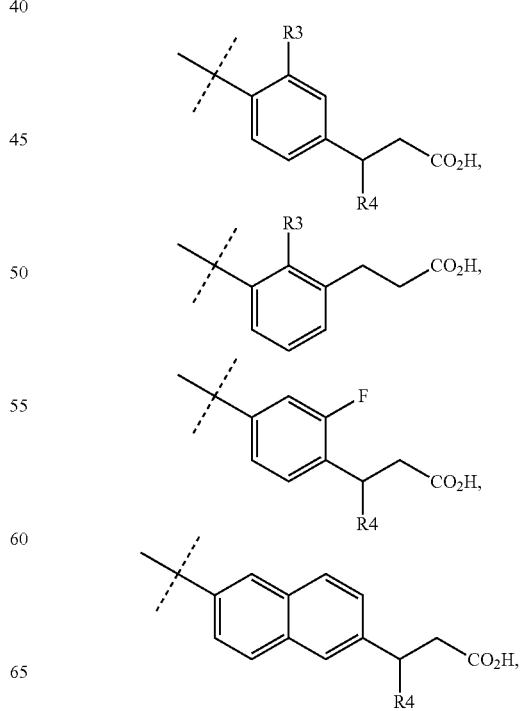
and
R12 represents OH, NH$_2$,
2. The compound, or pharmaceutically acceptable salt or stereoisomer thereof according to claim 1, wherein S is selected from the following groups:

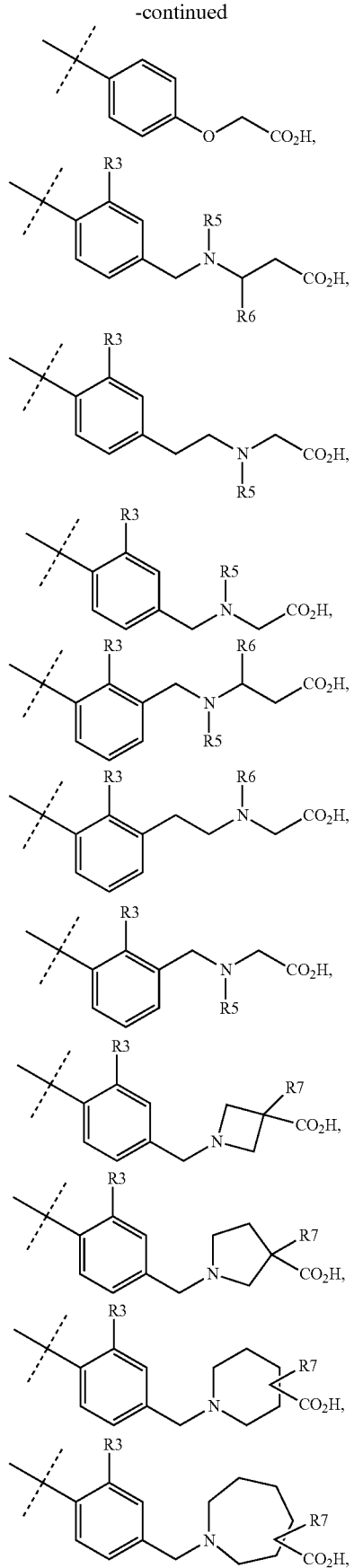
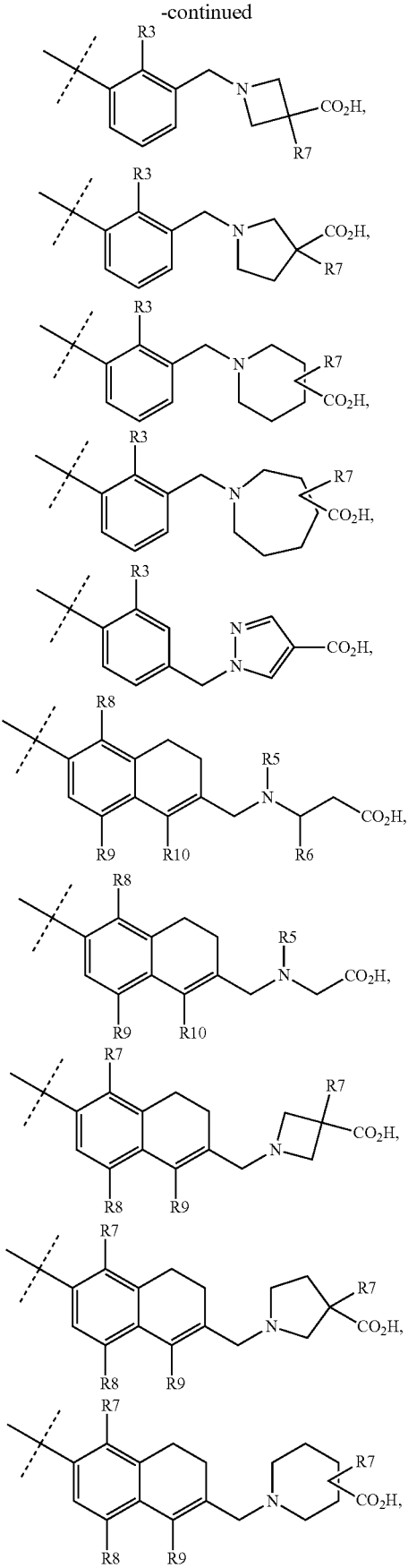

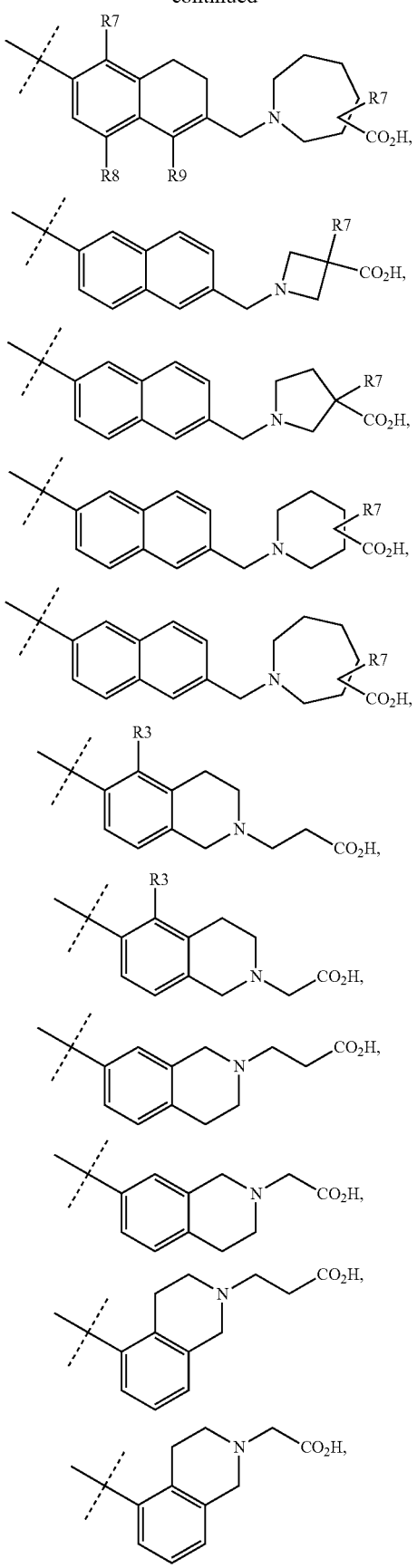

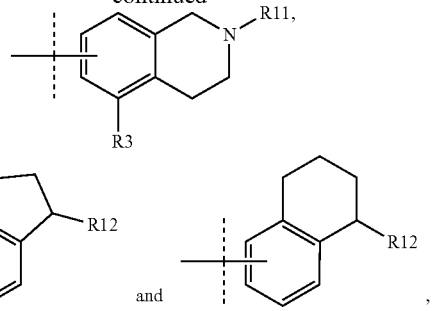

wherein
R3-R10 represent independently H, methyl, ethyl, fluoride, chloride, halogenomethyl, halogenoethyl, alkoxymethyl or alkoxyethyl,
R11 represents H,

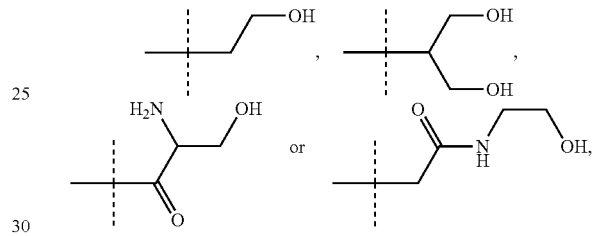

and
R12 represents OH, NH₂,

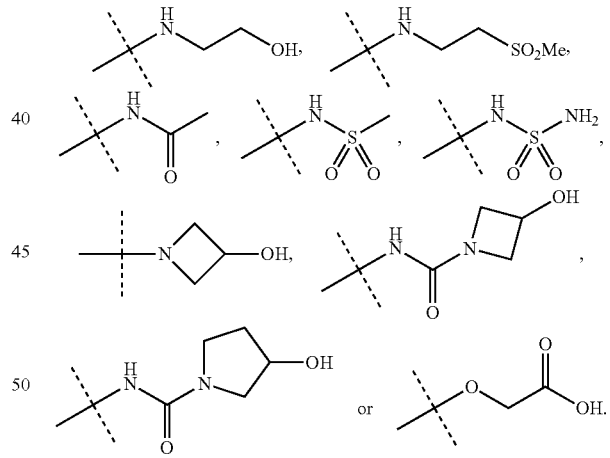

3. A compound, or pharmaceutically acceptable salt or stereoisomer thereof, wherein the compound is selected from the group consisting of:

3-{4-[5-(1-isopropyl-1H-indol-5-yl)-[1,2,4]oxadiazol-3-yl]-3-methyl-phenyl}-propanoic acid;

1-{4-[5-(1-isopropyl-1H-indol-5-yl)-[1,2,4]oxadiazol-3-yl]-benzyl}-azetidine-3-carboxylic acid;

1-{4-[5-(3-chloro-1-isopropyl-1H-indol-5-yl)-[1,2,4]oxadiazol-3-yl]-3-methyl-benzyl}-azetidine-3-carboxylic acid;

1-{4-[5-(3-cyano-1-isopropyl-1H-indol-5-yl)-[1,2,4]oxadiazol-3-yl]-3-methyl-benzyl}-azetidine-3-carboxylic acid;

1-{4-[5-(1-isopropyl-1H-indol-5-yl)-[1,2,4]oxadiazol-3-yl]-3-methyl-benzyl}-azetidine-3-carboxylic acid;
1-(4-{5-[1-isopropyl-3-(2,2,2-trifluoro-acetyl)-1H-indol-5-yl]-[1,2,4]oxadiazol-3-yl}-3-methyl-benzyl)-azetidine-3-carboxylic acid;
1-{4-[5-(1-isobutyl-1H-indol-5-yl)-[1,2,4]oxadiazol-3-yl]-3-methyl-benzyl}-azetidine-3-carboxylic acid;
1-{4-[5-(3-chloro-1-isopropyl-1H-indol-5-yl)-[1,2,4]oxadiazol-3-yl]-benzyl}-1H-pyrazole-4-carboxylic acid;
1-{4-[5-(3-chloro-1-isopropyl-1H-indol-5-yl)-[1,2,4]oxadiazol-3-yl]-3-methyl-benzyl}-1H-pyrazole-4-carboxylic acid;
3-{4-[5-(3-chloro-1-isopropyl-1H-indol-5-yl)-[1,2,4]oxadiazol-3-yl]-benzylamino}-propanoic acid;
{4-[5-(1-isopropyl-1H-indol-5-yl)-[1,2,4]oxadiazol-3-yl]-phenoxy}-acetic acid;
{4-[5-(3-chloro-1-isopropyl-1H-indol-5-yl)-[1,2,4]oxadiazol-3-yl]-phenoxy}-acetic acid;
3-{4-[5-(1-isopropyl-1H-indol-5-yl)-[1,2,4]oxadiazol-3-yl]-phenoxy}-propanoic acid;
(R)-1-{4-[5-(1-isopropyl-1H-indol-5-yl)-[1,2,4]oxadiazol-3-yl]-3-methyl-benzyl}-piperidine-3-carboxylic acid;
(S)-1-{4-[5-(1-isopropyl-1H-indol-5-yl)-[1,2,4]oxadiazol-3-yl]-3-methyl-benzyl}-piperidine-3-carboxylic acid;
1-{4-[5-(1-isopropyl-1H-indol-5-yl)-[1,2,4]oxadiazol-3-yl]-3-methyl-benzyl}-piperidine-4-carboxylic acid;
(S)-1-{4-[5-(1-isopropyl-1H-indol-5-yl)-[1,2,4]oxadiazol-3-yl]-3-methyl-benzyl}-pyrrolidine-3-carboxylic acid;
({4-[5-(1-isopropyl-1H-indol-5-yl)-[1,2,4]oxadiazol-3-yl]-3-methyl-benzyl}-methyl-amino)-acetic acid;
3-{4-[5-(1-isopropyl-1H-indol-5-yl)-[1,2,4]oxadiazol-3-yl]-3-methyl-benzylamino}-propanoic acid;
3-{3-[5-(1-isopropyl-1H-indol-5-yl)-[1,2,4]oxadiazol-3-yl]-2-methyl-phenyl}-propanoic acid;
1-{3-[5-(1-isopropyl-1H-indol-5-yl)-[1,2,4]oxadiazol-3-yl]-benzyl}-azetidine-3-carboxylic acid;
{3-[5-(1-isopropyl-1H-indol-5-yl)-[1,2,4]oxadiazol-3-yl]-benzylamino}-acetic acid;
({3-[5-(1-isopropyl-1H-indol-5-yl)-[1,2,4]oxadiazol-3-yl]-benzyl}-methyl-amino)-acetic acid;
(1S,3R)-3-{4-[5-(1-isopropyl-1H-indol-5-yl)-[1,2,4]oxadiazol-3-yl]-3-methyl-benzylamino}-cyclopentanecarboxylic acid;
3-({4-[5-(1-isopropyl-1H-indol-5-yl)-[1,2,4]oxadiazol-3-yl]-3-methyl-benzyl}-methyl-amino)-propanoic acid;
1-{3-[5-(1-isopropyl-1H-indol-5-yl)-[1,2,4]oxadiazol-3-yl]-2-methyl-benzyl}-azetidine-3-carboxylic acid;
5-[5-(1-isopropyl-1H-indol-5-yl)-[1,2,4]oxadiazol-3-yl]-1,2,3,4-tetrahydro-isoquinoline, hydrochloride;
{5-[5-(1-isopropyl-1H-indol-5-yl)-[1,2,4]oxadiazol-3-yl]-3,4-dihydro-1H-isoquinolin-2-yl}-acetic acid;
3-{5-[5-(1-isopropyl-1H-indol-5-yl)-[1,2,4]oxadiazol-3-yl]-3,4-dihydro-1H-isoquinolin-2-yl}-propanoic acid;
4-[5-(1-isopropyl-1H-indol-5-yl)-[1,2,4]oxadiazol-3-yl]-indan-1-ol;
2-{4-[5-(1-isopropyl-1H-indol-5-yl)-[1,2,4]oxadiazol-3-yl]-indan-1-ylamino}-ethanol;
(S)-2-amino-3-hydroxy-1-{5-[5-(1-isopropyl-1H-indol-5-yl)-[1,2,4]oxadiazol-3-yl]-3,4-dihydro-1H-isoquinolin-2-yl}-propan-1-on;
2-{5-[5-(1-isopropyl-1H-indol-5-yl)-[1,2,4]oxadiazol-3-yl]-3,4-dihydro-1H-isoquinolin-2-yl}-propan-1,3-diol;
N—{(S)-4-[5-(1-isopropyl-1H-indol-5-yl)-[1,2,4]oxadiazol-3-yl]-indan-1-yl}-methanesulfonamide;
N—{(S)-4-[5-(1-isopropyl-1H-indol-5-yl)-[1,2,4]oxadiazol-3-yl]-indan-1-yl}-acetamide;
N-{5-[5-(1-isopropyl-1H-indol-5-yl)-[1,2,4]oxadiazol-3-yl]-1,2,3,4-tetrahydro-naphthalen-1-yl}-acetamide;
N-{5-[5-(1-isopropyl-1H-indol-5-yl)-[1,2,4]oxadiazol-3-yl]-1,2,3,4-tetrahydro-naphthalen-1-yl}-methanesulfonamide;
N-{5-[5-(1-isopropyl-1H-indol-5-yl)-[1,2,4]oxadiazol-3-yl]-1,2,3,4-tetrahydro-naphthalen-1-yl}-sulfamide;
3-hydroxy-pyrrolidine-1-carboxylic acid {5-[5-(1-isopropyl-1H-indol-5-yl)-[1,2,4]oxadiazol-3-yl]-1,2,3,4-tetrahydro-naphthalen-1-yl}-amide;
5-[5-(3-chloro-1-isopropyl-1H-indol-5-yl)-[1,2,4]oxadiazol-3-yl]-1,2,3,4-tetrahydro-isoquinoline, hydrochloride;
7-[5-(1-isopropyl-1H-indol-5-yl)-[1,2,4]oxadiazol-3-yl]-1,2,3,4-tetrahydro-isoquinoline, hydrochloride;
3-hydroxy-azetidine-1-carboxylic acid {5-[5-(1-isopropyl-1H-indol-5-yl)-[1,2,4]oxadiazol-3-yl]-1,2,3,4-tetrahydro-naphthalen-1-yl}-amide;
{5-[5-(3-chloro-1-isopropyl-1H-indol-5-yl)-[1,2,4]oxadiazol-3-yl]-3,4-dihydro-1H-isoquinolin-2-yl}-acetic acid, fluoroacetate;
2-{5-[5-(3-chloro-1-isopropyl-1H-indol-5-yl)-[1,2,4]oxadiazol-3-yl]-3,4-dihydro-1H-isoquinolin-2-yl}-ethanol;
5-[5-(1-isopropyl-1H-indol-5-yl)-[1,2,4]oxadiazol-3-yl]-1,2,3,4-tetrahydro-naphthalen-1-ylamine, hydrochloride;
1-{4-[5-(1-isopropyl-1H-indol-5-yl)-[1,2,4]oxadiazol-3-yl]-indan-1-yl}-azetidin-3-ol;
2-{5-[5-(3-chloro-1-isopropyl-1H-indol-5-yl)-[1,2,4]oxadiazol-3-yl]-3,4-dihydro-1H-isoquinolin-2-yl}-N-(2-hydroxy-ethyl)-acetamide;
2-{7-[5-(1-isopropyl-1H-indol-5-yl)-[1,2,4]oxadiazol-3-yl]-3,4-dihydro-1H-isoquinolin-2-yl}-ethanol;
{5-[5-(1-isopropyl-1H-indol-5-yl)-[1,2,4]oxadiazol-3-yl]-1,2,3,4-tetrahydro-naphthalen-1-yl}-(2-methanesulfonyl-ethyl)-amine, hydrochloride;
{7-[5-(1-isopropyl-1H-indol-5-yl)-[1,2,4]oxadiazol-3-yl]-3,4-dihydro-1H-isoquinolin-2-yl}-acetic acid, hydrochloride;
N-(2-hydroxy-ethyl)-2-{7-[5-(1-isopropyl-1H-indol-5-yl)-[1,2,4]oxadiazol-3-yl]-3,4-dihydro-1H-isoquinolin-2-yl}-acetamide;
3-{4-[5-(3-chloro-1-isopropyl-1H-indol-5-yl)-[1,2,4]oxadiazol-3-yl]-3-methyl-phenyl}-propanoic acid;
3-{4-[5-(3-cyano-1-isopropyl-1H-indol-5-yl)-[1,2,4]oxadiazol-3-yl]-3-methyl-phenyl}-propanoic acid;
3-{3-methyl-4-[5-(1-methyl-1H-indol-5-yl)-[1,2,4]oxadiazol-3-yl]-phenyl}-propanoic acid;
5-[5-(1-isopropyl-1H-indol-5-yl)-[1,2,4]oxadiazol-3-yl]-indan-1-ol;
6-[5-(3-chloro-1-isopropyl-1H-indol-5-yl)-[1,2,4]oxadiazol-3-yl]-5-methyl-1,2,3,4-tetrahydro-isoquinoline, hydrochloride;
2-{6-[5-(3-chloro-1-isopropyl-1H-indol-5-yl)-[1,2,4]oxadiazol-3-yl]-5-methyl-3,4-dihydro-1H-isoquinolin-2-yl}-ethanol;
{6-[5-(3-chloro-1-isopropyl-1H-indol-5-yl)-[1,2,4]oxadiazol-3-yl]-5-methyl-3,4-dihydro-1H-isoquinolin-2-yl}-acetic acid, hydrochloride;
{5-[5-(1-isopropyl-1H-indol-5-yl)-[1,2,4]oxadiazol-3-yl]-indan-1-yloxy}-acetic acid;
2-{6-[5-(3-chloro-1-isopropyl-1H-indol-5-yl)-[1,2,4]oxadiazol-3-yl]-5-methyl-3,4-dihydro-1H-isoquinolin-2-yl}-N-(2-hydroxy-ethyl)-acetamide;

6-[5-(1-isopropyl-1H-indol-5-yl)-[1,2,4]oxadiazol-3-yl]-5-methyl-1,2,3,4-tetrahydro-isoquinoline, hydrochloride;
{6-[5-(3-cyano-1-isopropyl-1H-indol-5-yl)-[1,2,4]oxadiazol-3-yl]-5-methyl-3,4-dihydro-1H-isoquinolin-2-yl}-acetic acid, hydrochloride;
{6-[5-(1-isopropyl-1H-indol-5-yl)-[1,2,4]oxadiazol-3-yl]-5-methyl-3,4-dihydro-1H-isoquinolin-2-yl}-acetic acid, hydrochloride;
3-{4-[5-(7-chloro-2-methyl-1H-indol-5-yl)-[1,2,4]oxadiazol-3-yl]-3-methyl-phenyl}-propanoic acid;
1-isopropyl-5-[3-(1,2,3,4-tetrahydro-isoquinolin-5-yl)-[1,2,4]oxadiazol-5-yl]-1H-indol-3-carbonitrile, hydrochloride;
3-{4-[5-(2-cyclopentyl-1H-indol-5-yl)-[1,2,4]oxadiazol-3-yl]-3-methyl-phenyl}-propanoic acid;
{5-[5-(3-cyano-1-isopropyl-1H-indol-5-yl)-[1,2,4]oxadiazol-3-yl]-3,4-dihydro-1H-isoquinolin-2-yl}-acetic acid, hydrochloride;
3-{4-[5-(1-benzyl-1H-indol-5-yl)-[1,2,4]oxadiazol-3-yl]-3-methyl-phenyl}-propanoic acid;
3-{4-[5-(1-cyclopentyl-1H-indol-5-yl)-[1,2,4]oxadiazol-3-yl]-3-methyl-phenyl}-propanoic acid;
3-{4-[5-(7-cyano-2-methyl-1H-indol-5-yl)-[1,2,4]oxadiazol-3-yl]-3-methyl-phenyl}-propanoic acid;
3-{4-[5-(7-cyano-2-cyclopropyl-1H-indol-5-yl)-[1,2,4]oxadiazol-3-yl]-3-methyl-phenyl}-propanoic acid;
3-{4-[5-(7-cyano-1H-indol-5-yl)-[1,2,4]oxadiazol-3-yl]-3-methyl-phenyl}-propanoic acid;
3-{4-[5-(7-cyano-1-isopropyl-1H-indol-5-yl)-[1,2,4]oxadiazol-3-yl]-3-methyl-phenyl}-propanoic acid;
3-{4-[5-(7-cyano-1-methyl-1H-indol-5-yl)-[1,2,4]oxadiazol-3-yl]-3-methyl-phenyl}-propanoic acid;
3-{5-[5-(3-chloro-1-isopropyl-1H-indol-5-yl)-[1,2,4]oxadiazol-3-yl]-3,4-dihydro-1H-isoquinolin-2-yl}-propanoic acid, hydrochloride;
3-{6-[5-(1-isopropyl-1H-indol-5-yl)-[1,2,4]oxadiazol-3-yl]-5-methyl-3,4-dihydro-1H-isoquinolin-2-yl}-propanoic acid, hydrochloride;
3-{6-[5-(3-chloro-1-isopropyl-1H-indol-5-yl)-[1,2,4]oxadiazol-3-yl]-5-methyl-3,4-dihydro-1H-isoquinolin-2-yl}-propanoic acid, hydrochloride;
3-{4-[5-(7-methoxy-2-methyl-1H-indol-5-yl)-[1,2,4]oxadiazol-3-yl]-3-methyl-phenyl}-propanoic acid;
3-{4-[5-(7-chloro-1-isopropyl-1H-indol-5-yl)-[1,2,4]oxadiazol-3-yl]-3-methyl-phenyl}-propanoic acid;
3-{4-[5-(1-isopropyl-1H-indazol-5-yl)-[1,2,4]oxadiazol-3-yl]-3-methyl-phenyl}-propanoic acid;
{5-[5-(1-isopropyl-1H-indol-5-yl)-[1,2,4]oxadiazol-3-yl]-1,3-dihydro-isoindol-2-yl}-acetic acid;
3-{4-[5-(2-isopropyl-2H-indazol-5-yl)-[1,2,4]oxadiazol-3-yl]-3-methyl-phenyl}-propanoic acid;
{5-[5-(1-isopropyl-1H-indazol-5-yl)-[1,2,4]oxadiazol-3-yl]-3,4-dihydro-1H-isoquinolin-2-yl}-acetic acid;
3-{5-[5-(1-isopropyl-1H-indazol-5-yl)-[1,2,4]oxadiazol-3-yl]-3,4-dihydro-1H-isoquinolin-2-yl}-propanoic acid;
{6-[5-(1-isopropyl-1H-indazol-5-yl)-[1,2,4]oxadiazol-3-yl]-5-methyl-3,4-dihydro-1H-isoquinolin-2-yl}-acetic acid, trifluoroacetate;
3-{6-[5-(1-isopropyl-1H-indazol-5-yl)-[1,2,4]oxadiazol-3-yl]-5-methyl-3,4-dihydro-1H-isoquinolin-2-yl}-propanoic acid, trifluoroacetate;
{5-[5-(2-isopropyl-2H-indazol-5-yl)-[1,2,4]oxadiazol-3-yl]-3,4-dihydro-1H-isoquinolin-2-yl}-acetic acid, trifluoroacetate;
3-{5-[5-(2-isopropyl-2H-indazol-5-yl)-[1,2,4]oxadiazol-3-yl]-3,4-dihydro-1H-isoquinolin-2-yl}-propanoic acid, trifluoroacetate;
6-[5-(1-isopropyl-1H-indazol-5-yl)-[1,2,4]oxadiazol-3-yl]-5-methyl-1,2,3,4-tetrahydro-isoquinoline, hydrochloride;
5-[5-(2-isopropyl-2H-indazol-5-yl)-[1,2,4]oxadiazol-3-yl]-1,2,3,4-tetrahydro-isoquinoline, hydrochloride;
6-[5-(2-isopropyl-2H-indazol-5-yl)-[1,2,4]oxadiazol-3-yl]-5-methyl-1,2,3,4-tetrahydro-isoquinoline, hydrochloride;
6-[5-(3-chloro-1-isopropyl-1H-indazol-5-yl)-[1,2,4]oxadiazol-3-yl]-5-methyl-1,2,3,4-tetrahydro-isoquinoline, hydrochloride;
{6-[5-(3-chloro-1-isopropyl-1H-indazol-5-yl)-[1,2,4]oxadiazol-3-yl]-5-methyl-3,4-dihydro-1H-isoquinolin-2-yl}-acetic acid, trifluoroacetate;
3-{6-[5-(3-chloro-1-isopropyl-1H-indazol-5-yl)-[1,2,4]oxadiazol-3-yl]-5-methyl-3,4-dihydro-1H-isoquinolin-2-yl}-propanoic acid, trifluoroacetate;
{6-[5-(1-isopropyl-1H-pyrazolo[3,4-b]pyridin-5-yl)-[1,2,4]oxadiazol-3-yl]-5-methyl-3,4-dihydro-1H-isoquinolin-2-yl}-acetic acid;
5-[5-(1-isopropyl-1H-indazol-5-yl)-[1,2,4]oxadiazol-3-yl]-1,2,3,4-tetrahydro-isoquinoline, hydrochloride;
{6-[5-(2-isopropyl-2H-indazol-5-yl)-[1,2,4]oxadiazol-3-yl]-5-methyl-3,4-dihydro-1H-isoquinolin-2-yl}-acetic acid, trifluoroacetate;
3-{6-[5-(2-isopropyl-2H-indazol-5-yl)-[1,2,4]oxadiazol-3-yl]-5-methyl-3,4-dihydro-1H-isoquinolin-2-yl}-propanoic acid, trifluoroacetate;
{5-[5-(1-isopropyl-1H-pyrazolo[3,4-b]pyridin-5-yl)-[1,2,4]oxadiazol-3-yl]-3,4-dihydro-1H-isoquinolin-2-yl}-acetic acid;
({4-[5-(1-isopropyl-1H-indazol-5-yl)-[1,2,4]oxadiazol-3-yl]-3-methyl-benzyl}-methyl-amino)-acetic acid, trifluoroacetate;
5-[5-(3-chloro-1-isopropyl-1H-indazol-5-yl)-[1,2,4]oxadiazol-3-yl]-1,2,3,4-tetrahydro-isoquinoline, hydrochloride;
{5-[5-(3-chloro-1-isopropyl-1H-indazol-5-yl)-[1,2,4]oxadiazol-3-yl]-3,4-dihydro-1H-isoquinolin-2-yl}-acetic acid, trifluoroacetate;
3-{5-[5-(3-chloro-1-isopropyl-1H-indazol-5-yl)-[1,2,4]oxadiazol-3-yl]-3,4-dihydro-1H-isoquinolin-2-yl}-propanoic acid, trifluoroacetate;
{5-[5-(1-isopropyl-1H-pyrrolo[2,3-b]pyridin-5-yl)-[1,2,4]oxadiazol-3-yl]-3,4-dihydro-1H-isoquinolin-2-yl}-acetic acid;
6-[5-(3-chloro-1-isopropyl-1H-indazol-5-yl)-[1,2,4]oxadiazol-3-yl]-5-methyl-3,4-dihydro-1H-isoquinoline-2-sulfonic acid amide;
{6-[5-(1-isopropyl-1H-pyrrolo[2,3-b]pyridin-5-yl)-[1,2,4]oxadiazol-3-yl]-5-methyl-3,4-dihydro-1H-isoquinolin-2-yl}-acetic acid;
1-{4-[5-(1-isopropyl-1H-indazol-5-yl)-[1,2,4]oxadiazol-3-yl]-3-methyl-benzyl}-azetidine-3-carboxylic acid;
5-[5-(3-chloro-1-isopropyl-1H-indazol-5-yl)-[1,2,4]oxadiazol-3-yl]-3,4-dihydro-1H-isoquinoline-2-sulfonic acid amide;
{6-[5-(1-isopropyl-1H-indazol-5-yl)-[1,2,4]oxadiazol-3-yl]-3,4-dihydro-1H-isoquinolin-2-yl}-acetic acid, trifluoroacetate;
({4-[5-(1-isopropyl-1H-indazol-5-yl)-[1,2,4]oxadiazol-3-yl]-indan-1-yl}-methyl-amino)-acetic acid;

3-{6-[5-(1-isopropyl-1H-indazol-5-yl)-[1,2,4]oxadiazol-3-yl]-3,4-dihydro-1H-isoquinolin-2-yl}-propanoic acid, trifluoroacetate;
(R)-2-{4-[5-(1-isopropyl-1H-indazol-5-yl)-[1,2,4]oxadiazol-3-yl]-3-methyl-benzylamino}-propanoic acid;
{4-[5-(1-isopropyl-1H-indazol-5-yl)-[1,2,4]oxadiazol-3-yl]-3-methyl-benzylamino}-acetic acid, trifluoroacetate;
(ethyl-{4-[5-(1-isopropyl-1H-indazol-5-yl)-[1,2,4]oxadiazol-3-yl]-3-methyl-benzyl}-amino)-acetic acid, trifluoroacetate;
(R)-2-({4-[5-(1-isopropyl-1H-indazol-5-yl)-[1,2,4]oxadiazol-3-yl]-3-methyl-benzyl}-methyl-amino)-propanoic acid;
({4-[5-(1-isopropyl-1H-indazol-5-yl)-[1,2,4]oxadiazol-3-yl]-benzyl}-methyl-amino)-acetic acid, trifluoroacetate;
{6-[5-(1-isopropyl-3-methyl-1H-indazol-5-yl)-[1,2,4]oxadiazol-3-yl]-5-methyl-3,4-dihydro-1H-isoquinolin-2-yl}-acetic acid, trifluoroacetate;
({3-[5-(3-chloro-1-isopropyl-1H-indol-5-yl)-[1,2,4]oxadiazol-3-yl]-benzyl}-methyl-amino)-acetic acid, trifluoroacetate;
3-({3-[5-(3-chloro-1-isopropyl-1H-indol-5-yl)-[1,2,4]oxadiazol-3-yl]-benzyl}-methyl-amino)-propanoic acid, trifluoroacetate;
({3-[5-(3-chloro-1-isopropyl-1H-indol-5-yl)-[1,2,4]oxadiazol-3-yl]-2-methyl-benzyl}-methyl-amino)-acetic acid, trifluoroacetate;
3-{3-[5-(3-chloro-1-isopropyl-1H-indol-5-yl)-[1,2,4]oxadiazol-3-yl]-2-methyl-benzylamino}-propanoic acid, trifluoroacetate;
3-({3-[5-(3-chloro-1-isopropyl-1H-indol-5-yl)-[1,2,4]oxadiazol-3-yl]-2-methyl-benzyl}-methyl-amino)-propanoic acid, trifluoroacetate;
3-{4-[5-(3-chloro-1-isopropyl-1H-indazol-5-yl)-[1,2,4]oxadiazol-3-yl]-3-methyl-phenyl}-propanoic acid;
({3-[5-(3-chloro-1-isopropyl-1H-indazol-5-yl)-[1,2,4]oxadiazol-3-yl]-2-methyl-benzyl}-methyl-amino)-acetic acid, trifluoroacetate;
1-{3-[5-(3-chloro-1-isopropyl-1H-indazol-5-yl)-[1,2,4]oxadiazol-3-yl]-2-methyl-benzyl}-azetidine-3-carboxylic acid;
[(2-{3-[5-(3-chloro-1-isopropyl-1H-indol-5-yl)-[1,2,4]oxadiazol-3-yl]-phenyl}-ethyl)-methyl-amino]-acetic acid, trifluoroacetate;
1-(2-{3-[5-(3-chloro-1-isopropyl-1H-indol-5-yl)-[1,2,4]oxadiazol-3-yl]-phenyl}-ethyl)-piperidine-4-carboxylic acid;
3-{6-[5-(3-cyclopropyl-1-isopropyl-1H-indazol-5-yl)-[1,2,4]oxadiazol-3-yl]-5-methyl-3,4-dihydro-1H-isoquinolin-2-yl}-propanoic acid, trifluoroacetate;
3-{4-[5-(3-chloro-1-isopropyl-1H-indazol-5-yl)-[1,2,4]oxadiazol-3-yl]-3-methyl-phenyl}-butyric acid, trifluoroacetate;
3-{4-[5-(3-chloro-1-isopropyl-1H-indol-5-yl)-[1,2,4]oxadiazol-3-yl]-3-methyl-phenyl}-butyric acid, trifluoroacetate;
1-[4-(1-isopropyl-1H-indol-5-ylmethoxy)-benzyl]-azetidine-3-carboxylic acid;
3-[4-(1-isopropyl-1H-indol-5-ylmethoxy)-phenyl]-propanoic acid;
1-[4-(3-chloro-1-isopropyl-1H-indol-5-ylmethoxy)-3-methyl-benzyl]-azetidine-3-carboxylic acid;
[5-(1-isopropyl-1H-indazol-5-ylmethoxy)-3,4-dihydro-1H-isoquinolin-2-yl]-acetic acid, trifluoroacetate;
[6-(1-isopropyl-1H-indazol-5-ylmethoxy)-5-methyl-3,4-dihydro-1H-isoquinolin-2-yl]-acetic acid, trifluoroacetate;
[6-(2-isopropyl-2H-indazol-5-ylmethoxy)-5-methyl-3,4-dihydro-1H-isoquinolin-2-yl]-acetic acid, trifluoroacetate;
[5-(2-isopropyl-2H-indazol-5-ylmethoxy)-3,4-dihydro-1H-isoquinolin-2-yl]-acetic acid, trifluoroacetate;
3-[4-(3-chloro-1-isopropyl-1H-indol-5-ylmethoxy)-2-fluoro-phenyl]-propanoic acid;
3-[5-(1-isopropyl-1H-indazol-5-ylmethoxy)-3,4-dihydro-1H-isoquinolin-2-yl]-propanoic acid, trifluoroacetate;
3-[6-(3-chloro-1-isopropyl-1H-indol-5-ylmethoxy)-naphthalen-2-yl]-propanoic acid;
1-[6-(3-chloro-1-isopropyl-1H-indazol-5-ylmethoxy)-naphthalen-2-ylmethyl]-azetidine-3-carboxylic acid;
{[6-(3-chloro-1-isopropyl-1H-pyrrolo[2,3-b]pyridin-5-ylmethoxy)-naphthalen-2-ylmethyl]-methyl-amino}-acetic acid;
{[6-(3-chloro-1-isopropyl-1H-indazol-5-ylmethoxy)-naphthalen-2-ylmethyl]-methyl-amino}-acetic acid;
{[6-(3-chloro-1-isopropyl-1H-indazol-5-ylmethoxy)-1-methyl-3,4-dihydro-naphthalen-2-ylmethyl]-methyl-amino}-acetic acid;
1-[6-(3-chloro-1-isopropyl-1H-indazol-5-ylmethoxy)-1-methyl-3,4-dihydro-naphthalen-2-ylmethyl]-azetidine-3-carboxylic acid;
1-[6-(3-chloro-1-isopropyl-1H-pyrazolo[3,4-b]pyridin-5-ylmethoxy)-naphthalen-2-ylmethyl]-azetidine-3-carboxylic acid;
1-[6-(3-chloro-1-isopropyl-1H-indazol-5-ylmethoxy)-1-methyl-3,4-dihydro-naphthalen-2-ylmethyl]-piperidine-4-carboxylic acid;
1-[6-(3-chloro-1-isopropyl-1H-indazol-5-ylmethoxy)-1-methyl-3,4-dihydro-naphthalen-2-ylmethyl]-azepane-4-carboxylic acid;
1-[1-chloro-6-(3-chloro-1-isopropyl-1H-indazol-5-ylmethoxy)-3,4-dihydro-naphthalen-2-ylmethyl]-pyrrolidine-3-carboxylic acid;
(R)-1-[1-chloro-6-(3-chloro-1-isopropyl-1H-indazol-5-ylmethoxy)-3,4-dihydro-naphthalen-2-ylmethyl]-pyrrolidine-3-carboxylic acid;
1-[1-chloro-6-(3-chloro-1-isopropyl-1H-indazol-5-ylmethoxy)-3,4-dihydro-naphthalen-2-ylmethyl]-3-methyl-pyrrolidine-3-carboxylic acid;
1-[1-chloro-6-(3-chloro-1-isopropyl-1H-indazol-5-ylmethoxy)-3,4-dihydro-naphthalen-2-ylmethyl]-piperidine-4-carboxylic acid;
1-[1-chloro-6-(3-chloro-1-isopropyl-1H-indazol-5-ylmethoxy)-3,4-dihydro-naphthalen-2-ylmethyl]-4-fluoro-piperidine-4-carboxylic acid;
1-[1-chloro-6-(3-chloro-1-isopropyl-1H-indazol-5-ylmethoxy)-3,4-dihydro-naphthalen-2-ylmethyl]-piperidine-3-carboxylic acid;
(S)-1-[1-chloro-6-(3-chloro-1-isopropyl-1H-indazol-5-ylmethoxy)-3,4-dihydro-naphthalen-2-ylmethyl]-piperidine-3-carboxylic acid;
(R)-1-[1-chloro-6-(3-chloro-1-isopropyl-1H-indazol-5-ylmethoxy)-3,4-dihydro-naphthalen-2-ylmethyl]-piperidine-3-carboxylic acid;
1-[1-chloro-6-(3-chloro-1-isopropyl-1H-indazol-5-ylmethoxy)-3,4-dihydro-naphthalen-2-ylmethyl]-3-fluoro-piperidine-3-carboxylic acid;
1-[1-chloro-6-(3-chloro-1-isopropyl-1H-pyrazolo[3,4-b]pyridin-5-ylmethoxy)-3,4-dihydro-naphthalen-2-ylmethyl]-piperidine-4-carboxylic acid;

1-[6-(1-sec-butyl-3-chloro-1H-pyrazolo[3,4-b]pyridin-5-ylmethoxy)-1-chloro-3,4-dihydro-naphthalen-2-ylmethyl]-piperidine-4-carboxylic acid; and 1-[1-chloro-6-(3-chloro-1-isopropyl-1H-indazol-5-ylmethoxy)-3,4-dihydro-naphthalen-2-ylmethyl]-3-fluoro-pyrrolidine-3-carboxylic acid.

4. The compound of claim 1, wherein R1 is alkyl and R2 is H, alkyl, halogen, CN, $CF_3$ or $COCF_3$.

5. A pharmaceutical composition, comprising the compound, or pharmaceutically acceptable salt or stereoisomer thereof according to claim 1 as an active component, and a pharmaceutically acceptable carrier.

6. A pharmaceutical composition, comprising the compound, or pharmaceutically acceptable salt or stereoisomer thereof according to claim 4 as an active component, and pharmaceutically acceptable carrier.

7. A method for treating immunoregulation disorders selected from the group consisting of systemic lupus erythematosus, chronic rheumatoid arthritis, imflammatory bowel diseases, multiple sclerosis, amyotrophic lateral sclerosis (ALS), arteriosclerosis, artherosclerosis, scleroderma and autoimmune hepatitis, comprising the step of administering the compound, or pharmaceutically acceptable salt or stereoisomer thereof according to claim 1 to a subject in need thereof.

8. A method for treating autoimmune diseases in mammals, comprising the step of administering the compound, or pharmaceutically acceptable salt or stereoisomer thereof according to claim 1 to a subject in need thereof.

9. The method according to claim 8, wherein the autoimmune disease is multiple sclerosis.

10. A method for treating immunoregulation disorders selected from the group consisting of systemic lupus erythematosus, chronic rheumatoid arthritis, imflammatory bowel diseases, multiple sclerosis, amyotrophic lateral sclerosis (ALS), arteriosclerosis, artherosclerosis, scleroderma and autoimmune hepatitis, comprising the step of administering the compound, or pharmaceutically acceptable salt or stereoisomer thereof according to claim 4 to a subject in need thereof.

11. A method for treating an autoimmune disease in mammals, comprising the step of administering the compound, or pharmaceutically acceptable salt or stereoisomer thereof according to claim 4 to a subject in need thereof.

12. The method according to claim 11, wherein the autoimmune disease is multiple sclerosis.

* * * * *